(12) United States Patent
Jackson et al.

(10) Patent No.: US 8,357,501 B2
(45) Date of Patent: Jan. 22, 2013

(54) TISSUE PROTECTIVE ERYTHROPOIETIN RECEPTOR (NEPOR) AND METHODS OF USE

(75) Inventors: David B. Jackson, Heidelberg (DE);
Martin Stein, Mannheim (DE);
Hartmut Voss, Schriesheim (DE);
Stephan Brock, Weinheim (DE)

(73) Assignee: Molecular Health GmbH, Heidelberg (DE)

( * ) Notice: Subject to any disclaimer, the term of this patent is extended or adjusted under 35 U.S.C. 154(b) by 0 days.

(21) Appl. No.: 12/474,017

(22) Filed: May 28, 2009

(65) Prior Publication Data

US 2009/0306186 A1 Dec. 10, 2009

Related U.S. Application Data

(63) Continuation-in-part of application No. PCT/EP2008/066480, filed on Nov. 28, 2008.

(60) Provisional application No. 60/991,042, filed on Nov. 29, 2007.

(51) Int. Cl.
*G01N 33/53* (2006.01)
*G01N 33/15* (2006.01)
*G01N 33/48* (2006.01)
*A61K 38/18* (2006.01)
*C07K 14/505* (2006.01)

(52) U.S. Cl. ............ 435/7.9; 435/7.1; 514/7.7; 530/399

(58) Field of Classification Search ........................ None
See application file for complete search history.

(56) References Cited

FOREIGN PATENT DOCUMENTS

| WO | WO 2004/024773 A | 3/2004 |
| WO | WO 2004/080418 | 9/2004 |
| WO | WO 2004/096148 A | 11/2004 |
| WO | WO 2006/034456 | 3/2006 |

OTHER PUBLICATIONS

Wu et al. Expression of EPHB2 and EPHB4 in Breast Carcinoma. Pathology Oncology Research vol. 10/No. 1 (Feb. 2004).*
Hardee et al. Erythropoietin biology in Cancer. Clinical Cancer Research vol. 12(2) (Jan. 15, 2006).*
Sinha et al. The association between elevated EPBB4 expression, smoking status and advanced-stage disease in patients with head and neck squamous cell carcinoma. Arch Otolaryngol Head Neck Surgery vol. 132:1053-1059 (Oct. 2006).*
Koolpe et al. EphB receptor-binding peptides identified by phage display enable design of an antagonist with Ephrin-like Affinity. The Journal of Biological Chemistry, vol. 280/No. 17:17301-17311 (Jul. 29, 2005; published online Feb. 18, 2005).*
Muller-Ehmsen et al. Role of erythropoietin for angiogenesis and vasculogenesis: from embryonic development through adulthood. Am. J Physiol. Heart Circ Physiol vol. 290:H331-H340 (2006; first published Jul. 15, 2005).*
Sinha et al. Expression of EPH-B4 in head and neck squamous cell carcinoma. Ear, Nose & Throat Journal, vol. 82/11:866887; 4 pages (Nov. 2003).*
Henke et al. Do erythropoietin receptors on cancer cells explain unexpected clinical findings? Journal of Clinical Oncology, vol. 24/29:4708-4712 (Oct. 10, 2006).*
Konstantinopoulos, et al. "Selective modulation of the erythropoietic and tissue-protective effects erythropoietin: Time to reach the full therapeutic potential of erythropoietin", Biochimica et Biophysica Acta, vol. 1776, pp. 1-9, 2007.
Xia et al. "Up-Regulation of EphB4 in Mesothelioma and Its Biological Significance", Clinical Cancer Research, vol. 11, No. 12, pp. 4305-4315, 2005.
Brines, Michael et al. "Erythropoietin mediates tissue protection through an erythropoietin and common beta-subunit heteroreceptor", Proceedings of the National Academy of Sciences of the United States of America, vol. 101, No. 41; pp. 14907-14912, 2004.
Jubinsky, Paul et al. "The beta chain of the interleukin-3 receptor functionally associates with the erythropoietin receptor", Blood, vol. 90, No. 5, pp. 1867-1873, 1997.
Habashy et al, "Transferrin receptor (CD71) is a marker of poor prognosis in breast cancer and can predict response to tamoxifen," Breast Cancer Res Treat., 119(2):283-93. Epub Feb. 24, 2009 PubMed PMID: 19238537, 2010, Abstract.
Taneja et al, "Classical and novel prognostic biomarkers for breast cancer and their clinical significance," Clin. Med. Insights Oncol., 4: 15-34, 2010.
Turner et al, "FGFR1 amplification drives endocrine therapy resistance and is a therapeutic target in breast cancer," Cancer Research; 70(5) 2085-94. 3), 2010.
Khodarev et al. "Cooperativity of the MUC1 oncoproitein and STAT1 pathway in poor prognosis human breast cancer," Oncogene. 29(6):920-9, 2010.
Bierie et al., "Gain or loss of TGFbeta signaling in mammary carcinoma cells can promote metastasis," Cell Cycle, 8(20):3319-27, 2009.
Buess et al.,"Tumor-endothelial interaction links the CD44(+)/CD24(-) phenotype with poor prognosis in early stage breast cancer," Neoplasia, (10):987-1002, 2009.

(Continued)

Primary Examiner — Elizabeth C Kemmerer
Assistant Examiner — Regina M Deberry
(74) Attorney, Agent, or Firm — Foley & Lardner LLP

(57) ABSTRACT

There is disclosed a molecular composition(s) of a novel tissue protective erythropoietin (EPO) binding receptor protein complex, termed NEPOR. Presence of NEPOR components on a tumor allows EPO to impinge on the survival of associated cells thereby enhancing tumor progression and negatively effecting patient survival. Presence of NEPOR represents a prognostic biomarker for poorer patient outcome. Thus, methods are provided for stratifying patients having a tumor as suitable (i.e. NEPOR not present) or non-suitable (i.e., NEPOR present) for EPO treatment, comprising: (a) isolating a tissue sample from an individual who is receiving or is a candidate for receiving erythropoietin, (b) determining the level of expression of the NEPOR gene(s) (mRNA) and/or the presence of the NEPOR gene product (protein) from the isolated tissue, and (c) correlating the presence of an NEPOR gene expression product or the presence of NEPOR protein to a physiological response to the treatment with erythropoietin. Furthermore, by disclosing the molecular compositions of NEPOR species, there are disclosed methods for rationally identifying/designing NEPOR modulating therapeutics. Methods also are provided for treating neurological insults such as stroke (via enhancement of NEPOR activity) and cancer (via down-regulation of cytoprotective signaling from NEPOR).

4 Claims, 21 Drawing Sheets

OTHER PUBLICATIONS

Yasuoka H, et al., "Neuropilin-2 expression in breast cancer: correlation with lymph node metastasis, poor prognosis, and regulation of CXCR4 expression," *BMC Cancer*, 9:220, 2009.

Zabouo et al., "CD146 expression is associated with a poor prognosis in human breast tumors and with enhanced motility in breast cancer cell lines," *Breast Cancer Res.*, 11(1):R1. Epub Jan. 5, 2009. PubMed PMID: 19123925; PubMed Central PMCID: PMC2687703, 2009.

Sasaki et al., "REG1A expression is an independent factor predictive of poor prognosis in patients with breast cancer," *Ann Surg Oncol.*, (11):3244-51. Epub Sep. 10, 2008. PubMed PMID: 18781363, 2008 (Abstract).

Kuvaja et al., "High serum TIMP-1 correlates with poor prognosis in breast carcinoma—a validation study," *Cancer Biomark.*, 3(6):293-300. PubMed PMID: 18048967, 2007 (Abstract).

Marot et al., "High tumoral levels of Kiss1 and G-protein-coupled receptor 54 expression are correlated with poor prognosis of estrogen receptor-positive breast tumors," *Endocr Relat Cancer*, 14(3):691-702, PubMed PMID: 17914099, 2007.

Welm et al., "The macrophage-stimulating protein pathway promotes metastasis in a mouse model for breast cancer and predicts poor prognosis in humans," *Proc Natl Acad Sci U S A.*, 1;104(18):7570-5, PubMed PMID: 17456594; PubMed Central PMCID: PMC1855278, 2007.

Garcia et al., "Poor prognosis in breast carcinomas correlates with increased expression of targetable CD146 and c-Met and with proteomic basal-like phenotype," *Hum Pathol.*, 38(6):830-41, PubMed PMID: 17316758, 2007 (Abstract).

Westenfelder et al., "Erythropoietin stimulates proliferation of human renal carcinoma cells," *Kidney Int.* 58:647-657, 2000.

Acs et al., "Erythropoietin and erythropoietin receptor expression in human cancer," *Cancer Res.* 61:3561-3565, 2001.

Solar et al., Erythropoietin treatment of human ovarian cancer cells results in enhanced signaling and a paclitaxel-resistant phenotype, *Int. J. Cancer* 122:281-288, 2008 (Abstact).

Jeong et al., "An erythropoietin autocrine/paracrine axis modulates the growth and survival of human prostate cancer cells," *Mol. Cancer Res.*, 7:1150-1157, 2009.

Lai et al.,"Erythropoietin-mediated activation of JAK-STAT signaling contributes to cellular invasion in head and neck squamous cell carcinoma," *Oncogene*, 24:4442-4449, 2005.

Gewirtz, et al., "Erythropoietin fails to interfere with the antiproliferative and cytotoxic effects of antitumor drugs," *Clin. Cancer Res.* 12:2232-2238, 2006.

Liu et al., "Effect of haemopoietic growth factors on cancer cell lines and their role in chemosensitivity," *Oncogene* 23:981-990, 2004.

Laugsch et al., "Lack of functional erythropoietin receptors of cancer cell lines," *Int. J. Cancer* 122:1005-1011, 2008.

Jeong et al., "Characterization of erythropoietin receptor and erythropoietin expression and function in human ovarian cancer cells," *Int. J. Cancer.*, 122:274-280, 2008.

Paragh et al., "RNA interferencemediated inhibition of erythropoietin receptor expression suppresses tumor growth and invasiveness in A2780 human ovarian carcinoma cells," *Am. J. Pathol.* 174:1504-1514, 2009.

Sinclair et al., "Expression and function of erythropoietin receptors in tumors: implications for the use of erythropoiesis-stimulating agents in cancer patients," *Cancer*, 110(3):477-88, 2007.

Martiny-Baron et al., "The small molecule specific EphB4 kinase inhibitor NVP-BHG712 inhibits VEGF driven angiogenesis," *Angiogenesis*, (3):259-67, PubMed PMID: 20803239; PubMed Central PMCID: PMC2941628, 2010.

Davies et al, "Soluble ephrin-B2 mediates apoptosis in retinal neovascularization and in endothelial cells," *Microvasc Res.*, 77(3):382-6, PubMed PMID: 19232363; PubMed Central PMCID: PMC2679415, 2009.

He et al., "Soluble EphB4 regulates choroidal endothelial cell function and inhibits laser-induced choroidal neovascularization," *Invest Ophthalmol Vis Sci.*, 46(12):4772-9. PubMed PMID: 16303978, 2005.

Zamora et al., "Soluble forms of EphrinB2 and EphB4 reduce retinal neovascularization in a model of proliferative retinopathy," *Invest Ophthalmol Vis Sci.*, 46(6):2175-82. PubMed PMID: 15914639, 2005.

Martiny-Baron et al., "Inhibition of tumor growth and angiogenesis by soluble EphB4," *Neoplasia*, 6(3):248-57. PubMed PMID: 15153337; PubMed Central PMCID: PMC1502094, 2004.

Shin et all, Expression of ephrinB2 identifies a stable genetic difference between arterial and venous vascular smooth muscle as well as endothelial cells, and marks subsets of microvessels at sites of adult neovascularization. *Dev Biol.*, 230(2):139-50. PubMed PMID: 11161568, 2001 (Abstract).

\* cited by examiner

EPH Receptor domain architecture

Ephrin domain architecture

FIG. 11

| Cell Line | EpoR | EphB4 |
|---|---|---|
| Igrov | + | ++ |
| Skov3ip | 0 | ++ |
| HeyA8 | ++ | 0 |
| HeyA8MDR | +++ | + |

HeyA8-MDR
mouse tumor samples

| percent reduction | t-test | |
|---|---|---|
| 0.360976 | 1 v 2 | 0.065056 |
| -0.33573 | 1 v 3 | 0.024901 |
| -1.09027 | 2 v 3 | 0.024901 |
| -0.19542 | 2 v 4 | 0.284385 |
| 0.428102 | 3 v 4 | 0.055284 |
| 0.236098 | 1 v 4 | 0.155481 |

Immunoprecipitated- EphB4
wb- Epo

Survival (median years):

Epo-R neg 3.06

Epo-R pos 4.62 p=0.61

Survival (median years):

EphB4 neg 7.67

EphB4 pos 3.29 p<0.001

Survival (median years):

0 = 5.93

1 = 2.53

2 = 7.67

3 = 4.02

SEQUENCE LISTING

```
<160> NUMBER OF SEQ ID NOS: 273

<210> SEQ ID NO 1
<211> LENGTH: 508
<212> TYPE: PRT
<213> ORGANISM: Homo sapiens

<400> SEQUENCE: 1

Met Asp His Leu Gly Ala Ser Leu Trp Pro Gln Val Gly Ser Leu Cys
1               5                   10                  15

Leu Leu Leu Ala Gly Ala Ala Trp Ala Pro Pro Asn Leu Pro Asp
            20                  25                  30

Pro Lys Phe Glu Ser Lys Ala Ala Leu Leu Ala Ala Arg Gly Pro Glu
            35                  40                  45

Glu Leu Leu Cys Phe Thr Glu Arg Leu Glu Asp Leu Val Cys Phe Trp
        50                  55                  60

Glu Glu Ala Ala Ser Ala Gly Val Gly Pro Gly Asn Tyr Ser Phe Ser
65                  70                  75                  80

Tyr Gln Leu Glu Asp Glu Pro Trp Lys Leu Cys Arg Leu His Gln Ala
                85                  90                  95

Pro Thr Ala Arg Gly Ala Val Arg Phe Trp Cys Ser Leu Pro Thr Ala
            100                 105                 110

Asp Thr Ser Ser Phe Val Pro Leu Glu Leu Arg Val Thr Ala Ala Ser
            115                 120                 125

Gly Ala Pro Arg Tyr His Arg Val Ile His Ile Asn Glu Val Val Leu
        130                 135                 140

Leu Asp Ala Pro Val Gly Leu Val Ala Arg Leu Ala Asp Glu Ser Gly
145                 150                 155                 160

His Val Val Leu Arg Trp Leu Pro Pro Glu Thr Pro Met Thr Ser
                165                 170                 175

His Ile Arg Tyr Glu Val Asp Val Ser Ala Gly Asn Gly Ala Gly Ser
            180                 185                 190

Val Gln Arg Val Glu Ile Leu Glu Gly Arg Thr Glu Cys Val Leu Ser
        195                 200                 205

Asn Leu Arg Gly Arg Thr Arg Tyr Thr Phe Ala Val Arg Ala Arg Met
    210                 215                 220

Ala Glu Pro Ser Phe Gly Gly Phe Trp Ser Ala Trp Ser Glu Pro Val
225                 230                 235                 240

Ser Leu Leu Thr Pro Ser Asp Leu Asp Pro Leu Ile Leu Thr Leu Ser
                245                 250                 255

Leu Ile Leu Val Val Ile Leu Val Leu Leu Thr Val Leu Ala Leu Leu
            260                 265                 270

Ser His Arg Arg Ala Leu Lys Gln Lys Ile Trp Pro Gly Ile Pro Ser
        275                 280                 285

Pro Glu Ser Glu Phe Glu Gly Leu Phe Thr Thr His Lys Gly Asn Phe
    290                 295                 300

Gln Leu Trp Leu Tyr Gln Asn Asp Gly Cys Leu Trp Trp Ser Pro Cys
305                 310                 315                 320
```

Thr Pro Phe Thr Glu Asp Pro Pro Ala Ser Leu Glu Val Leu Ser Glu
             325                 330                 335

Arg Cys Trp Gly Thr Met Gln Ala Val Glu Pro Gly Thr Asp Asp Glu
             340                 345                 350

Gly Pro Leu Leu Glu Pro Val Gly Ser Glu His Ala Gln Asp Thr Tyr
             355                 360                 365

Leu Val Leu Asp Lys Trp Leu Leu Pro Arg Asn Pro Pro Ser Glu Asp
370                 375                 380

Leu Pro Gly Pro Gly Gly Ser Val Asp Ile Val Ala Met Asp Glu Gly
385                 390                 395                 400

Ser Glu Ala Ser Ser Cys Ser Ser Ala Leu Ala Ser Lys Pro Ser Pro
             405                 410                 415

Glu Gly Ala Ser Ala Ser Phe Glu Tyr Thr Ile Leu Asp Pro Ser
             420                 425                 430

Ser Gln Leu Leu Arg Pro Trp Thr Leu Cys Pro Glu Leu Pro Pro Thr
             435                 440                 445

Pro Pro His Leu Lys Tyr Leu Tyr Leu Val Val Ser Asp Ser Gly Ile
             450                 455                 460

Ser Thr Asp Tyr Ser Ser Gly Asp Ser Gln Gly Ala Gln Gly Gly Leu
465                 470                 475                 480

Ser Asp Gly Pro Tyr Ser Asn Pro Tyr Glu Asn Ser Leu Ile Pro Ala
             485                 490                 495

Ala Glu Pro Leu Pro Pro Ser Tyr Val Ala Cys Ser
             500                 505

<210> SEQ ID NO 2
<211> LENGTH: 987
<212> TYPE: PRT
<213> ORGANISM: Homo sapiens

<400> SEQUENCE: 2

Met Glu Leu Arg Val Leu Leu Cys Trp Ala Ser Leu Ala Ala Ala Leu
1               5                   10                  15

Glu Glu Thr Leu Leu Asn Thr Lys Leu Glu Thr Ala Asp Leu Lys Trp
             20                  25                  30

Val Thr Phe Pro Gln Val Asp Gly Gln Trp Glu Glu Leu Ser Gly Leu
             35                  40                  45

Asp Glu Glu Gln His Ser Val Arg Thr Tyr Glu Val Cys Asp Val Gln
         50                  55                  60

Arg Ala Pro Gly Gln Ala His Trp Leu Arg Thr Gly Trp Val Pro Arg
65                  70                  75                  80

Arg Gly Ala Val His Val Tyr Ala Thr Leu Arg Phe Thr Met Leu Glu
             85                  90                  95

Cys Leu Ser Leu Pro Arg Ala Gly Arg Ser Cys Lys Glu Thr Phe Thr
             100                 105                 110

Val Phe Tyr Tyr Glu Ser Asp Ala Asp Thr Ala Thr Ala Leu Thr Pro
         115                 120                 125

Ala Trp Met Glu Asn Pro Tyr Ile Lys Val Asp Thr Val Ala Ala Glu
             130                 135                 140

His Leu Thr Arg Lys Arg Pro Gly Ala Glu Ala Thr Gly Lys Val Asn
145                 150                 155                 160

Val Lys Thr Leu Arg Leu Gly Pro Leu Ser Lys Ala Gly Phe Tyr Leu
             165                 170                 175

Ala Phe Gln Asp Gln Gly Ala Cys Met Ala Leu Leu Ser Leu His Leu
         180                 185                 190

```
Phe Tyr Lys Lys Cys Ala Gln Leu Thr Val Asn Leu Thr Arg Phe Pro
        195                 200                 205

Glu Thr Val Pro Arg Glu Leu Val Pro Val Ala Gly Ser Cys Val
    210                 215                 220

Val Asp Ala Val Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Ala
                245                 250                 255

Pro Gly Phe Glu Ala Ala Glu Gly Asn Thr Lys Cys Arg Ala Cys Ala
            260                 265                 270

Gln Gly Thr Phe Lys Pro Leu Ser Gly Glu Gly Ser Cys Gln Pro Cys
        275                 280                 285

Pro Ala Asn Ser His Ser Asn Thr Ile Gly Ser Ala Val Cys Gln Cys
        290                 295                 300

Arg Val Gly Tyr Phe Arg Ala Arg Thr Asp Pro Arg Gly Ala Pro Cys
305                 310                 315                 320

Thr Thr Pro Pro Ser Ala Pro Arg Ser Val Val Ser Arg Leu Asn Gly
                325                 330                 335

Ser Ser Leu His Leu Glu Trp Ser Ala Pro Leu Glu Ser Gly Gly Arg
            340                 345                 350

Glu Asp Leu Thr Tyr Ala Leu Arg Cys Arg Glu Cys Arg Pro Gly Gly
        355                 360                 365

Ser Cys Ala Pro Cys Gly Gly Asp Leu Thr Phe Asp Pro Gly Pro Arg
    370                 375                 380

Asp Leu Val Glu Pro Trp Val Val Arg Gly Leu Arg Pro Asp Phe
385                 390                 395                 400

Thr Tyr Thr Phe Glu Val Thr Ala Leu Asn Gly Val Ser Ser Leu Ala
                405                 410                 415

Thr Gly Pro Val Pro Phe Glu Pro Val Asn Val Thr Thr Asp Arg Glu
            420                 425                 430

Val Pro Pro Ala Val Ser Asp Ile Arg Val Thr Arg Ser Ser Pro Ser
        435                 440                 445

Ser Leu Ser Leu Ala Trp Ala Val Pro Arg Ala Pro Ser Gly Ala Val
    450                 455                 460

Leu Asp Tyr Glu Val Lys Tyr His Glu Lys Gly Ala Glu Gly Pro Ser
465                 470                 475                 480

Ser Val Arg Phe Leu Lys Thr Ser Glu Asn Arg Ala Glu Leu Arg Gly
                485                 490                 495

Leu Lys Arg Gly Ala Ser Tyr Leu Val Gln Val Arg Ala Arg Ser Glu
            500                 505                 510

Ala Gly Tyr Gly Pro Phe Gly Gln Glu His His Ser Gln Thr Gln Leu
        515                 520                 525

Asp Glu Ser Glu Gly Trp Arg Glu Gln Leu Ala Leu Ile Ala Gly Thr
    530                 535                 540

Ala Val Val Gly Val Val Leu Val Leu Val Val Ile Val Val Ala Val
545                 550                 555                 560

Leu Cys Leu Arg Lys Gln Ser Asn Gly Arg Glu Ala Glu Tyr Ser Asp
                565                 570                 575

Lys His Gly Gln Tyr Leu Ile Gly His Gly Thr Lys Val Tyr Ile Asp
            580                 585                 590

Pro Phe Thr Tyr Glu Asp Pro Asn Glu Ala Val Arg Glu Phe Ala Lys
        595                 600                 605

Glu Ile Asp Val Ser Tyr Val Lys Ile Glu Glu Val Ile Gly Ala Gly
```

```
                610                 615                 620
Glu Phe Gly Glu Val Cys Arg Gly Arg Leu Lys Ala Pro Gly Lys Lys
625                 630                 635                 640

Glu Ser Cys Val Ala Ile Lys Thr Leu Lys Gly Gly Tyr Thr Glu Arg
                645                 650                 655

Gln Arg Arg Glu Phe Leu Ser Glu Ala Ser Ile Met Gly Gln Phe Glu
                660                 665                 670

His Pro Asn Ile Ile Arg Leu Glu Gly Val Val Thr Asn Ser Met Pro
                675                 680                 685

Val Met Ile Leu Thr Glu Phe Met Glu Asn Gly Ala Leu Asp Ser Phe
690                 695                 700

Leu Arg Leu Asn Asp Gly Gln Phe Thr Val Ile Gln Leu Val Gly Met
705                 710                 715                 720

Leu Arg Gly Ile Ala Ser Gly Met Arg Tyr Leu Ala Glu Met Ser Tyr
                725                 730                 735

Val His Arg Asp Leu Ala Ala Arg Asn Ile Leu Val Asn Ser Asn Leu
                740                 745                 750

Val Cys Lys Val Ser Asp Phe Gly Leu Ser Arg Phe Leu Glu Glu Asn
                755                 760                 765

Ser Ser Asp Pro Thr Tyr Thr Ser Ser Leu Gly Gly Lys Ile Pro Ile
770                 775                 780

Arg Trp Thr Ala Pro Glu Ala Ile Ala Phe Arg Lys Phe Thr Ser Ala
785                 790                 795                 800

Ser Asp Ala Trp Ser Tyr Gly Ile Val Met Trp Glu Val Met Ser Phe
                805                 810                 815

Gly Glu Arg Pro Tyr Trp Asp Met Ser Asn Gln Asp Val Ile Asn Ala
                820                 825                 830

Ile Glu Gln Asp Tyr Arg Leu Pro Pro Pro Asp Cys Pro Thr Ser
                835                 840                 845

Leu His Gln Leu Met Leu Asp Cys Trp Gln Lys Asp Arg Asn Ala Arg
850                 855                 860

Pro Arg Phe Pro Gln Val Val Ser Ala Leu Asp Lys Met Ile Arg Asn
865                 870                 875                 880

Pro Ala Ser Leu Lys Ile Val Ala Arg Glu Asn Gly Gly Ala Ser His
                885                 890                 895

Pro Leu Leu Asp Gln Arg Gln Pro His Tyr Ser Ala Phe Gly Ser Val
                900                 905                 910

Gly Glu Trp Leu Arg Ala Ile Lys Met Gly Arg Tyr Glu Glu Ser Phe
                915                 920                 925

Ala Ala Ala Gly Phe Gly Ser Phe Glu Leu Val Ser Gln Ile Ser Ala
930                 935                 940

Glu Asp Leu Leu Arg Ile Gly Val Thr Leu Ala Gly His Gln Lys Lys
945                 950                 955                 960

Ile Leu Ala Ser Val Gln His Met Lys Ser Gln Ala Lys Pro Gly Thr
                965                 970                 975

Pro Gly Gly Thr Gly Gly Pro Ala Pro Gln Tyr
                980                 985

<210> SEQ ID NO 3
<211> LENGTH: 205
<212> TYPE: PRT
<213> ORGANISM: Homo sapiens

<400> SEQUENCE: 3

Met Glu Phe Leu Trp Ala Pro Leu Leu Gly Leu Cys Cys Ser Leu Ala
```

```
  1               5                  10                 15
Ala Ala Asp Arg His Thr Val Phe Trp Asn Ser Ser Asn Pro Lys Phe
            20                  25                  30

Arg Asn Glu Asp Tyr Thr Ile His Val Gln Leu Asn Asp Tyr Val Asp
            35                  40                  45

Ile Ile Cys Pro His Tyr Glu Asp His Ser Val Ala Asp Ala Ala Met
 50                  55                  60

Glu Gln Tyr Ile Leu Tyr Leu Val Glu His Glu Tyr Gln Leu Cys
 65                  70                  75                  80

Gln Pro Gln Ser Lys Asp Gln Val Arg Trp Gln Cys Asn Arg Pro Ser
            85                  90                  95

Ala Lys His Gly Pro Glu Lys Leu Ser Glu Lys Phe Gln Arg Phe Thr
            100                 105                 110

Pro Phe Thr Leu Gly Lys Glu Phe Lys Glu Gly His Ser Tyr Tyr Tyr
            115                 120                 125

Ile Ser Lys Pro Ile His Gln His Glu Asp Arg Cys Leu Arg Leu Lys
            130                 135                 140

Val Thr Val Ser Gly Lys Ile Thr His Ser Pro Gln Ala His Asp Asn
145                 150                 155                 160

Pro Gln Glu Lys Arg Leu Ala Ala Asp Asp Pro Glu Val Arg Val Leu
            165                 170                 175

His Ser Ile Gly His Ser Ala Ala Pro Arg Leu Phe Pro Leu Ala Trp
            180                 185                 190

Thr Val Leu Leu Leu Pro Leu Leu Leu Leu Gln Thr Pro
            195                 200                 205

<210> SEQ ID NO 4
<211> LENGTH: 333
<212> TYPE: PRT
<213> ORGANISM: Homo sapiens

<400> SEQUENCE: 4

Met Ala Val Arg Arg Asp Ser Val Trp Lys Tyr Cys Trp Gly Val Leu
 1               5                  10                 15

Met Val Leu Cys Arg Thr Ala Ile Ser Lys Ser Ile Val Leu Glu Pro
            20                  25                  30

Ile Tyr Trp Asn Ser Ser Asn Ser Lys Phe Leu Pro Gly Gln Gly Leu
            35                  40                  45

Val Leu Tyr Pro Gln Ile Gly Asp Lys Leu Asp Ile Ile Cys Pro Lys
 50                  55                  60

Val Asp Ser Lys Thr Val Gly Gln Tyr Glu Tyr Tyr Lys Val Tyr Met
 65                  70                  75                  80

Val Asp Lys Asp Gln Ala Asp Arg Cys Thr Ile Lys Lys Glu Asn Thr
            85                  90                  95

Pro Leu Leu Asn Cys Ala Lys Pro Asp Gln Asp Ile Lys Phe Thr Ile
            100                 105                 110

Lys Phe Gln Glu Phe Ser Pro Asn Leu Trp Gly Leu Glu Phe Gln Lys
            115                 120                 125

Asn Lys Asp Tyr Tyr Ile Ile Ser Thr Ser Asn Gly Ser Leu Glu Gly
            130                 135                 140

Leu Asp Asn Gln Glu Gly Gly Val Cys Gln Thr Arg Ala Met Lys Ile
145                 150                 155                 160

Leu Met Lys Val Gly Gln Asp Ala Ser Ser Ala Gly Ser Thr Arg Asn
            165                 170                 175

Lys Asp Pro Thr Arg Arg Pro Glu Leu Glu Ala Gly Thr Asn Gly Arg
```

```
                        180                 185                 190
Ser Ser Thr Thr Ser Pro Phe Val Lys Pro Asn Pro Gly Ser Ser Thr
            195                 200                 205

Asp Gly Asn Ser Ala Gly His Ser Gly Asn Asn Ile Leu Gly Ser Glu
        210                 215                 220

Val Ala Leu Phe Ala Gly Ile Ala Ser Gly Cys Ile Ile Phe Ile Val
225                 230                 235                 240

Ile Ile Ile Thr Leu Val Val Leu Leu Lys Tyr Arg Arg Arg His
                245                 250                 255

Arg Lys His Ser Pro Gln His Thr Thr Thr Leu Ser Leu Ser Thr Leu
            260                 265                 270

Ala Thr Pro Lys Arg Ser Gly Asn Asn Asn Gly Ser Glu Pro Ser Asp
        275                 280                 285

Ile Ile Ile Pro Leu Arg Thr Ala Asp Ser Val Phe Cys Pro His Tyr
        290                 295                 300

Glu Lys Val Ser Gly Asp Tyr Gly His Pro Val Tyr Ile Val Gln Glu
305                 310                 315                 320

Met Pro Pro Gln Ser Pro Ala Asn Ile Tyr Tyr Lys Val
                325                 330

<210> SEQ ID NO 5
<211> LENGTH: 1849
<212> TYPE: DNA
<213> ORGANISM: Homo sapiens

<400> SEQUENCE: 5
acttagaggc gcctggtcgg gaagggcctg gtcagctgcg tccggcggag gcagctgctg      60
acccagctgt ggactgtgcc gggggcgggg gacggagggg caggagccct gggctccccg     120 tggcggggc  tgtatcatgg accacctcgg ggcgtccctc tggccccagg tcggctccct    180
ttgtctcctg ctcgctgggg ccgcctgggc gccccgcct  aacctcccgg accccaagtt    240
cgagagcaaa gcggccttgc tggcggcccg ggggcccgaa gagcttctgt gcttcaccga    300
gcggttggag gacttggtgt gtttctggga ggaagcggcg agcgctgggg tgggcccggg    360
caactacagc ttctcctacc agctcgagga tgagccatgg aagctgtgtc gcctgcacca    420
ggctcccacg gctcgtggtg cggtgcgctt ctggtgttcg ctgcctacag ccgacacgtc    480
gagcttcgtg cccctagagt tgcgcgtcac agcagcctcc ggcgctccgc gatatcaccg    540
tgtcatccac atcaatgaag tagtgctcct agacgccccc gtggggctgg tggcgcggtt    600
ggctgacgag agcggccacg tagtgttgcg ctggctcccg ccgcctgaga cacccatgac    660
gtctcacatc cgctacgagg tggacgtctc ggccggcaac ggcgcaggga gcgtacagag    720
ggtggagatc ctggagggcc gcaccgagtg tgtgctgagc aacctgcggg gccggacgcg    780
ctacaccttc gccgtccgcg cgcgtatggc tgagccgagc ttcggcggct tctggagcgc    840
ctggtcggag cctgtgtcgc tgctgacgcc tagcgacctg accccctca  tcctgacgct    900 ctccctcatc ctcgtggtca tcctggtgct gctgaccgtg ctcgcgctgc tctcccaccg    960
ccgggctctg aagcagaaga tctggcctgg catcccgagc ccagagagcg agtttgaagg   1020
cctcttcacc acccacaagg gtaacttcca gctgtggctg taccagaatg atggctgcct   1080
gtggtggagc ccctgcaccc ccttcacgga ggacccacct gcttccctgg aagtcctctc   1140
agagcgctgc tgggggacga tgcaggcagt ggagccgggg acagatgatg agggcccct    1200 gctggagcca gtgggcagtg agcatgccca ggatacctat ctggtgctgg acaaatggtt   1260
gctgccccgg aacccgccca gtgaggacct cccagggcct ggtggcagtg tggacatagt   1320
```

```
ggccatggat gaaggctcag aagcatcctc ctgctcatct gctttggcct cgaagcccag      1380
cccagaggga gcctctgctg ccagctttga gtacactatc ctggacccca gctcccagct      1440
cttgcgtcca tggacactgt gccctgagct gcccctacc ccaccccacc taaagtacct       1500
gtaccttgtg gtatctgact ctggcatctc aactgactac agctcagggg actcccaggg      1560
agcccaaggg ggcttatccg atggccccta ctccaaccct tatgagaaca gccttatccc      1620
agccgctgag cctctgcccc ccagctatgt ggcttgctct taggacacca ggctgcagat      1680
gatcagggat ccaatatgac tcagagaacc agtgcagact caagacttat ggaacaggga      1740
tggcgaggcc tctctcagga gcaggggcat tgctgatttt gtctgcccaa tccatcctgc      1800
tcaggaaacc acaaccttgc agtattttta aatatgtata gttttttttg                 1849

<210> SEQ ID NO 6
<211> LENGTH: 4369
<212> TYPE: DNA
<213> ORGANISM: Homo sapiens

<400> SEQUENCE: 6
ttccagcgca gctcagcccc tgcccggccc ggcccgcccg gctccgcgcc gcagtctccc        60
tccctcccgc tccgtccccg ctcgggctcc caccatcccc gcccgcgagg agagcactcg       120
gcccggcggc gcgagcagag ccactccagg gagggggga gaccgcgagc ggccggctca       180
gcccccgcca cccggggcgg gaccccgagg ccccggaggg accccaactc cagccacgtc      240
ttgctgcgcg cccgcccggc gcggccactg ccagcacgct ccgggcccgc cgcccgcgcg      300
cgcggcacag acgcggggcc acacttggcg ccgccgcccg gtgccccgca cgctcgcatg      360
ggcccgcgct gagggccccg acgaggagtc ccgcgcggag tatcggcgtc cacccgccca      420
gggagagtca gacctggggg ggcgagggcc ccccaaactc agttcggatc ctacccgagt      480
gaggcggcgc catggagctc cgggtgctgc tctgctgggc ttcgttggcc gcagctttgg      540
aagagaccct gctgaacaca aaattggaaa ctgctgatct gaagtgggtg acattccctc      600
aggtggacgg gcagtgggag gaactgagcg gcctggatga ggaacagcac agcgtgcgca      660
cctacgaagt gtgtgacgtg cagcgtgccc cgggccaggc ccactggctt cgcacaggtt      720 gggtccacg gcggggcgcc gtccacgtgt acgccacgct gcgcttcacc atgctcgagt      780
gcctgtccct gcctcgggct gggcgctcct gcaaggagac cttcaccgtc ttctactatg      840
agagcgatgc ggacacggcc acggcccctca cgccagcctg gatggagaac ccctacatca      900
aggtggacac ggtggccgcg gagcatctca cccggaagcg ccctggggcc gaggccaccg      960
ggaaggtgaa tgtcaagacg ctgcgtctgg gaccgctcag caaggctggc ttctacctgg     1020
ccttccagga ccagggtgcc tgcatggccc tgctatccct gcacctcttc tacaaaaagt     1080
gcgcccagct gactgtgaac ctgactcgat tccggagac tgtgcctcgg agctggttg       1140 tgcccgtggc cggtagctgc gtggtggatg ccgtccccgc cctggcccc agccccagcc     1200 tctactgccg tgaggatggc cagtgggccg aacagccggt cacgggctgc agctgtgctc      1260
cggggttcga ggcagctgag gggaacacca agtgccgagc ctgtgcccag gcaccttca    1320 agcccctgtc aggagaaggg tcctgccagc catgccagc caatagccac tctaacacca     1380
ttggatcagc cgtctgccag tgccgcgtcg gtacttccg ggcacgcaca gaccccccggg      1440 gtgcaccctg caccaccccct ccttcggctc cgcggagcgt ggtttccgc ctgaacggct     1500 cctccctgca cctggaatgg agtgcccccc tggagtctgg tggccgagag gacctcacct     1560 acgcccctccg ctgccgggag tgccgaccccg gaggctcctg tgcgccctgc ggggagacc    1620
```

```
tgactttga ccccggcccc cgggacctgg tggagccctg ggtggtggtt cgagggctac    1680
gtcctgactt cacctatacc tttgaggtca ctgcattgaa cggggtatcc tccttagcca    1740
cggggcccgt cccatttgag cctgtcaatg tcaccactga ccgagaggta cctcctgcag    1800
tgtctgacat ccgggtgacg cggtcctcac ccagcagctt gagcctggcc tgggctgttc    1860
cccgggcacc cagtgggct gtgctggact acgaggtcaa ataccatgag aagggcgccg    1920
agggtcccag cagcgtgcgg ttcctgaaga cgtcagaaaa ccgggcagag ctgcggggc    1980 tgaagcgggg agccagctac ctggtgcagg tacgggcgcg ctctgaggcc ggctacgggc    2040
ccttcggcca ggaacatcac agccagaccc aactggatga gagcgagggc tggcgggagc    2100
agctggccct gattgcgggc acggcagtcg tgggtgtggt cctggtcctg gtggtcattg    2160
tggtcgcagt tctctgcctc aggaagcaga gcaatgggag agaagcagaa tattcggaca    2220
aacacggaca gtatctcatc ggacatggta ctaaggtcta catcgacccc ttcacttatg    2280
aagaccctaa tgaggctgtg agggaatttg caaaagagat cgatgtctcc tacgtcaaga    2340
ttgaagaggt gattggtgca ggtgagtttg gcgaggtgtg ccgggggcgg ctcaaggccc    2400
cagggaagaa ggagagctgt gtggcaatca agaccctgaa gggtggctac acggagcggc    2460
agcggcgtga gtttctgagc gaggcctcca tcatgggcca gttcgagcac cccaatatca    2520
tccgcctgga gggcgtggtc accaacagca tgccgtcat gattctcaca gagttcatgg    2580
agaacggcgc cctggactcc ttcctgcggc taaacgacgg acagttcaca gtcatccagc    2640
tcgtgggcat gctgcgggc atcgcctcgg gcatgcggta ccttgccgag atgagctacg    2700
tccaccgaga cctggctgct cgcaacatcc tagtcaacag caacctcgtc tgcaaagtgt    2760
ctgactttgg cctttcccga ttcctggagg agaactcttc cgatcccacc tacacgagct    2820
ccctgggagg aaagattccc atccgatgga ctgccccgga ggccattgcc ttccggaagt    2880
tcacttccgc cagtgatgcc tggagttacg ggattgtgat gtgggaggtg atgtcatttg    2940
gggagaggcc gtactgggac atgagcaatc aggacgtgat caatgccatt gaacaggact    3000
accggctgcc cccgcccca gactgtccca cctccctcca ccagctcatg ctggactgtt    3060
ggcagaaaga ccggaatgcc cggccccgct tcccccaggt ggtcagcgcc ctggacaaga    3120
tgatccggaa ccccgccagc ctcaaaatcg tggcccggga gaatggcggg cctcacacc    3180 ctctcctgga ccagcggcag cctcactact cagcttttgg ctctgtgggc gagtggcttc    3240
gggccatcaa aatgggaaga tacgaagaaa gtttcgcagc cgctggcttt ggctccttcg    3300
agctggtcag ccagatctct gctgaggacc tgctccgaat cggagtcact ctggcgggac    3360
accagaagaa aatcttggcc agtgtccagc acatgaagtc ccaggccaag ccgggaaccc    3420
cgggtgggac aggaggaccg gccccgcagt actgacctgc aggaactccc caccccaggg    3480
acaccgcctc cccatttcc ggggcagagt ggggactcac agaggccccc agccctgtgc    3540
cccgctggat tgcactttga ccccgtgggg tgaggagttg gcaatttgga gagacaggat    3600 ttggggttc tgccataata ggagggaaa atcaccccc agccacctcg gggaactcca    3660
gaccaagggt gagggcgcct ttccctcagg actgggtgtg accagaggaa aaggaagtgc    3720
ccaacatctc ccagcctccc caggtgcccc cctcaccttg atgggtgcgt tcccgcagac    3780
caaagagagt gtgactccct tgccagctcc agagtggggg ggctgtccca gggggcaaga    3840
aggggtgtca gggcccagtg acaaaatcat tggggtttgt agtcccaact tgctgctgtc    3900
accaccaaac tcaatcattt ttttcccttg taaatgcccc tccccagct gctgccttca    3960 tattgaaggt ttttgagttt tgtttttggt cttaattttt ctccccgttc cctttttgtt    4020
```

| | |
|---|---|
| tcttcgtttt gttttcctac cgtccttgtc ataactttgt gttggaggga acctgtttca | 4080 |
| ctatggcctc ctttgcccaa gttgaaacag gggcccatca tcatgtctgt ttccagaaca | 4140 |
| gtgccttggt catcccacat ccccggaccc cgcctgggac ccccaagctg tgtcctatga | 4200 |
| aggggtgtgg ggtgaggtag tgaaaagggc ggtagttggt ggtggaaccc agaaacggac | 4260 |
| gccggtgctt ggaggggttc ttaaattata tttaaaaaag taactttttg tataaataaa | 4320 |
| agaaaatggg acgtgtccca gctccagggg taaaaaaaaa aaaaaaaa | 4369 |

<210> SEQ ID NO 7
<211> LENGTH: 1590
<212> TYPE: DNA
<213> ORGANISM: Homo sapiens

<400> SEQUENCE: 7

| | |
|---|---|
| gccagatctg tgagcccagc gctgactgcg ccgcggagaa agccagtggg aacccagacc | 60 |
| cataggagac ccgcgtcccc gctcggcctg gccaggcccc gcgctatgga gttcctctgg | 120 |
| gcccctctct tgggtctgtg ctgcagtctg gccgctgctg atcgccacac cgtcttctgg | 180 |
| aacagttcaa atcccaagtt ccggaatgag gactacacca tacatgtgca gctgaatgac | 240 |
| tacgtggaca tcatctgtcc gcactatgaa gatcactctg tggcagacgc tgccatggag | 300 |
| cagtacatac tgtacctggt ggagcatgag gagtaccagc tgtgccagcc ccagtccaag | 360 |
| gaccaagtcc gctggcagtg caaccggccc agtgccaagc atggcccgga gaagctgtct | 420 |
| gagaagttcc agcgcttcac accttttcacc ctgggcaagg agttcaaaga aggacacagc | 480 |
| tactactaca tctccaaacc catccaccag catgaagacc gctgcttgag gttgaaggtg | 540 |
| actgtcagtg gcaaaatcac tcacagtcct caggcccatg acaatccaca ggagaagaga | 600 |
| cttgcagcag atgacccaga ggtgcgggtt ctacatagca tcggtcacag tgctgcccca | 660 |
| cgcctcttcc cacttgcctg gactgtgctg ctccttccac ttctgctgct gcaaaccccg | 720 |
| tgaaggtgta tgccacacct ggccttaaag agggacaggc tgaagagagg gacaggcact | 780 |
| ccaaacctgt cttggggcca cttttcagagc ccccagccct gggaaccact cccaccacag | 840 |
| gcataagcta tcacctagca gcctcaaaac gggtcagtat taaggttttc aaccggaagg | 900 |
| aggccaacca gcccgacagt gccatcccca ccttcacctc ggagggatgg agaaagaagt | 960 |
| ggagacagtc ctttcccacc attcctgcct ttaagccaaa gaaacaagct gtgcaggcat | 1020 |
| ggtcccttaa ggcacagtgg gagctgagct ggaaggggcc acgtggatgg gcaaagcttg | 1080 |
| tcaaagatgc cccctccagg agagagccag gatgcccaga tgaactgact gaaggaaaag | 1140 |
| caagaaacag tttcttgctt ggaagccagg tacaggagag gcagcatgct gggctgacc | 1200 |
| cagcatctcc cagcaagacc tcatctgtgg agctgccaca gagaagtttg tagccaggta | 1260 |
| ctgcattctc tcccatcctg gggcagcact ccccagagct gtgccagcag gggggctgtg | 1320 |
| ccaacctgtt cttagagtgt agctgtaagg gcagtgccca tgtgtacatt ctgcctagag | 1380 |
| tgtagcctaa agggcagggc ccacgtgtat agtatctgta tataagttgc tgtgtgtctg | 1440 |
| tcctgatttc tacaactgga gtttttttat acaatgttct ttgtctcaaa ataaagcaat | 1500 |
| gtgttttttc ggacatgctt ttctgccact ccatattaaa acatatgacc attgagtccc | 1560 |
| tgctaaaaaa aaaaaaaaaa aaaaaaaaa | 1590 |

<210> SEQ ID NO 8
<211> LENGTH: 4335
<212> TYPE: DNA
<213> ORGANISM: Homo sapiens

<400> SEQUENCE: 8

```
gcgcggagct gggagtggct tcgccatggc tgtgagaagg gactccgtgt ggaagtactg      60
ctggggtgtt ttgatggttt tatgcagaac tgcgatttcc aaatcgatag ttttagagcc     120
tatctattgg aattcctcga actccaaatt tctacctgga caaggactgg tactataccc     180
acagatagga gacaaattgg atattatttg ccccaaagtg gactctaaaa ctgttggcca     240
gtatgaatat tataaagttt atatggttga taaagaccaa gcagacagat gcactattaa     300
gaaggaaaat accccctctcc tcaactgtgc caaaccagac caagtatca aattcaccat      360
caagtttcaa gaattcagcc ctaacctctg ggtctagaa tttcagaaga caaagatta      420
ttacattata tctacatcaa atgggtcttt ggagggcctg gataaccagg agggaggggt     480
gtgccagaca agagccatga agatcctcat gaaagttgga caagatgcaa gttctgctgg     540
atcaaccagg aataaagatc caacaagacg tccagaacta gaagctggta caaatggaag      600
aagttcgaca acaagtccct tgtaaaacc aaatccaggt tctagcacag acggcaacag      660
cgccggacat tcggggaaca acatcctcgg ttccgaagtg gccttatttg cagggattgc     720
ttcaggatgc atcatcttca tcgtcatcat catcacgctg tggtcctct tgctgaagta      780
ccggaggaga cacaggaagc actcgccgca gcacgacc acgctgtcgc tcagcacact      840
ggccacaccc aagcgcagcg gcaacaacaa cggctcagag cccagtgaca ttatcatccc     900
gctaaggact gcggacagcg tcttctgccc tcactacgag aaggtcagcg gggactacgg      960
gcacccggtg tacatcgtcc aggagatgcc cccgcagagc ccggcgaaca tttactacaa    1020
ggtctgagag ggaccctggt ggtacctgtg cttcccaga ggacacctaa tgtcccgatg     1080
cctcccttga gggttgaga gcccgcgtgc tggagaattg actgaagcac agcaccgggg     1140
gagagggaca ctcctcctcg gaagagcccg tcgcgctgga cagcttacct agtcttgtag    1200
cattcggcct tggtgaacac acacgctccc tggaagctgg aagactgtgc agaagacgcc    1260
cattcggact gctgtgccgc gtcccacgtc tcctcctcga agccatgtgc tgcggtcact    1320
caggcctctg cagaagccaa gggaagacag tggtttgtgg acgagagggc tgtgagcatc    1380
ctggcaggtg ccccaggatg ccacgcctgg aagggccggc ttctgcctgg ggtgcatttc    1440
ccccgcagtg catacccgac ttgtcacacg gacctcgggc tagttaaggt gtgcaaagat    1500
ctctagagtt tagtccttac tgtctcactc gttctgttac ccagggctct gcagcacctc    1560
acctgagacc tccactccac atctgcatca ctcatggaac actcatgtct ggagtcccct    1620
cctccagccg ctggcaacaa cagcttcagt ccatgggtaa tccgttcata gaaattgtgt    1680
ttgctaacaa ggtgcccttt agccagatgc taggctgtct gcgaagaagg ctaggagttc    1740
atagaaggga gtggggctgg ggaaagggct ggctgcaatt gcagctcact gctgctgcct    1800
ctgaaacaga aagttggaaa ggaaaaaaga aaaagcaat taggtagcac agcactttgg    1860
ttttgctgag atcgaagagg ccagtaggag acacgacagc acacacagtg gattccagtg    1920
catgggagg cactcgctgt tatcaaatag cgatgtgcag gaagaaaagc ccctcttcat     1980
tccgggaac aaagacgggt attgttggga aggaacagg cttggaggga agggagaaag    2040
taggccgctg atgatatatt cgggcaggac tgttgtggta ctggcaataa gatacacagc    2100
tccgagctgt aggagagtcg gtctgctttg gatgattttt taagcagact cagctgctat    2160
acttatcaca ttttattaaa cacgggaaa gcatttagga gaatagcaga gagccaaatc    2220
tgacctaaaa gttgaaaagc caaggtcaa acaggctgta attccatcat catcgttgtt    2280
attaaagaat ccttatctat aaaaggtagg tcagatcccc ctccccccag gttcctcctt    2340
```

```
cccctcccga ttgagcctta cgacactttg gtttatgcgg tgctgtccgg gtgccagggc    2400
tgcagggtcg gtactgatgg aggctgcagc gcccggtgct ctgtgtcaag gtgaagcaca    2460
tacggcagac ctcttagagt ccttaagacg gaagtaaatt atgatgtcca gggggagaag    2520
gaagatagga cgtatttata ataggtatat agaacacaag ggatataaaa tgaaagattt    2580
ttactaatat atattttaag gttgcacaca gtacacacca gaagatgtga aattcatttg    2640
tggcaattaa gtggtcccaa tgctcagcgc ttaaaaaaac aaattggaca gctacttctg    2700
ggaaaaacaa catcattcca aaaagaacaa taatgagagc aaatgcaaaa ataaccaagt    2760
cctccgaagg catctcacgg aaccgtagac taggaagtac gagccccaca gagcaggaag    2820
ccgatgtgac tgcatcatat atttaacaat gacaagatgt tccggcgttt atttctgcgt    2880
tgggttttcc cttgccttat gggctgaagt gttctctaga atccagcagg tcacactggg    2940
ggcttcaggt gacgatttag ctgtggctcc ctcctcctgt cctcccccgc accccctccc    3000
ttctgggaaa caagaagagt aaacaggaaa cctactttt atgtgctatg caaaatagac    3060
atctttaaca tagtcctgtt actatggtaa cactttgctt tctgaattgg aagggaaaaa    3120
aaatgtagcg acagcatttt aaggttctca gacctccagt gagtacctgc aaaaatgagt    3180
tgtcacagaa attatgatcc tctatttcct gaacctggaa atgatgttgg tccaaagtgc    3240
gtgtgtgtat gtgtgagtgg gtgcgtggta tacatgtgta catatatgta taatatatat    3300
ctacaatata tattatatat atctatatca tatttctgtg gagggttgcc atggtaacca    3360
gccacagtac atatgtaatt ctttccatca ccccaacctc tcctttctgt gcattcatgc    3420
aagagtttct tgtaagccat cagaagttac ttttaggatg ggggagaggg gcgagaaggg    3480
gaaaaatggg aaatagtctg attttaatga aatcaaatgt atgtatcatc agttggctac    3540
gttttggttc tatgctaaac tgtgaaaaat cagatgaatt gataaaagag ttccctgcaa    3600
ccaattgaaa agtgttctgt gcgtctgttt tgtgtctggt gcagaatatg acaatctacc    3660
aactgtccct ttgtttgaag ttggtttagc tttggaaagt tactgtaaat gccttgcttg    3720
tatgatcgtc cctggtcacc cgactttgga atttgcacca tcatgtttca gtgaagatgc    3780
tgtaaatagg ttcagatttt actgtctatg gatttggggt gttacagtag ccttattcac    3840 cttttttaata aaaatacaca tgaaaacaag aaagaaatgg cttttcttac ccagattgtg    3900
tacatagagc aatgttggtt ttttataaag tctaagcaag atgttttgta taaaatctga    3960
attttgcaat gtatttagct acagcttgtt taacggcagt gtcattcccc tttgcactgt    4020
aatgaggaaa aaatggtata aaaggttgcc aaattgctgc atatttgtgc cgtaattatg    4080
taccatgaat atttatttaa aatttcgttg tccaatttgt aagtaacaca gtattatgcc    4140
tgagttataa atattttttt ctttctttgt tttatttaa tagcctgtca taggttttaa    4200
atctgcttta gttcacatt gcagttagcc ccagaaaatg aaatccgtga agtcacattc    4260
cacatctgtt tcaaactgaa tttgttctta aaaaaataaa atattttttt cctatggaaa    4320
aaaaaaaaaa aaaaa                                                    4335
```

```
<210> SEQ ID NO 9
<211> LENGTH: 642
<212> TYPE: DNA
<213> ORGANISM: Homo sapiens

<400> SEQUENCE: 9
agcaaagcgg ccttgctggc ggcccggggg cccgaagagc ttctgtgctt caccgagcgg      60
ttggaggact tggtgtgttt ctgggaggaa gcggcgagcg ctggggtggg cccgggcaac     120
```

```
tacagcttct cctaccagct cgaggatgag ccatggaagc tgtgtcgcct gcaccaggct    180
cccacggctc gtggtgcggt gcgcttctgg tgttcgctgc ctacagccga cacgtcgagc    240
ttcgtgcccc tagagttgcg cgtcacagca gcctccggcg ctccgcgata tcaccgtgtc    300
atccacatca atgaagtagt gctcctagac gcccccgtgg ggctggtggc gcggttggct    360
gacgagagcg gccacgtagt gttgcgctgg ctcccgccgc ctgagacacc catgacgtct    420
cacatccgct acgaggtgga cgtctcggcc ggcaacggcg cagggagcgt acagagggtg    480
gagatcctgg agggccgcac cgagtgtgtg ctgagcaacc tgcggggccg gacgcgctac    540
accttcgccg tccgcgcgcg tatggctgag ccagcttcg gcggcttctg gagcgcctgg    600
tcggagcctg tgtcgctgct gacgcctagc gacctggacc cc                      642
```

`<210>` SEQ ID NO 10
`<211>` LENGTH: 651
`<212>` TYPE: DNA
`<213>` ORGANISM: Homo sapiens

`<400>` SEQUENCE: 10

```
ccttcggctc cgcggagcgt ggtttcccgc ctgaacggct cctccctgca cctggaatgg     60 agtgccccc tggagtctgg tggccgagag gacctcacct acgccctccg ctgccgggag    120
tgccgacccg gaggctcctg tgcgcccgtgc ggggagacc tgactttga ccccggcccc    180 cgggacctgg tggagccctg ggtggtggtt cgagggctac gtcctgactt cacctatacc    240
tttgaggtca ctgcattgaa cggggtatcc tccttagcca cggggcccgt cccatttgag    300
cctgtcaatg tcaccactga ccgagaggta cctcctgcag tgtctgacat ccgggtgacg    360
cggtcctcac ccagcagctt gagcctggcc tgggctgttc cccgggcacc cagtggggct    420
gtgctggact acgaggtcaa ataccatgag aagggcgccg agggtcccag cagcgtgcgg    480
ttcctgaaga cgtcagaaaa ccgggcagag ctgcgggggc tgaagcgggg agccagctac    540
ctggtgcagg tacgggcgcg ctctgaggcc ggctacgggc ccttcggcca ggaacatcac    600
agccagaccc aactggatga gagcgagggc tggcgggagc agctggccct g             651
```

`<210>` SEQ ID NO 11
`<211>` LENGTH: 417
`<212>` TYPE: DNA
`<213>` ORGANISM: Homo sapiens

`<400>` SEQUENCE: 11

```
ctggccgctg ctgatcgcca caccgtcttc tggaacagtt caaatcccaa gttccggaat     60
gaggactaca ccatacatgt gcagctgaat gactacgtgg acatcatctg tccgcactat    120
gaagatcact ctgtggcaga cgctgccatg gagcagtaca tactgtacct ggtggagcat    180
gaggagtacc agctgtgcca gccccagtcc aaggaccaag tccgctggca gtgcaaccgg    240
cccagtgcca agcatggccc ggagaagctg tctgagaagt tccagcgctt cacacctttc    300 acccctgggca aggagttcaa agaaggacac agctactact acatctccaa acccatccac    360
cagcatgaag accgctgctt gaggttgaag gtgactgtca gtggcaaaat cactcac      417
```

`<210>` SEQ ID NO 12
`<211>` LENGTH: 426
`<212>` TYPE: DNA
`<213>` ORGANISM: Homo sapiens

`<400>` SEQUENCE: 12

```
tccaaatcga tagtttaga gcctatctat tggaattcct cgaactccaa atttctacct     60
```

-continued

```
ggacaaggac tggtactata cccacagata ggagacaaat tggatattat ttgccccaaa    120
gtggactcta aaactgttgg ccagtatgaa tattataaag tttatatggt tgataaagac    180
caagcagaca gatgcactat taagaaggaa aatacccctc tcctcaactg tgccaaacca    240
gaccaagata tcaaattcac catcaagttt caagaattca gccctaacct ctggggtcta    300
gaatttcaga gaacaaaga ttattacatt atatctacat caaatgggtc tttggagggc    360
ctggataacc aggagggagg ggtgtgccag acaagagcca tgaagatcct catgaaagtt    420
ggacaa                                                              426
```

<210> SEQ ID NO 13
<211> LENGTH: 214
<212> TYPE: PRT
<213> ORGANISM: Homo sapiens

<400> SEQUENCE: 13

Ser Lys Ala Ala Leu Leu Ala Ala Arg Gly Pro Glu Glu Leu Leu Cys
1               5                   10                  15
Phe Thr Glu Arg Leu Glu Asp Leu Val Cys Phe Trp Glu Glu Ala Ala
                20                  25                  30
Ser Ala Gly Val Gly Pro Gly Asn Tyr Ser Phe Ser Tyr Gln Leu Glu
            35                  40                  45
Asp Glu Pro Trp Lys Leu Cys Arg Leu His Gln Ala Pro Thr Ala Arg
        50                  55                  60
Gly Ala Val Arg Phe Trp Cys Ser Leu Pro Thr Ala Asp Thr Ser Ser
65                  70                  75                  80
Phe Val Pro Leu Glu Leu Arg Val Thr Ala Ala Ser Gly Ala Pro Arg
                85                  90                  95
Tyr His Arg Val Ile His Ile Asn Glu Val Val Leu Leu Asp Ala Pro
            100                 105                 110
Val Gly Leu Val Ala Arg Leu Ala Asp Glu Ser Gly His Val Val Leu
        115                 120                 125
Arg Trp Leu Pro Pro Pro Glu Thr Pro Met Thr Ser His Ile Arg Tyr
130                 135                 140
Glu Val Asp Val Ser Ala Gly Asn Gly Ala Gly Ser Val Gln Arg Val
145                 150                 155                 160
Glu Ile Leu Glu Gly Arg Thr Glu Cys Val Leu Ser Asn Leu Arg Gly
                165                 170                 175
Arg Thr Arg Tyr Thr Phe Ala Val Arg Ala Arg Met Ala Glu Pro Ser
            180                 185                 190
Phe Gly Gly Phe Trp Ser Ala Trp Ser Glu Pro Val Ser Leu Leu Thr
        195                 200                 205
Pro Ser Asp Leu Asp Pro
    210

<210> SEQ ID NO 14
<211> LENGTH: 217
<212> TYPE: PRT
<213> ORGANISM: Homo sapiens

<400> SEQUENCE: 14

Pro Ser Ala Pro Arg Ser Val Val Ser Arg Leu Asn Gly Ser Ser Leu
1               5                   10                  15
His Leu Glu Trp Ser Ala Pro Leu Glu Ser Gly Gly Arg Glu Asp Leu
                20                  25                  30
Thr Tyr Ala Leu Arg Cys Arg Glu Cys Arg Pro Gly Gly Ser Cys Ala

```
                35                  40                  45
Pro Cys Gly Gly Asp Leu Thr Phe Asp Pro Pro Arg Asp Leu Val
         50                  55                  60
Glu Pro Trp Val Val Arg Gly Leu Arg Pro Asp Phe Thr Tyr Thr
 65                  70                  75                  80
Phe Glu Val Thr Ala Leu Asn Gly Val Ser Ser Leu Ala Thr Gly Pro
                 85                  90                  95
Val Pro Phe Glu Pro Val Asn Val Thr Thr Asp Arg Glu Val Pro Pro
                100                 105                 110
Ala Val Ser Asp Ile Arg Val Thr Arg Ser Ser Pro Ser Ser Leu Ser
                115                 120                 125
Leu Ala Trp Ala Val Pro Arg Ala Pro Ser Gly Ala Val Leu Asp Tyr
            130                 135                 140
Glu Val Lys Tyr His Glu Lys Gly Ala Glu Gly Pro Ser Ser Val Arg
145                 150                 155                 160
Phe Leu Lys Thr Ser Glu Asn Arg Ala Glu Leu Arg Gly Leu Lys Arg
                165                 170                 175
Gly Ala Ser Tyr Leu Val Gln Val Arg Ala Arg Ser Glu Ala Gly Tyr
            180                 185                 190
Gly Pro Phe Gly Gln Glu His His Ser Gln Thr Gln Leu Asp Glu Ser
            195                 200                 205
Glu Gly Trp Arg Glu Gln Leu Ala Leu
        210                 215

<210> SEQ ID NO 15
<211> LENGTH: 139
<212> TYPE: PRT
<213> ORGANISM: Homo sapiens

<400> SEQUENCE: 15

Leu Ala Ala Ala Asp Arg His Thr Val Phe Trp Asn Ser Ser Asn Pro
 1               5                  10                  15
Lys Phe Arg Asn Glu Asp Tyr Thr Ile His Val Gln Leu Asn Asp Tyr
                20                  25                  30
Val Asp Ile Ile Cys Pro His Tyr Glu Asp His Ser Val Ala Asp Ala
            35                  40                  45
Ala Met Glu Gln Tyr Ile Leu Tyr Leu Val Glu His Glu Glu Tyr Gln
         50                  55                  60
Leu Cys Gln Pro Gln Ser Lys Asp Gln Val Arg Trp Gln Cys Asn Arg
 65                  70                  75                  80
Pro Ser Ala Lys His Gly Pro Glu Lys Leu Ser Glu Lys Phe Gln Arg
                85                  90                  95
Phe Thr Pro Phe Thr Leu Gly Lys Glu Phe Lys Glu Gly His Ser Tyr
                100                 105                 110
Tyr Tyr Ile Ser Lys Pro Ile His Gln His Glu Asp Arg Cys Leu Arg
            115                 120                 125
Leu Lys Val Thr Val Ser Gly Lys Ile Thr His
        130                 135

<210> SEQ ID NO 16
<211> LENGTH: 142
<212> TYPE: PRT
<213> ORGANISM: Homo sapiens

<400> SEQUENCE: 16

Ser Lys Ser Ile Val Leu Glu Pro Ile Tyr Trp Asn Ser Ser Asn Ser
 1               5                  10                  15
```

```
Lys Phe Leu Pro Gly Gln Gly Leu Val Leu Tyr Pro Gln Ile Gly Asp
            20                  25                  30

Lys Leu Asp Ile Ile Cys Pro Lys Val Asp Ser Lys Thr Val Gly Gln
        35                  40                  45

Tyr Glu Tyr Tyr Lys Val Tyr Met Val Asp Lys Asp Gln Ala Asp Arg
50                  55                  60

Cys Thr Ile Lys Lys Glu Asn Thr Pro Leu Leu Asn Cys Ala Lys Pro
65                  70                  75                  80

Asp Gln Asp Ile Lys Phe Thr Ile Lys Phe Gln Glu Phe Ser Pro Asn
                85                  90                  95

Leu Trp Gly Leu Glu Phe Gln Lys Asn Lys Asp Tyr Tyr Ile Ile Ser
            100                 105                 110

Thr Ser Asn Gly Ser Leu Glu Gly Leu Asp Asn Gln Glu Gly Gly Val
            115                 120                 125

Cys Gln Thr Arg Ala Met Lys Ile Leu Met Lys Val Gly Gln
        130                 135                 140

<210> SEQ ID NO 17
<211> LENGTH: 138
<212> TYPE: PRT
<213> ORGANISM: Homo sapiens

<400> SEQUENCE: 17

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Arg Val Gln Gln Ala
            20                  25                  30

Val Glu Val Trp Gln Gly Leu Ala Leu Leu Ser Glu Ala Val Leu Arg
        35                  40                  45

Gly Gln Ala Leu Leu Val Asn Ser Ser Gln Pro Trp Glu Pro Leu Gln
    50                  55                  60

Leu His Val Asp Lys Ala Val Ser Gly Leu Arg Ser Leu Thr Thr Leu
65                  70                  75                  80

Leu Arg Ala Leu Gly Ala Gln Lys Glu Ala Ile Ser Pro Pro Asp Ala
                85                  90                  95

Ala Ser Ala Ala Pro Leu Arg Thr Ile Thr Ala Asp Thr Phe Arg Lys
            100                 105                 110

Leu Phe Arg Val Tyr Ser Asn Phe Leu Arg Gly Lys Leu Lys Leu Tyr
        115                 120                 125

Thr Gly Glu Ala Cys Arg Thr Gly Asp Arg
    130                 135

<210> SEQ ID NO 18
<211> LENGTH: 147
<212> TYPE: PRT
<213> ORGANISM: Homo sapiens

<400> SEQUENCE: 18

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Leu Leu Val Asn
    50                  55                  60
```

```
Ser Ser Gln Pro Trp Glu Pro Leu Gln Leu His Val Asp Lys Ala Val
 65                  70                  75                  80

Ser Gly Leu Arg Ser Leu Thr Thr Leu Leu Arg Ala Leu Gly Ala Gln
                 85                  90                  95

Lys Glu Ala Ile Ser Pro Pro Asp Ala Ala Ser Ala Ala Pro Leu Arg
            100                 105                 110

Thr Ile Thr Ala Asp Thr Phe Arg Lys Leu Phe Arg Val Tyr Ser Asn
        115                 120                 125

Phe Leu Arg Gly Lys Leu Lys Leu Tyr Thr Gly Glu Ala Cys Arg Thr
130                 135                 140

Gly Asp Arg
145

<210> SEQ ID NO 19
<211> LENGTH: 137
<212> TYPE: PRT
<213> ORGANISM: Homo sapiens

<400> SEQUENCE: 19

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Leu Leu Val Asn Ser Ser Gln Pro Trp Glu Pro Leu Gln Leu
    50                  55                  60

His Val Asp Lys Ala Val Ser Gly Leu Arg Ser Leu Thr Thr Leu Leu
 65                  70                  75                  80

Arg Ala Leu Gly Ala Gln Lys Glu Ala Ile Ser Pro Pro Asp Ala Ala
                 85                  90                  95

Ser Ala Ala Pro Leu Arg Thr Ile Thr Ala Asp Thr Phe Arg Lys Leu
            100                 105                 110

Phe Arg Val Tyr Ser Asn Phe Leu Arg Gly Lys Leu Lys Leu Tyr Thr
        115                 120                 125

Gly Glu Ala Cys Arg Thr Gly Asp Arg
    130                 135

<210> SEQ ID NO 20
<211> LENGTH: 135
<212> TYPE: PRT
<213> ORGANISM: Homo sapiens

<400> SEQUENCE: 20

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Pro Trp Glu Pro Leu Gln Leu His Val
    50                  55                  60

Asp Lys Ala Val Ser Gly Leu Arg Ser Leu Thr Thr Leu Leu Arg Ala
 65                  70                  75                  80

Leu Gly Ala Gln Lys Glu Ala Ile Ser Pro Pro Asp Ala Ala Ser Ala
                 85                  90                  95

Ala Pro Leu Arg Thr Ile Thr Ala Asp Thr Phe Arg Lys Leu Phe Arg
```

```
                100                 105                 110
Val Tyr Ser Asn Phe Leu Arg Gly Lys Leu Lys Leu Tyr Thr Gly Glu
        115                 120                 125

Ala Cys Arg Thr Gly Asp Arg
        130                 135

<210> SEQ ID NO 21
<211> LENGTH: 60
<212> TYPE: PRT
<213> ORGANISM: Homo sapiens

<400> SEQUENCE: 21

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Pro Gly Val Gly Gln Leu
        35                  40                  45

Phe Pro Ala Val Gly Ala Pro Ala Ala Cys Gly
    50                  55                  60

<210> SEQ ID NO 22
<211> LENGTH: 41
<212> TYPE: PRT
<213> ORGANISM: Homo sapiens

<400> SEQUENCE: 22

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Asn His Cys
        35                  40

<210> SEQ ID NO 23
<211> LENGTH: 26
<212> TYPE: PRT
<213> ORGANISM: Homo sapiens

<400> SEQUENCE: 23

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr
            20                  25

<210> SEQ ID NO 24
<211> LENGTH: 26
<212> TYPE: PRT
<213> ORGANISM: Homo sapiens

<400> SEQUENCE: 24

Ala Pro Pro Arg Leu Ile Cys Asp Ser Arg Val Leu Glu Ala Tyr Leu
1               5                   10                  15

Leu Glu Ala Lys Glu Ala Glu Asn Ile Thr
            20                  25

<210> SEQ ID NO 25
<211> LENGTH: 26
<212> TYPE: PRT
<213> ORGANISM: Homo sapiens

<400> SEQUENCE: 25
```

-continued

Ala Pro Pro Arg Leu Ile Cys Asp Ser Arg Val Leu Glu Glu Tyr Leu
1               5                   10                  15

Leu Glu Ala Lys Glu Ala Glu Asn Ile Thr
            20                  25

<210> SEQ ID NO 26
<211> LENGTH: 16
<212> TYPE: PRT
<213> ORGANISM: Homo sapiens

<400> SEQUENCE: 26

Ala Pro Pro Arg Leu Ile Cys Asp Ser Arg Val Leu Glu Arg Tyr Leu
1               5                   10                  15

<210> SEQ ID NO 27
<211> LENGTH: 6
<212> TYPE: PRT
<213> ORGANISM: Homo sapiens

<400> SEQUENCE: 27

Ala Pro Pro Arg Leu Ile
1               5

<210> SEQ ID NO 28
<211> LENGTH: 106
<212> TYPE: PRT
<213> ORGANISM: Homo sapiens

<400> SEQUENCE: 28

Ala Pro Pro Arg Leu Ile Cys Asp Ser Arg Val Leu Glu Arg Tyr Ile
1               5                   10                  15

Leu Glu Ala Lys Glu Ala Glu Asn Val Thr Met Gly Cys Ala Glu Gly
            20                  25                  30

Pro Arg Leu Ser Glu Asn Ile Thr Val Pro Asp Thr Lys Val Asn Phe
        35                  40                  45

Tyr Ala Trp Lys Arg Met Glu Lys Glu Leu Met Ser Pro Pro Asp Thr
    50                  55                  60

Thr Pro Pro Ala Pro Leu Arg Thr Leu Thr Val Asp Thr Phe Cys Lys
65                  70                  75                  80

Leu Phe Arg Val Tyr Ala Asn Phe Leu Arg Gly Lys Leu Lys Leu Tyr
                85                  90                  95

Thr Gly Glu Val Cys Arg Arg Gly Asp Arg
            100                 105

<210> SEQ ID NO 29
<211> LENGTH: 153
<212> TYPE: PRT
<213> ORGANISM: Homo sapiens

<400> SEQUENCE: 29

Ala Pro Pro Arg Leu Ile Cys Glu Ala Glu Asn Ile Thr Thr Gly Cys
1               5                   10                  15

Ala Glu His Cys Ser Leu Asn Glu Asn Ile Thr Val Pro Asp Thr Lys
            20                  25                  30

Val Asn Phe Tyr Ala Trp Lys Arg Met Glu Val Gly Gln Gln Ala Val
        35                  40                  45

Glu Val Trp Gln Gly Leu Ala Leu Leu Ser Glu Ala Val Leu Arg Gly
    50                  55                  60

Gln Ala Leu Leu Val Asn Ser Ser Gln Pro Trp Glu Pro Leu Gln Leu
65                  70                  75                  80

His Val Asp Lys Ala Val Ser Gly Leu Arg Ser Leu Thr Thr Leu Leu
                85                  90                  95
Arg Ala Leu Gly Ala Gln Lys Glu Ala Ile Ser Pro Pro Asp Ala Ala
            100                 105                 110
Ser Ala Ala Pro Leu Arg Thr Ile Thr Ala Asp Thr Phe Arg Lys Leu
            115                 120                 125
Phe Arg Val Tyr Ser Asn Phe Leu Arg Gly Lys Leu Lys Leu Tyr Thr
        130                 135                 140
Gly Glu Ala Cys Arg Thr Gly Asp Arg
145                 150

<210> SEQ ID NO 30
<211> LENGTH: 162
<212> TYPE: PRT
<213> ORGANISM: Homo sapiens

<400> SEQUENCE: 30

Ala Pro Pro Arg Leu Ile Cys Asp Ser Arg Val Leu Glu Arg Tyr Leu
1               5                   10                  15
Leu Glu Ala Lys Glu Ala Glu Asn Ile Thr Thr Gly Cys Ala Glu His
            20                  25                  30
Cys Ser Leu Asn Glu Asn Ile Thr Val Pro Asp Phe Tyr Ala Trp Lys
        35                  40                  45
Arg Met Glu Val Gly Gln Gln Ala Val Glu Val Trp Gln Gly Leu Ala
    50                  55                  60
Leu Leu Ser Glu Ala Val Leu Arg Gly Gln Ala Leu Leu Val Asn Ser
65                  70                  75                  80
Ser Gln Pro Trp Glu Pro Leu Gln Leu His Val Asp Lys Ala Val Ser
                85                  90                  95
Gly Leu Arg Ser Leu Thr Thr Leu Leu Arg Ala Leu Gly Ala Gln Lys
            100                 105                 110
Glu Ala Ile Ser Pro Pro Asp Ala Ala Ser Ala Ala Pro Leu Arg Thr
            115                 120                 125
Ile Thr Ala Asp Thr Phe Arg Lys Leu Phe Arg Val Tyr Ser Asn Phe
        130                 135                 140
Leu Arg Gly Lys Leu Lys Leu Tyr Thr Gly Glu Ala Cys Arg Thr Gly
145                 150                 155                 160
Asp Arg

<210> SEQ ID NO 31
<211> LENGTH: 158
<212> TYPE: PRT
<213> ORGANISM: Homo sapiens

<400> SEQUENCE: 31

Ala Pro Pro Arg Leu Ile Cys Asp Ser Arg Val Leu Glu Arg Tyr Leu
1               5                   10                  15
Leu Glu Ala Lys Glu Ala Glu Asn Ile Thr Thr Gly Cys Ala Glu His
            20                  25                  30
Cys Ser Leu Asn Glu Asn Ile Thr Val Pro Asp Thr Lys Val Asn Phe
        35                  40                  45
Tyr Ala Trp Lys Arg Met Glu Val Gly Gln Gln Ala Val Glu Val Trp
    50                  55                  60
Gln Gly Leu Ala Leu Leu Ser Glu Ala Val Leu Arg Gly Gln Ala Leu
65                  70                  75                  80
Leu Val Asn Ser Ser Gln Pro Trp Glu Pro Leu Gln Leu His Val Asp

```
                85                  90                  95
Leu Thr Thr Leu Leu Arg Ala Leu Gly Ala Gln Lys Glu Ala Ile Ser
            100                 105                 110

Pro Pro Asp Ala Ala Ser Ala Ala Pro Leu Arg Thr Ile Thr Ala Asp
        115                 120                 125

Thr Phe Arg Lys Leu Phe Arg Val Tyr Ser Asn Phe Leu Arg Gly Lys
    130                 135                 140

Leu Lys Leu Tyr Thr Gly Glu Ala Cys Arg Thr Gly Asp Arg
145                 150                 155

<210> SEQ ID NO 32
<211> LENGTH: 158
<212> TYPE: PRT
<213> ORGANISM: Homo sapiens

<400> SEQUENCE: 32

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Gly Lys
    130                 135                 140

Leu Lys Leu Tyr Thr Gly Glu Ala Cys Arg Thr Gly Asp Arg
145                 150                 155

<210> SEQ ID NO 33
<211> LENGTH: 160
<212> TYPE: PRT
<213> ORGANISM: Homo sapiens

<400> SEQUENCE: 33

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110
```

```
Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

<210> SEQ ID NO 34
<211> LENGTH: 159
<212> TYPE: PRT
<213> ORGANISM: Homo sapiens

<400> SEQUENCE: 34

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu
145                 150                 155

<210> SEQ ID NO 35
<211> LENGTH: 158
<212> TYPE: PRT
<213> ORGANISM: Homo sapiens

<400> SEQUENCE: 35

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125
```

```
Pro Leu Arg Thr Ile Thr Ala Asp Thr Phe Arg Lys Leu Phe Arg Val
            130                 135                 140

Tyr Ser Asn Phe Leu Arg Gly Lys Leu Lys Leu Tyr Thr Gly
145                 150                 155
```

<210> SEQ ID NO 36
<211> LENGTH: 157
<212> TYPE: PRT
<213> ORGANISM: Homo sapiens

<400> SEQUENCE: 36

```
Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr
145                 150                 155
```

<210> SEQ ID NO 37
<211> LENGTH: 156
<212> TYPE: PRT
<213> ORGANISM: Homo sapiens

<400> SEQUENCE: 37

```
Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr
145                 150                 155
```

-continued

```
145                150                155

<210> SEQ ID NO 38
<211> LENGTH: 155
<212> TYPE: PRT
<213> ORGANISM: Homo sapiens

<400> SEQUENCE: 38

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu
145                 150                 155

<210> SEQ ID NO 39
<211> LENGTH: 154
<212> TYPE: PRT
<213> ORGANISM: Homo sapiens

<400> SEQUENCE: 39

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys
145                 150

<210> SEQ ID NO 40
```

```
<211> LENGTH: 153
<212> TYPE: PRT
<213> ORGANISM: Homo sapiens

<400> SEQUENCE: 40

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu
145                 150

<210> SEQ ID NO 41
<211> LENGTH: 152
<212> TYPE: PRT
<213> ORGANISM: Homo sapiens

<400> SEQUENCE: 41

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys
145                 150

<210> SEQ ID NO 42
<211> LENGTH: 151
<212> TYPE: PRT
<213> ORGANISM: Homo sapiens
```

-continued

<400> SEQUENCE: 42

```
Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
130                 135                 140

Tyr Ser Asn Phe Leu Arg Gly
145                 150
```

<210> SEQ ID NO 43
<211> LENGTH: 150
<212> TYPE: PRT
<213> ORGANISM: Homo sapiens

<400> SEQUENCE: 43

```
Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
130                 135                 140

Tyr Ser Asn Phe Leu Arg
145                 150
```

<210> SEQ ID NO 44
<211> LENGTH: 149
<212> TYPE: PRT
<213> ORGANISM: Homo sapiens

<400> SEQUENCE: 44

```
Ala Pro Pro Arg Leu Ile Cys Asp Ser Arg Val Leu Glu Arg Tyr Leu
1               5                   10                  15
```

```
Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
130                 135                 140

Tyr Ser Asn Phe Leu
145

<210> SEQ ID NO 45
<211> LENGTH: 148
<212> TYPE: PRT
<213> ORGANISM: Homo sapiens

<400> SEQUENCE: 45

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
130                 135                 140

Tyr Ser Asn Phe
145

<210> SEQ ID NO 46
<211> LENGTH: 147
<212> TYPE: PRT
<213> ORGANISM: Homo sapiens

<400> SEQUENCE: 46

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
             20                  25                  30
```

```
Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
             100                 105                 110

Gly Ala Gln Lys Glu Ala Ile Ser Pro Pro Asp Ala Ala Ser Ala Ala
             115                 120                 125

Pro Leu Arg Thr Ile Thr Ala Asp Thr Phe Arg Lys Leu Phe Arg Val
     130                 135                 140

Tyr Ser Asn
145

<210> SEQ ID NO 47
<211> LENGTH: 146
<212> TYPE: PRT
<213> ORGANISM: Homo sapiens

<400> SEQUENCE: 47

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
             100                 105                 110

Gly Ala Gln Lys Glu Ala Ile Ser Pro Pro Asp Ala Ala Ser Ala Ala
             115                 120                 125

Pro Leu Arg Thr Ile Thr Ala Asp Thr Phe Arg Lys Leu Phe Arg Val
     130                 135                 140

Tyr Ser
145

<210> SEQ ID NO 48
<211> LENGTH: 145
<212> TYPE: PRT
<213> ORGANISM: Homo sapiens

<400> SEQUENCE: 48

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
```

```
                50                  55                  60
Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
                130                 135                 140

Tyr
145

<210> SEQ ID NO 49
<211> LENGTH: 144
<212> TYPE: PRT
<213> ORGANISM: Homo sapiens

<400> SEQUENCE: 49

Ala Pro Pro Arg Leu Ile Cys Asp Ser Arg Val Leu Glu Arg Tyr Leu
  1               5                  10                  15

Leu Glu Ala Lys Glu Ala Glu Asn Ile Thr Thr Gly Cys Ala Glu His
                 20                  25                  30

Cys Ser Leu Asn Glu Asn Ile Thr Val Pro Asp Thr Lys Val Asn Phe
             35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
                130                 135                 140

<210> SEQ ID NO 50
<211> LENGTH: 143
<212> TYPE: PRT
<213> ORGANISM: Homo sapiens

<400> SEQUENCE: 50

Ala Pro Pro Arg Leu Ile Cys Asp Ser Arg Val Leu Glu Arg Tyr Leu
  1               5                  10                  15

Leu Glu Ala Lys Glu Ala Glu Asn Ile Thr Thr Gly Cys Ala Glu His
                 20                  25                  30

Cys Ser Leu Asn Glu Asn Ile Thr Val Pro Asp Thr Lys Val Asn Phe
             35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95
```

```
Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg
        130                 135                 140

<210> SEQ ID NO 51
<211> LENGTH: 142
<212> TYPE: PRT
<213> ORGANISM: Homo sapiens

<400> SEQUENCE: 51

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe
        130                 135                 140

<210> SEQ ID NO 52
<211> LENGTH: 141
<212> TYPE: PRT
<213> ORGANISM: Homo sapiens

<400> SEQUENCE: 52

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu
        130                 135                 140
```

```
<210> SEQ ID NO 53
<211> LENGTH: 140
<212> TYPE: PRT
<213> ORGANISM: Homo sapiens

<400> SEQUENCE: 53
```

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys
    130                 135                 140

```
<210> SEQ ID NO 54
<211> LENGTH: 139
<212> TYPE: PRT
<213> ORGANISM: Homo sapiens

<400> SEQUENCE: 54
```

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg
    130                 135

```
<210> SEQ ID NO 55
<211> LENGTH: 138
<212> TYPE: PRT
<213> ORGANISM: Homo sapiens

<400> SEQUENCE: 55
```

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe
        130                 135

<210> SEQ ID NO 56
<211> LENGTH: 137
<212> TYPE: PRT
<213> ORGANISM: Homo sapiens

<400> SEQUENCE: 56

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr
        130                 135

<210> SEQ ID NO 57
<211> LENGTH: 136
<212> TYPE: PRT
<213> ORGANISM: Homo sapiens

<400> SEQUENCE: 57

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
 50                  55                  60

```
Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp
    130                 135

<210> SEQ ID NO 58
<211> LENGTH: 135
<212> TYPE: PRT
<213> ORGANISM: Homo sapiens

<400> SEQUENCE: 58

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala
    130                 135

<210> SEQ ID NO 59
<211> LENGTH: 134
<212> TYPE: PRT
<213> ORGANISM: Homo sapiens

<400> SEQUENCE: 59

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
```

```
                115                 120                 125

Pro Leu Arg Thr Ile Thr
    130

<210> SEQ ID NO 60
<211> LENGTH: 133
<212> TYPE: PRT
<213> ORGANISM: Homo sapiens

<400> SEQUENCE: 60

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile
    130

<210> SEQ ID NO 61
<211> LENGTH: 132
<212> TYPE: PRT
<213> ORGANISM: Homo sapiens

<400> SEQUENCE: 61

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr
    130

<210> SEQ ID NO 62
<211> LENGTH: 131
<212> TYPE: PRT
<213> ORGANISM: Homo sapiens
```

<400> SEQUENCE: 62

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg
    130

<210> SEQ ID NO 63
<211> LENGTH: 130
<212> TYPE: PRT
<213> ORGANISM: Homo sapiens

<400> SEQUENCE: 63

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu
    130

<210> SEQ ID NO 64
<211> LENGTH: 129
<212> TYPE: PRT
<213> ORGANISM: Homo sapiens

<400> SEQUENCE: 64

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe

```
                35                  40                  45
Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro

<210> SEQ ID NO 65
<211> LENGTH: 128
<212> TYPE: PRT
<213> ORGANISM: Homo sapiens

<400> SEQUENCE: 65

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

<210> SEQ ID NO 66
<211> LENGTH: 127
<212> TYPE: PRT
<213> ORGANISM: Homo sapiens

<400> SEQUENCE: 66

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110
```

```
Gly Ala Gln Lys Glu Ala Ile Ser Pro Pro Asp Ala Ala Ser Ala
            115                 120                 125

<210> SEQ ID NO 67
<211> LENGTH: 126
<212> TYPE: PRT
<213> ORGANISM: Homo sapiens

<400> SEQUENCE: 67

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser
            115                 120                 125

<210> SEQ ID NO 68
<211> LENGTH: 125
<212> TYPE: PRT
<213> ORGANISM: Homo sapiens

<400> SEQUENCE: 68

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala
            115                 120                 125

<210> SEQ ID NO 69
<211> LENGTH: 124
<212> TYPE: PRT
<213> ORGANISM: Homo sapiens

<400> SEQUENCE: 69

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30
```

```
Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala
                115                 120
```

<210> SEQ ID NO 70
<211> LENGTH: 123
<212> TYPE: PRT
<213> ORGANISM: Homo sapiens

<400> SEQUENCE: 70

```
Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                 20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp
                115                 120
```

<210> SEQ ID NO 71
<211> LENGTH: 122
<212> TYPE: PRT
<213> ORGANISM: Homo sapiens

<400> SEQUENCE: 71

```
Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                 20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110
```

Gly Ala Gln Lys Glu Ala Ile Ser Pro Pro
        115                 120

<210> SEQ ID NO 72
<211> LENGTH: 121
<212> TYPE: PRT
<213> ORGANISM: Homo sapiens

<400> SEQUENCE: 72

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro
        115                 120

<210> SEQ ID NO 73
<211> LENGTH: 120
<212> TYPE: PRT
<213> ORGANISM: Homo sapiens

<400> SEQUENCE: 73

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser
        115                 120

<210> SEQ ID NO 74
<211> LENGTH: 119
<212> TYPE: PRT
<213> ORGANISM: Homo sapiens

<400> SEQUENCE: 74

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile
            115

<210> SEQ ID NO 75
<211> LENGTH: 118
<212> TYPE: PRT
<213> ORGANISM: Homo sapiens

<400> SEQUENCE: 75

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala
            115

<210> SEQ ID NO 76
<211> LENGTH: 117
<212> TYPE: PRT
<213> ORGANISM: Homo sapiens

<400> SEQUENCE: 76

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu
        115

<210> SEQ ID NO 77
<211> LENGTH: 116
<212> TYPE: PRT
<213> ORGANISM: Homo sapiens

<400> SEQUENCE: 77

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys
        115

<210> SEQ ID NO 78
<211> LENGTH: 115
<212> TYPE: PRT
<213> ORGANISM: Homo sapiens

<400> SEQUENCE: 78

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln
        115

<210> SEQ ID NO 79
<211> LENGTH: 114
<212> TYPE: PRT
<213> ORGANISM: Homo sapiens

<400> SEQUENCE: 79

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

```
Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
 50                      55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala

<210> SEQ ID NO 80
<211> LENGTH: 113
<212> TYPE: PRT
<213> ORGANISM: Homo sapiens

<400> SEQUENCE: 80

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
 50                      55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly

<210> SEQ ID NO 81
<211> LENGTH: 112
<212> TYPE: PRT
<213> ORGANISM: Homo sapiens

<400> SEQUENCE: 81

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
 50                      55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

<210> SEQ ID NO 82
```

```
<211> LENGTH: 111
<212> TYPE: PRT
<213> ORGANISM: Homo sapiens

<400> SEQUENCE: 82

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala
            100                 105                 110

<210> SEQ ID NO 83
<211> LENGTH: 110
<212> TYPE: PRT
<213> ORGANISM: Homo sapiens

<400> SEQUENCE: 83

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg
            100                 105                 110

<210> SEQ ID NO 84
<211> LENGTH: 109
<212> TYPE: PRT
<213> ORGANISM: Homo sapiens

<400> SEQUENCE: 84

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
```

```
              85                  90                  95

Lys Ala Val Ser Gly Leu Arg Ser Leu Thr Thr Leu Leu
            100                 105

<210> SEQ ID NO 85
<211> LENGTH: 108
<212> TYPE: PRT
<213> ORGANISM: Homo sapiens

<400> SEQUENCE: 85

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu
            100                 105

<210> SEQ ID NO 86
<211> LENGTH: 107
<212> TYPE: PRT
<213> ORGANISM: Homo sapiens

<400> SEQUENCE: 86

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr
            100                 105

<210> SEQ ID NO 87
<211> LENGTH: 106
<212> TYPE: PRT
<213> ORGANISM: Homo sapiens

<400> SEQUENCE: 87

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45
```

```
Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr
            100                 105
```

<210> SEQ ID NO 88
<211> LENGTH: 105
<212> TYPE: PRT
<213> ORGANISM: Homo sapiens

<400> SEQUENCE: 88

```
Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                 20                  25                  30

Cys Ser Leu Asn Glu Asn Ile Thr Val Pro Asp Thr Lys Val Asn Phe
             35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu
            100                 105
```

<210> SEQ ID NO 89
<211> LENGTH: 104
<212> TYPE: PRT
<213> ORGANISM: Homo sapiens

<400> SEQUENCE: 89

```
Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                 20                  25                  30

Cys Ser Leu Asn Glu Asn Ile Thr Val Pro Asp Thr Lys Val Asn Phe
             35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser
            100
```

<210> SEQ ID NO 90
<211> LENGTH: 103
<212> TYPE: PRT
<213> ORGANISM: Homo sapiens

<400> SEQUENCE: 90

```
Ala Pro Pro Arg Leu Ile Cys Asp Ser Arg Val Leu Glu Arg Tyr Leu
 1               5                  10                  15
```

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg
            100

<210> SEQ ID NO 91
<211> LENGTH: 102
<212> TYPE: PRT
<213> ORGANISM: Homo sapiens

<400> SEQUENCE: 91

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu
            100

<210> SEQ ID NO 92
<211> LENGTH: 101
<212> TYPE: PRT
<213> ORGANISM: Homo sapiens

<400> SEQUENCE: 92

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly
            100

<210> SEQ ID NO 93
<211> LENGTH: 100

```
<212> TYPE: PRT
<213> ORGANISM: Homo sapiens

<400> SEQUENCE: 93

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser
            100

<210> SEQ ID NO 94
<211> LENGTH: 99
<212> TYPE: PRT
<213> ORGANISM: Homo sapiens

<400> SEQUENCE: 94

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val

<210> SEQ ID NO 95
<211> LENGTH: 98
<212> TYPE: PRT
<213> ORGANISM: Homo sapiens

<400> SEQUENCE: 95

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95
```

Lys Ala

<210> SEQ ID NO 96
<211> LENGTH: 97
<212> TYPE: PRT
<213> ORGANISM: Homo sapiens

<400> SEQUENCE: 96

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
        50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys

<210> SEQ ID NO 97
<211> LENGTH: 96
<212> TYPE: PRT
<213> ORGANISM: Homo sapiens

<400> SEQUENCE: 97

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
        50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

<210> SEQ ID NO 98
<211> LENGTH: 95
<212> TYPE: PRT
<213> ORGANISM: Homo sapiens

<400> SEQUENCE: 98

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
        50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val

<210> SEQ ID NO 99
<211> LENGTH: 94
<212> TYPE: PRT
<213> ORGANISM: Homo sapiens

<400> SEQUENCE: 99

Ala Pro Pro Arg Leu Ile Cys Asp Ser Arg Val Leu Glu Arg Tyr Leu
1               5                   10                  15
Leu Glu Ala Lys Glu Ala Glu Asn Ile Thr Thr Gly Cys Ala Glu His
            20                  25                  30
Cys Ser Leu Asn Glu Asn Ile Thr Val Pro Asp Thr Lys Val Asn Phe
        35                  40                  45
Tyr Ala Trp Lys Arg Met Glu Val Gly Gln Gln Ala Val Glu Val Trp
    50                  55                  60
Gln Gly Leu Ala Leu Leu Ser Glu Ala Val Leu Arg Gly Gln Ala Leu
65                  70                  75                  80
Leu Val Asn Ser Ser Gln Pro Trp Glu Pro Leu Gln Leu His
                85                  90

<210> SEQ ID NO 100
<211> LENGTH: 93
<212> TYPE: PRT
<213> ORGANISM: Homo sapiens

<400> SEQUENCE: 100

Ala Pro Pro Arg Leu Ile Cys Asp Ser Arg Val Leu Glu Arg Tyr Leu
1               5                   10                  15
Leu Glu Ala Lys Glu Ala Glu Asn Ile Thr Thr Gly Cys Ala Glu His
            20                  25                  30
Cys Ser Leu Asn Glu Asn Ile Thr Val Pro Asp Thr Lys Val Asn Phe
        35                  40                  45
Tyr Ala Trp Lys Arg Met Glu Val Gly Gln Gln Ala Val Glu Val Trp
    50                  55                  60
Gln Gly Leu Ala Leu Leu Ser Glu Ala Val Leu Arg Gly Gln Ala Leu
65                  70                  75                  80
Leu Val Asn Ser Ser Gln Pro Trp Glu Pro Leu Gln Leu
                85                  90

<210> SEQ ID NO 101
<211> LENGTH: 92
<212> TYPE: PRT
<213> ORGANISM: Homo sapiens

<400> SEQUENCE: 101

Ala Pro Pro Arg Leu Ile Cys Asp Ser Arg Val Leu Glu Arg Tyr Leu
1               5                   10                  15
Leu Glu Ala Lys Glu Ala Glu Asn Ile Thr Thr Gly Cys Ala Glu His
            20                  25                  30
Cys Ser Leu Asn Glu Asn Ile Thr Val Pro Asp Thr Lys Val Asn Phe
        35                  40                  45
Tyr Ala Trp Lys Arg Met Glu Val Gly Gln Gln Ala Val Glu Val Trp
    50                  55                  60
Gln Gly Leu Ala Leu Leu Ser Glu Ala Val Leu Arg Gly Gln Ala Leu
65                  70                  75                  80
Leu Val Asn Ser Ser Gln Pro Trp Glu Pro Leu Gln
                85                  90

<210> SEQ ID NO 102
<211> LENGTH: 91
<212> TYPE: PRT
<213> ORGANISM: Homo sapiens

<400> SEQUENCE: 102

Ala Pro Pro Arg Leu Ile Cys Asp Ser Arg Val Leu Glu Arg Tyr Leu
1               5                   10                  15
Leu Glu Ala Lys Glu Ala Glu Asn Ile Thr Thr Gly Cys Ala Glu His
            20                  25                  30
Cys Ser Leu Asn Glu Asn Ile Thr Val Pro Asp Thr Lys Val Asn Phe
        35                  40                  45
Tyr Ala Trp Lys Arg Met Glu Val Gly Gln Gln Ala Val Glu Val Trp
    50                  55                  60
Gln Gly Leu Ala Leu Leu Ser Glu Ala Val Leu Arg Gly Gln Ala Leu
65                  70                  75                  80
Leu Val Asn Ser Ser Gln Pro Trp Glu Pro Leu
                85                  90

<210> SEQ ID NO 103
<211> LENGTH: 90
<212> TYPE: PRT
<213> ORGANISM: Homo sapiens

<400> SEQUENCE: 103

Ala Pro Pro Arg Leu Ile Cys Asp Ser Arg Val Leu Glu Arg Tyr Leu
1               5                   10                  15
Leu Glu Ala Lys Glu Ala Glu Asn Ile Thr Thr Gly Cys Ala Glu His
            20                  25                  30
Cys Ser Leu Asn Glu Asn Ile Thr Val Pro Asp Thr Lys Val Asn Phe
        35                  40                  45
Tyr Ala Trp Lys Arg Met Glu Val Gly Gln Gln Ala Val Glu Val Trp
    50                  55                  60
Gln Gly Leu Ala Leu Leu Ser Glu Ala Val Leu Arg Gly Gln Ala Leu
65                  70                  75                  80
Leu Val Asn Ser Ser Gln Pro Trp Glu Pro
                85                  90

<210> SEQ ID NO 104
<211> LENGTH: 89
<212> TYPE: PRT
<213> ORGANISM: Homo sapiens

<400> SEQUENCE: 104

Ala Pro Pro Arg Leu Ile Cys Asp Ser Arg Val Leu Glu Arg Tyr Leu
1               5                   10                  15
Leu Glu Ala Lys Glu Ala Glu Asn Ile Thr Thr Gly Cys Ala Glu His
            20                  25                  30
Cys Ser Leu Asn Glu Asn Ile Thr Val Pro Asp Thr Lys Val Asn Phe
        35                  40                  45
Tyr Ala Trp Lys Arg Met Glu Val Gly Gln Gln Ala Val Glu Val Trp
    50                  55                  60
Gln Gly Leu Ala Leu Leu Ser Glu Ala Val Leu Arg Gly Gln Ala Leu
65                  70                  75                  80
Leu Val Asn Ser Ser Gln Pro Trp Glu
                85

<210> SEQ ID NO 105

```
<211> LENGTH: 88
<212> TYPE: PRT
<213> ORGANISM: Homo sapiens

<400> SEQUENCE: 105

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp
                85

<210> SEQ ID NO 106
<211> LENGTH: 87
<212> TYPE: PRT
<213> ORGANISM: Homo sapiens

<400> SEQUENCE: 106

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro
                85

<210> SEQ ID NO 107
<211> LENGTH: 86
<212> TYPE: PRT
<213> ORGANISM: Homo sapiens

<400> SEQUENCE: 107

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln
                85

<210> SEQ ID NO 108
<211> LENGTH: 85
<212> TYPE: PRT
```

<213> ORGANISM: Homo sapiens

<400> SEQUENCE: 108

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser
                85

<210> SEQ ID NO 109
<211> LENGTH: 84
<212> TYPE: PRT
<213> ORGANISM: Homo sapiens

<400> SEQUENCE: 109

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser

<210> SEQ ID NO 110
<211> LENGTH: 83
<212> TYPE: PRT
<213> ORGANISM: Homo sapiens

<400> SEQUENCE: 110

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn

<210> SEQ ID NO 111
<211> LENGTH: 82
<212> TYPE: PRT
<213> ORGANISM: Homo sapiens

<400> SEQUENCE: 111

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val

<210> SEQ ID NO 112
<211> LENGTH: 81
<212> TYPE: PRT
<213> ORGANISM: Homo sapiens

<400> SEQUENCE: 112

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu

<210> SEQ ID NO 113
<211> LENGTH: 80
<212> TYPE: PRT
<213> ORGANISM: Homo sapiens

<400> SEQUENCE: 113

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

<210> SEQ ID NO 114
<211> LENGTH: 79
<212> TYPE: PRT
<213> ORGANISM: Homo sapiens

<400> SEQUENCE: 114

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe

```
            35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala
 65                  70                  75

<210> SEQ ID NO 115
<211> LENGTH: 78
<212> TYPE: PRT
<213> ORGANISM: Homo sapiens

<400> SEQUENCE: 115

Ala Pro Pro Arg Leu Ile Cys Asp Ser Arg Val Leu Glu Arg Tyr Leu
  1               5                  10                  15

Leu Glu Ala Lys Glu Ala Glu Asn Ile Thr Thr Gly Cys Ala Glu His
                 20                  25                  30

Cys Ser Leu Asn Glu Asn Ile Thr Val Pro Asp Thr Lys Val Asn Phe
             35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln
 65                  70                  75

<210> SEQ ID NO 116
<211> LENGTH: 77
<212> TYPE: PRT
<213> ORGANISM: Homo sapiens

<400> SEQUENCE: 116

Ala Pro Pro Arg Leu Ile Cys Asp Ser Arg Val Leu Glu Arg Tyr Leu
  1               5                  10                  15

Leu Glu Ala Lys Glu Ala Glu Asn Ile Thr Thr Gly Cys Ala Glu His
                 20                  25                  30

Cys Ser Leu Asn Glu Asn Ile Thr Val Pro Asp Thr Lys Val Asn Phe
             35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly
 65                  70                  75

<210> SEQ ID NO 117
<211> LENGTH: 76
<212> TYPE: PRT
<213> ORGANISM: Homo sapiens

<400> SEQUENCE: 117

Ala Pro Pro Arg Leu Ile Cys Asp Ser Arg Val Leu Glu Arg Tyr Leu
  1               5                  10                  15

Leu Glu Ala Lys Glu Ala Glu Asn Ile Thr Thr Gly Cys Ala Glu His
                 20                  25                  30

Cys Ser Leu Asn Glu Asn Ile Thr Val Pro Asp Thr Lys Val Asn Phe
             35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg
 65                  70                  75

<210> SEQ ID NO 118
<211> LENGTH: 75
```

```
<212> TYPE: PRT
<213> ORGANISM: Homo sapiens

<400> SEQUENCE: 118

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu
65                  70                  75

<210> SEQ ID NO 119
<211> LENGTH: 74
<212> TYPE: PRT
<213> ORGANISM: Homo sapiens

<400> SEQUENCE: 119

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val
65                  70

<210> SEQ ID NO 120
<211> LENGTH: 73
<212> TYPE: PRT
<213> ORGANISM: Homo sapiens

<400> SEQUENCE: 120

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala
65                  70

<210> SEQ ID NO 121
<211> LENGTH: 72
<212> TYPE: PRT
<213> ORGANISM: Homo sapiens

<400> SEQUENCE: 121

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30
```

```
Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
 50                  55                  60

Gln Gly Leu Ala Leu Leu Ser Glu
 65                  70

<210> SEQ ID NO 122
<211> LENGTH: 71
<212> TYPE: PRT
<213> ORGANISM: Homo sapiens

<400> SEQUENCE: 122

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
 50                  55                  60

Gln Gly Leu Ala Leu Leu Ser
 65                  70

<210> SEQ ID NO 123
<211> LENGTH: 70
<212> TYPE: PRT
<213> ORGANISM: Homo sapiens

<400> SEQUENCE: 123

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
 50                  55                  60

Gln Gly Leu Ala Leu Leu
 65                  70

<210> SEQ ID NO 124
<211> LENGTH: 69
<212> TYPE: PRT
<213> ORGANISM: Homo sapiens

<400> SEQUENCE: 124

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
 50                  55                  60

Gln Gly Leu Ala Leu
 65

<210> SEQ ID NO 125
```

```
<211> LENGTH: 68
<212> TYPE: PRT
<213> ORGANISM: Homo sapiens

<400> SEQUENCE: 125

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala
65

<210> SEQ ID NO 126
<211> LENGTH: 67
<212> TYPE: PRT
<213> ORGANISM: Homo sapiens

<400> SEQUENCE: 126

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu
65

<210> SEQ ID NO 127
<211> LENGTH: 66
<212> TYPE: PRT
<213> ORGANISM: Homo sapiens

<400> SEQUENCE: 127

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly
65

<210> SEQ ID NO 128
<211> LENGTH: 65
<212> TYPE: PRT
<213> ORGANISM: Homo sapiens

<400> SEQUENCE: 128

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30
```

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
    50                  55                  60

Gln
65

<210> SEQ ID NO 129
<211> LENGTH: 64
<212> TYPE: PRT
<213> ORGANISM: Homo sapiens

<400> SEQUENCE: 129

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
    50                  55                  60

<210> SEQ ID NO 130
<211> LENGTH: 63
<212> TYPE: PRT
<213> ORGANISM: Homo sapiens

<400> SEQUENCE: 130

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val
    50                  55                  60

<210> SEQ ID NO 131
<211> LENGTH: 62
<212> TYPE: PRT
<213> ORGANISM: Homo sapiens

<400> SEQUENCE: 131

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu
    50                  55                  60

<210> SEQ ID NO 132
<211> LENGTH: 61
<212> TYPE: PRT
<213> ORGANISM: Homo sapiens

<400> SEQUENCE: 132

Ala Pro Pro Arg Leu Ile Cys Asp Ser Arg Val Leu Glu Arg Tyr Leu
1               5                   10                  15

```
Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val
    50                  55                  60

<210> SEQ ID NO 133
<211> LENGTH: 60
<212> TYPE: PRT
<213> ORGANISM: Homo sapiens

<400> SEQUENCE: 133

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala
    50                  55                  60

<210> SEQ ID NO 134
<211> LENGTH: 59
<212> TYPE: PRT
<213> ORGANISM: Homo sapiens

<400> SEQUENCE: 134

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln
    50                  55

<210> SEQ ID NO 135
<211> LENGTH: 58
<212> TYPE: PRT
<213> ORGANISM: Homo sapiens

<400> SEQUENCE: 135

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln
    50                  55

<210> SEQ ID NO 136
<211> LENGTH: 57
<212> TYPE: PRT
<213> ORGANISM: Homo sapiens

<400> SEQUENCE: 136

Ala Pro Pro Arg Leu Ile Cys Asp Ser Arg Val Leu Glu Arg Tyr Leu
1               5                   10                  15
```

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly
        50                  55

<210> SEQ ID NO 137
<211> LENGTH: 56
<212> TYPE: PRT
<213> ORGANISM: Homo sapiens

<400> SEQUENCE: 137

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
            35                  40                  45

Tyr Ala Trp Lys Arg Met Glu Val
        50                  55

<210> SEQ ID NO 138
<211> LENGTH: 55
<212> TYPE: PRT
<213> ORGANISM: Homo sapiens

<400> SEQUENCE: 138

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
            35                  40                  45

Tyr Ala Trp Lys Arg Met Glu
        50                  55

<210> SEQ ID NO 139
<211> LENGTH: 54
<212> TYPE: PRT
<213> ORGANISM: Homo sapiens

<400> SEQUENCE: 139

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
            35                  40                  45

Tyr Ala Trp Lys Arg Met
        50

<210> SEQ ID NO 140
<211> LENGTH: 53
<212> TYPE: PRT
<213> ORGANISM: Homo sapiens

<400> SEQUENCE: 140

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
            35                  40                  45

Tyr Ala Trp Lys Arg
            50

<210> SEQ ID NO 141
<211> LENGTH: 52
<212> TYPE: PRT
<213> ORGANISM: Homo sapiens

<400> SEQUENCE: 141

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
            35                  40                  45

Tyr Ala Trp Lys
            50

<210> SEQ ID NO 142
<211> LENGTH: 51
<212> TYPE: PRT
<213> ORGANISM: Homo sapiens

<400> SEQUENCE: 142

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
            35                  40                  45

Tyr Ala Trp
            50

<210> SEQ ID NO 143
<211> LENGTH: 50
<212> TYPE: PRT
<213> ORGANISM: Homo sapiens

<400> SEQUENCE: 143

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
            35                  40                  45

Tyr Ala
            50

<210> SEQ ID NO 144
<211> LENGTH: 49
<212> TYPE: PRT
<213> ORGANISM: Homo sapiens

<400> SEQUENCE: 144

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr

<210> SEQ ID NO 145
<211> LENGTH: 48
<212> TYPE: PRT
<213> ORGANISM: Homo sapiens

<400> SEQUENCE: 145

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

<210> SEQ ID NO 146
<211> LENGTH: 47
<212> TYPE: PRT
<213> ORGANISM: Homo sapiens

<400> SEQUENCE: 146

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn
        35                  40                  45

<210> SEQ ID NO 147
<211> LENGTH: 46
<212> TYPE: PRT
<213> ORGANISM: Homo sapiens

<400> SEQUENCE: 147

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val
        35                  40                  45

<210> SEQ ID NO 148
<211> LENGTH: 45
<212> TYPE: PRT
<213> ORGANISM: Homo sapiens

<400> SEQUENCE: 148

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys
        35                  40                  45

<210> SEQ ID NO 149
<211> LENGTH: 44

```
<212> TYPE: PRT
<213> ORGANISM: Homo sapiens

<400> SEQUENCE: 149

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr
        35                  40

<210> SEQ ID NO 150
<211> LENGTH: 43
<212> TYPE: PRT
<213> ORGANISM: Homo sapiens

<400> SEQUENCE: 150

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp
        35                  40

<210> SEQ ID NO 151
<211> LENGTH: 42
<212> TYPE: PRT
<213> ORGANISM: Homo sapiens

<400> SEQUENCE: 151

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro
        35                  40

<210> SEQ ID NO 152
<211> LENGTH: 41
<212> TYPE: PRT
<213> ORGANISM: Homo sapiens

<400> SEQUENCE: 152

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val
        35                  40

<210> SEQ ID NO 153
<211> LENGTH: 40
<212> TYPE: PRT
<213> ORGANISM: Homo sapiens

<400> SEQUENCE: 153

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr
```

<210> SEQ ID NO 154
<211> LENGTH: 39
<212> TYPE: PRT
<213> ORGANISM: Homo sapiens

<400> SEQUENCE: 154

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile
        35

<210> SEQ ID NO 155
<211> LENGTH: 38
<212> TYPE: PRT
<213> ORGANISM: Homo sapiens

<400> SEQUENCE: 155

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn
        35

<210> SEQ ID NO 156
<211> LENGTH: 37
<212> TYPE: PRT
<213> ORGANISM: Homo sapiens

<400> SEQUENCE: 156

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu
        35

<210> SEQ ID NO 157
<211> LENGTH: 36
<212> TYPE: PRT
<213> ORGANISM: Homo sapiens

<400> SEQUENCE: 157

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn
        35

<210> SEQ ID NO 158
<211> LENGTH: 35
<212> TYPE: PRT
<213> ORGANISM: Homo sapiens

<400> SEQUENCE: 158

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu
        35

<210> SEQ ID NO 159
<211> LENGTH: 34
<212> TYPE: PRT
<213> ORGANISM: Homo sapiens

<400> SEQUENCE: 159

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser

<210> SEQ ID NO 160
<211> LENGTH: 33
<212> TYPE: PRT
<213> ORGANISM: Homo sapiens

<400> SEQUENCE: 160

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys

<210> SEQ ID NO 161
<211> LENGTH: 32
<212> TYPE: PRT
<213> ORGANISM: Homo sapiens

<400> SEQUENCE: 161

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

<210> SEQ ID NO 162
<211> LENGTH: 31
<212> TYPE: PRT
<213> ORGANISM: Homo sapiens

<400> SEQUENCE: 162

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu
            20                  25                  30

<210> SEQ ID NO 163
<211> LENGTH: 30
<212> TYPE: PRT
<213> ORGANISM: Homo sapiens

<400> SEQUENCE: 163

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala
            20                  25                  30

<210> SEQ ID NO 164
<211> LENGTH: 29
<212> TYPE: PRT
<213> ORGANISM: Homo sapiens

<400> SEQUENCE: 164

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys
            20                  25

<210> SEQ ID NO 165
<211> LENGTH: 28
<212> TYPE: PRT
<213> ORGANISM: Homo sapiens

<400> SEQUENCE: 165

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly
            20                  25

<210> SEQ ID NO 166
<211> LENGTH: 27
<212> TYPE: PRT
<213> ORGANISM: Homo sapiens

<400> SEQUENCE: 166

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr
            20                  25

<210> SEQ ID NO 167
<211> LENGTH: 26
<212> TYPE: PRT
<213> ORGANISM: Homo sapiens

<400> SEQUENCE: 167

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr
            20                  25

<210> SEQ ID NO 168
<211> LENGTH: 25
<212> TYPE: PRT
<213> ORGANISM: Homo sapiens

<400> SEQUENCE: 168

Ala Pro Pro Arg Leu Ile Cys Asp Ser Arg Val Leu Glu Arg Tyr Leu
1               5                   10                  15

Leu Glu Ala Lys Glu Ala Glu Asn Ile
            20                  25

<210> SEQ ID NO 169
<211> LENGTH: 24
<212> TYPE: PRT
<213> ORGANISM: Homo sapiens

<400> SEQUENCE: 169

Ala Pro Pro Arg Leu Ile Cys Asp Ser Arg Val Leu Glu Arg Tyr Leu

```
                1               5                  10                  15
Leu Glu Ala Lys Glu Ala Glu Asn
            20

<210> SEQ ID NO 170
<211> LENGTH: 23
<212> TYPE: PRT
<213> ORGANISM: Homo sapiens

<400> SEQUENCE: 170

Ala Pro Pro Arg Leu Ile Cys Asp Ser Arg Val Leu Glu Arg Tyr Leu
1               5                  10                  15

Leu Glu Ala Lys Glu Ala Glu
            20

<210> SEQ ID NO 171
<211> LENGTH: 22
<212> TYPE: PRT
<213> ORGANISM: Homo sapiens

<400> SEQUENCE: 171

Ala Pro Pro Arg Leu Ile Cys Asp Ser Arg Val Leu Glu Arg Tyr Leu
1               5                  10                  15

Leu Glu Ala Lys Glu Ala
            20

<210> SEQ ID NO 172
<211> LENGTH: 21
<212> TYPE: PRT
<213> ORGANISM: Homo sapiens

<400> SEQUENCE: 172

Ala Pro Pro Arg Leu Ile Cys Asp Ser Arg Val Leu Glu Arg Tyr Leu
1               5                  10                  15

Leu Glu Ala Lys Glu
            20

<210> SEQ ID NO 173
<211> LENGTH: 20
<212> TYPE: PRT
<213> ORGANISM: Homo sapiens

<400> SEQUENCE: 173

Ala Pro Pro Arg Leu Ile Cys Asp Ser Arg Val Leu Glu Arg Tyr Leu
1               5                  10                  15

Leu Glu Ala Lys
            20

<210> SEQ ID NO 174
<211> LENGTH: 19
<212> TYPE: PRT
<213> ORGANISM: Homo sapiens

<400> SEQUENCE: 174

Ala Pro Pro Arg Leu Ile Cys Asp Ser Arg Val Leu Glu Arg Tyr Leu
1               5                  10                  15

Leu Glu Ala

<210> SEQ ID NO 175
<211> LENGTH: 18
<212> TYPE: PRT
<213> ORGANISM: Homo sapiens
```

```
<400> SEQUENCE: 175

Ala Pro Pro Arg Leu Ile Cys Asp Ser Arg Val Leu Glu Arg Tyr Leu
1               5                   10                  15

Leu Glu

<210> SEQ ID NO 176
<211> LENGTH: 17
<212> TYPE: PRT
<213> ORGANISM: Homo sapiens

<400> SEQUENCE: 176

Ala Pro Pro Arg Leu Ile Cys Asp Ser Arg Val Leu Glu Arg Tyr Leu
1               5                   10                  15

Leu

<210> SEQ ID NO 177
<211> LENGTH: 16
<212> TYPE: PRT
<213> ORGANISM: Homo sapiens

<400> SEQUENCE: 177

Ala Pro Pro Arg Leu Ile Cys Asp Ser Arg Val Leu Glu Arg Tyr Leu
1               5                   10                  15

<210> SEQ ID NO 178
<211> LENGTH: 15
<212> TYPE: PRT
<213> ORGANISM: Homo sapiens

<400> SEQUENCE: 178

Ala Pro Pro Arg Leu Ile Cys Asp Ser Arg Val Leu Glu Arg Tyr
1               5                   10                  15

<210> SEQ ID NO 179
<211> LENGTH: 14
<212> TYPE: PRT
<213> ORGANISM: Homo sapiens

<400> SEQUENCE: 179

Ala Pro Pro Arg Leu Ile Cys Asp Ser Arg Val Leu Glu Arg
1               5                   10

<210> SEQ ID NO 180
<211> LENGTH: 13
<212> TYPE: PRT
<213> ORGANISM: Homo sapiens

<400> SEQUENCE: 180

Ala Pro Pro Arg Leu Ile Cys Asp Ser Arg Val Leu Glu
1               5                   10

<210> SEQ ID NO 181
<211> LENGTH: 12
<212> TYPE: PRT
<213> ORGANISM: Homo sapiens

<400> SEQUENCE: 181

Ala Pro Pro Arg Leu Ile Cys Asp Ser Arg Val Leu
1               5                   10

<210> SEQ ID NO 182
<211> LENGTH: 11
<212> TYPE: PRT
<213> ORGANISM: Homo sapiens
```

<400> SEQUENCE: 182

Ala Pro Pro Arg Leu Ile Cys Asp Ser Arg Val
1               5                   10

<210> SEQ ID NO 183
<211> LENGTH: 10
<212> TYPE: PRT
<213> ORGANISM: Homo sapiens

<400> SEQUENCE: 183

Ala Pro Pro Arg Leu Ile Cys Asp Ser Arg
1               5                   10

<210> SEQ ID NO 184
<211> LENGTH: 9
<212> TYPE: PRT
<213> ORGANISM: Homo sapiens

<400> SEQUENCE: 184

Ala Pro Pro Arg Leu Ile Cys Asp Ser
1               5

<210> SEQ ID NO 185
<211> LENGTH: 8
<212> TYPE: PRT
<213> ORGANISM: Homo sapiens

<400> SEQUENCE: 185

Ala Pro Pro Arg Leu Ile Cys Asp
1               5

<210> SEQ ID NO 186
<211> LENGTH: 7
<212> TYPE: PRT
<213> ORGANISM: Homo sapiens

<400> SEQUENCE: 186

Ala Pro Pro Arg Leu Ile Cys
1               5

<210> SEQ ID NO 187
<211> LENGTH: 166
<212> TYPE: PRT
<213> ORGANISM: Homo sapiens

<400> SEQUENCE: 187

Ala Pro Pro Arg Leu Ile Cys Ala Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
        50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala

```
            115                 120                 125
Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 188
<211> LENGTH: 166
<212> TYPE: PRT
<213> ORGANISM: Homo sapiens

<400> SEQUENCE: 188

Ala Pro Pro Arg Leu Ile Cys Arg Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 189
<211> LENGTH: 166
<212> TYPE: PRT
<213> ORGANISM: Homo sapiens

<400> SEQUENCE: 189

Ala Pro Pro Arg Leu Ile Cys Asp Ser Arg Val Leu Glu Ala Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110
```

```
Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 190
<211> LENGTH: 166
<212> TYPE: PRT
<213> ORGANISM: Homo sapiens

<400> SEQUENCE: 190

Ala Pro Pro Arg Leu Ile Cys Asp Ser Arg Val Leu Glu Glu Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 191
<211> LENGTH: 166
<212> TYPE: PRT
<213> ORGANISM: Homo sapiens

<400> SEQUENCE: 191

Ala Pro Pro Arg Leu Ile Cys Asp Ser Arg Val Leu Glu Arg Tyr Leu
1               5                   10                  15

Leu Glu Ala Ala Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95
```

```
Lys Ala Val Ser Gly Leu Arg Ser Leu Thr Thr Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 192
<211> LENGTH: 166
<212> TYPE: PRT
<213> ORGANISM: Homo sapiens

<400> SEQUENCE: 192

Ala Pro Pro Arg Leu Ile Cys Asp Ser Arg Val Leu Glu Arg Tyr Leu
1               5                   10                  15

Leu Glu Ala Glu Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 193
<211> LENGTH: 166
<212> TYPE: PRT
<213> ORGANISM: Homo sapiens

<400> SEQUENCE: 193

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Ala Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
```

```
                85                  90                  95
Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 194
<211> LENGTH: 166
<212> TYPE: PRT
<213> ORGANISM: Homo sapiens

<400> SEQUENCE: 194

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Ala Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 195
<211> LENGTH: 166
<212> TYPE: PRT
<213> ORGANISM: Homo sapiens

<400> SEQUENCE: 195

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Glu Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80
```

```
Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 196
<211> LENGTH: 166
<212> TYPE: PRT
<213> ORGANISM: Homo sapiens

<400> SEQUENCE: 196

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Ala Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 197
<211> LENGTH: 166
<212> TYPE: PRT
<213> ORGANISM: Homo sapiens

<400> SEQUENCE: 197

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Ala Phe
        35                  40                  45

Tyr Ala Trp Lys Arg Met Glu Val Gly Gln Gln Ala Val Glu Val Trp
    50                  55                  60
```

-continued

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 198
<211> LENGTH: 166
<212> TYPE: PRT
<213> ORGANISM: Homo sapiens

<400> SEQUENCE: 198

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Ala Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 199
<211> LENGTH: 166
<212> TYPE: PRT
<213> ORGANISM: Homo sapiens

<400> SEQUENCE: 199

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

```
                  50                  55                  60
Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Glu Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 200
<211> LENGTH: 166
<212> TYPE: PRT
<213> ORGANISM: Homo sapiens

<400> SEQUENCE: 200

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                 20                  25                  30

Cys Ser Leu Asn Glu Asn Ile Thr Val Pro Asp Thr Lys Val Asn Phe
             35                  40                  45

Tyr Ala Trp Lys Arg Met Glu Val Gly Gln Gln Ala Val Glu Val Trp
     50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ala Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 201
<211> LENGTH: 166
<212> TYPE: PRT
<213> ORGANISM: Homo sapiens

<400> SEQUENCE: 201

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                 20                  25                  30

Cys Ser Leu Asn Glu Asn Ile Thr Val Pro Asp Thr Lys Val Asn Phe
             35                  40                  45
```

```
Tyr Ala Trp Lys Arg Met Glu Val Gly Gln Gln Ala Val Glu Val Trp
             50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Ala Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 202
<211> LENGTH: 166
<212> TYPE: PRT
<213> ORGANISM: Homo sapiens

<400> SEQUENCE: 202

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                 20                  25                  30

Cys Ser Leu Asn Glu Asn Ile Thr Val Pro Asp Thr Lys Val Asn Phe
                 35                  40                  45

Tyr Ala Trp Lys Arg Met Glu Val Gly Gln Gln Ala Val Glu Val Trp
             50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Glu Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 203
<211> LENGTH: 166
<212> TYPE: PRT
<213> ORGANISM: Homo sapiens

<400> SEQUENCE: 203

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                 20                  25                  30
```

```
Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ala Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
                130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 204
<211> LENGTH: 166
<212> TYPE: PRT
<213> ORGANISM: Homo sapiens

<400> SEQUENCE: 204

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                 20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Ala Val
                130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 205
<211> LENGTH: 166
<212> TYPE: PRT
<213> ORGANISM: Homo sapiens

<400> SEQUENCE: 205

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
```

```
                   20                  25                  30
Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Glu Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 206
<211> LENGTH: 166
<212> TYPE: PRT
<213> ORGANISM: Homo sapiens

<400> SEQUENCE: 206

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Ala Phe Leu Arg Gly Lys Leu Lys Leu Tyr Thr Gly Glu Ala
145                 150                 155                 160

Cys Arg Thr Gly Asp Arg
                165

<210> SEQ ID NO 207
<211> LENGTH: 166
<212> TYPE: PRT
<213> ORGANISM: Homo sapiens

<400> SEQUENCE: 207

Ala Pro Pro Arg Leu Ile Cys Asp Ser Arg Val Leu Glu Arg Tyr Leu
1               5                   10                  15
```

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Ala Gly Lys Leu Lys Leu Tyr Thr Gly Glu Ala
145                 150                 155                 160

Cys Arg Thr Gly Asp Arg
                165

<210> SEQ ID NO 208
<211> LENGTH: 166
<212> TYPE: PRT
<213> ORGANISM: Homo sapiens

<400> SEQUENCE: 208

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Glu Gly Lys Leu Lys Leu Tyr Thr Gly Glu Ala
145                 150                 155                 160

Cys Arg Thr Gly Asp Arg
                165

<210> SEQ ID NO 209
<211> LENGTH: 27
<212> TYPE: PRT
<213> ORGANISM: Homo sapiens

<400> SEQUENCE: 209

```
Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr
            20                  25
```

<210> SEQ ID NO 210
<211> LENGTH: 21
<212> TYPE: PRT
<213> ORGANISM: Homo sapiens

<400> SEQUENCE: 210

```
Asn Glu Asn Ile Thr Val Pro Asp Thr Lys Val Asn Phe Tyr Ala Trp
1               5                   10                  15

Lys Arg Met Glu Val
            20
```

<210> SEQ ID NO 211
<211> LENGTH: 27
<212> TYPE: PRT
<213> ORGANISM: Homo sapiens

<400> SEQUENCE: 211

```
Asn Ser Ser Gln Pro Trp Glu Pro Leu Gln Leu His Val Asp Lys Ala
1               5                   10                  15

Val Ser Gly Leu Arg Ser Leu Thr Thr Leu Leu
            20                  25
```

<210> SEQ ID NO 212
<211> LENGTH: 18
<212> TYPE: PRT
<213> ORGANISM: Homo sapiens

<400> SEQUENCE: 212

```
Phe Arg Lys Leu Phe Arg Val Tyr Ser Asn Phe Leu Arg Gly Lys Leu
1               5                   10                  15

Lys Leu
```

<210> SEQ ID NO 213
<211> LENGTH: 193
<212> TYPE: PRT
<213> ORGANISM: Homo sapiens

<400> SEQUENCE: 213

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
```

```
                130                 135                 140
Ala Ile Ser Pro Pro Asp Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg

<210> SEQ ID NO 214
<211> LENGTH: 181
<212> TYPE: PRT
<213> ORGANISM: Homo sapiens

<400> SEQUENCE: 214

Glu Glu Thr Leu Leu Asn Thr Lys Leu Glu Thr Ala Asp Leu Lys Trp
1               5                   10                  15

Val Thr Phe Pro Gln Val Asp Gly Gln Trp Glu Glu Leu Ser Gly Leu
                20                  25                  30

Asp Glu Glu Gln His Ser Val Arg Thr Tyr Glu Val Cys Asp Val Gln
                35                  40                  45

Arg Ala Pro Gly Gln Ala His Trp Leu Arg Thr Gly Trp Val Pro Arg
        50                  55                  60

Arg Gly Ala Val His Val Tyr Ala Thr Leu Arg Phe Thr Met Leu Glu
65                  70                  75                  80

Cys Leu Ser Leu Pro Arg Ala Gly Arg Ser Cys Lys Glu Thr Phe Thr
                85                  90                  95

Val Phe Tyr Tyr Glu Ser Asp Ala Asp Thr Ala Thr Ala Leu Thr Pro
                100                 105                 110

Ala Trp Met Glu Asn Pro Tyr Ile Lys Val Asp Thr Val Ala Ala Glu
            115                 120                 125

His Leu Thr Arg Lys Arg Pro Gly Ala Glu Ala Thr Gly Lys Val Asn
        130                 135                 140

Val Lys Thr Leu Arg Leu Gly Pro Leu Ser Lys Ala Gly Phe Tyr Leu
145                 150                 155                 160

Ala Phe Gln Asp Gln Gly Ala Cys Met Ala Leu Leu Ser Leu His Leu
                165                 170                 175

Phe Tyr Lys Lys Cys
                180

<210> SEQ ID NO 215
<211> LENGTH: 199
<212> TYPE: PRT
<213> ORGANISM: Homo sapiens

<400> SEQUENCE: 215

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
        50                  55                  60

Gln Gly Leu Ala Leu Leu Ser Glu Ala Val Leu Arg Gly Gln Ala Leu
65                  70                  75                  80
```

-continued

```
Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Leu
        115                 120                 125

Thr Pro Ala Trp Met Glu Asn Pro Tyr Ile Lys Val Asp Thr Val Ala
    130                 135                 140

Ala Glu His Leu Thr Arg Lys Arg Pro Gly Ala Glu Ala Thr Gly Lys
145                 150                 155                 160

Val Asn Val Lys Thr Leu Arg Leu Gly Pro Leu Ser Lys Ala Gly Phe
                165                 170                 175

Tyr Leu Ala Phe Gln Asp Gln Gly Ala Cys Met Ala Leu Leu Ser Leu
            180                 185                 190

His Leu Phe Tyr Lys Lys Cys
            195

<210> SEQ ID NO 216
<211> LENGTH: 206
<212> TYPE: PRT
<213> ORGANISM: Homo sapiens

<400> SEQUENCE: 216

Glu Glu Thr Leu Leu Asn Thr Lys Leu Glu Thr Ala Asp Leu Lys Trp
1               5                   10                  15

Val Thr Phe Pro Gln Val Asp Gly Gln Trp Glu Glu Leu Ser Gly Leu
            20                  25                  30

Asp Glu Glu Gln His Ser Val Arg Thr Tyr Glu Val Cys Asp Val Gln
        35                  40                  45

Arg Ala Pro Gly Gln Ala His Trp Leu Arg Thr Gly Trp Val Pro Arg
    50                  55                  60

Arg Gly Ala Val His Val Tyr Ala Thr Leu Arg Phe Thr Met Leu Glu
65                  70                  75                  80

Cys Leu Ser Leu Pro Arg Ala Gly Arg Ser Cys Lys Glu Thr Phe Thr
                85                  90                  95

Val Phe Tyr Tyr Glu Ser Asp Ala Asp Thr Ala Thr Ala Leu Ser Glu
            100                 105                 110

Ala Val Leu Arg Gly Gln Ala Leu Val Asn Ser Ser Gln Pro Trp
        115                 120                 125

Glu Pro Leu Gln Leu His Val Asp Lys Ala Val Ser Gly Leu Arg Ser
    130                 135                 140

Leu Thr Thr Leu Leu Arg Ala Leu Gly Ala Gln Lys Glu Ala Ile Ser
145                 150                 155                 160

Pro Pro Asp Ala Ala Ser Ala Ala Pro Leu Arg Thr Ile Thr Ala Asp
                165                 170                 175

Thr Phe Arg Lys Leu Phe Arg Val Tyr Ser Asn Phe Leu Arg Gly Lys
            180                 185                 190

Leu Lys Leu Tyr Thr Gly Glu Ala Cys Arg Thr Gly Asp Arg
        195                 200                 205

<210> SEQ ID NO 217
<211> LENGTH: 20
<212> TYPE: DNA
<213> ORGANISM: Homo sapiens

<400> SEQUENCE: 217
atggaggcct cgctcagaaa                                              20
```

```
<210> SEQ ID NO 218
<211> LENGTH: 20
<212> TYPE: DNA
<213> ORGANISM: Homo sapiens

<400> SEQUENCE: 218
tacctgaagg tcaggcgaac                                              20

<210> SEQ ID NO 219
<211> LENGTH: 21
<212> TYPE: RNA
<213> ORGANISM: Homo sapiens

<400> SEQUENCE: 219
ggugaauguc aagacgcugu u                                            21

<210> SEQ ID NO 220
<211> LENGTH: 21
<212> TYPE: RNA
<213> ORGANISM: Homo sapiens

<400> SEQUENCE: 220
cagcgucuug acauucaccu u                                            21

<210> SEQ ID NO 221
<211> LENGTH: 21
<212> TYPE: RNA
<213> ORGANISM: Homo sapiens

<400> SEQUENCE: 221
aguuaauauc aagacgcugu u                                            21

<210> SEQ ID NO 222
<211> LENGTH: 21
<212> TYPE: RNA
<213> ORGANISM: Homo sapiens

<400> SEQUENCE: 222
cagcgucuug auauuaacuu u                                            21

<210> SEQ ID NO 223
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence:
      Synthetic oligonucleotide

<400> SEQUENCE: 223
cgcugacccu gaaguucatu u                                            21

<210> SEQ ID NO 224
<211> LENGTH: 21
<212> TYPE: RNA
<213> ORGANISM: Artificial Sequence
<220> FEATURE:
<223> OTHER INFORMATION: Description of Artificial Sequence:
      Synthetic oligonucleotide

<400> SEQUENCE: 224
augaacuuca gggucagcgu u                                            21
```

```
<210> SEQ ID NO 225
<211> LENGTH: 16
<212> TYPE: DNA
<213> ORGANISM: Homo sapiens

<400> SEQUENCE: 225
cgcggagatg ggggtg                                                   16

<210> SEQ ID NO 226
<211> LENGTH: 17
<212> TYPE: DNA
<213> ORGANISM: Homo sapiens

<400> SEQUENCE: 226
acagatgacc aggtgtg                                                  17

<210> SEQ ID NO 227
<211> LENGTH: 10
<212> TYPE: DNA
<213> ORGANISM: Homo sapiens

<400> SEQUENCE: 227
ttccagcgca                                                          10

<210> SEQ ID NO 228
<211> LENGTH: 15
<212> TYPE: DNA
<213> ORGANISM: Homo sapiens

<400> SEQUENCE: 228
ggcgccatgg agctc                                                    15

<210> SEQ ID NO 229
<211> LENGTH: 16
<212> TYPE: DNA
<213> ORGANISM: Homo sapiens

<400> SEQUENCE: 229
gcagtactga cctgca                                                   16

<210> SEQ ID NO 230
<211> LENGTH: 14
<212> TYPE: DNA
<213> ORGANISM: Homo sapiens

<400> SEQUENCE: 230
ccagctccag gggt                                                     14

<210> SEQ ID NO 231
<211> LENGTH: 15
<212> TYPE: DNA
<213> ORGANISM: Homo sapiens

<400> SEQUENCE: 231
tgtatcatgg accac                                                    15

<210> SEQ ID NO 232
<211> LENGTH: 16
<212> TYPE: DNA
<213> ORGANISM: Homo sapiens

<400> SEQUENCE: 232
ttgctcttag gacacc                                                   16
```

```
<210> SEQ ID NO 233
<211> LENGTH: 14
<212> TYPE: DNA
<213> ORGANISM: Homo sapiens

<400> SEQUENCE: 233
tgtatagttt tttt                                                      14

<210> SEQ ID NO 234
<211> LENGTH: 107
<212> TYPE: PRT
<213> ORGANISM: Homo sapiens

<400> SEQUENCE: 234

Leu Glu Pro Val Ser Trp Ser Ser Leu Asn Pro Lys Phe Leu Ser Gly
1               5                   10                  15

Lys Gly Leu Val Ile Tyr Pro Lys Ile Gly Asp Lys Leu Asp Ile Ile
            20                  25                  30

Cys Pro Arg Ala Glu Ala Gly Arg Pro Tyr Glu Tyr Tyr Lys Leu Tyr
        35                  40                  45

Leu Val Arg Pro Glu Gln Ala Ala Ala Cys Ser Thr Val Leu Asp Pro
    50                  55                  60

Asn Val Leu Val Thr Cys Asn Arg Pro Glu Gln Glu Ile Arg Phe Thr
65                  70                  75                  80

Ile Lys Phe Gln Glu Phe Ser Pro Asn Tyr Met Gly Leu Glu Phe Lys
                85                  90                  95

Lys His His Asp Tyr Tyr Ile Thr Ser Thr Ser
            100                 105

<210> SEQ ID NO 235
<211> LENGTH: 109
<212> TYPE: PRT
<213> ORGANISM: Homo sapiens

<400> SEQUENCE: 235

Leu Glu Pro Ile Tyr Trp Asn Ser Ser Asn Ser Lys Phe Leu Pro Gly
1               5                   10                  15

Gln Gly Leu Val Leu Tyr Pro Gln Ile Gly Asp Lys Leu Asp Ile Ile
            20                  25                  30

Cys Pro Lys Val Asp Ser Lys Thr Val Gly Gln Tyr Glu Tyr Tyr Lys
        35                  40                  45

Val Tyr Met Val Asp Lys Asp Gln Ala Asp Arg Cys Thr Ile Lys Lys
    50                  55                  60

Glu Asn Thr Pro Leu Leu Asn Cys Ala Lys Pro Asp Gln Asp Ile Lys
65                  70                  75                  80

Phe Thr Ile Lys Phe Gln Glu Phe Ser Pro Asn Leu Trp Gly Leu Glu
                85                  90                  95

Phe Gln Lys Asn Lys Asp Tyr Tyr Ile Ile Ser Thr Ser
            100                 105

<210> SEQ ID NO 236
<211> LENGTH: 119
<212> TYPE: PRT
<213> ORGANISM: Homo sapiens

<400> SEQUENCE: 236

Val Ala Asp Arg Tyr Ala Val Tyr Trp Asn Ser Ser Asn Pro Arg Phe
1               5                   10                  15

Gln Arg Gly Asp Tyr His Ile Asp Val Cys Ile Asn Asp Tyr Leu Asp
```

-continued

```
                    20                  25                  30
Val Phe Cys Pro His Tyr Glu Asp Ser Val Pro Glu Asp Lys Thr Glu
             35                  40                  45

Arg Tyr Val Leu Tyr Met Val Asn Phe Asp Gly Tyr Ser Ala Cys Asp
         50                  55                  60

His Thr Ser Lys Gly Phe Lys Arg Trp Glu Cys Asn Arg Pro His Ser
 65                  70                  75                  80

Pro Asn Gly Pro Leu Lys Phe Ser Glu Lys Phe Gln Leu Phe Thr Pro
                 85                  90                  95

Phe Ser Leu Gly Phe Glu Phe Arg Pro Gly Arg Glu Tyr Phe Tyr Ile
            100                 105                 110

Ser Ser Ala Ile Pro Asp Asn
            115

<210> SEQ ID NO 237
<211> LENGTH: 123
<212> TYPE: PRT
<213> ORGANISM: Homo sapiens

<400> SEQUENCE: 237

Arg Tyr Ala Val Tyr Trp Asn Arg Ser Asn Pro Arg Phe His Ala Gly
 1               5                  10                  15

Ala Gly Asp Asp Gly Gly Gly Tyr Thr Val Glu Val Ser Ile Asn Asp
             20                  25                  30

Tyr Leu Asp Ile Tyr Cys Pro His Tyr Gly Ala Pro Leu Pro Pro Ala
         35                  40                  45

Glu Arg Met Glu His Tyr Val Leu Tyr Met Val Asn Gly Glu Gly His
     50                  55                  60

Ala Ser Cys Asp His Arg Gln Arg Gly Phe Lys Arg Trp Glu Cys Asn
 65                  70                  75                  80

Arg Pro Ala Ala Pro Gly Gly Pro Leu Lys Phe Ser Glu Lys Phe Gln
                 85                  90                  95

Leu Phe Thr Pro Phe Ser Leu Gly Phe Glu Phe Arg Pro Gly His Glu
            100                 105                 110

Tyr Tyr Tyr Ile Ser Ala Thr Pro Pro Asn Ala
            115                 120

<210> SEQ ID NO 238
<211> LENGTH: 114
<212> TYPE: PRT
<213> ORGANISM: Homo sapiens

<400> SEQUENCE: 238

Arg His Val Val Tyr Trp Asn Ser Ser Asn Pro Arg Leu Leu Arg Gly
 1               5                  10                  15

Asp Ala Val Val Glu Leu Gly Leu Asn Asp Tyr Leu Asp Ile Val Cys
             20                  25                  30

Pro His Tyr Glu Gly Pro Gly Pro Glu Gly Pro Glu Thr Phe Ala
         35                  40                  45

Leu Tyr Met Val Asp Trp Pro Gly Tyr Glu Ser Cys Gln Ala Glu Gly
     50                  55                  60

Pro Arg Ala Tyr Lys Arg Trp Val Cys Ser Leu Pro Phe Gly His Val
 65                  70                  75                  80

Gln Phe Ser Glu Lys Ile Gln Arg Phe Thr Pro Phe Ser Leu Gly Phe
                 85                  90                  95

Glu Phe Leu Pro Gly Glu Thr Tyr Tyr Ile Ser Val Pro Thr Pro
            100                 105                 110
```

Glu Ser

<210> SEQ ID NO 239
<211> LENGTH: 117
<212> TYPE: PRT
<213> ORGANISM: Homo sapiens

<400> SEQUENCE: 239

```
Arg His Thr Val Phe Trp Asn Ser Ser Asn Pro Lys Phe Arg Asn Glu
1               5                   10                  15
Asp Tyr Thr Ile His Val Gln Leu Asn Asp Tyr Val Asp Ile Ile Cys
            20                  25                  30
Pro His Tyr Glu Asp His Ser Val Ala Asp Ala Ala Met Glu Gln Tyr
        35                  40                  45
Ile Leu Tyr Leu Val Glu His Glu Glu Tyr Gln Leu Cys Gln Pro Gln
    50                  55                  60
Ser Lys Asp Gln Val Arg Trp Gln Cys Asn Arg Pro Ser Ala Lys His
65                  70                  75                  80
Gly Pro Glu Lys Leu Ser Glu Lys Phe Gln Arg Phe Thr Pro Phe Thr
                85                  90                  95
Leu Gly Lys Glu Phe Lys Glu Gly His Ser Tyr Tyr Tyr Ile Ser Lys
            100                 105                 110
Pro Ile His Gln His
            115
```

<210> SEQ ID NO 240
<211> LENGTH: 105
<212> TYPE: PRT
<213> ORGANISM: Homo sapiens

<400> SEQUENCE: 240

```
Asp Pro Lys Phe Glu Ser Lys Ala Ala Leu Leu Ala Ala Arg Gly Pro
1               5                   10                  15
Glu Glu Leu Leu Cys Phe Thr Glu Arg Leu Glu Asp Leu Val Cys Phe
            20                  25                  30
Trp Glu Glu Ala Ala Ser Ala Gly Val Gly Pro Gly Asn Tyr Ser Phe
        35                  40                  45
Ser Tyr Gln Leu Glu Asp Glu Pro Trp Lys Leu Cys Arg Leu His Gln
    50                  55                  60
Ala Pro Thr Ala Arg Phe Trp Cys Ser Leu Pro Thr Ala Asp Thr Ser
65                  70                  75                  80
Ser Phe Val Pro Leu Glu Leu Arg Val Thr Ala Ala Ser Gly Ala Pro
                85                  90                  95
Arg Tyr His Arg Val Ile His Ile Asn
            100                 105
```

<210> SEQ ID NO 241
<211> LENGTH: 166
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 241

```
Ala Pro Pro Arg Leu Ile Cys Asp Ser Arg Val Leu Glu Arg Tyr Leu
1               5                   10                  15
Leu Glu Ala Lys Glu Ala Glu Asn Ile Thr Thr Gly Cys Ala Glu His
            20                  25                  30
```

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
            165

<210> SEQ ID NO 242
<211> LENGTH: 21
<212> TYPE: RNA
<213> ORGANISM: Homo sapiens

<400> SEQUENCE: 242
caauagccac ucuaacaccu u                                              21

<210> SEQ ID NO 243
<211> LENGTH: 21
<212> TYPE: RNA
<213> ORGANISM: Homo sapiens

<400> SEQUENCE: 243
gguguuagag uggcuauugu u                                              21

<210> SEQ ID NO 244
<211> LENGTH: 21
<212> TYPE: RNA
<213> ORGANISM: Homo sapiens

<400> SEQUENCE: 244
ggggcccguc ccauuugagu u                                              21

<210> SEQ ID NO 245
<211> LENGTH: 21
<212> TYPE: RNA
<213> ORGANISM: Homo sapiens

<400> SEQUENCE: 245
cucaaauggg acgggccccu u                                              21

<210> SEQ ID NO 246
<211> LENGTH: 21
<212> TYPE: RNA
<213> ORGANISM: Homo sapiens

<400> SEQUENCE: 246
cugaucugaa gugggugacu u                                              21

<210> SEQ ID NO 247

```
<211> LENGTH: 21
<212> TYPE: RNA
<213> ORGANISM: Homo sapiens

<400> SEQUENCE: 247
gucacccacu ucagaucagu u                                              21

<210> SEQ ID NO 248
<211> LENGTH: 21
<212> TYPE: RNA
<213> ORGANISM: Homo sapiens

<400> SEQUENCE: 248
aagacccuaa ugaggcuguu u                                              21

<210> SEQ ID NO 249
<211> LENGTH: 21
<212> TYPE: RNA
<213> ORGANISM: Homo sapiens

<400> SEQUENCE: 249
acagccucau uagggucuuu u                                              21

<210> SEQ ID NO 250
<211> LENGTH: 21
<212> TYPE: RNA
<213> ORGANISM: Homo sapiens

<400> SEQUENCE: 250
ucgaugucuc cuacgucaau u                                              21

<210> SEQ ID NO 251
<211> LENGTH: 21
<212> TYPE: RNA
<213> ORGANISM: Homo sapiens

<400> SEQUENCE: 251
uugacguagg agacaucgau u                                              21

<210> SEQ ID NO 252
<211> LENGTH: 21
<212> TYPE: RNA
<213> ORGANISM: Homo sapiens

<400> SEQUENCE: 252
auugaagagg ugauuggugu u                                              21

<210> SEQ ID NO 253
<211> LENGTH: 21
<212> TYPE: RNA
<213> ORGANISM: Homo sapiens

<400> SEQUENCE: 253
caccaaucac cucuucaauu u                                              21

<210> SEQ ID NO 254
<211> LENGTH: 21
<212> TYPE: RNA
<213> ORGANISM: Homo sapiens

<400> SEQUENCE: 254
ggaguuacgg gauugugauu u                                              21

<210> SEQ ID NO 255
```

```
<211> LENGTH: 21
<212> TYPE: RNA
<213> ORGANISM: Homo sapiens

<400> SEQUENCE: 255
aucacaaucc cguaacuccu u                                              21

<210> SEQ ID NO 256
<211> LENGTH: 21
<212> TYPE: RNA
<213> ORGANISM: Homo sapiens

<400> SEQUENCE: 256
gguacuaagg ucuacaucgu u                                              21

<210> SEQ ID NO 257
<211> LENGTH: 21
<212> TYPE: RNA
<213> ORGANISM: Homo sapiens

<400> SEQUENCE: 257
cgauguagac cuuaguaccu u                                              21

<210> SEQ ID NO 258
<211> LENGTH: 21
<212> TYPE: RNA
<213> ORGANISM: Homo sapiens

<400> SEQUENCE: 258
guccugacuu caccuauacu u                                              21

<210> SEQ ID NO 259
<211> LENGTH: 21
<212> TYPE: RNA
<213> ORGANISM: Homo sapiens

<400> SEQUENCE: 259
guauagguga agucaggacu u                                              21

<210> SEQ ID NO 260
<211> LENGTH: 21
<212> TYPE: RNA
<213> ORGANISM: Homo sapiens

<400> SEQUENCE: 260
ugccgcgucg gguacuuccu u                                              21

<210> SEQ ID NO 261
<211> LENGTH: 21
<212> TYPE: RNA
<213> ORGANISM: Homo sapiens

<400> SEQUENCE: 261
ggaaguaccc gacgcggcau u                                              21

<210> SEQ ID NO 262
<211> LENGTH: 19
<212> TYPE: RNA
<213> ORGANISM: Homo sapiens

<400> SEQUENCE: 262
ccgaagagcu ucugugcuu                                                 19

<210> SEQ ID NO 263
```

```
<211> LENGTH: 19
<212> TYPE: RNA
<213> ORGANISM: Homo sapiens

<400> SEQUENCE: 263
aagcacagaa gcucuucgg                                                   19

<210> SEQ ID NO 264
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
uucuccgaac guugucacgu                                                  20

<210> SEQ ID NO 265
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 265
acgugacacg uucggagaa                                                   19

<210> SEQ ID NO 266
<211> LENGTH: 19
<212> TYPE: RNA
<213> ORGANISM: Homo sapiens

<400> SEQUENCE: 266
cagccaauag ccacucuaa                                                   19

<210> SEQ ID NO 267
<211> LENGTH: 19
<212> TYPE: RNA
<213> ORGANISM: Homo sapiens

<400> SEQUENCE: 267
uuagaguggc uauuggcug                                                   19

<210> SEQ ID NO 268
<211> LENGTH: 4
<212> TYPE: PRT
<213> ORGANISM: Homo sapiens

<400> SEQUENCE: 268

Met Gly Val His
1

<210> SEQ ID NO 269
<211> LENGTH: 6
<212> TYPE: PRT
<213> ORGANISM: Homo sapiens

<400> SEQUENCE: 269

Cys Arg Thr Gly Asp Arg
1               5

<210> SEQ ID NO 270
<211> LENGTH: 5
<212> TYPE: PRT
```

```
<213> ORGANISM: Homo sapiens

<400> SEQUENCE: 270

Met Glu Leu Arg Val
1               5

<210> SEQ ID NO 271
<211> LENGTH: 7
<212> TYPE: PRT
<213> ORGANISM: Homo sapiens

<400> SEQUENCE: 271

Gly Gly Pro Ala Pro Gln Tyr
1               5

<210> SEQ ID NO 272
<211> LENGTH: 5
<212> TYPE: PRT
<213> ORGANISM: Homo sapiens

<400> SEQUENCE: 272

Met Asp His Leu Gly
1               5

<210> SEQ ID NO 273
<211> LENGTH: 5
<212> TYPE: PRT
<213> ORGANISM: Homo sapiens

<400> SEQUENCE: 273

Tyr Val Ala Cys Ser
1               5
```

TISSUE PROTECTIVE ERYTHROPOIETIN RECEPTOR (NEPOR) AND METHODS OF USE

INFORMATION ON RELATED APPLICATIONS

This application is a continuation-in-part of International Application No. PCT/EP2008/066480 filed Nov. 28, 2008, which claims the benefit of U.S. Provisional Application 60/991,042, filed Nov. 29, 2007, both of which are herein incorporated by reference.

BACKGROUND

Approved by the FDA in 1993 for treatment of anemia, Erythropoietin (EPO) is a 193 amino acid glycoprotein hormone, produced by the kidneys to regulate red blood cell (RBC) production; a process commonly termed erythropoiesis. EPO was originally identified as a cytokine that promotes erythrocyte progenitor survival and differentiation, but has also been shown to possess neuroprotective functions, particularly in response to ischemic injury in the central nervous system, (CNS). Clinical use of EPO has been prevalent in the treatment of anemic cancer patients, while ongoing studies are exploring EPO's potential in the treatment of neurological diseases (e.g. stroke). Notwithstanding, recent clinical studies in cancer patients have begun to uncover highly worrying adverse events, suggesting that administration of recombinant human EPO (rHuEPO) can adversely effect overall patient survival. An urgent need thus exists in medical oncology to better understand and predict the prevalence or susceptibility to this effect, so that administration of rHuEPO can be contra-indicated, continued or stopped.

SUMMARY

The present invention discloses members of the ephrin family (ephrinA1 and EPH-B4) as mediators of cytoprotective EPO signalling, either as homodimers and/or as heterodimeric partners of EPOR and/or each other. Our data emphasize the importance of EPH-B4 and EphrinA1 in mediating this function. As such, NEPOR represents a novel EPO receptor derived from a unique combination (i.e. via homo- and/or hetero-dimerization) of components derived from ephrin biology and possibly the EPO receptor. See FIG. 3 for summary.

The present disclosure is based upon the data that EPH-B4 and EphrinA1 are the components of a novel EPO receptor (NEPOR). We are able to show that EPO stimulates enhanced tumor growth in a mouse tumor model system. EPO stimulates the Akt signalling pathway in cell lines lacking EPO receptor expression. These cells express EPH-B4 which is a receptor that stimulates signalling via the Akt pathway. Furthermore in a mouse tumor model it can be shown that EPO is capable of stimulating significant tumor growth. Such activity is inhibited via knock-down of the EPH-B4 receptor highlighting the EPH-B4 dependant nature of a EPO mediated tumor genesis. As such, NEPOR is primarily composed of EPH-B4 as a homodimer and/or in heterodimeric association with EPOR or an Ephrin. Furthermore, in silico analyses points to structural complementarity between EPO and Ephrin molecules, particularly Ephrin A1. Thus, NEPOR may also be composed of EphrinA1 as a homodimer and/or in heterodimeric association EPH-B4. A summary of these putative NEPOR species is provided in FIG. 3 and Table 5.

The present disclosure provides a method for assessing a tissue for expression of the tissue protective NEPOR receptor complex and/or EPH-B4 and/or Ephrin A1. In so doing, the present disclosure provides a prognostic method to stratify patients having a tumour as suitable (NEPOR not present on the tumour; NEPOR−) or non-suitable (NEPOR present on the tumour; NEPOR+) for EPO treatment. Specifically, the method for assessing tumour tissue NEPOR and/or gene expression components comprises:

(a) isolating a tissue sample from an individual who is receiving or shall receive erythropoietin, (b) determining the level of expression of the NEPOR gene transcript(s) (i.e. EPH-B4, and/or Ephrin A1 mRNA) and/or the presence of the NEPOR gene products (i.e. EPH-B4, and/or Ephrin A1 proteins) from the isolated tissue, and (c) correlating the presence of these NEPOR component gene expression products to a negative physiological response to the treatment with erythropoietin.

In one aspect, methods are provided for determining whether a patient is suitable for erythropoietin (EPO) therapy, comprising (A) isolating a tissue sample from said patient; (B) determining the level of expression of EPH-B4 in said sample; and (C) correlating a presence of EPH-B4 expression to a negative physiological response to EPO therapy. In one embodiment, the level of expression is determined by measuring the amount of EPH-B4 protein (SEQ ID NO: 2) in said sample. In another embodiment, the level of expression is determined by measuring the amount of EPH-B4 mRNA (SEQ ID NO: 6) in said sample.

In another embodiment, the methods further comprise determining the level of expression in the sample of at least one of Ephrin A1 protein (SEQ ID NO: 3) or EPOR protein (SEQ ID NO: 1). Similarly, the methods can comprise determining the level of expression in the sample of at least one of Ephrin A1 mRNA (SEQ ID NO: 7) or EPOR mRNA (SEQ ID NO: 5).

Methods of determining the level of expression of EPH-B4 are further explained below.

In one embodiment, the presence of EPH-B4 expression is defined by the percentage of cells in said sample showing detectable levels of EPH-B4 protein and the concentration of EPH-B4 protein in said cells. In one example, the presence of EPH-B4 expression is defined by the formula P×C wherein P is the percentage of cells in said sample showing detectable levels of EPH-B4 protein and C is the relative concentration of EPH-B4 protein in said cells, wherein a score of 0, 1, 2, 3 or 4 is assigned to a sample comprising a percentage of cells showing detectable levels of EPH-B4 protein of, respectively, 0%, <25%, 25-50%, 50-75% and 75-100%, wherein a score of 1, 2 or 3 is assigned to relative concentrations of EPH-B4 protein of, respectively, weak, moderate and heavy, and wherein a resulting product of >3 denotes EPH-B4 expression in the sample.

In one embodiment of the present invention, the level of expression of EPH-B4, but not of EPH-A1 is determined. Alternatively, the level of expression of EPH-B4, but not of other components of NEPOR is determined. This includes the possibility that the level of other proteins not being part of NEPOR is determined.

In a further embodiment, only the level of expression of EPH-B4 is determined.

In one embodiment, the level of expression of EPH-B4 is determined by immunohistochemistry. In another embodiment, the level of expression of EPH-B4 is determined by ELISA. In another embodiment, the level of expression of EPH-B4 is determined by RT-PCR.

Preferably, the expression of the NEPOR component genes (i.e. EPH-B4, and/or Ephrin A1 mRNA) is determined by a molecular biological technique selected from the group consisting of PCR, QPCR, R-PCR, gene expression microarray analysis, northern-blot analysis, reverse transcription and amplification, zymography, ligase-chain-reaction, NASBA, RNase Protection Assay (RPA), capillary electrophoresis with laser induced fluorescence (CE-LIF) and combinations thereof.

Preferably, the determination of the presence of the NEPOR gene products is done by detecting the respective proteins with an immunoassay procedure, where the immunoassay procedure is selected from the group of immunoprecipitation, enzyme immunoassay (EIA), radioimmunoassay (RIA) or fluorescent immunoassay, a chemiluminescent assay, an agglutination assay, nephelometric assay, turbidimetric assay, a Western blot, a competitive immunoassay, a noncompetitive immunoassay, a homogeneous immunoassay a heterogeneous immunoassay, a bioassay and a reporter-assay such as a luciferase-assay. The immunoassay procedure is most preferably based on ELISA.

Preferably, the method for detection of NEPOR and/or EPH-B4, and/or Ephrin A1 on tumour tissue can also be an in situ imaging method, comprising administering an anti-NEPOR antibody or NEPOR binding peptide linked to a radio-ligand or other imaging agent, and measuring for tissue distribution and location of the radio-ligand or other imaging agent. Preferably, the tissue sample is selected from the cancerous tissue or circulating cells derived from same, or from a group of biological tissues and fluids such as blood, lymph, urine, cerebral fluid. Specifically, the individual is a cancer patient who is to be treated with erythropoietin or is being treated with erythropoietin. Preferably, the negative physiological effect is increased tumor progression and/or poorer patient survival. Preferably, the presence of NEPOR gene products and/or EPH-B4, and/or Ephrin A1 is indicative of increased tumor progression and/or poorer patient survival upon treatment with erythropoietin. Preferably the cancer is one of head and neck cancer, breast cancer, liver cancer, colorectal cancer, small intestine cancer, leukemia, prostate cancer, lung cancer, ovarian cancer, pancreatic cancer, endometrial cancer, stomach cancer, non-Hodgkin lymphoma, kidney cancer, Renal cell carcinoma (RCC), malignant melanoma, gallbladder cancer, bladder cancer, vulvar cancer, Penile cancer, testicular cancer, thymus cancer, Kaposi's sarcoma, eye cancer, adrenal gland cancer, brain cancer, cervical cancer, appendix cancer, adenoid cancer, bile duct cancer, urethral cancer, spinal cancer, Ewing's family of tumors, extragonal germ cell cancer, extra hepatic bile duct cancer, fallopian tube cancer, soft tissue cancers, bone cancer, Hodgkin's lymphoma, anal cancer, malignant mesothelioma, vaginal cancer skin cancer, central nervous system cancer (craniopharyngioma), pleuropulmonary blastoma, nasal cavity and paranasal sinus cancer transitional cell cancer of renal pelvis and ureter, pituitary gland cancer, sqamous cell carcinoma of the head and neck (HNSCC), prostate cancer, colorectal cancer, lung cancer, brain cancer, bladder cancer, and salivary gland cancer. It is particularly preferred that the cancer is selected from the group of squamous cell carcinoma of the head and neck (HNSCC), prostate cancer, colorectal cancer, lung cancer, kidney cancer, brain cancer, bladder cancer and breast cancer.

The present disclosure further provides a method for designing a therapy which modulates the activity of NEPOR and/or EPH-B4, and/or Ephrin A1, comprising:

1) performing an in vitro screening assay for NEPOR and/or EPH-B4, and/or Ephrin A1 specific therapies; by measuring the binding of test compounds to a tissue protective NEPOR receptor complex and/or EPH-B4, and/or Ephrin A1 (also in comparison to EPOR homodimer complexes), wherein the test compound is labelled (binding of the labelled test compound to the receptor complexes detailed in FIG. 10) and is measured by detecting the label attached to the test compound;

2) performing a label-free screening approach such as surface plasmon resonance. In this case the test compound is not labelled and its binding to NEPOR receptor complexes (as detailed in FIG. 10) is measured by a label independent (optical) method.

3) testing NEPOR and/or EPH-B4, and/or Ephrin A1 activity by (a) contacting a test compound with a tissue protective NEPOR receptor complex (N) or tissue protective NEPOR receptor complex-expressing cell; measuring the level of the activity of (N) in the cell; identifying a test compound that increases or decreases the level of activity of (N) as compared to the level of activity of (N) measured in the absence of the test compound; and assaying the identified test compound for tissue protective activity;

4) testing the modulation of NEPOR/ligand binding and/or EPH-B4, and/or Ephrin A1 ligand binding by (a) contacting (N) with a tissue protective NEPOR receptor complex ligand and/or EPH-B4, and/or Ephrin A1 ligand attached to a first label, and an equivalent amount of a test compound attached to a second label under conditions conducive to binding, removing unbound material from (N), and detecting the level of the first and second labels, where if the second label is present the compound binds (N) and if the level of the first label decreases relative to the level of the first label when the labelled ligand is contacted with (N) under conditions conducive to binding in the absence of a test compound after removal of unbound material, then a compound that binds to (N) is identified.

5) identifying a compound that modulates a tissue protective activity in a mammal, comprising: (a) administering the compound to a first animal immediately following infliction of an injury, wherein the first animal endogenously expresses a tissue protective NEPOR receptor complex; and (b) administering the compound to a second animal immediately following infliction of the same injury as in step (a), wherein the second animal is deficient in expression of a tissue protective NEPOR receptor complex and/or EPH-B4, and/or Ephrin A1 or components thereof; such that if recovery from the injury differs in the animal of step (a) as compared to the animal of step (b), a compound that modulates a tissue protective activity is identified.

The present disclosure further provides methods for treating or preventing a disease or disorder in a human comprising administering a therapeutically effective amount of a compound that modulates the activity of a tissue protective NEPOR receptor complex to a human in need of such treatment or prevention, with the proviso that the compound is not EPO. The compound is selected from the group consisting of an antibody specific for the tissue protective NEPOR receptor complex, an antibody is specific for a tissue protective NEPOR receptor complex ligand, a small molecule, a peptide, an EPO mutant, an EPO:Ephrin_ligand_binding domain chimera, a member of a library, and a combination thereof. Preferably, such compounds negatively modulate the tissue protective function of the NEPOR receptor complex in the aforementioned mentioned cancers. Preferably such compounds positively modulate the tissue protective function of the NEPOR receptor complex wherein the disease or disorder is caused by hypoxia, seizure disorders, neurodegenerative diseases, neurotoxin poisoning, multiple sclerosis, hypotension, cardiac arrest, radiation, or hypoglycemia.

The present disclosure further provides a method for identifying compounds that modulate NEPOR's tissue protective signalling activity, comprising (a) contacting a test compound with the NEPOR receptor complex expressing cell; (b) measuring the level of tissue protective activity initiated by NEPOR activation in the cell; (c) identifying a test compound which increases or decreases the level of tissue protective NEPOR complex activity in a cell; (d) assaying the identified compounds for tissue protective activity mediated via NEPOR; and (e) assaying the identified therapeutics for NEPOR inhibitory activity. Preferably, the assay in step (d) is a tissue protective NEPOR receptor complex activity is measured by a cell proliferation/differentiation assay. More preferably, the cells in the cell proliferentiation/differentiation assay are recombinantly engineered to express EPH-B4, and/or EPOR, and/or Ephrin A1. More preferably, the cells endogenously express an EPO receptor and are transformed with a nucleic acid comprising a nucleotide sequence that (i) is operably linked to a promoter, and (ii) encodes either EPH-B4 and/or Ephrin A1. Most preferably, the cells endogenously express EPH-B4 and/or Ephrin A1 and are transformed with a nucleic acid comprising a nucleotide sequence that (i) is operably linked to a promoter, and (ii) encodes an EPO receptor polypeptide.

The present disclosure further provides a method for identifying a compound that modulates the interaction between a tissue protective NEPOR receptor complex and a tissue protective NEPOR receptor complex ligand, comprising: (a) contacting a tissue protective NEPOR receptor complex with one or more test compounds; and (b) measuring the tissue protective NEPOR receptor complex activity, whereby if the activity measured in (b) differs from the tissue protective NEPOR receptor complex activity in the absence of the one or more test compounds, then a compound that modulates the interaction between the tissue protective NEPOR receptor complex and the tissue protective NEPOR receptor complex ligand is identified. Preferably, the tissue protective NEPOR receptor complex activity is measured by cell proliferation or cell differentiation. Preferably, the tissue protective NEPOR receptor complex activity measured is the ability of the tissue protective NEPOR receptor complex to interact with a tissue protective NEPOR receptor complex ligand. Preferably, the step of assaying the identified compound for tissue protective activity comprises detecting the presence of nucleolin in the cell. Preferably, the step of assaying the identified compound for tissue protective activity comprises detecting or measuring an increased level of activity of neuroglobin or cytoglobin in a cell. Preferably, the tissue protective NEPOR receptor complex is in solution. Preferably, the tissue protective NEPOR receptor complex is in a cell. Preferably, the compound inhibits the binding of a tissue protective NEPOR receptor complex ligand to a tissue protective NEPOR receptor complex. Preferably, the compound enhances the binding of a tissue protective NEPOR receptor complex ligand to a tissue protective NEPOR receptor complex. Preferably, the tissue protective NEPOR receptor complex contacted in step (a) is on a cell surface. Preferably, the tissue protective NEPOR receptor complex is on an isolated cell membrane. Preferably, the tissue protective NEPOR receptor complex activity is compared to EPOR receptor activation to identify NEPOR specific compounds. Preferably, the tissue protective NEPOR receptor complex is immobilized to a solid surface and more preferably, the solid surface is a microtiter dish or a chip.

The present disclosure further provides a method for identifying a compound that binds a tissue protective NEPOR receptor complex, comprising: (a) contacting a test compound with a ligand-binding tissue protective NEPOR receptor complex fragment comprising at least one EPO receptor or EPH-B4 receptor or Ephrin A1 receptor extracellular domain and at least one EPO receptor or EPH-B4 receptor or Ephrin A1 receptor, extracellular domain fused to an Fc fragment attached to a solid support; and (b) contacting a test compound with a ligand-binding EPOR receptor complex fragment comprising at least two EPO receptor extracellular domains fused to an Fc fragment attached to a solid support (c) removing unbound test compounds from the solid supports; (d) identifying the compound attached to the tissue protective NEPOR receptor complex fragment, but not the EPOR receptor complex (and vice versa), whereby a compound bound to the solid support is identified as a compound that binds specifically to a tissue protective NEPOR receptor complex or a compound that binds specifically to an EPOR receptor complex.

The present disclosure further provides a method for identifying a compound that binds a tissue protective NEPOR receptor complex, comprising: (a) contacting a test compound with a ligand-binding tissue protective NEPOR receptor complex fragment comprising at least one EPO receptor or EPH-B4 receptor or Ephrin A1 receptor, extracellular domain fused to an Fc fragment attached to a solid support; (b) removing unbound test compounds from the solid supports; (c) identifying the compound attached to the tissue protective NEPOR receptor complex fragment, whereby a compound bound to the solid support is identified as a compound that binds specifically to a tissue protective NEPOR receptor complex.

The present disclosure further provides a method for identifying a compound that binds to a tissue protective NEPOR receptor complex, comprising: (a) contacting a tissue protective NEPOR receptor complex fragment comprising at least one EPO receptor or EPH-B4 receptor or Ephrin A1 receptor extracellular domain and at least one EPO receptor or EPH-B4 receptor or Ephrin A1 receptor, extracellular domain fused to an Fc fragment attached to a solid support with (i) a tissue protective NEPOR receptor complex ligand attached to a first label and (ii) an equivalent amount of a test compound attached to a second label under conditions conducive to binding; (b) removing unbound material from the tissue protective NEPOR receptor complex; and (c) detecting the level of the first and second labels wherein if the second label is present the compound binds the complex and if the level of the first label decreases relative to the level of the first label where the labelled ligand is contacted with a tissue protective NEPOR receptor complex under conditions conducive to binding in the absence of a test compound after removal of unbound material, then a compound that binds to a tissue protective NEPOR receptor complex is identified.

The present disclosure further provides a method for identifying a compound that modulates the binding of a tissue protective NEPOR receptor complex ligand to a tissue protective NEPOR receptor complex, comprising: (a) contacting a tissue protective NEPOR receptor complex ligand with a tissue protective NEPOR receptor complex fragment comprising at least one EPO receptor or EPH-B4 receptor or Ephrin A1 receptor extracellular domain and at least one EPO receptor or EPH-B4 receptor or Ephrin A1 receptor, extracellular domain fused to an Fc fragment attached to a solid support; in the presence of one or more test compounds under conditions conducive to binding; and (b) measuring the amount of tissue protective NEPOR receptor complex ligated bound to the tissue protective NEPOR receptor complex; whereby if the amount of bound tissue protective NEPOR receptor complex ligand measured in (b) differs from the amount of bound tissue protective NEPOR receptor complex ligand measured in the absence of the one or more test compounds, then a compound that modulates the binding of a tissue protective NEPOR receptor complex ligand to the tissue protective NEPOR receptor complex is identified.

Preferably, the amount of bound tissue protective NEPOR receptor complex ligand is measured using a tissue protective NEPOR receptor complex ligand-specific antibody. Preferably, the tissue protective NEPOR receptor complex ligand is labelled and binding of the tissue protective NEPOR receptor complex ligand to the tissue protective NEPOR receptor complex is measured by detecting the label attached to the tissue protective NEPOR receptor complex ligand. Preferably, the tissue protective NEPOR receptor complex ligand is labelled and binding of the labelled ligand to the tissue protective NEPOR receptor complex is measured by detecting the label attached to the tissue protective NEPOR receptor complex ligand. Preferably, the label is fluorescent. Preferably, the test compound is an antibody specific for the tissue protective NEPOR receptor complex. Preferably, the test compound is a small molecule. Preferably, the test compound is a peptide or a member of a library. Preferably, the tissue protective NEPOR receptor complex ligand is EPO, or derivatives thereof. Preferably, the compound binds the tissue protective NEPOR receptor complex or ligand thereof. Preferably, the tissue protective NEPOR receptor complex activity is compared to EPOR receptor activation to identify NEPOR specific compounds.

The present disclosure further provides a method for identifying a compound that modulates a tissue protective activity in a mammal, comprising: (a) administering the compound to a first animal immediately following infliction of an injury, wherein the first animal endogenously expresses a tissue protective NEPOR receptor complex; and (b) administering the compound to a second animal immediately following infliction of the same injury as in step (a), wherein the second animal is deficient in expression of a tissue protective NEPOR receptor complex or components thereof; such that if recovery from the injury differs in the animal of step (a) as compared to the animal of step (b), a compound that modulates a tissue protective activity is identified.

The present disclosure further provides a method for designing a compound which interferes with NEPOR's survival promoting activity, comprising:
(a) providing the molecular makeup of the NEPOR species and providing amino acid sequences of a component NEPOR polypeptides;
(b) using software comprised by the digital computer to design a chemical compound/protein construct which is predicted to bind to NEPOR; and
(c) optionally designing protein constructs which mimic NEPOR in its dimerised/multimerised state (e.g. Fc constructs).

The present disclosure further provides a method for identifying compounds that modulate NEPOR's tissue protective signalling activity, comprising (a) contacting a test compound with the NEPOR receptor complex; (b) measuring the level of tissue protective activity initiated by NEPOR activation; (c) identifying a test compound which increases or decreases the level of tissue protective NEPOR complex activity; (d) assaying the identified therapeutics for tissue protective activity mediated via NEPOR; and (e) assaying the identified therapeutics for NEPOR inhibitory activity. Preferably, the tissue protective NEPOR receptor complex activity is measured by measuring the binding of the test compound to the NEPOR receptor complex. More preferably, the test compound is labelled and binding of the labelled test compound to the tissue protective NEPOR receptor complex is measured by detecting the label attached to the test compound. Most preferably, the tissue protective NEPOR receptor complex activity is measured by measuring the binding of the test compound to the tissue protective NEPOR receptor complex.

The present disclosure further provides a method for imaging tumour tissue that is susceptible to enhanced survival in response to EPO treatment, comprising administering an anti-NEPOR antibody or NEPOR binding peptide linked to a radio-ligand or other imaging agent, and measuring for tissue distribution and location of the radio-ligand or other imaging agent. Preferably, the anti-NEPOR antibody is a monoclonal or polyclonal antibody selected from the group of antibodies listed in Table 6.

The present disclosure further provides a method for modulating cell survival in NEPOR positive tissue comprising administering an EPO mutants and peptides selected from the group consisting of peptides from SEQ ID NO. 17 through SEQ ID NO. 212.

The present disclosure further provides a method for modulating cell survival in NEPOR positive tissue comprising administering an effective amount of an EPO chimera, comprising an ephrin receptor ligand binding domain selected from the group consisting of SEQ ID NO. 215, and SEQ ID NO. 216.

In another aspect, methods are provided for enhancing the effectiveness of EPO therapy in a patient, comprising administering to the patient, in conjunction with EPO therapy, an siRNA specific for EPH-B4. In one embodiment, the siRNA is selected from the group of nucleic acid duplexes consisting of SEQ ID NO: 242 and SEQ ID NO: 243; SEQ ID NO: 244 and SEQ ID NO: 245; SEQ ID NO: 246 and SEQ ID NO: 247; SEQ ID NO: 248 and SEQ ID NO: 249; SEQ ID NO: 250 and SEQ ID NO: 251; SEQ ID NO: 252 and SEQ ID NO: 253; SEQ ID NO: 254 and SEQ ID NO: 255; SEQ ID NO: 256 and SEQ ID NO: 257; SEQ ID NO: 258 and SEQ ID NO: 259; and SEQ ID NO: 260 and SEQ ID NO: 261.

In another embodiment, the siRNA is a duplex of SEQ ID NO: 266 and SEQ ID NO: 267. In another, the siRNA is a duplex of ID NO: 219 and SEQ ID NO: 220.

BRIEF DESCRIPTION OF THE FIGURES

Figure 11:
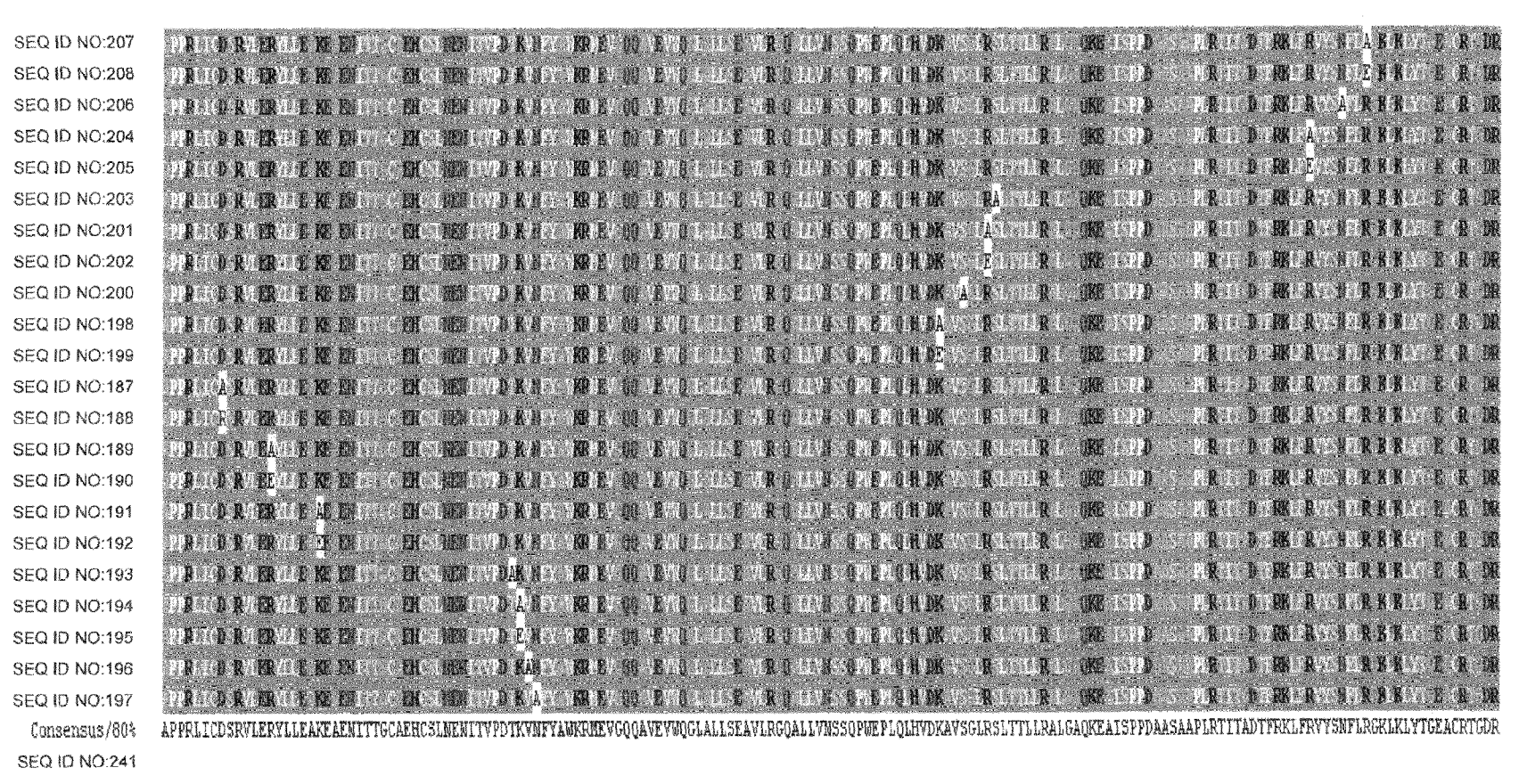

FIG. 11 shows an alignment of EPO protein mutants which are predicted to bind NEPOR more favourably than EPOR. Such mutants are predicted to be primarily tissue protective as opposed to haematopoietic, particularly those versions combining the described mutations.

DETAILED DESCRIPTION

Figure 1:
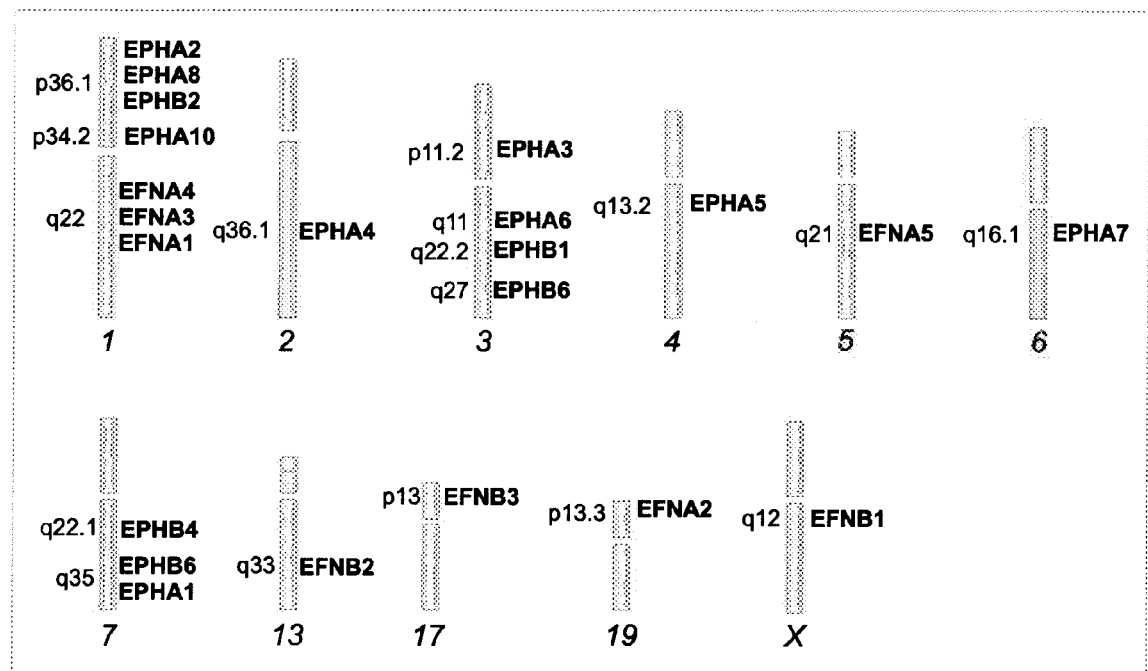
FIG. 1 shows the genomic localization of human Eph receptor (EPH) and ephrin (EFN) genes on human chromosomes.

The present disclosure results from the identification of a novel EPO receptor, henceforth referred to as NEPOR. NEPOR was identified using a bioinformatics workflow encompassing both a functional and sequence based analysis of the human genome/proteome. Homology analysis involving an extracellular protein database (termed XtraCellDB) was used in conjunction text-mining and genome context analysis. These in silico predictions were subsequently verified in lab-based experiments. Thus, the present disclosure provides genomic, proteomic and experiment evidence that the protein EPH-B4 (Erythropoietin Producing Hepatoma protein B4) and/or Ephrin A1 act as EPO receptors.

EPO: Biological Function

Erythropoietin (EPO) is a 193 amino acid type I cytokine, produced by cells of the renal cortex to regulate red blood cell (RBC) production in a process termed erythropoiesis. Erythropoiesis is multistage in nature, involving the differentiation of pluripotent hematopoietic stem cells through the lineage-committed burst-forming unit-erythroid (BFU-E) and colony-forming unit-erythroid (CFU-E) progenitor cells, which give rise to a series of early and late erythroblasts, eventually leading to the formation of reticulocytes and mature erythrocytes. During this process, the sequential formation of pro-erythroblasts, basophilic, polychromatophilic, and orthochromatic erythroblasts is positively regulated by EPO. EPO induces multiple positive effects on early erythroblasts, including increased proliferation, progression through maturation, and protection from programmed cell death.

In terms of molecular mechanism, EPO binds to two identical receptors (EpoR), an event which activates several intracellular signaling pathways. These include Janus kinase 2-signal transducer and activator of transcription 5 (JAK2-STAT5), phosphatidylinositol 3-kinase (PI3K), protein kinase C (PKC), and Ras-Raf-MEK (mitogen-activated or extracellular signal-regulated protein kinase kinase)-ERK (extracellular signal-regulated protein kinase). The JAK2-STAT5 and RAS-RAF-MEK-ERK pathways are thought to be associated with Epo's mitogenic action, while the PI3K pathway, acting through Akt (PI3K-Akt), is viewed as a mediator of EPO's anti-apoptotic activities.

EPO: Clinical Use

Anemia (AmE) or anemia/anaemia (BrE), from the Greek (ναιμία)(an-haîma) meaning "without blood", is a deficiency of red blood cells (RBCs) and/or hemoglobin. The condition is commonly observed in patients with chronic diseases, and is particularly common in cancer where about 50% of patients are anaemic at presentation and some 70-90% developing the condition during the course of treatment (typically termed chemotherapy induced anemia (CIA)). In a recent review of the European Cancer Anemia Survey (ECAS), Ludwig et al. cited a 50% baseline anemia rate (hemoglobin [Hb]<12 g/dL) among 3010 patients with hematological malignancies and a 41% baseline anemia rate among 11,453 patients with solid tumours (Blood, 2002; 100:234a-235a. Abstract 884). Further longitudinal analysis revealed that 72% of 2780 patients with haematologic malignancies and 66% of 10,067 patients with solid tumours succumbed to CIA. Other published studies have reported varying high rates in patients at different phases and with different types of treatment (Table 1). Notwithstanding, all studies demonstrate the extremely high prevalence of anemia amongst cancer patients.

TABLE 1

Prevalence of Anemia in Cancer Patients Undergoing Treatment

| Type of Cancer | Prevalence of Anemia (Hb < 12 g/dL) |
| --- | --- |
| Cervical cancer[3] | 82% |
| Solid tumors[1] | 66% |

TABLE 1-continued

Prevalence of Anemia in Cancer Patients Undergoing Treatment

| Type of Cancer | Prevalence of Anemia (Hb < 12 g/dL) |
| --- | --- |
| Colorectal cancer[3] | 67% |
| Lung cancer[3] | 63% |
| Haematological malignancies | 72% |

A number of factors contribute to the high incidence of anemia among cancer patients, including not only chemotherapy and radiation-induced myelosuppression, but also cytokine-mediated anemia of chronic disease, bleeding, marrow infiltration by tumour, hemolysis, and nutritional deficiencies. Whatever the source, anemia results in a reduced ability of blood to transfer oxygen to the tissues, leading to tissue hypoxia and an associated range of clinical consequences, affecting all realms of patient health: physiologic status, psychosocial well-being and quality of life. Not surprising, anemia can negatively affect a patient's response to cancer therapy, a fact which highlights the important supportive role of rHuEPO in restoring normal RBC counts.

EPO: Clinical Safety

ESA's were for many years considered to be extremely safe in their labelled indications of chronic kidney disease and chemotherapy-induced anemia. The first hints of safety issues came in 2003 when results from a pair of studies examining EPO's potentiation of radiation and chemotherapy prompted an FDA meeting in May 2004. This first study (the ENHANCE study: *Lancet* 2003; 362:1255-1260) suggested the relative risk of progression-free survival was worse for patients who received radiotherapy plus NeoRecormon epoetin beta from Roche than for patients receiving placebo plus radiotherapy. A randomized, double-blind, multi-institutional trial that included a study population of 351 patients who were receiving radiotherapy was performed. The patients were treated 3 times per week with either placebo or EPO in the form of epoetin beta starting 10 to 14 days before and continuing through radiation therapy. Although haemoglobin levels increased in 82% of patients receiving EPO, compared with 15% in patients receiving placebo, the rate of loco-regional progression-free survival was significantly lower. In addition, the EPO group had a higher relative risk for loco-regional progression and death.

In the second trial involving 939 breast cancer patients receiving chemotherapy (the BEST study: *J. Clin. Oncol.* 2005; 23:5960-5972; see table 2), those given Eprex epoetin alfa from Johnson & Johnson had a higher 4-month mortality rate and a lower 12-month survival rate than those on placebo. Both studies attempted to push the limits of hemoglobin levels beyond that permitted for marketing by the FDA—the recommended haemoglobin target for Aranesp was at the time up to 12 g/dL, while the labels for Epogen and Procrit recommended 10-12 g/dL. Henke treated men to target levels of at least 15 g/dL, while women were treated to at least 14 g/dL. The target level in the BEST study was 12-14 g/dL.

TABLE 2

Summary of the results from Leyland-Jones et al. (J. Clin. Oncol. 2005; 23: 5960-5972) showing that 8.7% of patients from the EPO treatment arm died within 4 months of treatment, compared to 3.4% in the non-treated arm. ITT = Intention to treat.

Table 2 Causes of Death Among Patients Who Died Within 4 Months of Random Assignment (ITT population, N = 939)

| Outcome | Epoetin Alfa (n = 469) | | Placebo (n = 470) | |
|---|---|---|---|---|
| | No. of Patients | % | No. of Patients | % |
| Alive at 4 months | 428 | 91.3 | 454 | 96.6 |
| Died within 4 months | 41 | 8.7 | 16 | 3.4 |

Johnson & Johnson (JNJ, New Brunswick, N.J.) have since reported data from the Phase IV CHOIR trial (*N. Engl. J. Med.* 2006 Nov. 16; 355(20):2085-98.) that tested whether using Procrit epoetin alfa to get hemoglobin levels to 13.5 g/dL would improve outcomes vs. treating to 11.3 g/dL (within the 10-12 g/dL range on the drug's label). Patients in the higher haemoglobin group had a significantly increased incidence of mortality and cardiovascular events. While this study was carried out in the renal disease space, the safety implications were further emphasized in a more recent study—DAHANCA10. In February 2007, Amgen disclosed that this independent study had been halted three months earlier after interim data showed that Aranesp plus radiation missed the primary endpoint of 3-year loco-regional control vs. radiation alone. The study also showed a non-significant increase in death in the Aranesp arm. DAHANCA10 explored whether the use of Aranesp to maintain a hemoglobin level of 14-15.5 g/dL during radiotherapy could improve loco-regional disease control in patients with primary head and neck squamous cell carcinoma (HNSCC).

Safety signals also emerged from the use of Aranesp in the AoC space (study 103). In January 2007, Amgen reported that the risk/benefit profile of Aranesp was "at best neutral" in a Phase III trial in patients who had AoC and who were not receiving chemo- or radio-therapy. Here the data revealed significantly more deaths in Aranesp patients than in placebo patients. The trial, which treated patients to a haemoglobin level of 12-13 g/dL, also missed its primary endpoint of a significant reduction in transfusion frequency at 16 weeks. Study 103 enrolled patients with various cancers, including non-small cell lung cancer (NSCLC), breast cancer and prostate cancer. Canadian researchers have published similar findings (*J. Clin. Oncol.* 2007 Mar. 20; 25(9):1027-32). Here the authors showed that of the 70 advanced NSCLC patients with AoC, those receiving Procrit, had a significantly higher mortality rate than those receiving placebo. A synopsis of each of these studies is provided in Table 3 below:

TABLE 3

Summary of results from EPO safety studies highlighting survival issues.

| STUDY | EPO type | POPULATION | DESIGN | STATUS |
|---|---|---|---|---|
| DAHANCA (SE20029001) | Aranesp | HNSCC; Baseline Hb <= 14.5 | Multicenter, open-label trial of radiotherapy +/− Aranesp | Terminated early by DMC (after 522 of 600 planned patients enrolled) based on lower LRC rates and increased deaths in the ESA arm at planned interim analysis; 522 of 600 planned pts; summary results 12/06; CSR anticipated 9/08 |
| EPO-CAN-20 | Eprex/Procrit | NSCLC not receiving chemo; baseline Hb <= 12 | Double-blind, placebo controlled, randomized (1:1) +/− Eprex | Terminated early by DSMB for increased deaths in ESA arm; 70 of 300 patients enrolled; results published in abstract in 2004 and in the journal of clinical oncology 3/07 |
| BEST (EPO-INT-76) | Eprex/Procrit | Metastatic breast cancer | Randomised, double blind, placebo controlled | Terminated in April 2002, after review of data in the first 938 pts by the DMC, due to evidence of excess mortality in the Eprex arm |
| RTOG 9903 | Eprex/Procrit | HNSCC; baseline Hb 9-12.5 (female), 9-13.5 (male) | Open-label, randomized (1:1), chemo/radiation +/− procrit | Terminated early by DSMB for trend to poorer LRC and OS in EPO arm. 148 of 372 patients enrolled. Results published in abstract 2004 |
| Study 103 (Amgen) | Aranesp | NSCLC, prostate, breast cancer | | |

These clinical findings have led many investigators to suggest a possible role for ESA's in promoting tumour growth through stimulation of EPO receptor survival signalling in tumour cells, and via the stimulation of angiogenesis. Implicit in these proposed activities is the notion that the EPO receptor can somehow confer survival advantage to cancer cells, a negative side effect. This, in turn, suggests that EPO receptor is both present and activated by EPO binding in such cells. Using real-time, quantitative RT-PCR, the EPOR gene has not only been shown to be strongly expressed in bone marrow (containing the EPO-responsive erythroid progenitors), but also at significant levels in normal tissues (e.g. kidney, heart, brain, endothelium, and smooth muscle). Moreover, EPOR transcript levels in breast, colon, ovary, prostate, lung, lymphoma, ileum, stomach, and kidney tumour tissues and tumour cell lines were no higher than those levels observed in normal tissue counterparts. These findings are in concordance other reports which demonstrated that EPOR transcript levels are basically equivalent in matched tumour and non-tumour samples from patients with lung, colon and prostate cancer.

From the perspective of these data, it is questionable whether the EPOR gene might somehow provide selective advantage to tumour cells, at least via abnormal expression levels.

Therefore, there is a possible role for EPOR in mediating tumour cell survival in response to EPO. From a molecular perspective, the ability of cancer cells to subvert the EPO/EPOR system would not be surprising. A number of preclinical studies have demonstrated EPO-mediated activation of the mitogen-activated protein kinase (MAPK), phosphatidylinositol 3-kinase (PI₃K)-Akt, JAK-STAT (Janus kinase-Signal Transducer and Activator of Transcription), and nuclear factor-kappa B (NFκB) signalling pathways in a variety of human cancers. Each of these signalling cascades has been associated with cellular functions that promote tumour progression. EPO stimulated not only chemotaxis of endothelial cells, together with migration and invasion of breast cancer and HNSCC cells, but also appears to induce cancer cell proliferation and inhibit apoptosis. Moreover, pretreatment with rHuEPO protects some cancer cell lines from the cytotoxic effects of the chemotherapeutic agent, cisplatin. Thus, EPO/EPOR signalling appears to contribute to a wide variety of tumour-promoting functions in different cancer types.

Despite this evidence, the possible contribution of EPO/EPOR signalling to cancer progression is anything but straightforward. The influence of EPO/EPOR on different cancer types appears to be quite variable and remains incompletely understood. Studies have shown that EPO does not influence the proliferation of cancer cell lines. Rosti et al. (*Haematologica* 1993 July-August; 78(4):208-12.), for example, investigated the proliferative potential of rHuEPO by testing the effects of this factor on clonogenic growth and DNA synthesis in 10 different cell lines derived from haematologic malignancies and solid tumours. The cell lines K-562 and HEL were included in this study, both of which express EPO receptors. Results showed that rHuEPO had no effect on either colony growth or DNA synthesis (see Table 4).

TABLE 4

Showing the lack of effect of rHuEPO on the percentage of cells in S phase in human cell lines.

| Cell line | EPO (IU/ml) | | |
|---|---|---|---|
| K-562 | 37.0 ± 2.0 | 37.1 ± 2.1 | 36.8 ± 1.7 |
| HEL | 27.3 ± 1.9 | 26.2 ± 1.3 | 25.8 ± 1.4 |
| HL-60 | 26.4 ± 1.8 | 24.8 ± 2.1 | 25.6 ± 2.0 |
| PLB 985 | 30.0 ± 1.7 | 27.8 ± 2.3 | 28.2 ± 2.5 |
| KG-1 | 14.2 ± 1.3 | 14.0 ± 1.7 | 15.5 ± 1.8 |
| H69 | 15.3 ± 1.5 | 15.8 ± 1.3 | 14.9 ± 1.6 |
| N417 | 16.6 ± 1.8 | 17.0 ± 1.4 | 16.3 ± 2.2 |
| MCF-7 | 20.0 ± 0.9 | 21.1 ± 1.2 | 19.7 ± 1.0 |
| OCUM-1 | 16.1 ± 2.1 | 17.3 ± 2.4 | 15.3 ± 2.3 |
| GBL-HU12 | 19.2 ± 1.5 | 20.9 ± 1.6 | 19.1 ± 2.0 |

In a similar study, Westphal et al. (*Tumori* 2002 March-April; 88(2): 150-9.) investigated the effects of EPO on more than 25 different benign and malignant human cell lines. Expression of EPO receptor mRNA and protein was analyzed with RT-PCR, Western blot, and immunocytochemistry. Cellular responses to various concentrations of EPO were evaluated using tritiated thymidine uptake, Northern blot analysis of c-fos expression, and tyrosine-kinase activity assay. EPO receptor mRNA and protein were identified in the majority of the tumour cell lines evaluated. Despite these findings, treatment with rHuEPO did not significantly influence the proliferation rate of EPO-receptor-positive tumour cell lines. Moreover, treatment with EPO neither affected the gene c-fos mRNA of those cell lines nor stimulated tyrosine-kinase activation. Based on their findings, the authors concluded that expression of the EPO receptor in tumour cells does not appear to be essential for growth and therefore should not have a deleterious effect in cancer patients.

Results by Lu et al. (*J. Biol. Chem.*, Vol. 281, Issue 11, 7002-7011, 2006) establish that receptor activation is not simply accomplished by bringing two receptors into close proximity through disulfide linkages in the transmembrane or extracellular domains. Instead, the relative orientation of the two transmembrane domains of an EpoR dimer, rather than their proximity, determines the extent of receptor activation. More specifically, these authors propose that Epo binding to the inactive, symmetric EpoR dimer causes the repositioning of the two fibronectinIII domains to an asymmetric 120° relative orientation, which in turn changes the orientation of the transmembrane domains and intracellular domains, and juxtaposes the appended JAK2s to initiate the phosphorylation cascade. EPO mutants would not necessarily be expected to be capable of initiating EPOR-signalling, due to their inability to induce the correct relative conformation of the fibronectinIII domains. Interestingly, it appears that certain aspects of EPO function can be decoupled from EPOR activity. Leist et al. (*Science* 305, 239-242.) have shown that the haematopoietic and tissue-protective activities of Epo are distinct and separate, demonstrating for example that carbamylated Epo (CEpo) does not stimulate erythropoiesis, yet prevents tissue injury in a wide variety of in vivo and in vitro models.

EPO's efficacy in treating nervous system disease has been demonstrated in several experimental models of brain and spinal cord injury. As such, EPO has become a candidate for therapeutic neuro-protection. Notwithstanding, the use of EPO as a neuro-protectant raises several safety issues. Although recombinant EPO seems to be potentially safe at neuroprotective proven doses, cardiovascular or cerebrovascular events can occur as a result of its bone marrow stimulating activities. Interestingly, as highlighted above, EPO's neuronal protective function appears molecularly separable from the haematopoietic activity, as carbamylated EPO and certain EPO mutants are neuroprotective but fail to induce haematopoiesis. Such mutants fail to bind EPOR (Leist et al. *Science* 305, 239-242).

EPO was for a long time considered to act solely on haematopoietic cells, a fact which led to its emergence as a leading treatment for chemotherapy-induced anemia. However, emerging evidence has shown that EPO is expressed in a variety of tissue and cell types, including cancer, vascular endothelial, and neuronal cells. Expression of EPO is induced in response to hypoxia, an event mediated by the HIF-1 transcription factor. EPO is prototypically thought to exert its biological effects via binding to its cell surface receptor EPOR, resulting in tyrosine phosphorylation of the receptor and other intracellular proteins, including JAK2 and STAT5. The JAK/STAT pathway is utilized both in haematopoietic and non-haematopoietic cells (including brain cells) following binding of EPO to the EPO receptor. The recent findings of EPO-receptor expression in human breast and renal cancer cells, as well as in several tumour cell lines, have raised important questions in the oncology setting about a possible tumour-growth-promoting effect of rHuEPO on EPO-receptor-bearing tumours. This possibility has been borne out in several clinical trials. Interestingly, other studies have shown that certain EPO mutants which are cytoprotective but not longer able to induce haematopoiesis, function independently of EPOR. This suggests that another EPO receptor may exist which lacks EPOR's strict binding conformation requirements.

Ephrin and Ephrin Receptor Biology

Erythropoietin-producing hepatocellular carcinoma (Eph) receptors form the largest family of receptor tyrosine kinases. Eph receptors are divided into two groups (Eph-A's and Eph-B's) based on the similarity of their extracellular domain sequences and the distinct structural properties of the ephrin ligands (Eph Nomenclature Committee, 1997). About 16 ephrin receptor genes (EphA1-10, EphB1-6) have been identified in the vertebrate genome (Pasquale, Nat. Rev., Mol. Cell Biol. 6 (2005), pp. 462-475.), 14 of which are present in humans (FIG. 1) and other mammals (EphA1-8, EphA10, EphB1-4, EphB6).

Figure 2:
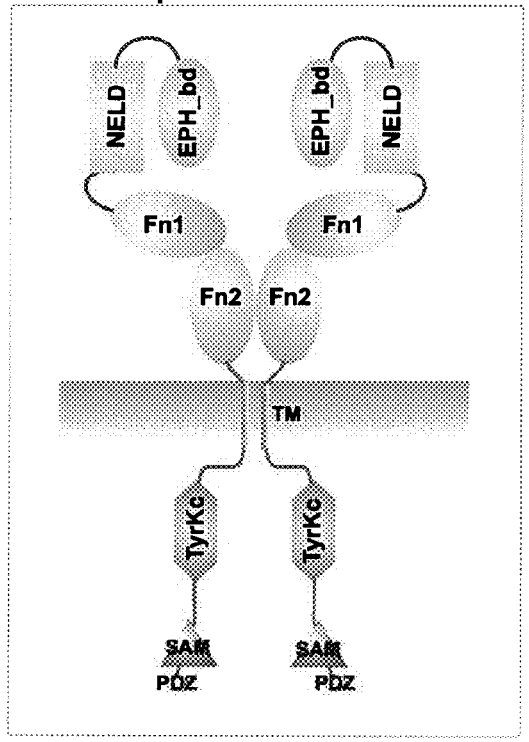
FIG. 2 shows the domain architecture of Eph receptors and Ephrins (A and B subclasses).
Figure 2:
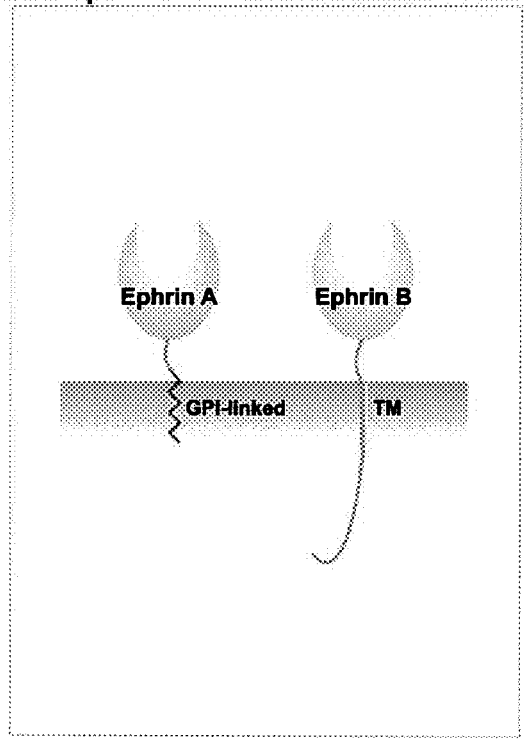

Eph receptors are single-pass transmembrane proteins with highly conserved extracellular and intracellular domains. The former domains consists of an N-terminal ligand binding domain, a cysteine-rich EGF-like region and two fibronectin type III repeats (Yamaguchi and Pasquale, Curr. Opin. Neurobiol. 14 (2004), pp. 288-296.). Intracellularly, the juxtamembrane region is followed by a tyrosine kinase domain, followed by a sterile-α-motif (SAM), and a type-II PSD-95/Disc large/ZO-1 (PDZ) binding motif at the carboxyl terminus (Kullander and Klein, Nat. Rev., Mol. Cell Biol. 3 (2002), pp. 475-486.). The tyrosine kinase domain of one receptor from each class (EphA10 and EphB6) lacks residues that are essential for catalytic activity. Eph receptor variants are generated by alternative splicing and their structures differ from the prototypical domain structure. The domain architecture of Eph receptors and Ephrins (A and B subclasses) are shown in FIG. 2.

Eph receptors can undergo cis-oriented homo—as well as heterodimerization (Freywald et al., J. Biol. Chem. 277 (2002), pp. 3823-3828.), which is mediated directly by the extracellular cysteine-rich region, the fibronectin type III repeats (Lackmann et al., J. Biol. Chem. 273 (1998), pp. 20228-20237.) and the SAM motif (Stapleton et al., Nat. Struct. Biol. 6 (1999), pp. 44-49. and Thanos et al., Science 283 (1999), pp. 833-836.) or indirectly through PDZ protein interactions (Fanning and Anderson, J. Clin. Invest. 103 (1999), pp. 767-772). Trans-oriented interactions typically occur with select ephrin molecules on opposing cells. In common with their receptors, the ephrins (named derived from Eph family receptor interacting proteins or ephoros) are divided into two distinct subclasses A and B. Ephrin-A ligands are GPI-anchored peripheral membrane molecules. In contrast, ephrin-B ligands are transmembrane molecules whose short cytoplasmic domain is capable of participating in various signalling events. The ephrin-A and ephrin-B molecules were initially described as selectively interacting with EphA and EphB receptors, respectively. However, there may be crosstalk between A and B family members. For example, ephrin-A5 is capable of binding EphB2, while EphA4 binds to ephrin-A and ephrin-B family members. Although interactions across classes are limited, within a class they are promiscuous, with multiple EphA receptors binding to a given ephrina and vice versa.

While neither class of ephrins possesses a catalytic activity, both can activate signal transduction pathways after interaction with Eph receptors (reverse signalling). Reverse signalling activated by transmembrane ephrins includes tyrosine phosphorylation of their cytoplasmic tail and interaction with various signalling molecules. The mechanism by which GPI-linked ephrins stimulate downstream signalling is still unclear.

Signalling sometimes involves formation of signalling assemblies, a process that begins with a monovalent interaction (nanomolar affinity) between an Eph receptor and an ephrin on a juxtaposed cell. Crystallographic work has shown that the globular ephrin-binding domain of EphB2 contains a cavity that accommodates a hydrophobic protrusion from the ephrins. Structural changes occur upon binding. For example, EphB2 undergoes different structural rearrangements upon binding to ephrin-B2 or ephrin-A5.

A lower affinity binding interface is also present on the opposite side of the EphB2 ligand binding domain (Eph_lb), with complementary interfaces also present in the Eph-receptor-binding domain of ephrin-B2. While only of micromolar binding affinity, the second interface can mediate the dimerization of two Eph-ephrin dimers into a tetramer that comprises two receptor and two ephrin molecules extending from adjacent cell surfaces. The lower-affinity interface contains important determinants of subclass specificity and is not engaged in the EphB2-ephrin-A5 complex.

Signalling is initiated upon transphosphorylation via correctly orientated kinase domains. Eph receptors become extensively phosphorylated upon activation by ephrins and via src-kinase association. Phosphorylation promotes conformational order on the activation segment of the kinase domain that favours substrate binding and also disrupts intra-molecular inhibitory interactions that occur between the juxtamembrane segment and the kinase domain. Src-family mediated phosphorylation of Eph receptors has also been shown to act in a similar manner.

Discussion

Working on the theory that the adverse effects of EPO seen in many cancer patients may be mediated by a receptor complex distinct from the prototypical EPO receptor (EPOR) homodimer, we initiated an in silico discovery project to try to identify a novel EPO receptor. Should such a novel EPO receptor species exist, we hypothesized that it will be responsible for mediating EPO-induced cell survival activity, as opposed to EPO mediated haematopoietic activity. Thus, we proposed the existence of at least two species of EPO receptor; the prototypical EPOR homodimer which is primarily responsible for EPO's haematopoietic activity, and a novel EPO receptor, termed NEPOR, which is primarily responsible for EPO's cytoprotective activities. The existence of such a novel EPO receptor is compelling for three main reasons. Firstly it allows the prediction of a cancer patients response to EPO. Presence of NEPOR on a tumour cell would imply a negative response to EPO, since binding of EPO by NEPOR would induce a cascade of survival signals within tumour cells and tissues, thus contributing to cancer progression and poorer patient survival. Thus, detection of NEPOR expression in a tumour provides a novel biomarker for stratify cancer patients as suitable (i.e. NEPOR not present) or unsuitable (i.e. NEPOR present) for EPO treatment. A corollary of this model is a second interesting perspective. If NEPOR is capable of initiating survival signals on cancer cells, then it represents an excellent therapeutic target for treatment of cancers expressing this receptor. Thus, therapeutic molecules targeting and antagonizing the tissue protective function of this receptor should be efficacious anti-cancer agents. Finally, under conditions where induction of cell survival is favourable, such as in response to ischemic stroke, therapeutic molecules capable of activating NEPOR-mediated survival signals provide an efficacious path to treating a variety of neurological diseases. Definition of NEPOR's molecular composition therefore provides the molecular basis for designing such therapies.

It had previously been proposed that rHuEPO can promote tumour growth through stimulation of Epo receptor (EPOR) signalling in tumour cells, and via the stimulation of angiogenesis. Binding of EPO to EPOR homodimers was assumed to somehow confer survival advantage to cancer cells, leading to increased loco-regional progression and poorer survival rates in patients having a form of cancer. However, aware of the binding promiscuity of exogenously administered therapeutics, we were anxious to address the possibility as to whether another receptor might be responsible for the observed negative outcomes, either alone or in functional interaction with EPOR.

In an effort to identify such a novel cytoprotective EPO receptor, we developed an in silico based analysis approach specifically designed to mine the human proteome for candidate molecules. Combining the power of text-mining and in-depth bioinformatics analysis, this multi-evidence based approach successfully identified a putative novel EPO receptor. Subsequent lab-based validation supports these findings. Given its established physiological role, we propose that by impinging on this receptors activity, EPO can confer survival advantage to certain cells, including cancer cells and neurons. As a consequence, the expression of this protein on cancer cells can be used to stratify the suitability of cancer patients for EPO treatment. Patients with cancer associated NEPOR expression should be contraindicated for EPO treatment. However, a corollary of this finding is that these same individuals represent excellent candidates for treatment with antagonistic anti-NEPOR therapies. In addition, we also propose that by mediating EPO's cyto-protective activity, NEPOR represents an excellent therapeutic target for a variety of diseases involving tissue ischaemia (e.g. stroke).

Thus, in the first instance, the present disclosure provides a method for assessing a tumour for expression of NEPOR. The disclosure provides a method to stratify patients having a tumour as suitable (i.e. NEPOR not present) or non-suitable (i.e., NEPOR present) for EPO treatment. The method disclosed comprises: (a) isolating a tissue sample from an individual who is receiving or shall receive erythropoietin, (b) determining the level of expression of the NEPOR gene(s) (mRNA) and/or the presence of the NEPOR gene product (protein) from the isolated tissue, and (c) correlating the presence of an NEPOR gene expression product or the presence of NEPOR protein to a physiological response to the treatment with erythropoietin. In a second instance, the present disclosure provides a method for treating patients possessing NEPOR positive tumors. Furthermore, the present disclosure provides a method for treating stroke. Finally, by providing a means of comparing binding affinities of putative therapeutics to both NEPOR and EPOR, the present disclosure provides a method for screening for NEPOR specific therapeutics (both antagonistic therapeutics for cancer, and agonistic therapeutics for treatment of hypoxia associated disease such as stroke). Such therapeutics will lack the haematopoietic activity associated with EPOR binding and signaling.

NEPOR—Molecular Definition

Figure 3:
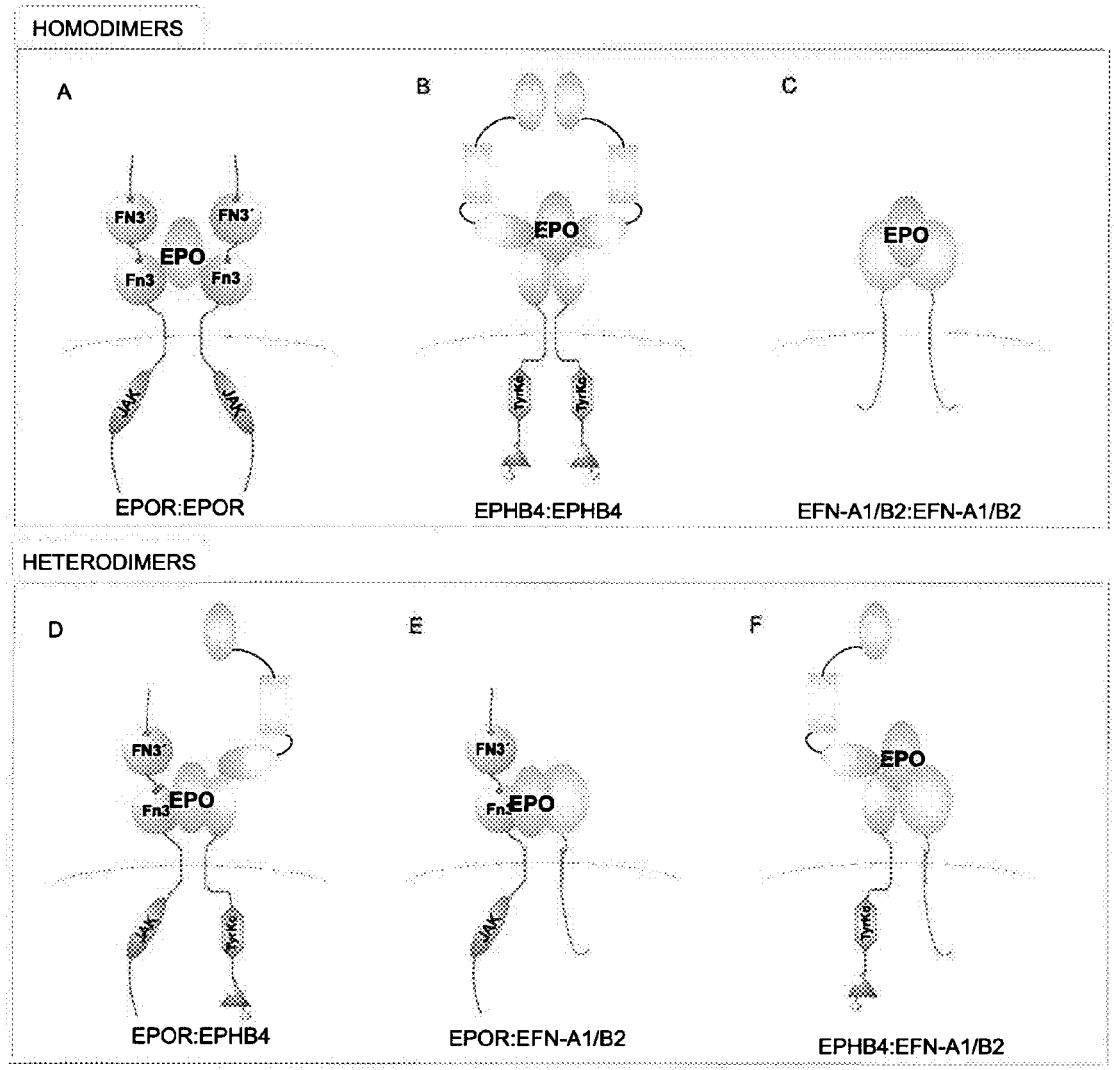
FIG. 3 shows the theoretical combinations of receptors that might have EPO binding capacity.

We have identified a novel multimeric EPO receptor, which we term NEPOR. NEPOR comprises EPHB4 and/or Ephrin A1 molecules either as homodimers or heterodimers. Without being bound by theory, these components may also heterodimerize with the EPO receptor. A synopsis of the possible molecular compositions of NEPOR is provided in FIG. 3. Despite the room for molecular promiscuity involving other components from ephrin biology, EPH-B4 and/or EphrinA1 are components of a novel EPO receptor (NEPOR). As such NEPOR is primarily composed of EPH-B4 and Ephrin A1, either as a homodimers and/or in heterodimeric association with each other, or the EPO receptor. Without being bound by theory, given the strong functional association between EPH-B4 and Ephrin B2, NEPOR may also comprise Ephrin B2 disclosed herein as SEQ ID NO. 4 (amino acid sequence), SEQ ID NO. 8 (mRNA sequence), and SEQ ID NO. 12 (binding region).

Table 5 shows, without being bound by theory, the possible molecular composition of dimeric EPO receptors. The prototypical haematopoietic EPO receptor (EPOR) represents a homodimer of two EPOR (SEQ ID NO. 1) monomers (1). Our results suggest that a novel tissue protective EPO receptor dimer is comprised of Ephrin A1 (SEQ ID NO. 3) and EPH-B4 (SEQ ID NO.2). Possible scenarios are shown in Table 5.

TABLE 5

|    | Description | Monomer 1     | Monomer 2     |
|----|-------------|---------------|---------------|
| 1  | EPOR        | SEQ ID NO. 1  | SEQ ID NO. 1  |
| 2  | NEPOR       | SEQ ID NO. 1  | SEQ ID NO. 2  |
| 3  | NEPOR       | SEQ ID NO. 1  | SEQ ID NO. 3  |
| 4  | NEPOR       | SEQ ID NO. 2  | SEQ ID NO. 2  |
| 5  | NEPOR       | SEQ ID NO. 2  | SEQ ID NO. 3  |
| 6  | NEPOR       | SEQ ID NO. 3  | SEQ ID NO. 3  |
| 7  | NEPOR       | SEQ ID NO. 1  | SEQ ID NO. 4  |
| 8  | NEPOR       | SEQ ID NO. 2  | SEQ ID NO. 4  |
| 9  | NEPOR       | SEQ ID NO. 3  | SEQ ID NO. 4  |
| 10 | NEPOR       | SEQ ID NO. 4  | SEQ ID NO. 4  |

>EPOR

SEQ ID NO. 1

MDHLGASLWPQVGSLCLLLAGAAWAPPPNLPDPKFESKAALLAARGPEEL

LCFTERLEDLVCFWEEAASAGVGPGNYSFSYQLEDEPWKLCRLHQAPTAR

GAVRFWCSLPTADTSSFVPLELRVTAASGAPRYHRVIHINEVVLLDAPVG

LVARLADESGHVVLRWLPPPETPMTSHIRYEVDVSAGNGAGSVQRVEILE

GRTECVLSNLRGRTRYTFAVRARMAEPSFGGFWSAWSEPVSLLTPSDLDP

LILTLSLILVVILVLLTVLALLSHRRALKQKIWPGIPSPESEFEGLFTTH

KGNFQLWLYQNDGCLWWSPCTPFTEDPPASLEVLSERCWGTMQAVEPGTD

DEGPLLEPVGSEHAQDTYLVLDKWLLPRNPPSEDLPGPGGSVDIVAMDEG

SEASSCSSALASKPSPEGASAASFEYTILDPSSQLLRPWTLCPELPPTPP

HLKYLYLVVSDSGISTDYSSGDSQGAQGGLSDGPYSNPYENSLIPAAEPL

PPSYVACS

>EPH-B4

SEQ ID NO. 2

MELRVLLCWASLAAALEETLLNTKLETADLKWVTFPQVDGQWEELSGLDE

EQHSVRTYEVCDVQRAPGQAHWLRTGWVPRRGAVHVYATLRFTMLECLSL

PRAGRSCKETFTVFYYESDADTATALTPAWMENPYIKVDTVAAEHLTRKR

PGAEATGKVNVKTLRLGPLSKAGFYLAFQDQGACMALLSLHLFYKKCAQL

TVNLTRFPETVPRELVVPVAGSCVVDAVPAPGPSPSLYCREDGQWAEQPV

TGCSCAPGFEAAEGNTKCRACAQGTFKPLSGEGSCQPCPANSHSNTIGSA

VCQCRVGYFRARTDPRGAPCTTPPSAPRSVVSRLNGSSLHLEWSAPLESG

TABLE 5-continued

```
GREDLTYALRCRECRPGGSCAPCGGDLTFDPGPRDLVEPWVVVRGLRPDF

TYTFEVTALNGVSSLATGPVPFEPVNVTTDREVPPAVSDIRVTRSSPSSL

SLAWAVPRAPSGAVLDYEVKYHEKGAEGPSSVRFLKTSENRAELRGLKRG

ASYLVQVRARSEAGYGPFGQEHHSQTQLDESEGWREQLALIAGTAVVGVV

LVLVVIVVAVLCLRKQSNGREAEYSDKHGQYLIGHGTKVYIDPFTYEDPN

EAVREFAKEIDVSYVKIEEVIGAGEFGEVCRGRLKAPGKKESCVAIKTLK

GGYTERQRREFLSEASIMGQFEHPNIIRLEGVVTNSMPVMILTEFMENGA

LDSFLRLNDGQFTVIQLVGMLRGIASGMRYLAEMSYVHRDLAARNILVNS

NLVCKVSDFGLSRFLEENSSDPTYTSSLGGKIPIRWTAPEAIAFRKFTSA

SDAWSYGIVMWEVMSFGERPYWDMSNQDVINAIEQDYRLPPPPDCPTSLH

QLMLDCWQKDRNARPRFPQVVSALDKMIRNPASLKIVARENGGASHPLLD

QRQPHYSAFGSVGEWLRAIKMGRYEESFAAAGFGSFELVSQISAEDLLRI

GVTLAGHQKKILASVQHMKSQAKPGTPGGTGGPAPQY

>EphrinA1
                                         SEQ ID NO. 3
MEFLWAPLLGLCCSLAAADRHTVFWNSSNPKFRNEDYTIHVQLNDYVDII

CPHYEDHSVADAAMEQYILYLVEHEEYQLCQPQSKDQVRWQCNRPSAKHG

PEKLSEKFQRFTPFTLGKEFKEGHSYYYISKPIHQHEDRCLRLKVTVSGK

ITHSPQAHDNPQEKRLAADDPEVRVLHSIGHSAAPRLFPLAWTVLLLPLL

LLQTP

>EphrinB2
                                         SEQ ID NO. 4
MAVRRDSVWKYCWGVLMVLCRTAISKSIVLEPIYWNSSNSKFLPGQGLVL

YPQIGDKLDIICPKVDSKTVGQYEYYKVYMVDKDQADRCTIKKENTPLLN

CAKPDQDIKFTIKFQEFSPNLWGLEFQKNKDYYIISTSNGSLEGLDNQEG

GVCQTRAMKILMKVGQDASSAGSTRNKDPTRRPELEAGTNGRSSTTSPFV

KPNPGSSTDGNSAGHSGNNILGSEVALFAGIASGCIIFIVIIITLVVLLL

KYRRRHRKHSPQHTTTLSLSTLATPKRSGNNNGSEPSDIIIPLRTADSVF

CPHYEKVSGDYGHPVYIVQEMPPQSPANIYYKV
```

The present disclosure includes any splice variant of the polypeptides of SEQ ID NOS 1-4 components possessing the extracellular EPO binding region (for EPH-B4 this region of proposed to encompass the two fibronectinIII domains; the oval structures adjacent to Epo in FIGS. 3B, D and F) and the intracellular signalling part, is also capable of mediating EPO's (and derivatives thereof) cyto-protective effect.

NEPOR: Prognostic Implications

The type 1 cytokine, Erythropoietin (EPO), possesses both haematopoietic and tissue protective activities. The present disclosure provides that the latter functionality is mediated via interactions of EPO with a novel EPO receptor, termed NEPOR. The model provides that binding of EPO to NEPOR receptor complexes, on NEPOR positive cancer cells, confers survival advantage to such cells. The implicit physiological outcome for patients possessing NEPOR positive cancers is therefore increased loco-regional cancer progression and poorer overall survival.

Thus, the present disclosure provides a diagnostic or prognostic test that can predict whether or not cancer patients administered EPO will respond negatively in terms of survival outcome. The prognostic test comprises determining NEPOR (i.e. EPH-B4, and/or Ephrin A1) in tumour tissue, or more particularly cancer cells. In another embodiment NEPOR component gene expression levels in tumour cells can be compared to baseline levels or levels in surrounding normal cells or tissue. Therefore, a comparative analysis looking at elevated or normal baseline expression levels of NEPOR component expression, using standard gene expression analysis methods (such as q-PCR and DNA microarray analyses) provides a diagnostic test that can determine whether or not administration of EPO to cancer patients will unwittingly enhance tumour cell survival (a negative outcome).

As stated, one method that can be used for comparing levels of gene expression of components of NEPOR and/or EPH-B4, and/or Ephrin A1 is Quantitative polymerase chain reaction (qPCR). This is a modification of PCR or polymerase chain reaction used to rapidly measure the quantity of DNA present in a tissue sample. Like other forms of polymerase chain reaction, the process is used to amplify nucleic acid samples, via the temperature-mediated enzyme DNA polymerase. PCR amplifies DNA exponentially, doubling the number of molecules present with each amplification cycle. The number of amplification cycles and the amount of PCR end-product should allow one to calculate the initial quantity of NEPOR-specific genetic material and/or EPH-B4 and/or Ephrin A1 genetic material in particular mRNA molecules using NEPOR-specific component sequences in particular and/or EPH-B4, and/or Ephrin A1 sequences for the two primers used for amplification.

In addition, gene expression analysis of NEPOR components and/or EPH-B4, and/or Ephrin A1 can be done with a microarray analysis containing a plurality of capture probes specific for sequences of the NEPOR complex in particular and/or EPH-B4, and/or Ephrin A1. As EPO is proposed to stimulate survival of NEPOR positive cancer cells and/or EPH-B4, and/or Ephrin A1 positive cells, it is important to test all cancer patients for NEPOR status and/or and/or EPH-B4, and/or Ephrin A1 status prior to and during EPO administration. This is best done with a microarray analysis for expression status of NEPOR component genes in tumour tissue and with mRNA samples taken from tumour tissue. Ascertaining the levels of endogenous tumour associated NEPOR (i.e. EPH-B4, and/or EphrinA1) expression, provide correlations as to patient prognosis/survival rate.

The present disclosure thus provides a method to stratify patients having a tumour as suitable (i.e. NEPOR not present and/or EPH-B4, and/or Ephrin A1 present) or non-suitable (i.e., NEPOR present and/or and/or EPH-B4, and/or Ephrin A1 present) for EPO treatment. The method disclosed comprises: (a) isolating a tissue sample from an individual who is receiving or shall receive erythropoietin, (b) determining the level of expression of EPH-B4 and/or Ephrin A1 from the isolated tissue, and (c) correlating the presence of these component gene expression products to a negative physiological response to the treatment with erythropoietin.

```
>erythropoietin receptor (EPOR), mRNA
                                         SEQ ID NO. 5
ACTTAGAGGCGCCTGGTCGGGAAGGGCCTGGTCAGCTGCGTCCGGCGGAG
GCAGCTGCTGACCCAGCTGTGGACTGTGCCGGGGCGGGGACGGAGGGG
CAGGAGCCCTGGGCTCCCCGTGGCGGGGCTGTATCATGGACCACCTCGG
GGCGTCCCTCTGGCCCCAGGTCGGCTCCCTTTGTCTCCTGCTCGCTGGGG
CCGCCTGGGCGCCCCCGCCTAACCTCCCGGACCCCAAGTTCGAGAGCAAA
GCGGCCTTGCTGGCGGCCCGGGGGCCCGAAGAGCTTCTGTGCTTCACCGA
```

-continued

GCGGTTGGAGGACTTGGTGTGTTTCTGGGAGGAAGCGGCGAGCGCTGGGG
TGGGCCCGGGCAACTACAGCTTCTCCTACCAGCTCGAGGATGAGCCATGG
AAGCTGTGTCGCCTGCACCAGGCTCCCACGGCTCGTGGTGCGGTGCGCTT
CTGGTGTTCGCTGCCTACAGCCGACACGTCGAGCTTCGTGCCCCTAGAGT
TGCGCGTCACAGCAGCCTCCGGCGCTCCGCGATATCACCGTGTCATCCAC
ATCAATGAAGTAGTGCTCCTAGACGCCCCCGTGGGGCTGGTGGCGCGGTT
GGCTGACGAGAGCGGCCACGTAGTGTTGCGCTGGCTCCCGCCGCCTGAGA
CACCCATGACGTCTCACATCCGCTACGAGGTGGACGTCTCGGCCGGCAAC
GGCGCAGGGAGCGTACAGAGGGTGGAGATCCTGGAGGGCCGCACCGAGTG
TGTGCTGAGCAACCTGCGGGGCCGGACGCGCTACACCTTCGCCGTCCGCG
CGCGTATGGCTGAGCCGAGCTTCGGCGGCTTCTGGAGCGCCTGGTCGGAG
CCTGTGTCGCTGCTGACGCCTAGCGACCTGGACCCCCTCATCCTGACGCT
CTCCCTCATCCTCGTGGTCATCCTGGTGCTGCTGACCGTGCTCGCGCTGC
TCTCCCACCGCCGGGCTCTGAAGCAGAAGATCTGGCCTGGCATCCCGAGC
CCAGAGAGCGAGTTTGAAGGCCTCTTCACCACCCACAAGGGTAACTTCCA
GCTGTGGCTGTACCAGAATGATGGCTGCCTGTGGTGGAGCCCCTGCACCC
CCTTCACGGAGGACCCACCTGCTTCCCTGGAAGTCCTCTCAGAGCGCTGC
TGGGGGACGATGCAGGCAGTGGAGCCGGGGACAGATGATGAGGGCCCCT
GCTGGAGCCAGTGGGCAGTGAGCATGCCCAGGATACCTATCTGGTGCTGG
ACAAATGGTTGCTGCCCCGGAACCCGCCCAGTGAGGACCTCCCAGGGCCT
GGTGGCAGTGTGGACATAGTGGCCATGGATGAAGGCTCAGAAGCATCCTC
CTGCTCATCTGCTTTGGCCTCGAAGCCCAGCCCAGAGGGAGCCTCTGCTG
CCAGCTTTGAGTACACTATCCTGGACCCCAGCTCCCAGCTCTTGCGTCCA
TGGACACTGTGCCCTGAGCTGCCCCTACCCCACCCCACCTAAAGTACCT
GTACCTTGTGGTATCTGACTCTGGCATCTCAACTGACTACAGCTCAGGGG
ACTCCCAGGGAGCCAAGGGGGCTTATCCGATGGCCCCTACTCCAACCCT
TATGAGAACAGCCTTATCCCAGCCGCTGAGCCTCTGCCCCCCAGCTATGT
GGCTTGCTCTTAGGACACCAGGCTGCAGATGATCAGGGATCCAATATGAC
TCAGAGAACCAGTGCAGACTCAAGACTTATGGAACAGGGATGGCGAGGCC
TCTCTCAGGAGCAGGGGCATTGCTGATTTTGTCTGCCCAATCCATCCTGC
TCAGGAAACCACAACCTTGCAGTATTTTTAAATATGTATAGTTTTTTG

>EPH receptor B4 (EPHB4), mRNA

SEQ ID NO. 6

TTCCAGCGCAGCTCAGCCCCTGCCCGGCCCGGCCCGCCCGGCTCCGCGCC
GCAGTCTCCCTCCCTCCCGCTCCGTCCCCGCTCGGGCTCCCACCATCCCC
GCCCGCGAGGAGAGCACTCGGCCCGGCGGCGCGAGCAGAGCCACTCCAGG
GAGGGGGGAGACCGCGAGCGGCCGGCTCAGCCCCCGCCACCCGGGGCGG
GACCCCGAGGCCCCGGAGGGGACCCCAACTCCAGCCACGTCTTGCTGCGCG
CCCGCCCGGCCGCGGCCACTGCCAGCACGCTCCGGGCCCGCCGCCCGCG
CGCGGCACAGACGCGGGGCCACACTTGGCGCCGCCGCCCGGTGCCCCGCA
CGCTCGCATGGGCCCGCGCTGAGGGCCCCGACGAGGAGTCCCGCGCGGAG
TATCGGCGTCCACCCGCCCAGGGAGAGTCAGACCTGGGGGGGCGAGGGCC
CCCCAAACTCAGTTCGGATCCTACCCGAGTGAGGCGGCGCCATGGAGCTC
CGGGTGCTGCTCTGCTGGGCTTCGTTGGCCGCAGCTTTGGAAGAGACCCT
GCTGAACACAAAATTGGAAACTGCTGATCGAAGTGGGTGACATTCCCTC
AGGTGGACGGCAGTGGGAGGAACTGAGCGGCCTGGATGAGGAACAGCAC
AGCGTGCGCACCTACGAAGTGTGACGTGCAGCGTGCCCGGGCCAGGC
CCACTGGCTTCGCACAGGTTGGGTCCCACGGCGGGGCGCCGTCCACGTGT
ACGCCACGCTGCGCTTCACCATGCTCGAGTGCCTGTCCCTGCCTCGGGCT
GGGCGCTCCTGCAAGGAGACCTTCACCGTCTTCTACTATGAGAGCGATGC
GGACACGGCCACGGCCCTCACGCCAGCCTGGATGGAGAACCCCTACATCA
AGGTGGACACGGTGGCCGCGGAGCATCTCACCCGGAAGCGCCCTGGGGCC
GAGGCCACCGGGAAGGTGAATGTCAAGACGCTGCGTCTGGGACCGCTCAG
CAAGGCTGGCTTCTACCTGGCCTTCCAGGACCAGGGTGCCTGCATGGCCC
TGCTATCCCTGCACCTCTTCTACAAAAAGTGCCCCAGCTGACTGTGAAC
CTGACTCGATTCCCGGAGACTGTGCCTCGGGAGCTGGTTGTGCCCGTGGC
CGGTAGCTGCGTGGTGGATGCCGTCCCCGCCCCTGGCCCCAGCCCCAGCC
TCTACTGCCGTGAGGATGGCCAGTGGGCCGAACAGCCGGTCACGGGCTGC
AGCTGTGCTCCGGGGTTCGAGGCAGCTGAGGGGAACACCAAGTGCCGAGC
CTGTGCCCAGGGCACCTTCAAGCCCCTGTCAGGAGAGGGTCCTGCCAGC
CATGCCCAGCCAATAGCCACTCTAACACCATTGGATCAGCCGTCTGCCAG
TGCCGCGTCGGGTACTTCCGGGCACGCACAGACCCCCGGGGTGCACCCTG
CACCACCCCTCCTTCGGCTCCGCGGAGCGTGGTTTCCCGCCTGAACCGGT
CCTCCCTGCACCTGGAATGGAGTGCCCCCCTGGAGTCTGGTGGCCGAGAT
GACCTCACCTACGCCCTCCGCTGCCGGGAGTGCCGACCCGGAGGCTCCTG
TGCGCCCTGCGGGGAGACCTGACTTTTGACCCCGGCCCCCGGGACCTGG
TGGAGCCCTGGGTGGTTGTTGAGGGCTACGTCTTGGCTGACTTCACCTATCC
TTTGAGGTCACTGCATTGAACGGGTATCCTCCTTAGCCACGGGGCCCGT
CCCATTTGAGCCTGTCAATGTCACCACTGACCGAGAGGTACCTCCTGCAG
TGTCTGACATCCGGGTGACGCGGTCCTCACCCAGCAGCTTGAGCCTGGCC
TGGGCTGTTCCCCAGGCGACCCAGTGGGGCTGTGCTGGACTACGAGGTCAA
ATACCATGAGAAGGGCGCCGAGGGTCCCAGCAGCGTGCGGTTCCTGAAGA
CGTCAGAAAACCGGGCAGAGCTGCGGGGCTGAAGCGGGGAGCCAGCTAC
CTGGTGCAGGTACGGGCGCGCTCTGAGGCCGGCTACGGGCCCTTCGGCCA
GGAACATCACAGACCCAACTGGATGAGGACGGAGGCTGGCGGGCG
AGCTGGCCCTGATTCGGGCACGGCAGTCGTGGGTGTGGTCCTGGTCCTG
GTGGTCATTGTGGTCGCAGTTCTCTGCCTCAGGAAGCAGAGCAATGGGAG
AGAAGCAGAATATTCGGACAAACACGGACAGTATCTCATCGGACATGGTA
CTAAGGTCTACATCGACCCCTTCACTTATGAAGACCCTAATGAGGCTGTG
AGGGAATTTGCAAAAGAGATCGATGTCTCCACGTCAAGATTGAAGAGGT

-continued

GATTGGTGCAGGTGAGTTTGGCGAGGTGTGCCGGGGCGGCTCAAGGCCC
CAGGGAAGAAGGAGAGCTGTGTGGCAATCAAGACCCTGAAGGGTGGCTAC
ACGGAGCGGCAGCGGCGTGAGTTTCTGAGCGAGGCCTCCATCATGGGCCA
GTTCGAGCACCCCAATATCATCCGCCTGGAGGGCGTGGTCACCAACAGCA
TGCCCGTCATGATTCTCACAGAGTTCATGGAGAACGGCGCCCTGGACTCC
TTCCTGCGGCTAAACGACGGACAGTTCACAGTCATCCAGCTCGTGGGCAT
GCTGCGGGGCATCGCCTCGGGCATGCGGTACCTTGCCGAGATGAGCTACG
TCCACCGAGACCTGGCTGCTCGCAACATCCTAGTCAACAGCAACCTCGTC
TGCAAAGTGTCTGACTTTGGCCTTTCCCGATTCCTGGAGGAGAACTCTTC
CGATCCCACCTACACGAGCTCCCTGGGAGGAAAGATTCCCATCCGATGGA
CTGCCCCGGAGGCCATTGCCTTCCGGAAGTTCACTTCCGCCAGTGATGCC
TGGAGTTACGGGATTGTGATGTGGGAGGTGATGTCATTTGGGGAGAGGCC
GTACTGGGACATGAGCAATCAGGACGTGATCAATGCCATTGAACAGGACT
ACCGGCTGCCCCCGCCCCCAGACTGTCCCACCTCCCTCCACCAGCTCATG
CTGGACTGTTGGCAGAAAGACCGGAATGCCCGGCCCCGCTTCCCCCAGGT
GGTCAGCGCCCTGGACAAGATGATCCGGAACCCCGCCAGCCTCAAAATCG
TGGCCCGGGAGAATGGCGGGCCTCACACCCTCTCCTGGACCAGCGGCAG
CCTCACTACTCAGCTTTTGCTCTGTGGGCGAGTGGCTTCGGGCCATCAA
AATGGGAAGATACGAAGAAAGTTTCGCACGCGCTGGCTTTGGCTCCTTCG
AGCTGGTCAGCCAGATCTCTGCTGAGGACCTGCTCCGAATCGGAGTCACT
CTGGCGGGACACCAGAAGAAAATCTTGGCCAGTGTCCAGCACATGAAGTC
CCAGGCCAGCCGGGAACCCCGGGTGGGACAGGAGGACCGGCCCCGCAGT
ACTGACCTGCAGGAACTCCCCACCCCAGGGACACCGCCTCCCCATTTTCC
GGGGCAGAGTGGGGACTCACAGAGGCCCCCAGCCCTGTGCCCGCTGGAT
TGCACTTTGAGCCCGTGGGGTGAGGAGTTGGCAATTTGGAGAGACAGGAT
TTGGGGGTTCTGCCATAATAGGAGGGGAAAATCACCCCCAGCCACCTCG
GGGAACTCCAGACCAAGGGTGAGGGCGCCTTTCCCTCAGGACTGGGTGTG
ACCAGAGGAAAGGAAGTGCCCAACATCTCCCAGCCTCCCCAGGTGCCCC
CCTCACCTTGATGGGTGCGTTCCCGCAGACCAAAGAGAGTGTGACTCCCT
TGCCAGCTCCAGAGTGGGGGGGCTGTCCCAGGGGGCAAGAAGGGGTGTCA
GGGCCCAGTGACAAAATCATTGGGGTTTGTAGTCCCAACTTGCTGCTGTC
ACCACCAAACTCAATCATTTTTTTCCCTTGTAAATGCCCCTCCCCCAGCT
GCTGCCTTCATATTGAAGGTTTTTGAGTTTTGTTTTTGGTCTTAATTTTT
CTCCCCGTTCCCTTTTTGTTTCTTCGTTTTGTTTTTCTACCGTCCTTGTC
ATAACTTTTGTTGGAGGGAACCTGTTTCACTATGGCCTCCTTTGCCCAA
GTTGAAACAGGGGCCCATCATCATGTCTGTTTCCAGAACAGTGCCTTGGT
CATCCCACATCCCCGGACCCCGCCTGGGACCCCAAGCTGTGTCCTATGA
AGGGGTGTGGGGTGAGGTAGTGAAAAGGCGGTAGTTGGTGGTGGAACCC
AGAAACGGACGCCGGTGCTTGGAGGGGTTCTTAAATTATATTTAAAAAAG
TAACTTTTTGTATAAATAAAAGAAAATGGGACGTGTCCCAGCTCCAGGGG
TAAAAAAAAAAAAAAAAAA

>Ephrin-A1 (EFNA1) mRNA

SEQ ID NO. 7

GCCAGATCTGTGAGCCCAGCGCTGACTGCGCCGCGGGAGAAAGCCAGTGGG
AACCCAGACCCATAGGAGACCCGCGTCCCCGCTCGGCCTGGCCAGGCCCC
GCGCTATGGAGTTCCTCTGGGCCCCTCTCTTGGGTCTGTGCTGCAGTCTG
GCCGCTGCTGATCGCCACACCGTCTTCTGGAACAGTTCAAATCCCAAGTT
CCGGAATGAGGACTACACCATACATGTGCAGCTGAATGACTACGTGGACA
TCATCTGTCCGCACTATGAAGATCACTCTGTGGCAGACGCTGCCATGGAG
CAGTACATACTGTACCTGGTGGAGCATGAGGAGTACCAGCTGTGCCAAGC
CCAGTCCAAGGACCAAGTCCGCTGGCAGTGCAACCGGCCCAGTGCCAAGC
ATGGCCCGAGAAGCTGTCTGAGAAGTTCCAGCGCTTCACACCTTTCACC
CTGGGCAAGGAGTTCAAAGAAGGACACAGCTACTACTACATCTCCAAACC
CATCCACCAGCATGAAGACCGCTGCTTGAGGTTGAAGGTGACTGTCAGTG
GCAAATCACTCACAGTCCTCAGGCCCATGACAATCACAGGAGAAGAGA
CTTGCAGCAGATGACCCAGAGGTGCGGGTTCTACATAGCATCGGTCACAG
TGCTGCCCCACGCCTCTTCCCACTTGCCTGGACTGTGCTGCTCCTTCCAC
TTCTGCTGCTGAAACCCGTGGATGTATGCCACACCTGGCCTTAAAG
AGGGACAGGCTGAAGAGAGGGACAGGCACTCCAAACCTGTCTTGGGGAA
CTTTCAGAGCCCCAGCCCTGGGAACCACTCCCACCACAGGCATAAGCTA
TCACCTAGCAGCCTCAAAACGGGTCAGTATTAAGGTTTTCAACCGGAAGG
AGGCCAACCAGCCCGACAGTGCCATCCCCACCTTCACCTCGGAGGGATGG
AGAAAGAAGTGGAGACAGTCCTTTTCCCACCATTCCTGCCTTTAAGCCAAA
GAAACAAGCTGTGCAGGCATGGTCCCTTAAGGCACAGTGGGAGCTGAGCT
GGAAGGGGCCACGTGGATGGGCAAAGCTTGTCAAAGATGCCCCTCCAGG
AGAGAGCCAGGATGCCCAGATGAACTGACTGAAGGAAAAGCAAGAAACAG
TTTCTTGCTTGGAACCCAGGTACAGGAAGAGGCAGCATGCTTGGGCTGACC
CAGCATCTCCCAGCAAGACCTCATCTGTGAGCTGCCACAGAGAAGTTTG
TAGCCAGGTACTGCATTCTCTCCCATCCTGGGGCAGCATCTCCCAGAGCT
GTGCCAGCAGGGGGCTGTGCCAACCTGTTCTTAGAGTGTAGCTGTAAGG
GCAGTGCCCATGTGTGCATTCTGCCTAGAGTGTAGCCTAAAGGGCAGGG
CCACGTGTATAGTATCTGTATATAAGTTGCTGTGTGTCTGTCCTGATTTC
TACAACTGGAGTTTTTTATACAATGTTCTTTGTCTCAAATATAAAGCAAT
GTGTTTTTCGGACATGCTTTTCTGCCACTCCATATTAAAACATATGACC
ATTGAGTCCCTGCTAAAAAAAAAAAAAAAAAAAAAAA

>ephrin-B2 (EFNB2), mRNA

SEQ ID NO. 8

GCGCGGAGCTGGGAGTGGCTTCGCCATGGCTGTGAGAAGGGACTCCGTGT
GGAAGTACTGCTGGGGTGTTTTGATGGTTTTATGCAGAACTGCGATTTCC

```
-continued
AAATCGATAGTTTTAGAGCCTATCTATTGGAATTCCTCGAACTCCAAATT
TCTACCTGGACAAGGACTGGTACTATACCCACAGATAGGAGACAAATTGG
ATATTATTTGCCCCAAAGTGGACTCTAAAACTGTTGGCCAGTATGAATAT
TATAAAGTTTATATGGTTGATAAAGACCAAGCAGACAGATGCACTATTAA
GAAGGAAAATACCCCTCTCCTCAACTGTGCCAAACCAGACCAAGATATCA
AATTCACCATCAAGTTTCAAGAATTCAGCCCTAACCTCTGGGGTCTAGAA
TTTCAGAAGAACAAAGATTATTACATTATATCTACATCAATGGGTCTTT
GGAGGGCCTGGATAACCAGGAGGGAGGGGTGTGCCAGACAAGAGCCATGA
AGATCCTCATGAAAGTTGGACAAGATGCAAGTTCTGCTGGATCAACCAGG
AATAAAGATCCAACAAGACGTCCAGAACTAGAAGCTGGTACAAATGGAAG
AAGTTCGACAACAAGTCCCTTTGTAAAACCAAATCCAGGTTCTAGCACAG
ACGGCAACAGCGCCGGACATTCGGGGAACAACATCCTCGGTTCCGAAGTG
GCCTTATTTGCAGGGATTGCTTCAGGATGCATCATCTTCATCGTCATCAT
CATCACGCTGGTGGTCCTCTTGCTGAAGTACCGGAGGAGACACAGGAAGC
ACTCGCCGCAGCACACGACCACGCTGTCGCTCAGCACACTGGCCACACCC
AAGCGCAGCGGCAACAACAACGGCTCAGAGCCCAGTGACATTATCATCCG
GCTAAGGACTGCGGACAGCGTCTTCTGCCCTCACTACGAGAAGGTCAGCG
GGGACTACGGGCACCCGGTGTACATCGTCCAGGAGATGCCCCCGCAGAGC
CCGGCGAACATTTACTACAAGGTCTGAGAGGGACCCTGGTGGTACCTGTG
CTTTCCCAGAGGACACCTAATGTCCCGATGCCTCCCTTGAGGGTTTGAGA
GCCCGCGTGCTGGAGAATTGACTGAAGCACAGCACCGGGGGAGAGGGACA
CTCCTCCTCGGAAGAGCCCGTCGCGCTGGACAGCTTACCTAGTCTTGTAG
CATTCGGCCTTGGTGAACACACACGCTCCCTGGAAGCTGGAAGACTGTGC
AGAAGCAGCCCATTCGGACTGCTGTGCCGCGTCCCACGTCTCCTCCTCGA
AGCCATGTGCTGCGGTCACTCAGGCCTCTGCAGAAGCCAAGGGAAGACAG
TGGTTTGTGCAGCAGAGGGCTGTGAGCATCCTGGCAGGTGCCCCAGGATG
CCACGCCTGGAAGGGCCGGCTTCTGCCTGGGGTGCATTTCCCCCGCAGTG
CATACCGGACTTGTCACACGGACCTCGGGCTAGTTAAGGTGTGCAAAGAT
CTCTAGAGTTTAGTCCTTACTGTCTCACTCGTTCTGTTACCCAGGGCTCT
GCAGCACCTCACCTGAGACCTCCACTCCACATCTGCATCACTCATGGAAC
ACTCATGTCTGGAGTCCCCTCCTCCAGCCGCTGGCAACAACAGCTTCAGT
CCATGGGTAATCCGTTCATAGAAATTGTGTTTGCTAACAAGGTGCCCTTT
AGCCAGATGCTAGGCTGTCTGCGAAGAAGGCTAGGAGTTCATAGAAGGGA
GTGGGGCTGGGGAAAGGGCTGGCTGCAATTGCAGCTCACTGCTGCTGCCT
CTGAAACAGAAAGTTGGAAAGGAAAAAAGAAAAAAGCAATTAGGTAGCAC
AGCACTTTGGTTTTGCTGAGATCGAAGAGGCCAGTAGGAGACACGACAGC
ACACACAGTGGATTCCAGTGCATGGGGAGGCACTCGCTGTTATCAAATAG
CGATGTGCAGGAAGAAAAGCCCCTCTTCATTCCGGGGAACAAAGACGGGT
ATTGTTGGGAAAGGAACAGGCTTGGAGGGAAAGGGAGAAAGTAGGCCGCTG
ATGATATATTCGGGCAGGACTGTTGTGGTACTGGCAATAAGATACACAGC
TCCGAGCTGTAGGAGAGTCGGTCTGCTTTGGATGATTTTTAAGCAGACT
CAGCTGCTATACTTATCACATTTTATTAAACACAGGGAAAGCATTTAGGA
GAATAGCAGAGAGCCAAATCTGACCTAAAAGTTGAAAAGCCAAAGGTCAA
ACAGGCTGTAATTCCATCATCATCGTTGTTATTAAAGAATCCTTATCTAT
AAAAGGTAGGTCAGATCCCCCTCCCCCCAGGTTCCTCCTTCCCCTCCCGA
TTGAGCCTTACGACACTTTGGTTTATGCGGTGCTGTCCGGGTGCCAGGGC
TGCAGGGTCGGTACTGATGGAGGCTGCAGCGCCCGGTGCTCTGTGTCAAG
GTGAAGCACATACGGCAGACCTCTTAGAGTCCTTAAGACGGAAGTAAATT
ATGATGTCCAGGGGAGAAGGAAGATAGGACGTATTTATAATAGGTATAT
AGAACACAAGGGATATAAAATGAAAGATTTTTACTAATATATATTTTAAG
GTTGCACACAGTACACACCAGAAGATGTGAAATTCATTTGTGGCAATTAA
GTGGTCCCAATGCTCAGCGCTTAAAAAAACAAATTGGACAGCTACTTCTG
GGAAAAACAACATCATTCCAAAAGAACAATAATGAGAGCAAATGCAAAA
ATAACCAAGTCCTCCGAAGGCATCTCACGGAACCGTAGACTAGGAAGTAC
GAGCCCCACAGACAGGAAGCCGATGTGACTGCATCATATATTTAACAAT
GACAAGATGTTCCGGCGTTTATTTCTGCGTTGGGTTTTCCCTTGCCTTAT
GGGCTGAAGTGTTCTCTAGAATCCAGCAGGTCACACTGGGGGCTTCAGGT
GACGATTTAGCTGTGGCTCCCTCCTCCTGTCCTCCCCCGCACCCCTCCC
TTCTGGGAAACAAGAAGAGTAAACAGGAAACCTACTTTTTATGTGCTATG
CAAAATAGACATCTTTAACATAGTCCTGTTACTATGGTAACACTTTGCTT
TCTGAATTGGAAGGGAAAAAAAATGTAGCGACAGCATTTTAAGGTTCTCA
GACCTCCAGTGAGTACCTGCAAAAATGAGTTGTCACAGAAATTATGATCC
TCTATTTCCTGAACCTGGAAATGATGTTGGTCCAAAGTGCGTGTGTGTAT
GTGTGAGTGGGTGCGTGGTATACATGTGTACATATATGTATAATATATAT
CTACAATATATATTATATATCTATATCATATTTCTGTGGAGGGTTGCC
ATGGTAACCAGCCACAGTACATATGTAATTCTTTCCATCACCCCAACCTC
TCCTTTCTGTGCATTCATGCAAGAGTTTCTTGTAAGCCATCAGAAGTTAC
TTTTAGGATGGGGGAGAGGGGCGAGAAGGGGAAAAATGGGAAATAGTCTG
ATTTTAATGAAATCAAATGTATGTATCATCAGTTGGCTACGTTTTGGTTC
TATGCTAAACTGTGAAAAATCAGATGAATTGATAAAAGAGTTCCCTGCAA
CCAATTGAAAAGTGTTCTGTCGTCTGTTTTGTGTCTGGTGCAGAATATG
ACAATCTACCAACTGTCCCTTTGTTTGAAGTTGGTTTAGCTTTGGAAAGT
TACTGTAAATGCCTTGCTTGTATGATCGTCCCTGGTCACCCGACTTTGGA
ATTTGCACCATCATGTTTCAGTGAAGATGCTGTAAATAGGTTCAGATTTT
ACTGTCTATGGATTTGGGGTGTTACAGTAGCCTTATTCACCTTTTTAATA
AAAATACACATGAAAACAAGAAAAAATGGCTTTTCTTACCCAGATTGTG
TACATAGAGCAATGTTGGTTTTTTATAAAGTCTAAGCAAGATGTTTTGTA
TAAAATCTGAATTTTGCAATGTATTTAGCTACAGCTTGTTTAACGGCAGT
GTCATTCCCCTTTGCACTGTAATGAGGAAAAAATGGTATAAAAGGTTGCC
AAATTGCTGCATATTTGTGCCGTAATTATGTACCATGAATATTTATTTAA
AATTTCGTTGTCCAATTTGTAAGTAACACAGTATTATGCCTGAGTTATAA
```

```
-continued
ATATTTTTTTCTTTCTTTGTTTTATTTTAATAGCCTGTCATAGGTTTTAA
ATCTGCTTTAGTTTCACATTGCAGTTAGCCCCAGAAAATGAAATCCGTGA
AGTCACATTCCACATCTGTTTCAAACTGAATTTGTTCTTAAAAAAATAAA
ATATTTTTTTCCTATGGAAAAAAAAAAAAAAAAAA
```

Detection of NEPOR component mRNA (SEQ ID NOs 5-8) should preferentially be performed using probes complementary to the sub-region of SEQ ID NO's 5-8, encoding the EPO binding domain and is particular SEQ Id NO. 6 and/or 7 encoding EPH-B4 and Ephrin A1. This implies for EPH-B4, probes complementary to SEQ ID NO. 10.; for Ephrin A1, probes complementary to SEQ ID NO. 11.

>epor_epobinding coding region
SEQ ID NO. 9
```
AGCAAAGCGGCCTTGCTGGCGGCCCGGGGGCCCGAAGAGCTTCTGTGCTT
CACCGAGCGGTTGGAGGACTTGGTGTGTTTCTGGGAGGAAGCGGCGAGCG
CTGGGGTGGGCCCGGGCAACTACAGCTTCTCCTACCAGCTCGAGGATGAG
CCATGGAAGCTGTGTCGCCTGCACCAGGCTCCCACGGCTCGTGGTGCGGT
GCGCTTCTGGTGTTCGCTGCCTACAGCCGACACGTCGAGCTTCGTGCCCC
TAGAGTTGCGCGTCACAGCAGCCTCCGGCGCTCCGCGATATCACCGTGTC
ATCCACATCAATGAAGTAGTGCTCCTAGACGCCCCCGTGGGGCTGGTGGC
GCGGTTGGCTGACGAGAGCGGCCACGTAGTGTTGCGCTGGCTCCCGCCGC
CTGAGACACCCATGACGTCTCACATCCGCTACGAGGTGGACGTCTCGGCC
GGCAACGGCGCAGGGAGCGTACAGAGGGTGGAGATCCTGGAGGGCCGCAC
CGAGTGTGTGCTGAGCAACCTGCGGGGCCGGACGCGCTACACCTTCGCCG
TCCGCGCGCGTATGGCTGAGCCGAGCTTCGGCGGCTTCTGGAGCGCCTGG
TCGGAGCCTGTGTCGCTGCTGACGCCTAGCGACCTGGACCCC
```

>ephb4_epobinding coding region
SEQ ID NO. 10
```
CCTTCGGCTCCGCGGAGCGTGGTTTCCCGCCTGAACGGCTCCTCCCTGCA
CCTGGAATGGAGTGCCCCCCTGGAGTCTGGTGGCCGAGAGGACCTCACCT
ACGCCCTCCGCTGCCGGGAGTGCCGACCCGGAGGCTCCTGTGCGCCCTGC
GGGGGAGACCTGACTTTTGACCCCGGCCCCCGGGACCTGGTGGAGCCCTG
GGTGGTGGTTCGAGGGCTACGTCCTGACTTCACCTATACCTTTGAGGTCA
CTGCATTGAACGGGGTATCCTCCTTAGCCACGGGGCCCGTCCCATTTGAG
CCTGTCAATGTCACCACTGACCGAGAGGTACCTCCTGCAGTGTCTGACAT
CCGGGTGACGCGGTCCTCACCCAGCAGCTTGAGCCTGGCCTGGGCTGTTC
CCCGGGCACCCAGTGGGGCTGTGCTGGACTACGAGGTCAAATACCATGAG
AAGGGCGCCGAGGGTCCCAGCAGCGTGCGGTTCCTGAAGACGTCAGAAAA
CCGGGCAGAGCTGCGGGGCTGAAGCGGGGAGCCAGCTACCTGGTGCAGG
TACGGGCGCGCTCTGAGGCCGGCTACGGGCCCTTCGGCCAGGAACATCAC
AGCCAGACCCAACTGGATGAGAGCGAGGGCTGGCGGGAGCAGCTGGCCC
TG
```

>ephrinA1_epobinding coding region
SEQ ID NO. 11
```
CTGGCCGCTGCTGATCGCCACACCGTCTTCTGGAACAGTTCAAATCCCAA
GTTCCGGAATGAGGACTACACCATACATGTGCAGCTGAATGACTACGTGG
ACATCATCTGTCCGCACTATGAAGATCACTCTGTGGCAGACGCTGCCATG
GAGCAGTACATACTGTACCTGGTGGAGCATGAGGAGTACCAGCTGTGCCA
GCCCCAGTCCAAGGACCAAGTCCGCTGGCAGTGCAACCGGCCCAGTGCCA
AGCATGGCCCGGAGAAGCTGTCTGAGAAGTTCCAGCGCTTCACACCTTTC
ACCCTGGGCAAGGAGTTCAAAGAAGGACACAGCTACTACTACATCTCCAA
ACCCATCCACCAGCATGAAGACCGCTGCTTGAGGTTGAAGGTGACTGTCA
GTGGCAAAATCACTCAC
```

>ephrinb2_epobinding coding region
SEQ ID NO. 12
```
TCCAAATCGATAGTTTTAGAGCCTATCTATTGGAATTCCTCGAACTCCAA
ATTTCTACCTGGACAAGGACTGGTACTATACCCACAGATAGGAGACAAAT
TGGATATTATTTGCCCCAAAGTGGACTCTAAAACTGTTGGCCAGTATGAA
TATTATAAAGTTTATATGGTTGATAAAGACCAAGCAGACAGATGCACTAT
TAAGAAGGAAAATACCCCTCTCCTCAACTGTGCCAAACCAGACCAAGATA
TCAAATTCACCATCAAGTTTCAAGAATTCAGCCCTAACCTCTGGGGTCTA
GAATTTCAGAAGAACAAAGATTATTACATTATATCTACATCAAATGGGTC
TTTGGAGGGCCTGGATAACCAGGAGGGAGGGGTGTGCCAGACAAGAGCCA
TGAAGATCCTCATGAAAGTTGGACAA
```

The determination of the presence of the Ephrin A1 and/or the determination of the presence of the EPH-B4 gene product (mRNA) may be done by using a hybridization technique or an amplification technique. It is preferred that the technique is selected from the group of real-time-PCR, northern-blot analysis, reverse transcription and amplification, zymography, ligase-chain-reaction, NASBA, RNase Protection Assay (RPA), capillary electrophoresis with laser induced fluorescence (CE-LIF) and combinations thereof.

Specifically, the individual is a cancer patient who is to be treated with erythropoietin or is being treated with erythropoietin. Preferably, the negative physiological effect is poorer patient survival due to enhanced tumor progression. Preferably, the presence of a higher level of NEPOR component genes (mRNA) and/or the presence of NEPOR component gene expression products (proteins) and/or EPH-B4 and/or Ephrin A1 on tumor tissues is indicative of poorer survival prognosis upon treatment with erythropoietin.

Preferably, the determination of the presence of the NEPOR dimer complex is done by detecting the respective NEPOR proteins with an immunoassay. Also peptides thereof may be detected. The immunoassay is selected from the group of immunoprecipitation, a protein array or binding to a mass microbalance instrument (for example, Q-Sense or Attana), enzyme immunoassay (EIA), radioimmunoassay (RIA) or fluorescent immunoassay, a chemiluminescent assay, an agglutination assay, nephelometric assay, turbidimetric assay, a Western blot, a competitive immunoassay, a noncompetitive immunoassay, a homogeneous immunoassay a heterogeneous immunoassay, a bioassay and a reporter-assay such as a luciferase-assay. Preferably, the immunoassay is an ELISA. Preferably, the anti-NEPOR antibody and/or EPH-B4 and/or Ephrin A1 antibody is a monoclonal or polyclonal antibody, for example selected from—or similar to—the antibodies listed in Table 6.

Preferably, detection of NEPOR component proteins should preferentially be performed using antibodies detecting the sub-regions of SEQ ID NOs 6 and 7, representing the EPO binding domain. This implies for EPH-B4, antibodies specific to SEQ ID NO. 14.; for Ephrin A1, antibodies specific to SEQ ID NO. 15.

```
>epor_epobinding_region
                                          SEQ ID NO. 13
SKAALLAARGPEELLCFTERLEDLVCFWEEAASAGVGPGNYSFSYQLEDE
PWKLCRLHQAPTARGAVRFWCSLPTADTSSFVPLELRVTAASGAPRYHRV
IHINEVVLLDAPVGLVARLADESGHVVLRWLPPPETPMTSHIRYEVDVSA
GNGAGSVQRVEILEGRTECVLSNLRGRTRYTFAVRARMAEPSFGGFWSAW
SEPVSLLTPSDLDP >ephb4_epobinding_region
                                          SEQ ID NO. 14
PSAPRSVVSRLNGSSLHLEWSAPLESGGREDLTYALRCRECRPGGSCAPC
GGDLTFDPGPRDLVEPWVVVRGLRPDFTYTFEVTALNGVSSLATGPVPFE
PVNVTTDREVPPAVSDIRVTRSSPSSLSLAWAVPRAPSGAVLDYEVKYHE
KGAEGPSSVRFLKTSENRAELRGLKRGASYLVQVRARSEAGYGPFGQEHH
SQTQLDESEGWREQLAL >ephrinA1_epobinding_region
                                          SEQ ID NO. 15
LAAADRHTVFWNSSNPKFRNEDYTIHVQLNDYVDIICPHYEDHSVADAAM
EQYILYLVEHEEYQLCQPQSKDQVRWQCNRPSAKHGPEKLSEKFQRFTPF
TLGKEFKEGHSYYYISKPIHQHEDRCLRLKVTVSGKITH >ephrinb2_epobinding_region
                                          SEQ ID NO. 16
SKSIVLEPIYWNSSNSKFLPGQGLVLYPQIGDKLDIICPKVDSKTVGQYE
YYKVYMVDKDQADRCTIKKENTPLLNCAKPDQDIKFTIKFQEFSPNLWGL
EFQKNKDYYIISTSNGSLEGLDNQEGGVCQTRAMKILMKVGQ
```

Preferably, the individual is a cancer patient who is to be treated with erythropoietin or is being treated with erythropoietin. The tissue sample may be selected from the group of biological tissues and fluids such as blood, lymph, urine, cerebral fluid. The tissue sample may also be a tumor biopsy sample. It is preferred that the tissue sample is from the cancer tissue or circulating cells derived from same.

It is preferred that the cancer of the cancer patient is selected from the group of, head and neck cancer, breast cancer, liver cancer, colorectal cancer, small intestine cancer, leukemia, prostate cancer, lung cancer, ovarian cancer, pancreatic cancer, endometrial cancer, stomach cancer, non-Hodgkin lymphoma, kidney cancer, Renal cell carcinoma (RCC), malignant melanoma, gallbladder cancer, bladder cancer, vulvar cancer, Penile cancer, testicular cancer, thymus cancer, Kaposi's sarcoma, eye cancer, adrenal gland cancer, brain cancer, cervical cancer, appendix cancer, adenoid cancer, bile duct cancer, urethral cancer, spinal cancer, Ewing's family of tumors, extragonal germ cell cancer, extra hepatic bile duct cancer, fallopian tube cancer, soft tissue cancers, bone cancer, Hodgkin's lymphoma, anal cancer, malignant mesothelioma, vaginal cancer skin cancer, central nervous system cancer (craniopharyngioma), pleuropulmonary blastoma, nasal cavity and paranasal sinus cancer transitional cell cancer of renal pelvis and ureter, pituitary gland cancer, sqamous cell carcinoma of the head and neck (HNSCC), prostate cancer, colorectal cancer, lung cancer, brain cancer, bladder cancer, and salivary gland cancer. It is particularly preferred that the cancer is selected from the group of squamous cell carcinoma of the head and neck (HNSCC), prostate cancer, colorectal cancer, lung cancer, kidney cancer, brain cancer and bladder cancer.

NEPOR and Disease Intervention and Therapy Design/Screening.

Without being bound by theory, NEPOR is proposed to mediate the cyto-protective effects of EPO and its variants. Thus, EPO and variants that have been shown to possess cyto-protective (but not haematopoietic) activity can affect NEPOR function. Therefore, the present disclosure provides knowledge of NEPOR's composition that can be used to optimize the structure and efficacy of such therapeutic molecules (that is, better manage the structure-activity relationship or SAR of the EPO pharmacophore). Moreover, the present disclosure provides knowledge of NEPOR's composition that can be used to identify novel NEPOR regulating compounds. For example, in diseases associated with hypoxic conditions (e.g., stroke, heart attack), NEPOR binding compounds of enhanced efficacy can be developed to mimic the effects of EPO on NEPOR. Similarly, NEPOR specific antagonists (such as those molecules that bind the active site of NEPOR yet do not transducer signal are antagonists of EPO function. Such EPO antagonist agents, when concomitantly administered with EPO, can allow for EPO effects to improve haematopoiesis (that is, treat the anaemia) yet prevent the side effect of promoting tumour cell growth, survival and angiogenesis in NEPOR positive cancers such as HNSCC. Moreover, contrasting the relative activity of compounds to the tissue protective NEPOR receptor complex in comparison to the EPOR receptor homodimer provides for generating NEPOR specific/directed therapies.

Definition of NEPOR provides methods for identifying therapeutic molecules that modulate NEPOR's tissue protective signalling activity. This comprises: (a) contacting a test compound with the NEPOR receptor complex and/or EPH-B4 and/or Ephrin A1 and an EPOR homodimer complex; (b) measuring and comparing the level of tissue protective activity initiated by NEPOR activation with the activation of EPOR homodimer signalling; (c) identifying a test compound which increases or decreases the level of tissue protective NEPOR complex activity as compared to the level of EPOR complex activation; and (d) assaying the identified therapeutics for tissue protective activity mediated via NEPOR, but lack of EPOR activation and (e) assaying the identified therapeutics for NEPOR inhibitory activity. The method is useful for identifying therapeutics that modulates the interaction between a tissue protective NEPOR complex and/or EPH-B4 and/or Ephrin A1 and the EPO ligand. The method is furthermore useful for identifying therapies for treating diseases of the central nervous system or peripheral nervous system which have primarily neurological or psychiatric symptoms, ophthalmic diseases, cardiovascular diseases, cardiopulmonary diseases, respiratory diseases, kidney, urinary and reproductive diseases, bone diseases, skin diseases, gastrointestinal diseases and endocrine and metabolic abnormalities and cancer.

More specifically, identification of NEPOR provides a method identifying (I1) a compound that modulates the tissue protective activity of NEPOR, comprising:

(a) contacting a test compound with a tissue protective NEPOR receptor complex (N) and/or EPH-B4 and/or Ephrin A1 or tissue protective cytokine receptor complex-expressing cell; measuring the level of the activity of (N) in the cell; identifying a test compound that increases or decreases the level of activity of (N) as compared to the level of activity of (N) measured in the absence of the test compound; and assaying the identified test compound for tissue protective activity;

(b) contacting a test compound with a cell that is recombinantly engineered to express (N), where the cell or the recombinant cell is transformed with a nucleic acid comprising a nucleotide sequence that is functionally linked to a promoter and encodes EPH-B4 and/or Ephrin A1 polypeptides; measuring the level of activity of (N) in the cell; and (c) contacting a test compound with a tissue protective NEPOR receptor complex-expressing cell, where the cell is transformed with a nucleic acid comprising a nucleotide sequence that encodes a reporter gene functionally linked to regulatory element associated with the activity of (N); identifying a test compound that increases or decreases the level of reporter gene expression relative to the level of reporter gene expression measured in the absence of the test compound; and assaying the identified test compound for a tissue protective activity.

The present disclosure further provides a method for identifying (I2) a compound that binds to (N), comprising:

(a) contacting (N) with a tissue protective NEPOR receptor complex ligand and/or EPH-B4 and/or Ephrin A1 ligand attached to a first label, and an equivalent amount of a test compound attached to a second label under conditions conducive to binding, removing unbound material from (N), and detecting the level of the first and second labels, where if the second label is present the compound binds (N) and if the level of the first label decreases relative to the level of the first label when the labelled ligand is contacted with (N) under conditions conducive to binding in the absence of a test compound after removal of unbound material, then a compound that binds to (N) is identified; or (b) contacting a test compound with a ligand-binding tissue protective receptor NEPOR complex fragment comprising at least one EPH-B4 receptor or Ephrin A1 receptor, extracellular domain fused to a Fc fragment attached to a solid support, removing unbound test compounds from the solid support, and identifying the compound attached to the tissue protective NEPOR receptor complex fragment, such that a compound bound to the solid support is identified as a compound that binds to a tissue protective NEPOR receptor complex; and identifying (I3) a compound that modulates the binding of a tissue protective NEPOR receptor complex ligand to (N), or compound that modulates the interaction between (N) and tissue protective cytokine receptor complex ligand, involves (i) contacting a tissue protective NEPOR receptor complex ligand with (N) in the presence of one or more test compounds under conditions conducive to binding, and measuring the amount of tissue protective cytokine receptor complex ligand bound to (N).

Figure 10:
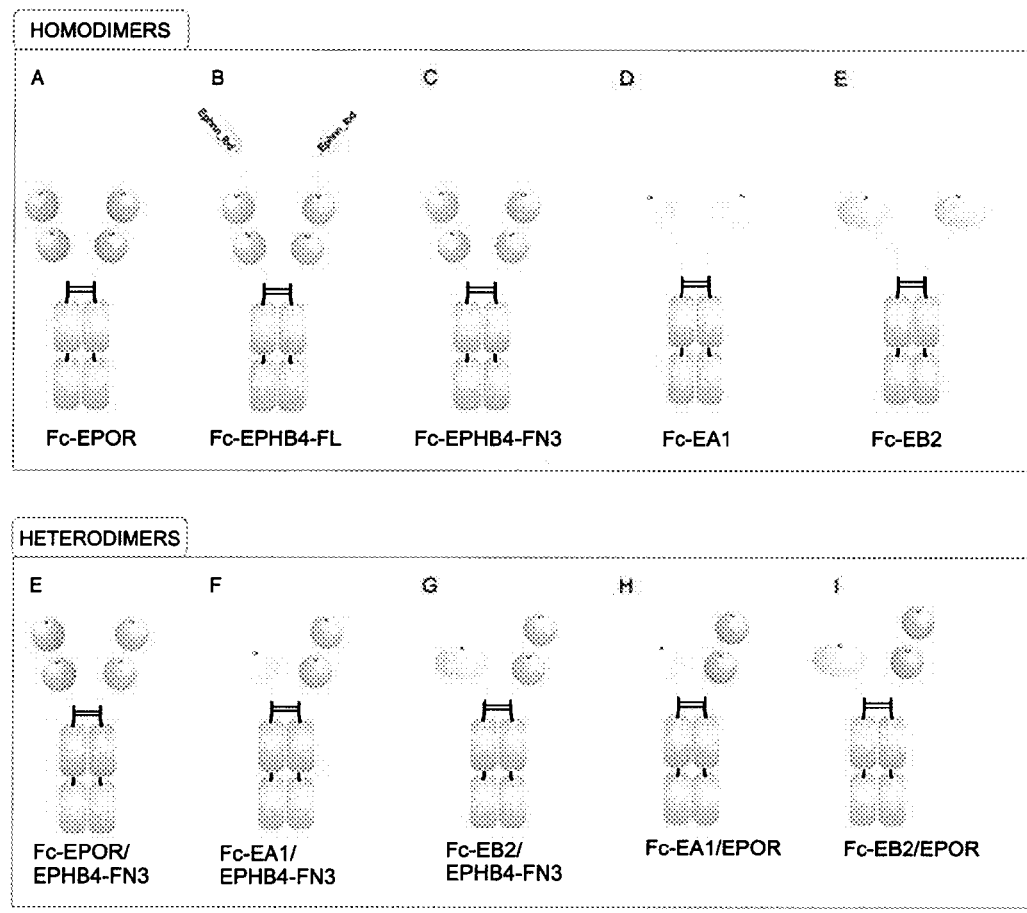
FIG. 10 shows the possible various species of NEPOR (without being bound by theory). In this representation, NEPOR homo/heterodimer species are shown as Fc constructs. This mimics the dimerization of separate receptor monomers. Any method which allows the production of such NEPOR dimers can be employed in screening for NEPOR specific agonists and antagonists, including small molecules, peptides, proteins and EPO variants.
Figure 12:
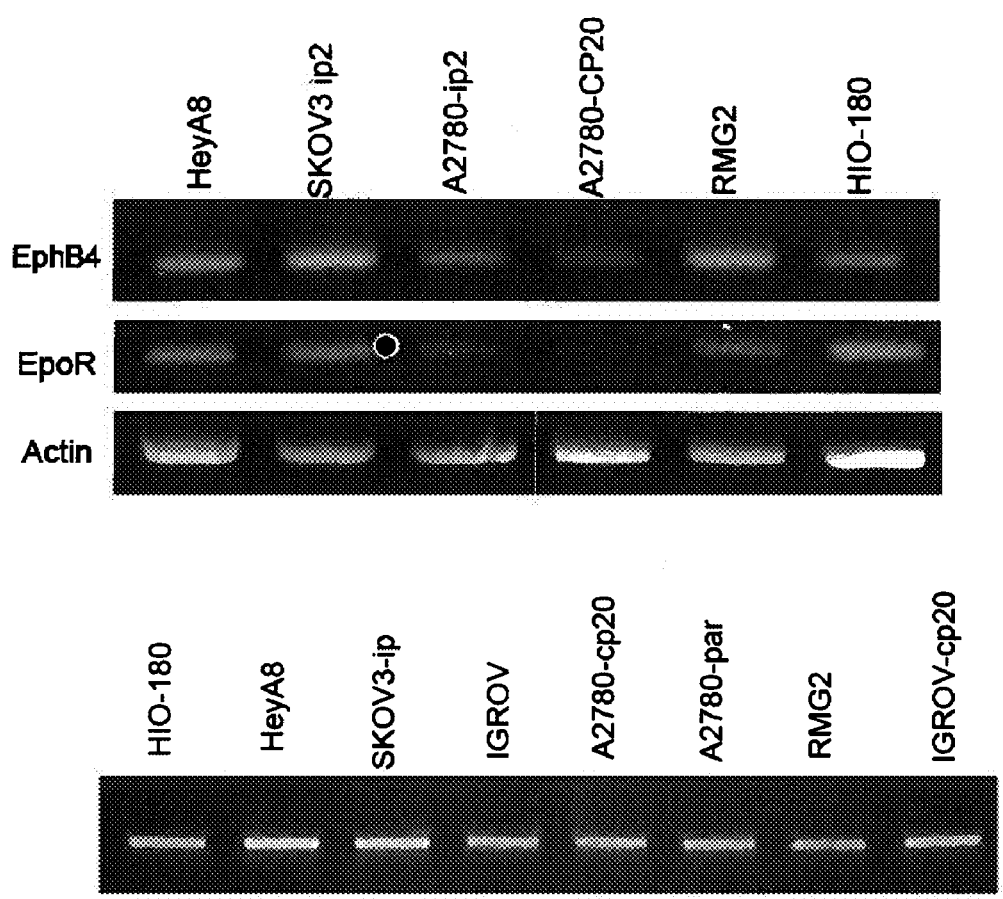
FIG. 12 shows mRNA levels of ovarian cancer cell lines. RNA was isolated from a panel ovarian cancer cell lines and was reverse transcribed into cDNA. PCR was done using primers specific for EPO receptor, EPH-B4, Ephrin A1 and actin.
Figure 13:
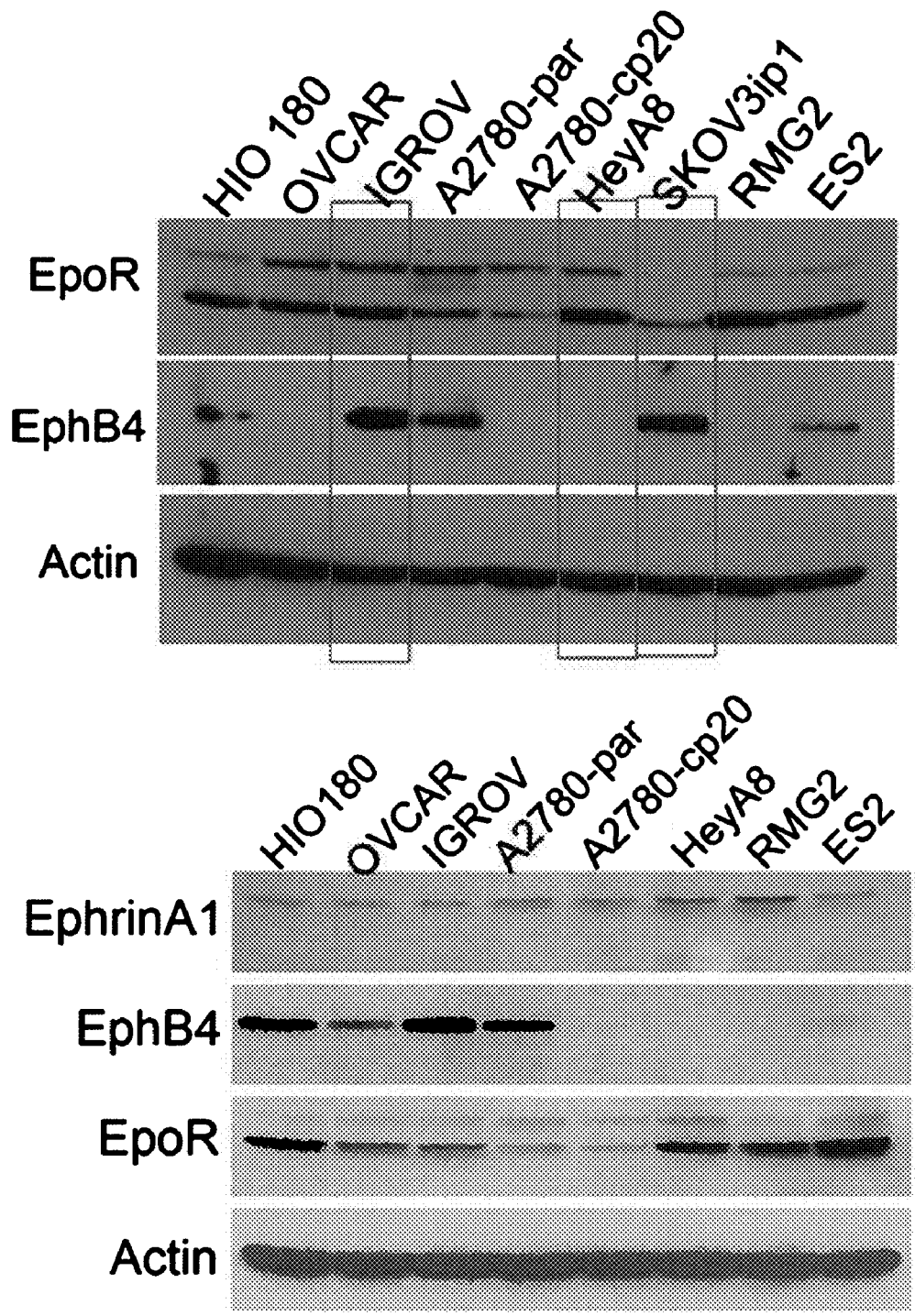
FIG. 13 shows protein expression in ovarian cancer cell lines. Protein extracts were isolated from a panel ovarian cancer cell lines. Samples were separated using SDS-Page gel electrophoresis. Immunoblots using antibodies for EPO Receptor (R&D biosystems), EPH-B4 (a gift from Prakash Gil), Ephrin A1 and acting (Sigma Aldrich) were used to compare protein expression.
Figure 14:
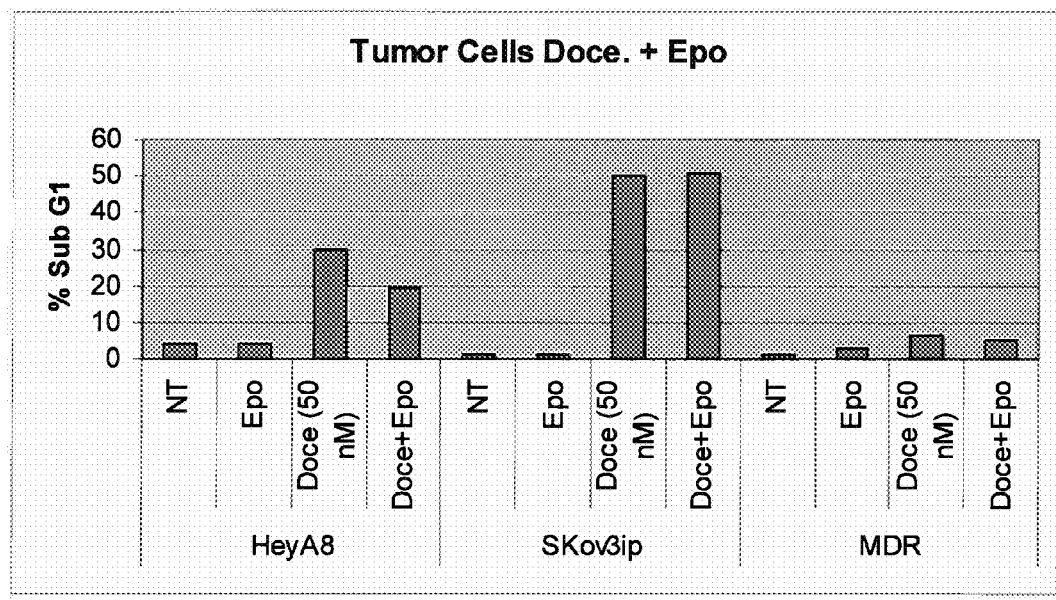
FIG. 14 shows ESA protection from chemotherapy induced apoptosis. Ovarian cancer cell lines Hey A8, SkoV3 ip1, and HeyA8-MDR (chemoresistant) were treated with 50 U erythropoietin (EPO), 50 nM docetaxel, or a combination of EPO and docetaxes for 48 hours. Cells were then fixed and DNA stained with propidium iodide. Percentage of sub G1 cells were then quantified using flow cytometer (BD).
Figure 15:
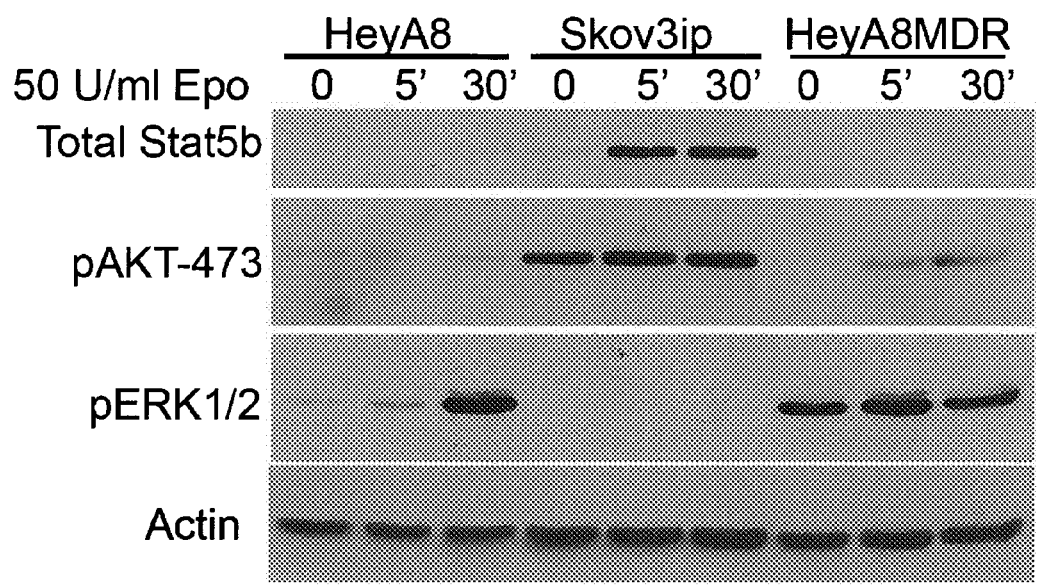
FIG. 15 shows signalling pathways activated in response to EPO in ovarian cancer cell lines. Cell lines previously characterized for expression levels of EPOR, EPH-B4, and Ephrin A1 were washed and grown in serum free media for two hours. Cells were then treated with 50 U EPO and collected and designated time points (0, 5 and 30 minutes). Protein extracts were isolated and analyzed by immunoblots using antibodies for phosphor-STAT5 (Invitrogen), phosphor-AKT, phosphor-ERK (Cell Signaling) and acting (Sigma Aldrich).
Figure 16:
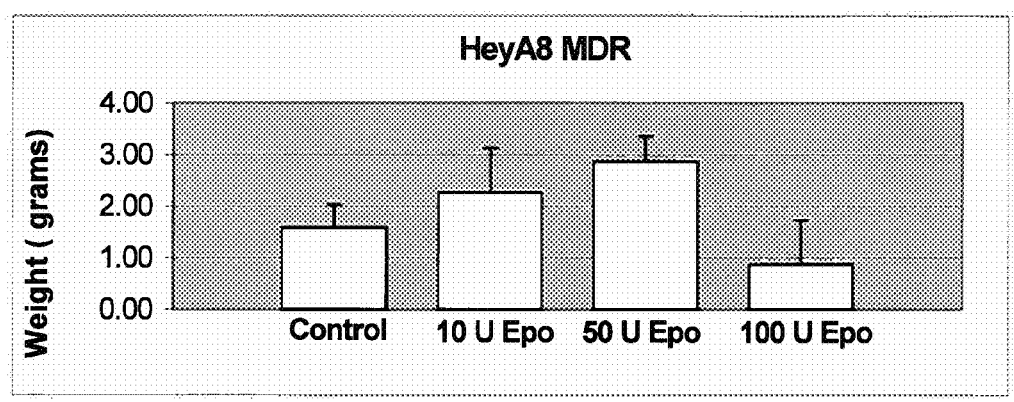
FIG. 16 shows erythropoietin induced tumor growth in nude mice. Mice were injected i.p. with $1\times10^6$ Hey MDR ovarian cancer cells. Day eight following injections mice were injected with designated amounts of EPO (10, 50, 100 U, three mice per group) every second day. A) Mice were sacrificed at day 26 and tumor weight was measured. B) Protein extracts were isolated from tumors and analyzed by immunoblot using antibodies specific for phosphor AKT ser 473, phosphor ERK (Cell Signaling) and pSTAT5b (Invitrogen).
Figure 16:
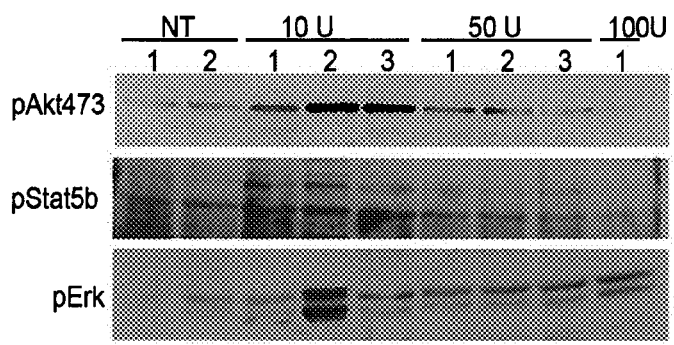
Figure 17:
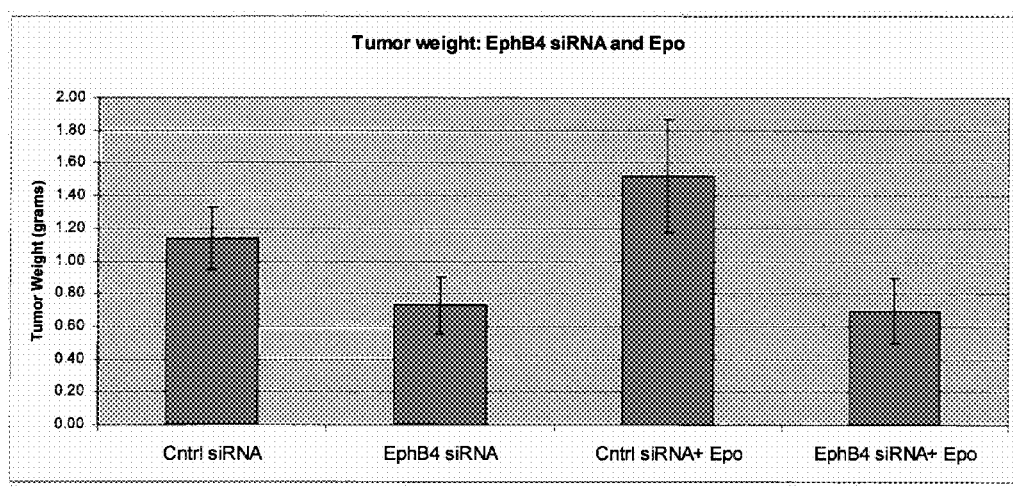
FIG. 17 shows EPH-B4 expression effects tumor promoting effect of EPO. Female nude mice were injected i.p. with $1\times10^6$ HeyA8-MDR cells. Day eight following injection the cells were treated with control siRNA-DOPC, EPH-B4 siRNA-DOPC, EPO, or in EPO+ control or EPH-B4 siRNA-DOPC (10 per group). (50 U EPO given 3× week, 5 µg siRNA 2× week). Mice were sacrificed on day 25 and tumor weights were measured. Statistics were done using students T-test. B) Distribution of tumor weight per group.
Figure 18:
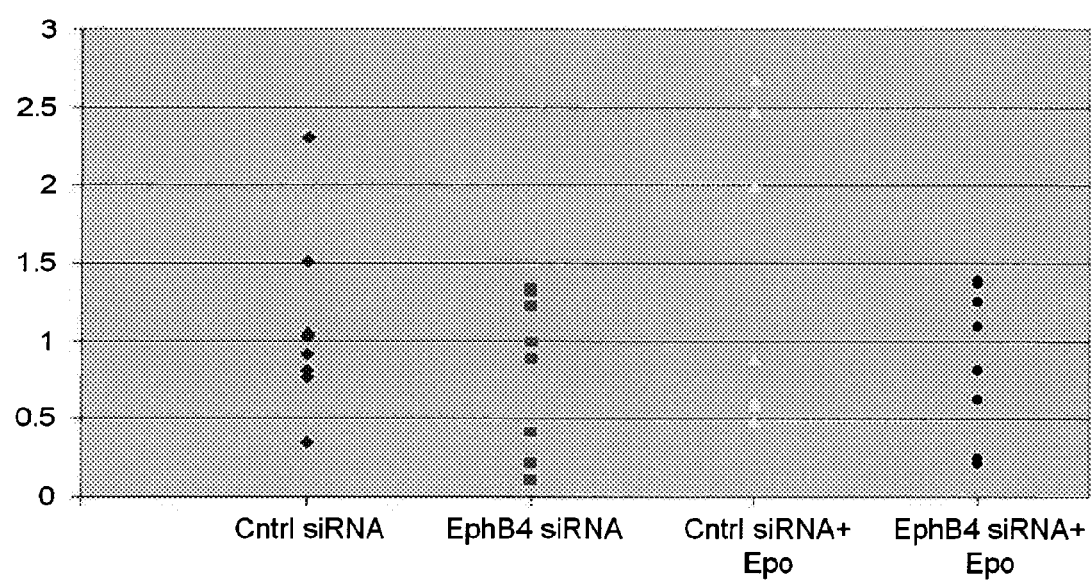
FIG. 18 shows tumor weight distributions.

The present disclosure further provides novel tissue protective NEPOR receptor complexes in particular EPH-B4 and/or Ephrin A1 containing complexes that can be used to provide an in vitro screening assay for NEPOR specific therapies; by measuring the binding of test compounds to the tissue protective NEPOR receptor complex in comparison to EPOR homodimer complexes. The test compound is labelled and binding of the labelled test compound to the receptor complexes detailed in FIG. 10 is measured by detecting the label attached to the test compound. Alternatively, a label free detection approach such as surface plasmon resonance may be employed. Such an approach can provide for novel neuroprotective therapies (i.e. NEPOR agonists) which lack haematopoietic activity. Such an approach can also provide for novel onco-therapies (i.e. NEPOR antagonists i.e. at least a and/or EPH-B4 and/or Ephrin A1 agonist) which do not inhibit haematopoiesis. The nature of such screening arrays involving recombinant receptor constructs is demonstrated in FIG. 10 (in the exemplified case as Fc constructs).

Use (I1) is useful for identifying a compound that modulates NEPOR's tissue protective activity. (I2) is useful for identifying a compound that binds to NEPOR. (I3) is useful for identifying a compound that modulates the binding of a tissue protective NEPOR receptor complex ligand to (N), or compound that modulates the interaction between (N) and tissue protective cytokine receptor complex ligand (claimed). The compounds identified using (I1)-(I3) are useful for treating various conditions of the central and peripheral nervous systems (e.g., hypoxia, and/or ischemia, epilepsy, chronic seizure disorders, neurotoxin poisoning, septic shock, anaphylactic shock), neuropsychologic disorders (senile dementia, Alzheimer's disease, Parkinson's disease, dermentia, multiple sclerosis, Creutzfeldt-Jakob disease, Huntington's disease), inflammatory diseases (e.g., chronic bronchitis, rheumatoid arthritis, glomerulonephritis, encephalitis, meningitis, polymyositis), opthalamic diseases (e.g., angiitis, retinal ischemia), cardiovascular diseases (e.g., myocardial infraction, myocarditis), cardiopulmonary diseases (e.g., asthma, pulmonary thrombosis), respiratory diseases, kidney, urinary, and reproductive diseases (e.g., myasthenia gravis, diabetes, autoimmune diseases), bone diseases (e.g., osteopenia, Paget's disease), gastrointestinal diseases and endocrine and metabolic abnormalities.

The compounds identified using (I1)-(I3) are also useful for treating NEPOR positive cancers in particular and/or EPH-B4 and/or Ephrin A1 positive cancers including, head and neck cancer, breast cancer, liver cancer, colorectal cancer, small intestine cancer, leukemia, prostate cancer, lung cancer, ovarian cancer, pancreatic cancer, endometrial cancer, stomach cancer, non-Hodgkin lymphoma, kidney cancer, Renal cell carcinoma (RCC), malignant melanoma, gallbladder cancer, bladder cancer, vulvar cancer, Penile cancer, testicular cancer, thymus cancer, Kaposi's sarcoma, eye cancer, adrenal gland cancer, brain cancer, cervical cancer, appendix cancer, adenoid cancer, bile duct cancer, urethral cancer, spinal cancer, Ewing's family of tumors, extragonal germ cell cancer, extra hepatic bile duct cancer, fallopian tube cancer, soft tissue cancers, bone cancer, Hodgkin's lymphoma, anal cancer, malignant mesothelioma, vaginal cancer skin cancer, central nervous system cancer (craniopharyngioma), pleuropulmonary blastoma, nasal cavity and paranasal sinus cancer transitional cell cancer of renal pelvis and ureter, pituitary gland cancer, sqamous cell carcinoma of the head and neck (HNSCC), prostate cancer, colorectal cancer, lung cancer, brain cancer, bladder cancer, and salivary gland cancer. It is particularly preferred that the cancer is selected from the group of squamous cell carcinoma of the head and neck (HNSCC), prostate cancer, colorectal cancer, lung cancer, kidney cancer, brain cancer and bladder cancer.

NEPOR in Oncology Therapy

The hypothesis of the present disclosure is that EPO results in poorer survival outcomes (at least in some cancers) because of its effects on NEPOR activity i.e. in particular EPH-B4 and/or Ephrin A1 activity. Therefore, treatment of these NEPOR positive patients with a NEPOR targeted therapy is a prudent path to disease intervention. Specific approaches to antagonising NEPOR mediated survival signals include, for example:

a) NEPOR specific antagonistic antibodies. Such antibodies block and antagonise the extracellular regions of the molecule specifically associated with the mediation of NEPOR's cyto-protective activity.

b) NEPOR specific small-molecules. Such small molecules block and antagonise the extracellular regions of the molecule specifically associated with the mediation of NEPOR's cytoprotective activity.

c) high-affinity peptides which specifically target NEPOR to block and antagonise the mediation of EPO's cytoprotective activity.

d) Small molecules targeting EPH-B4's intracellular tyrosine kinase domain (e.g. Dasatinib), including:

1: CID: 1095868, AKI-STT-00166305; ZINC00818264; BAS 09636496 IUPAC: N-[5-[(3-chlorophenyl)methyl]-1,3-thiazol-2-yl]-2-(4,6-dimethylpyrimidin-2-yl)sulfanylacetamide. MW: 404.93678|MF: C18H17ClN4OS2. (MW is molecular weight and MF is molecular formula)

2: CID: 1465558, IUPAC: 2-[(3-chlorobenzoyl)amino]-4-methyl-N-pyridin-3-yl-1,3-thiazole-5-carboxamide, MW: 372.82872|MF: C17H13ClN4O2S.

3: CID: 1468201, IUPAC: N-[5-[(2-chlorophenyl)carbamoyl]-4-methyl-1,3-thiazol-2-yl]pyridine-4-carboxamide, MW: 372.82872|MF: C17H13ClN4O2S.

4: CID: 3062316, Dasatinib; Sprycel; BMS Dasatinib, IUPAC: N-(2-chloro-6-methylphenyl)-2-[[6-[4-(2-hydroxyethyl)piperazin-1-yl]-2-methylpyrimidin-4-yl]amino]-1,3-thiazole-5-carboxamide, MW: 488.00554|MF: C22H26ClN7O2S.

5: CID: 3072360, 142287-40-9; Pyrimido(4,5-d)pyrimidin-4 (1H)-one, 7-methyl-1-phenyl-2-((3-(4-(2-thiazolyl)-1-piperazinyl)propyl)thio)-IUPAC: 2-methyl-8-phenyl-7-[3-[4-(1,3-thiazol-2-yl)piperazin-1-yl]propylsulfanyl]pyrimido[6,5-d]pyrimidin-5-one, MW: 479.6209|MF: C23H25N7OS2.

6: CID: 5041467, STK154706; ZINC04687922, IUPAC: [2-[(2-methylphenyl)amino]-1,3-thiazol-4-yl]-(4-pyrimidin-2-ylpiperazin-1-yl)methanone, MW: 380.4667|MF: C19H20N6OS.

7: CID: 9822929, IUPAC: N-(2-chloro-6-methylphenyl)-2-[(6-imidazol-1-ylpyridazin-3-yl)amino]-1,3-thiazole-5-carboxamide, MW: 411.869|MF: C18H14ClN7OS.

8: CID: 9927718, IUPAC: N-(2-chloro-6-methylphenyl)-2-(cyclopropanecarbonylamino)-1,3-thiazole-5-carboxamide, MW: 335.809|MF: C15H14ClN3O2S.

9: CID: 10006113, IUPAC: N-[4-chloro-2-[(5-chloropyridin-2-yl)carbamoyl]phenyl]-5-methyl-6,7-dihydro-4H-[1,3]thiazolo[5,4-c]pyridine-2-carboxamide hydrochloride, MW: 498.81322|MF: C20H18Cl3N5O2S.

10: CID: 10006114, IUPAC: N-[4-chloro-2-[(5-chloropyridin-2-yl)carbamoyl]phenyl]-5-methyl-6,7-dihydro-4H-[1,3]thiazolo[5,4-c]pyridine-2-carboxamide, MW: 462.35228|MF: C20H17Cl2N5O2S.

11: CID: 10052635, IUPAC: 2-[[2-methyl-5-[[6-[(4-methylpiperazin-1-yl)methyl]pyridin-2-yl]amino]phenyl]amino]-N-(2-methylphenyl)-1,3-thiazole-5-carboxamide, MW: 527.68362|MF: C29H33N7OS.

12: CID: 10195898, IUPAC: N-[(4-chlorophenyl)methyl]-2-[[[(2S)-2-hydroxy-2-pyrimidin-2-ylethyl]-methylamino]methyl]-4-methyl-7-oxothieno[2,3-e]pyridine-6-carboxamide, MW: 497.99706|MF: C24H24ClN5O3S.

13: CID: 10206276, IUPAC: N-[4-[(5-chloropyridin-2-yl)carbamoyl]-2-phenyl-1,3-thiazol-5-yl]-1-propan-2-ylpiperidine-4-carboxamide, MW: 484.01354|MF: C24H26ClN5O2S.

14: CID: 10252208, IUPAC: 2-[4-(5-amino-1,3-thiazol-2-yl)phenyl]-3-(5-chloropyridin-2-yl)quinazolin-4-one, MW: 431.89746|MF: C22H14ClN5OS.

15: CID: 10253695, IUPAC: 2-[4-[3-(5-chloropyridin-2-yl)-4-oxoquinazolin-2-yl]phenyl]-1,3-thiazole-5-carboxamide, MW: 459.90756|MF: C23H14ClN5O2S.

16: CID: 10301604, IUPAC: N-[4-[(5-chloropyridin-2-yl)carbamoyl]-2-(3,4-difluorophenyl)-1,3-thiazol-5-yl]-1-propan-2-ylpiperidine-4-carboxamide, MW: 519.99466|MF: C24H24ClF2N5O2S.

17: CID: 10344807, IUPAC: N-[2-[4-[3-(5-chloropyridin-2-yl)-4-oxoquinazolin-2-yl]phenyl]-1,3-thiazol-4-yl]acetamide, MW: 473.93414|MF: C24H16ClN5O2S.

18: CID: 10368624, IUPAC: N-[(4-chlorophenyl)methyl]-2-[[(2-hydroxy-2-pyrimidin-2-ylethyl)-methylamino]methyl]-7-methyl-4-oxothieno[3,2-e]pyridine-5-carboxamide, MW: 497.99706|MF: C24H24ClN5O3S.

19: CID: 10370949, IUPAC: (3Z)-4-[[(2S)-2-(3-chlorophenyl)-2-hydroxyethyl]amino]-3-[6-methyl-2-[4-(1,3-thiazol-2-ylmethyl)piperazin-1-yl]-7,9-dihydropurin-8-ylidene]pyridin-2-one, MW: 578.08832|MF: C27H28ClN9O2S.

20: CID: 10412586, IUPAC: N-[2-[4-[3-(5-chloropyridin-2-yl)-4-oxoquinazolin-2-yl]phenyl]-1,3-thiazol-5-yl]acetamide, MW: 473.93414|MF: C24H16ClN5O2S.

21: CID: 10413555, IUPAC: N-[(4-chlorophenyl)methyl]-2-[[[(2R)-2-hydroxy-2-pyrimidin-2-ylethyl]-methylamino]methyl]-7-methyl-4-oxothieno[3,2-e]pyridine-5-carboxamide, MW: 497.99706|MF: C24H24ClN5O3S.

22: CID: 10456156, IUPAC: 4-[(3-chlorothiophen-2-yl)methylamino]-2-[(4-morpholin-4-ylphenyl)amino]pyrimidine-5-carboxamide, MW: 444.93774|MF: C20H21ClN6O2S.

23: CID: 10458706, IUPAC: N-[5-[2-[(4-chlorophenyl)amino]pyrimidin-4-yl]-4-methyl-1,3-thiazol-2-yl]-3-(2-morpholin-4-ylethylamino)propanamide, MW: 502.03212 MF: C23H28ClN7O2S.

24: CID: 11153014, IUPAC: N-(2-chloro-6-methylphenyl)-2-[(2,6-dimethylpyrimidin-4-yl)amino]-1,3-thiazole-5-carboxamide, MW: 373.85984|MF: C17H16ClN5OS.

25: CID: 11167695, IUPAC: N-(2-chloro-6-methylphenyl)-2-[[2-methyl-6-(2-morpholin-4-ylethylamino)pyrimidin-4-yl]amino]-1,3-thiazole-5-carboxamide, MW: 488.00554|MF: C22H26ClN7O2S.

26: CID: 11168231, IUPAC: N-(2-chloro-6-methylphenyl)-2-[(6-chloro-2-methylpyrimidin-4-yl)amino]-N-[(4-methoxyphenyl)methyl]-1,3-thiazole-5-carboxamide, MW: 514.42684|MF: C24H21Cl2N5O2S.

27: CID: 11200510, IUPAC: N-(2-chloro-6-methylphenyl)-2-[[6-(2-hydroxyethylamino)pyridin-2-yl]amino]-1,3-thiazole-5-carboxamide, MW: 403.88582|MF: C18H18ClN5O2S.

28: CID: 11247793, IUPAC: N-(2-chloro-6-methylphenyl)-2-[[6-(methyl-(3-methylaminopropyl)amino)pyridin-2-yl]amino]-1,3-thiazole-5-carboxamide, MW: 444.9808|MF: C21H25ClN6OS.

29: CID: 11260009, IUPAC: N-(2-chloro-6-methylphenyl)-2-[[6-[4-(hydroxymethyl)piperidin-1-yl]-2-methylpyrimidin-4-yl]amino]-1,3-thiazole-5-carboxamide, MW: 472.9909|MF: C22H25ClN6O2S.

30: CID: 11269410, IUPAC: N-(2-chloro-6-methylphenyl)-2-[(6-chloro-2-methylpyrimidin-4-yl)amino]-1,3-thiazole-5-carboxamide, MW: 394.27832|MF: C16H13Cl2N5OS.

31: CID: 11282881, IUPAC: N-(2-chloro-6-methylphenyl)-2-[[6-(2-morpholin-4-ylethylamino)pyrimidin-4-yl]amino]-1,3-thiazole-5-carboxamide, MW: 473.97896|MF: C21H24ClN7O2S.

32: CID: 11283174, IUPAC: N-(2-chloro-6-methylphenyl)-2-[[6-(3-morpholin-4-ylpropylamino)pyridin-2-yl]amino]-1,3-thiazole-5-carboxamide, MW: 487.01748|MF: C23H27ClN6O2S.

33: CID: 11328827, IUPAC: N-(2-chloro-6-methylphenyl)-2-[[6-(3-imidazol-1-ylpropylamino)pyridin-2-yl]amino]-1,3-thiazole-5-carboxamide, MW: 467.97438|MF: C22H22ClN7OS.

34: CID: 11407465, IUPAC: N-(2-chloro-6-methylphenyl)-2-[[6-(2-hydroxyethylamino)-2-methylpyrimidin-4-yl]amino]-1,3-thiazole-5-carboxamide, MW: 418.90046|MF: C18H19ClN6O2S.

35: CID: 11466196, IUPAC: N-(2-chloro-6-methylphenyl)-2-[[2-methyl-6-(3-morpholin-4-ylpropylamino)pyrimidin-4-yl]amino]-1,3-thiazole-5-carboxamide. MW: 502.03212|MF: C23H28ClN7O2S.

36: CID: 11466607, IUPAC: N-(2-chloro-6-methylphenyl)-2-[[6-[4-(2-hydroxyethyl)piperazin-1-yl]-2-methylpyrimidin-4-yl]amino]-1,3-thiazole-5-carboxamide hydrochloride, MW: 524.46648|MF: C22H27Cl2N7O2S.

37: CID: 11487256, IUPAC: N-(2-chloro-6-methylphenyl)-2-[(6-morpholin-4-ylpyrimidin-4-yl)amino]-1,3-thiazole-5-carboxamide, MW: 430.91116|MF: C19H19ClN6O2S.

38: CID: 11505502, IUPAC: 2-[[6-[4-(2-hydroxyethyl)piperazin-1-yl]pyrimidin-4-yl]amino]-N-[2-methyl-5-[[3-(trifluoromethyl)benzoyl]amino]phenyl]-1,3-thiazole-5-carboxamide. MW: 626.65257|MF: C29H29F3N8O3S.

39: CID: 11512538, IUPAC: 2-[4-[6-[[5-[(2-chloro-6-methylphenyl)carbamoyl]-1,3-thiazol-2-yl]amino]-2-methylpyrimidin-4-yl]piperazin-1-yl]ethyl 2,2-dimethylpropanoate, MW: 572.12196|MF: C27H34ClN7O3S.

40: CID: 11539665, IUPAC: (3-chloro-2-fluorophenyl)-[4-[[6-[(5-fluoro-1,3-thiazol-2-yl)amino]pyridin-2-yl]methyl]piperazin-1-yl]methanone, MW: 449.904626|MF: C20H18ClF2N5OS.

41: CID: 11540687, IUPAC: N-(2-chloro-6-methylphenyl)-2-[[6-[4-(2-hydroxyethyl)piperazin-1-yl]-2-methylpyrimidin-4-yl]amino]-1,3-thiazole-5-carboxamide hydrate, MW: 506.02082|MF: C22H28ClN7O3S.

42: CID: 11569328, IUPAC: N-(2-chloro-6-methylphenyl)-2-[[3-[4-(2-hydroxyethyl)piperazin-1-yl]-5-methylphenyl]amino]-1,3-thiazole-5-carboxamide, MW: 486.02942|MF: C24H28ClN5O2S.

43: CID: 11570976, IUPAC: 2-[[6-[4-(2-hydroxyethyl)piperazin-1-yl]-2-methylpyrimidin-4-yl]amino]-N-[2-methyl-5-[[3-(trifluoromethyl)phenyl]carbamoyl]phenyl]-1,3-thiazole-5-carboxamide, MW: 640.67915|MF: C30H31F3N8O3S.

44: CID: 11577776, IUPAC: 2-[[6-(2-hydroxyethylamino)-2-methylpyrimidin-4-yl]amino]-N-[2-methyl-5-[[3-(trifluoromethyl)benzoyl]amino]phenyl]-1,3-thiazole-5-carboxamide, MW: 571.57407|MF: C26H24F3N7O3S.

45: CID: 11590089, IUPAC: (3-chloro-2-fluorophenyl)-[4-[5-methyl-6-(1,3-thiazol-2-ylamino)pyridin-2-yl]piperazin-1-yl]methanone, MW: 431.914163|MF: C20H19ClFN5OS.

46: CID: 11606973, IUPAC: N-[5-[[3-[4-(2-hydroxyethyl)piperazin-1-yl]-5-(trifluoromethyl)benzoyl]amino]-2-methylphenyl]-2-(pyridin-2-ylamino)-1,3-thiazole-5-carboxamide, MW: 625.66451|MF: C30H30F3N7O3S.

47: CID: 11650098, IUPAC: 2-[[6-(4-methylpiperazin-1-yl)pyrimidin-4-yl]amino]-N-[2-methyl-5-[[3-(trifluoromethyl)benzoyl]amino]phenyl]-1,3-thiazole-5-carboxamide, MW: 596.62659|MF: C28H27F3N8O2S.

48: CID: 11650132, IUPAC: pentyl N-[5-[(2-chloro-6-methylphenyl)carbamoyl]-1,3-thiazol-2-yl]-N-[6-[4-(2-hydroxyethyl)piperazin-1-yl]-2-methylpyrimidin-4-yl]carbamate, MW: 602.14794|MF: C28H36ClN7O4S.

49: CID: 11650511, IUPAC: N-[5-[[3-(4-ethylpiperazin-1-yl)-5-(trifluoromethyl)benzoyl]amino]-2-methylphenyl]-2-[[6-(2-hydroxyethylamino)-2-methylpyrimidin-4-yl]amino]-1,3-thiazole-5-carboxamide, MW: 683.74695|MF: C32H36F3N9O3S.

50: CID: 11664355, IUPAC: 2-[(2-methyl-6-morpholin-4-ylpyrimidin-4-yl)amino]-N-[2-methyl-5-[[3-(trifluoromethyl)benzoyl]amino]phenyl]-1,3-thiazole-5-carboxamide, MW: 597.61135|MF: C28H26F3N7O3S.

51: CID: 11664511, IUPAC: 2-[[4-[4-(2-hydroxyethyl)piperazin-1-yl]pyridin-2-yl]amino]-N-[2-methyl-5-[[3-(trifluoromethyl)benzoyl]amino]phenyl]-1,3-thiazole-5-carboxamide, MW: 625.66451|MF: C30H30F3N7O3S.

52: CID: 11669430, IUPAC: N-(2-chloro-6-methylphenyl)-2-[(2-methyl-6-piperazin-1-ylpyrimidin-4-yl)amino]-1,3-thiazole-5-carboxamide, MW: 443.95298|MF: C20H22ClN7OS.

53: CID: 11676373, IUPAC: (3-chloro-2-fluorophenyl)-[4-[[6-(1,3-thiazol-2-ylamino)pyridin-2-yl]methyl]piperazin-1-yl]methanone, MW: 431.914163|MF: C20H19ClFN5OS.

54: CID: 11684148, IUPAC: (3-chloro-2-fluorophenyl)-[4-[[6-[(5-chloro-1,3-thiazol-2-yl)amino]pyridin-2-yl]methyl]piperazin-1-yl]methanone, MW: 466.359223|MF: C20H18Cl2FN5OS.

55: CID: 11700117, IUPAC: 2-[[6-(4-ethylpiperazin-1-yl)-2-methylpyrimidin-4-yl]amino]-N-[2-methyl-5-[[3-(trifluoromethyl)benzoyl]amino]phenyl]-1,3-thiazole-5-carboxamide, MW: 624.67975|MF: C30H31F3N8O2S.

56: CID: 11707091, IUPAC: 2-[[2-methyl-6-(4-methylpiperazin-1-yl)pyrimidin-4-yl]amino]-N-[2-methyl-5-[[3-(trifluoromethyl)benzoyl]amino]phenyl]-1,3-thiazole-5-carboxamide, MW: 610.65317|MF: C29H29F3N8O2S.

57: CID: 11714286, IUPAC: 2-[[5-[4-(2-hydroxyethyl)piperazin-1-yl]pyridin-2-yl]amino]-N-[2-methyl-5-[[3-(trifluoromethyl)benzoyl]amino]phenyl]-1,3-thiazole-5-carboxamide, MW: 625.66451|MF: C30H30F3N7O3S.

58: CID: 11714353, IUPAC: 2-[[6-[4-(2-hydroxyethyl)piperazin-1-yl]-2-methylpyrimidin-4-yl]amino]-N-[2-methyl-5-[[3-(trifluoromethyl)benzoyl]amino]phenyl]-1,3-thiazole-5-carboxamide, MW: 640.67915|MF: C30H31F3N8O3S.

59: CID: 11752136, IUPAC: N-(2-chloro-6-methylphenyl)-2-[[5-[4-(2-hydroxyethyl)piperazin-1-yl]-2-methylpyri- 60: CID: 11772766, IUPAC: 4-[2-(3-chlorophenyl)ethylamino]-2-pyridin-4-yl-1,3-thiazole-5-carboxamide, MW: 358.8452|MF: C17H15ClN4OS.

61: CID: 11775143, IUPAC: N-(2-chloro-6-methylphenyl)-2-[(2-methyl-6-morpholin-4-ylpyrimidin-4-yl)amino]-1,3-thiazole-5-carboxamide, MW: 444.93774|MF: C20H21ClN6O2S.

62: CID: 11854012, IUPAC: 2-[4-[6-[[5-[(2-chloro-6-methylphenyl)carbamoyl]-1,3-thiazol-2-yl]amino]-2-methylpyrimidin-4-yl]piperazin-1-yl]acetic acid, MW: 501.98906|MF: C22H24ClN7O3S.

63: CID: 11854269, IUPAC: 2-[4-[6-[[5-[(2-chloro-6-methylphenyl)carbamoyl]-1,3-thiazol-2-yl]amino]-2-methylpyrimidin-4-yl]piperazin-1-yl]ethyl hydrogen sulfate, MW: 568.06874|MF: C22H26ClN7O5S2.

64: CID: 11854270, IUPAC: N-(2-chloro-6-methylphenyl)-2-[[6-[2-(2-hydroxyethylamino)ethylamino]-2-methylpyrimidin-4-yl]amino]-1,3-thiazole-5-carboxamide, MW: 461.96826|MF: C20H24ClN7O2S 65: CID: 11854271, IUPAC: 2-[[6-(2-aminoethylamino)-2-methylpyrimidin-4-yl]amino]-N-(2-chloro-6-methylphenyl)-1,3-thiazole-5-carboxamide, MW: 417.9157|MF: C18H20ClN7OS.

66: CID: 11854272, IUPAC: 2-[[2-[4-[6-[[5-[(2-chloro-6-methylphenyl)carbamoyl]-1,3-thiazol-2-yl]amino]-2-methylpyrimidin-4-yl]piperazin-1-yl]acetyl]amino]ethanesulfonic acid, MW: 609.12066|MF: C24H29ClN8O5S2.

67: CID: 11854533, IUPAC: N-(2-chloro-4-hydroxy-6-methylphenyl)-2-[[6-[4-(2-hydroxyethyl)piperazin-1-yl]-2-methylpyrimidin-4-yl]amino]-1,3-thiazole-5-carboxamide, MW: 504.00494|MF: C22H26ClN7O3S.

68: CID: 11854534, IUPAC: N-[2-chloro-6-(hydroxymethyl)phenyl]-2-[[6-[4-(2-hydroxyethyl)piperazin-1-yl]-2-methylpyrimidin-4-yl]amino]-1,3-thiazole-5-carboxamide, MW: 504.00494|MF: C22H26ClN7O3S.

69: CID: 11854535, IUPAC: N-(2-chloro-6-methylphenyl)-2-[[6-[4-(2-hydroxyethyl)-4-oxidopiperazin-4-ium-1-yl]-2-methylpyrimidin-4-yl]amino]-1,3-thiazole-5-carboxamide, MW: 504.00494|MF: C22H26ClN7O3S.

70: CID: 11854536, IUPAC: 2-[4-[6-[[5-[(2-chloro-6-methylphenyl)carbamoyl]-1,3-thiazol-2-yl]amino]-2-methylpyrimidin-4-yl]-1-oxidopiperazin-1-ium-1-yl]acetic acid, MW: 517.98846|MF: C22H24ClN7O4S.

71: CID: 11949914, IUPAC: 4-[[2-(5-chloro-2-fluorophenyl)-5-dimethylaminopyrimidin-4-yl]amino]-N-[2-(2-hydroxyethylamino)ethyl]pyridine-3-carboxamide, MW: 473.93100|MF: C22H25ClFN7O2.

72: CID: 11951866, IUPAC: 4-[[2-(5-chloro-2-fluorophenyl)-5-pyrrolidin-1-ylpyrimidin-4-yl]amino]-N-(2-hydroxyethyl)pyridine-3-carboxamide, MW: 456.900483|MF: C22H22ClFN6O2.

73: CID: 11952045, IUPAC: 4-[[2-(5-chloro-2-fluorophenyl)-5-pyrrolidin-1-ylpyrimidin-4-yl]amino]-N-[(2S)-2-hydroxypropyl]pyridine-3-carboxamide, MW: 470.927063|MF: C23H24ClFN6O2.

74: CID: 15979866, IUPAC: 5-[2-[[4-(4-acetylpiperazin-1-yl)pyridin-2-yl]amino]-1,3-thiazol-5-yl]-N-methylpyridine-3-carboxamide, MW: 437.51802|MF: C21H23N7O2S.

75: CID: 15980109, IUPAC: N-(2-aminoethyl)-5-[2-[(4-morpholin-4-ylpyridin-2-yl)amino]-1,3-thiazol-5-yl]pyridine-3-carboxamide, MW: 425.50732|MF: C20H23N7O2S 76: CID: 15980233, IUPAC: N-(2-hydroxyethyl)-5-[2-[(4-morpholin-4-ylpyridin-2-yl)amino]-1,3-thiazol-5-yl]pyridine-3-carboxamide, MW: 426.49208|MF: C20H22N6O3S.

77: CID: 15980347, IUPAC: N-(2-methylaminoethyl)-5-[2-[(4-morpholin-4-ylpyridin-2-yl)amino]-1,3-thiazol-5-yl]pyridine-3-carboxamide, MW: 439.5339|MF: C21H25N7O2S.

78: CID: 15980351, IUPAC: 5-[2-[[4-[4-(2-hydroxyacetyl)piperazin-1-yl]pyridin-2-yl]amino]-1,3-thiazol-5-yl]-N-(2,2,2-trifluoroethyl)pyridine-3-carboxamide, MW: 521.51539|MF: C22H22F3N7O3S.

79: CID: 15982537, IUPAC: (3-chloro-2-fluorophenyl)-[4-[6-[(5-fluoro-1,3-thiazol-2-yl)amino]-5-methylpyridin-2-yl]piperazin-1-yl]methanone, MW: 449.904626|MF: C20H18ClF2N5OS.

80: CID: 16034848, IUPAC: N-(2-chloro-6-methylphenyl)-2-[[6-[4-(2-hydroxyethyl)piperazin-1-yl]-2-methylpyrimidin-4-yl]amino]-1,3-thiazole-5-carboxamide; 2,3-dihydroxybutanedioic acid, MW: 638.09238|MF: C26H32ClN7O8S.

81: CID: 16037977, IUPAC: N-(2-chloro-6-methylphenyl)-2-[[6-[4-(2-hydroxyethyl)piperazin-1-yl]-5-methylpyrimidin-4-yl]amino]-1,3-thiazole-5-carboxamide, MW: 488.00554|MF: C22H26ClN7O2S.

82: CID: 16061431, IUPAC: N-(2-chloro-6-methylphenyl)-2-[[6-[4-(2-hydroxyethyl)piperazin-1-yl]-2-methylpyrimidin-4-yl]amino]-1,3-thiazole-5-carboxamide; 4-[(4-methylpiperazin-1-yl)methyl]-N-[4-methyl-3-[(4-pyridin-3-ylpyrimidin-2-yl)amino]phenyl]benzamide, MW: 981.60828|MF: C51H57ClN14O3S.

83: CID: 16223227, IUPAC: but-2-enedioic acid; N-(2-chloro-6-methylphenyl)-2-[[6-[4-(2-hydroxyethyl)piperazin-1-yl]-2-methylpyrimidin-4-yl]amino]-1,3-thiazole-5-carboxamide, MW: 604.0777|MF: C26H30ClN7O6S.

84: CID: 16223228, IUPAC: N-(2-chloro-6-methylphenyl)-2-[[6-[4-(2-hydroxyethyl)piperazin-1-yl]-2-methylpyrimidin-4-yl]amino]-1,3-thiazole-5-carboxamide hydrobromide, MW: 568.91748|MF: C22H27BrClN7O2S.

85: CID: 16223229, IUPAC: but-2-enedioic acid; N-(2-chloro-6-methylphenyl)-2-[[6-[4-(2-hydroxyethyl)piperazin-1-yl]-2-methylpyrimidin-4-yl]amino]-1,3-thiazole-5-carboxamide, MW: 604.0777|MF: C26H30ClN7O6S.

86: CID: 16223316, IUPAC: N-(2-chloro-6-methylphenyl)-2-[[6-[4-(2-hydroxyethyl)piperazin-1-yl]-2-methylpyrimidin-4-yl]amino]-1,3-thiazole-5-carboxamide; methanesulfonic acid, MW: 584.1112|MF: C23H30ClN7O5S2.

87: CID: 16223317, IUPAC: N-(2-chloro-6-methylphenyl)-2-[[6-[4-(2-hydroxyethyl)piperazin-1-yl]-2-methylpyrimidin-4-yl]amino]-1,3-thiazole-5-carboxamide; phosphoric acid, MW: 586.00072|MF: C22H29ClN7O6PS.

88: CID: 16223318, IUPAC: N-(2-chloro-6-methylphenyl)-2-[[6-[4-(2-hydroxyethyl)piperazin-1-yl]-2-methylpyrimidin-4-yl]amino]-1,3-thiazole-5-carboxamide; 2-hydroxybenzoic acid, MW: 626.12628|MF: C29H32ClN7O5S.

89: CID: 16223319, IUPAC: N-(2-chloro-6-methylphenyl)-2-[[6-[4-(2-hydroxyethyl)piperazin-1-yl]-2-methylpyrimidin-4-yl]amino]-1,3-thiazole-5-carboxamide; sulfuric acid, MW: 586.08402|MF: C22H28ClN7O6S2.

90: CID: 16223320, IUPAC: N-(2-chloro-6-methylphenyl)-2-[[6-[4-(2-hydroxyethyl)piperazin-1-yl]-2-methylpyrimidin-4-yl]amino]-1,3-thiazole-5-carboxamide; 4-methylbenzenesulfonic acid, MW: 660.20716|MF: C29H34ClN7O5S2.

91: CID: 16584134, AKE-PB223730486, IUPAC: N-(4-chlorophenyl)-2-[(4,5-dimethyl-1,3-thiazol-2-yl)amino]-

4-methylpyrimidine-5-carboxamide, MW: 373.85984|MF: C17H16ClN5OS.
92: CID: 16584137, AKE-PB223730492, IUPAC: N-(3-chlorophenyl)-2-[(4,5-dimethyl-1,3-thiazol-2-yl)amino]-4-methylpyrimidine-5-carboxamide, MW: 373.85984|MF: C17H16ClN5OS.
93: CID: 16584139, AKE-PB223730496, IUPAC: 2-[(4,5-dimethyl-1,3-thiazol-2-yl)amino]-4-methyl-N-(2-methylphenyl)pyrimidine-5-carboxamide, MW: 353.44136|MF: C18H19N5OS.
94: CID: 16655683, IUPAC: 2-[(6-chloro-2-methylpyrimidin-4-yl)amino]-N-(2,6-dichlorophenyl)-1,3-thiazole-5-carboxamide, MW: 414.6968|MF: C15H10Cl3N5OS.
95: CID: 16655839, IUPAC: N-(2,6-dichlorophenyl)-2-[[6-[4-(2-hydroxyethyl)piperazin-1-yl]-2-methylpyrimidin-4-yl]amino]-1,3-thiazole-5-carboxamide, MW: 508.42402|MF: C21H23Cl2N7O2S.
96: CID: 16660745, IUPAC: N-(4-fluorophenyl)-4-(2-hydroxyethylamino)-6-methylsulfanyl-2-pyridin-4-ylpyrimidine-5-carboxamide, MW: 399.441923|MF: C19H18FN5O2S.
97: CID: 16660747, IUPAC: N-(4-ethylphenyl)-4-(2-hydroxyethylamino)-6-methylsulfanyl-2-pyridin-4-ylpyrimidine-5-carboxamide, MW: 409.50462|MF: C21H23N5O2S.
98: CID: 16660907, IUPAC: 4-(2-hydroxyethylamino)-N-(4-methylphenyl)-6-methylsulfanyl-2-pyridin-4-ylpyrimidine-5-carboxamide, MW: 395.47804|MF: C20H21N5O2S.
99: CID: 16661063, IUPAC: N-(4-chlorophenyl)-4-(2-hydroxyethylamino)-6-methylsulfanyl-2-pyridin-4-ylpyrimidine-5-carboxamide, MW: 415.89652|MF: C19H18ClN5O2S.
100: CID: 16661212, IUPAC: N-(2,4-dimethylphenyl)-4-(2-hydroxyethylamino)-6-methylsulfanyl-2-pyridin-4-ylpyrimidine-5-carboxamide, MW: 409.50462|MF: C21H23N5O2S.
101: CID: 16661214, IUPAC: 4-(1-hydroxybutan-2-ylamino)-N-(4-methylphenyl)-6-methylsulfanyl-2-pyridin-4-ylpyrimidine-5-carboxamide, MW: 423.5312|MF: C22H25N5O2S.

Herein, CID is the compound identifier as defined in Pubchem.

e) Small molecules targeting and antagonising downstream components of the NEPOR signalling pathway, particularly EPH-B4 tyrosine kinase inhibitors.
f) Combination therapies involving one or more of approaches a-e.

g) The present disclosure also provides a combination therapy. Co-administration of EPO with an intracellular inhibitor of NEPOR signalling (e.g. Dasatinib) is proposed to maintain EPO signalling via EPOR (and thus promote haematopoiesis) while inhibiting survival of NEPOR positive tumour cells.

NEPOR Based Therapeutics to Treat Neuronal Insults

Without being bound by theory, the present disclosure provides that EPO is neuroprotective because of its effects on NEPOR activity, i.e. in particular and/or EPH-B4 and/or Ephrin A1 activity. Therefore, the present disclosure provides a method for treating ischemic stroke, trauma, epilepsy, neurodegenerative diseases, and cognitive dysfunction with an agonistic NEPOR targeted therapy. Specific approaches to positively enhance NEPOR mediated survival signals include:

a) NEPOR specific antibodies. Such antibodies bind and initiate/enhance the mediation of NEPOR's cyto-protective activity.

b) NEPOR specific small-molecules. Such small molecules bind and initiate/enhance the mediation of NEPOR's cytoprotective activity.

c) NEPOR-targeting EPO mutants and glycosylated versions thereof. Due to EPOR's strict conformational requirements for mediating signalling in response to EPO, the following EPOR mutants (SEQ ID NO. 17-SEQ ID NO. 212.) favour binding to NEPOR as opposed to EPOR and thus primarily act as tissue protective.

SEQ ID NO. 17
APPRLICDSRVLERYLLEAKEAENITRVGQQAVEVWQGLALLSEAVLRGQ
ALLVNSSQPWEPLQLHVDKAVSGLRSLTTLLRALGAQKEAISPPDAASAA
PLRTITADTFRKLFRVYSNFLRGKLKLYTGEACRTGDR

SEQ ID NO. 18
APPRLICDSRVLERYLLEAKEAENITTGCAEHCSLNENITVPDTKVNFYA
WKRMEVGQQALLVNSSQPWEPLQLHVDKAVSGLRSLTTLLRALGAQKEAI
SPPDAASAAPLRTITADTFRKLFRVYSNFLRGKLKLYTGEACRTGDR

SEQ ID NO. 19
APPRLICDSRVLERYLLEAKEAENITTGCAEHCSLNENITVPDTKVNFYA
LLVNSSQPWEPLQLHVDKAVSGLRSLTTLLRALGAQKEAISPPDAASAAP
LRTITADTFRKLFRVYSNFLRGKLKLYTGEACRTGDR

SEQ ID NO. 20
APPRLICDSRVLERYLLEAKEAENITTGCAEHCSLNENITVPDTKVNFYA
WKRMEPWEPLQLHVDKAVSGLRSLTTLLRALGAQKEAISPPDAASAAPLR
TITADTFRKLFRVYSNFLRGKLKLYTGEACRTGDR

SEQ ID NO. 21
APPRLICDSRVLERYLLEAKEAENITTGCAEHCSLNENITVPPGVGQLFP
AVGAPAAACG

SEQ ID NO. 22
APPRLICDSRVLERYLLEAKEAENITTGCAEHCSLNENNHC

SEQ ID NO. 23
APPRLICDSRVLERYLLEAKEAENIT

SEQ ID NO. 24
APPRLICDSRVLEAYLLEAKEAENIT

SEQ ID NO. 25
APPRLICDSRVLEEYLLEAKEAENIT

SEQ ID NO. 26
APPRLICDSRVLERYL

SEQ ID NO. 27
APPRLI

SEQ ID NO. 28
APPRLICDSRVLERYILEAKEAENVTMGCAEGPRLSENITVPDTKVNFYA
WKRMEKELMSPPDTTPPAPLRTLTVDTFCKLFRVYANFLRGKLKLYTGEV
CRRGDR

Deletions of hWT 4 EPOR Interaction Sites

SEQ ID NO. 29
APPRLICEAENITTGCAEHCSLNENITVPDTKVNFYAWKRMEVGQQAVEV
WQGLALLSEAVLRGQALLVNSSQPWEPLQLHVDKAVSGLRSLTTLLRALG
AQKEAISPPDAASAAPLRTITADTFRKLFRVYSNFLRGKLKLYTGEACRT
GDR

SEQ ID NO. 30
APPRLICDSRVLERYLLEAKEAENITTGCAEHCSLNENITVPDFYAWKRM
EVGQQAVEVWQGLALLSEAVLRGQALLVNSSQPWEPLQLHVDKAVSGLRS
LTTLLRALGAQKEAISPPDAASAAPLRTITADTFRKLFRVYSNFLRGKLK
LYTGEACRTGDR

SEQ ID NO. 31
APPRLICDSRVLERYLLEAKEAENITTGCAEHCSLNENITVPDTKVNFYA
WKRMEVGQQAVEVWQGLALLSEAVLRGQALLVNSSQPWEPLQLHVDLTTL
LRALGAQKEAISPPDAASAAPLRTITADTFRKLFRVYSNFLRGKLKLYTG
EACRTGDR

```
                                                    SEQ ID NO. 32
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFGKLKLYTG
EACRTGDR
```

C-Term Deletions Beginning at the Last Cysteine Bridge C161

```
                                                    SEQ ID NO. 33
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVYSNFLR
GKLKLYTGEA

SEQ ID NO. 34
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVYSNFLR
GKLKLYTGE

SEQ ID NO. 35
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVYSNFLR
GKLKLYTG

SEQ ID NO. 36
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVYSNFLR
GKLKLYT

SEQ ID NO. 37
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVYSNFLR
GKLKLY

SEQ ID NO. 38
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVYSNFLR
GKLKL

SEQ ID NO. 39
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVYSNFLR
GKLK

SEQ ID NO. 40
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVYSNFLR
GKL

SEQ ID NO. 41
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVYSNFLR
GK

SEQ ID NO. 42
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVYSNFLR
G

SEQ ID NO. 43
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVYSNFLR

SEQ ID NO. 44
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVYSNFL

SEQ ID NO. 45
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVYSNF

SEQ ID NO. 46
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVYSN

SEQ ID NO. 47
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVYS

SEQ ID NO. 48
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVY

SEQ ID NO. 49
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRV

SEQ ID NO. 50
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFR

SEQ ID NO. 51
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLF

SEQ ID NO. 52
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKL

SEQ ID NO. 53
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRK

SEQ ID NO. 54
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFR

SEQ ID NO. 55
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTF

SEQ ID NO. 56
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADT

SEQ ID NO. 57
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITAD

SEQ ID NO. 58
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITA

SEQ ID NO. 59
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTIT

SEQ ID NO. 60
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTI
```

SEQ ID NO. 61
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRT

SEQ ID NO. 62
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLR

SEQ ID NO. 63
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPL

SEQ ID NO. 64
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAP

SEQ ID NO. 65
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAA

SEQ ID NO. 66
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASA

SEQ ID NO. 67
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAAS

SEQ ID NO. 68
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAA

SEQ ID NO. 69
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDA

SEQ ID NO. 70
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPD

SEQ ID NO. 71
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPP

SEQ ID NO. 72
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISP

SEQ ID NO. 73
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAIS

SEQ ID NO. 74
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAI

SEQ ID NO. 75
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEA

SEQ ID NO. 76
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKE

SEQ ID NO. 77
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQK

SEQ ID NO. 78
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQ

SEQ ID NO. 79
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGA

SEQ ID NO. 80
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALG

SEQ ID NO. 81
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRAL

SEQ ID NO. 82
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRA

SEQ ID NO. 83
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLR

SEQ ID NO. 84
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLL

SEQ ID NO. 85
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTL

SEQ ID NO. 86
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTT

SEQ ID NO. 87
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLT

SEQ ID NO. 88
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSL

SEQ ID NO. 89
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRS

SEQ ID NO. 90
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLR

SEQ ID NO. 91
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GL

SEQ ID NO. 92
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
G

SEQ ID NO. 93
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS

SEQ ID NO. 94
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAV

SEQ ID NO. 95
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKA

SEQ ID NO. 96
APPRLICDSRVLERYLLEAKEAENITTGCAEHCSLNENITVPDTKVNFYA
WKRMEVGQQAVEVWQGLALLSEAVLRGQALLVNSSQPWEPLQLHVDK

SEQ ID NO. 97
APPRLICDSRVLERYLLEAKEAENITTGCAEHCSLNENITVPDTKVNFYA
WKRMEVGQQAVEVWQGLALLSEAVLRGQALLVNSSQPWEPLQLHVD

SEQ ID NO. 98
APPRLICDSRVLERYLLEAKEAENITTGCAEHCSLNENITVPDTKVNFYA
WKRMEVGQQAVEVWQGLALLSEAVLRGQALLVNSSQPWEPLQLHV

SEQ ID NO. 99
APPRLICDSRVLERYLLEAKEAENITTGCAEHCSLNENITVPDTKVNFYA
WKRMEVGQQAVEVWQGLALLSEAVLRGQALLVNSSQPWEPLQLH

SEQ ID NO. 100
APPRLICDSRVLERYLLEAKEAENITTGCAEHCSLNENITVPDTKVNFYA
WKRMEVGQQAVEVWQGLALLSEAVLRGQALLVNSSQPWEPLQL

SEQ ID NO. 101
APPRLICDSRVLERYLLEAKEAENITTGCAEHCSLNENITVPDTKVNFYA
WKRMEVGQQAVEVWQGLALLSEAVLRGQALLVNSSQPWEPLQ

SEQ ID NO. 102
APPRLICDSRVLERYLLEAKEAENITTGCAEHCSLNENITVPDTKVNFYA
WKRMEVGQQAVEVWQGLALLSEAVLRGQALLVNSSQPWEPL

SEQ ID NO. 103
APPRLICDSRVLERYLLEAKEAENITTGCAEHCSLNENITVPDTKVNFYA
WKRMEVGQQAVEVWQGLALLSEAVLRGQALLVNSSQPWEP

SEQ ID NO. 104
APPRLICDSRVLERYLLEAKEAENITTGCAEHCSLNENITVPDTKVNFYA
WKRMEVGQQAVEVWQGLALLSEAVLRGQALLVNSSQPWE

SEQ ID NO. 105
APPRLICDSRVLERYLLEAKEAENITTGCAEHCSLNENITVPDTKVNFYA
WKRMEVGQQAVEVWQGLALLSEAVLRGQALLVNSSQPW

SEQ ID NO. 106
APPRLICDSRVLERYLLEAKEAENITTGCAEHCSLNENITVPDTKVNFYA
WKRMEVGQQAVEVWQGLALLSEAVLRGQALLVNSSQP

SEQ ID NO. 107
APPRLICDSRVLERYLLEAKEAENITTGCAEHCSLNENITVPDTKVNFYA
WKRMEVGQQAVEVWQGLALLSEAVLRGQALLVNSSQ

SEQ ID NO. 108
APPRLICDSRVLERYLLEAKEAENITTGCAEHCSLNENITVPDTKVNFYA
WKRMEVGQQAVEVWQGLALLSEAVLRGQALLVNSS

SEQ ID NO. 109
APPRLICDSRVLERYLLEAKEAENITTGCAEHCSLNENITVPDTKVNFYA
WKRMEVGQQAVEVWQGLALLSEAVLRGQALLVNS

SEQ ID NO. 110
APPRLICDSRVLERYLLEAKEAENITTGCAEHCSLNENITVPDTKVNFYA
WKRMEVGQQAVEVWQGLALLSEAVLRGQALLVN

SEQ ID NO. 111
APPRLICDSRVLERYLLEAKEAENITTGCAEHCSLNENITVPDTKVNFYA
WKRMEVGQQAVEVWQGLALLSEAVLRGQALLV

SEQ ID NO. 112
APPRLICDSRVLERYLLEAKEAENITTGCAEHCSLNENITVPDTKVNFYA
WKRMEVGQQAVEVWQGLALLSEAVLRGQALL

SEQ ID NO. 113
APPRLICDSRVLERYLLEAKEAENITTGCAEHCSLNENITVPDTKVNFYA
WKRMEVGQQAVEVWQGLALLSEAVLRGQAL

SEQ ID NO. 114
APPRLICDSRVLERYLLEAKEAENITTGCAEHCSLNENITVPDTKVNFYA
WKRMEVGQQAVEVWQGLALLSEAVLRGQA

SEQ ID NO. 115
APPRLICDSRVLERYLLEAKEAENITTGCAEHCSLNENITVPDTKVNFYA
WKRMEVGQQAVEVWQGLALLSEAVLRGQ

SEQ ID NO. 116
APPRLICDSRVLERYLLEAKEAENITTGCAEHCSLNENITVPDTKVNFYA
WKRMEVGQQAVEVWQGLALLSEAVLRG

SEQ ID NO. 117
APPRLICDSRVLERYLLEAKEAENITTGCAEHCSLNENITVPDTKVNFYA
WKRMEVGQQAVEVWQGLALLSEAVLR

SEQ ID NO. 118
APPRLICDSRVLERYLLEAKEAENITTGCAEHCSLNENITVPDTKVNFYA
WKRMEVGQQAVEVWQGLALLSEAVL

SEQ ID NO. 119
APPRLICDSRVLERYLLEAKEAENITTGCAEHCSLNENITVPDTKVNFYA
WKRMEVGQQAVEVWQGLALLSEAV

SEQ ID NO. 120
APPRLICDSRVLERYLLEAKEAENITTGCAEHCSLNENITVPDTKVNFYA
WKRMEVGQQAVEVWQGLALLSEA

SEQ ID NO. 121
APPRLICDSRVLERYLLEAKEAENITTGCAEHCSLNENITVPDTKVNFYA
WKRMEVGQQAVEVWQGLALLSE

SEQ ID NO. 122
APPRLICDSRVLERYLLEAKEAENITTGCAEHCSLNENITVPDTKVNFYA
WKRMEVGQQAVEVWQGLALLS

SEQ ID NO. 123
APPRLICDSRVLERYLLEAKEAENITTGCAEHCSLNENITVPDTKVNFYA
WKRMEVGQQAVEVWQGLALL

SEQ ID NO. 124
APPRLICDSRVLERYLLEAKEAENITTGCAEHCSLNENITVPDTKVNFYA
WKRMEVGQQAVEVWQGLAL

SEQ ID NO. 125
APPRLICDSRVLERYLLEAKEAENITTGCAEHCSLNENITVPDTKVNFYA
WKRMEVGQQAVEVWQGLA

SEQ ID NO. 126
APPRLICDSRVLERYLLEAKEAENITTGCAEHCSLNENITVPDTKVNFYA
WKRMEVGQQAVEVWQGL

SEQ ID NO. 127
APPRLICDSRVLERYLLEAKEAENITTGCAEHCSLNENITVPDTKVNFYA
WKRMEVGQQAVEVWQG

SEQ ID NO. 128
APPRLICDSRVLERYLLEAKEAENITTGCAEHCSLNENITVPDTKVNFYA
WKRMEVGQQAVEVWQ

SEQ ID NO. 129
APPRLICDSRVLERYLLEAKEAENITTGCAEHCSLNENITVPDTKVNFYA
WKRMEVGQQAVEVW

SEQ ID NO. 130
APPRLICDSRVLERYLLEAKEAENITTGCAEHCSLNENITVPDTKVNFYA
WKRMEVGQQAVEV

SEQ ID NO. 131
APPRLICDSRVLERYLLEAKEAENITTGCAEHCSLNENITVPDTKVNFYA
WKRMEVGQQAVE

SEQ ID NO. 132
APPRLICDSRVLERYLLEAKEAENITTGCAEHCSLNENITVPDTKVNFYA
WKRMEVGQQAV

-continued

SEQ ID NO. 133
APPRLICDSRVLERYLLEAKEAENITTGCAEHCSLNENITVPDTKVNFYAWKRMEVGQQA

SEQ ID NO. 134
APPRLICDSRVLERYLLEAKEAENITTGCAEHCSLNENITVPDTKVNFYAWKRMEVGQQ

SEQ ID NO. 135
APPRLICDSRVLERYLLEAKEAENITTGCAEHCSLNENITVPDTKVNFYAWKRMEVGQ

SEQ ID NO. 136
APPRLICDSRVLERYLLEAKEAENITTGCAEHCSLNENITVPDTKVNFYAWKRMEVG

SEQ ID NO. 137
APPRLICDSRVLERYLLEAKEAENITTGCAEHCSLNENITVPDTKVNFYAWKRMEV

SEQ ID NO. 138
APPRLICDSRVLERYLLEAKEAENITTGCAEHCSLNENITVPDTKVNFYAWKRME

SEQ ID NO. 139
APPRLICDSRVLERYLLEAKEAENITTGCAEHCSLNENITVPDTKVNFYAWKRM

SEQ ID NO. 140
APPRLICDSRVLERYLLEAKEAENITTGCAEHCSLNENITVPDTKVNFYAWKR

SEQ ID NO. 141
APPRLICDSRVLERYLLEAKEAENITTGCAEHCSLNENITVPDTKVNFYAWK

SEQ ID NO. 142
APPRLICDSRVLERYLLEAKEAENITTGCAEHCSLNENITVPDTKVNFYAW

SEQ ID NO. 143
APPRLICDSRVLERYLLEAKEAENITTGCAEHCSLNENITVPDTKVNFYA

SEQ ID NO. 144
APPRLICDSRVLERYLLEAKEAENITTGCAEHCSLNENITVPDTKVNFY

SEQ ID NO. 145
APPRLICDSRVLERYLLEAKEAENITTGCAEHCSLNENITVPDTKVNF

SEQ ID NO. 146
APPRLICDSRVLERYLLEAKEAENITTGCAEHCSLNENITVPDTKVN

SEQ ID NO. 147
APPRLICDSRVLERYLLEAKEAENITTGCAEHCSLNENITVPDTKV

SEQ ID NO. 148
APPRLICDSRVLERYLLEAKEAENITTGCAEHCSLNENITVPDTK

SEQ ID NO. 149
APPRLICDSRVLERYLLEAKEAENITTGCAEHCSLNENITVPDT

SEQ ID NO. 150
APPRLICDSRVLERYLLEAKEAENITTGCAEHCSLNENITVPD

SEQ ID NO. 151
APPRLICDSRVLERYLLEAKEAENITTGCAEHCSLNENITVP

SEQ ID NO. 152
APPRLICDSRVLERYLLEAKEAENITTGCAEHCSLNENITV

SEQ ID NO. 153
APPRLICDSRVLERYLLEAKEAENITTGCAEHCSLNENIT

SEQ ID NO. 154
APPRLICDSRVLERYLLEAKEAENITTGCAEHCSLNENI

SEQ ID NO. 155
APPRLICDSRVLERYLLEAKEAENITTGCAEHCSLNEN

SEQ ID NO. 156
APPRLICDSRVLERYLLEAKEAENITTGCAEHCSLNE

-continued

SEQ ID NO. 157
APPRLICDSRVLERYLLEAKEAENITTGCAEHCSLN

SEQ ID NO. 158
APPRLICDSRVLERYLLEAKEAENITTGCAEHCSL

SEQ ID NO. 159
APPRLICDSRVLERYLLEAKEAENITTGCAEHCS

SEQ ID NO. 160
APPRLICDSRVLERYLLEAKEAENITTGCAEHC

SEQ ID NO. 161
APPRLICDSRVLERYLLEAKEAENITTGCAEH

SEQ ID NO. 162
APPRLICDSRVLERYLLEAKEAENITTGCAE

SEQ ID NO. 163
APPRLICDSRVLERYLLEAKEAENITTGCA

SEQ ID NO. 164
APPRLICDSRVLERYLLEAKEAENITTGC

SEQ ID NO. 165
APPRLICDSRVLERYLLEAKEAENITTG

SEQ ID NO. 166
APPRLICDSRVLERYLLEAKEAENITT

SEQ ID NO. 167
APPRLICDSRVLERYLLEAKEAENIT

SEQ ID NO. 168
APPRLICDSRVLERYLLEAKEAENI

SEQ ID NO. 169
APPRLICDSRVLERYLLEAKEAEN

SEQ ID NO. 170
APPRLICDSRVLERYLLEAKEAE

SEQ ID NO. 171
APPRLICDSRVLERYLLEAKEA

SEQ ID NO. 172
APPRLICDSRVLERYLLEAKE

SEQ ID NO. 173
APPRLICDSRVLERYLLEAK

SEQ ID NO. 174
APPRLICDSRVLERYLLEA

SEQ ID NO. 175
APPRLICDSRVLERYLLE

SEQ ID NO. 176
APPRLICDSRVLERYLL

SEQ ID NO. 177
APPRLICDSRVLERYL

SEQ ID NO. 178
APPRLICDSRVLERY

SEQ ID NO. 179
APPRLICDSRVLER

SEQ ID NO. 180
APPRLICDSRVLE

SEQ ID NO. 181
APPRLICDSRVL

SEQ ID NO. 182
APPRLICDSRV

SEQ ID NO. 183
APPRLICDSR

```
                                    SEQ ID NO. 184
APPRLICDS

SEQ ID NO. 185
APPRLICD

SEQ ID NO. 186
APPRLIC
```

Single Amino Acid Mutations (Ala/Conversions) and all combinations/permutations thereof and all glycosylated versions of same. All possible combinations/permutations of mutations contained in Single mutations of SEQ ID NOs. 187-208 and glycosylated versions thereof.

```
                                    SEQ ID NO. 187
APPRLICASRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVYSNFLR
GKLKLYTGEACRTGDR

SEQ ID NO. 188
APPRLICRSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVYSNFLR
GKLKLYTGEACRTGDR

SEQ ID NO. 189
APPRLICDSRVLEAYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVYSNFLR
GKLKLYTGEACRTGDR

SEQ ID NO. 190
APPRLICDSRVLEEYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVYSNFLR
GKLKLYTGEACRTGDR

SEQ ID NO. 191
APPRLICDSRVLERYLLEAAEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVYSNFLR
GKLKLYTGEACRTGDR

SEQ ID NO. 192
APPRLICDSRVLERYLLEAEEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVYSNFLR
GKLKLYTGEACRTGDR

SEQ ID NO. 193
APPRLICDSRVLERYLLEAKEAENITTGCAEHCSLNENITVPDAKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVYSNFLR
GKLKLYTGEACRTGDR

SEQ ID NO. 194
APPRLICDSRVLERYLLEAKEAENITTGCAEHCSLNENITVPDTAVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVYSNFLR
GKLKLYTGEACRTGDR

SEQ ID NO. 195
APPRLICDSRVLERYLLEAKEAENITTGCAEHCSLNENITVPDTEVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVYSNFLR
GKLKLYTGEACRTGDR

SEQ ID NO. 196
APPRLICDSRVLERYLLEAKEAENITTGCAEHCSLNENITVPDTKANFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVYSNFLR
GKLKLYTGEACRTGDR

SEQ ID NO. 197
APPRLICDSRVLERYLLEAKEAENITTGCAEHCSLNENITVPDTKVAFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVYSNFLR
GKLKLYTGEACRTGDR

SEQ ID NO. 198
APPRLICDSRVLERYLLEAKEAENITTGCAEHCSLNENITVPDTKVNFYA
WKRMEVGQQAVEVWQGLALLSEAVLRGQALLVNSSQPWEPLQLHVDAAVS
GLRSLTTLLRALGAQKEAISPPDAASAAPLRTITADTFRKLFRVYSNFLR
GKLKLYTGEACRTGDR

SEQ ID NO. 199
APPRLICDSRVLERYLLEAKEAENITTGCAEHCSLNENITVPDTKVNFYA
WKRMEVGQQAVEVWQGLALLSEAVLRGQALLVNSSQPWEPLQLHVDEAVS
GLRSLTTLLRALGAQKEAISPPDAASAAPLRTITADTFRKLFRVYSNFLR
GKLKLYTGEACRTGDR

SEQ ID NO. 200
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVA
GLRSLTTLLRALGAQKEAISPPDAASAAPLRTITADTFRKLFRVYSNFLR
GKLKLYTGEACRTGDR

SEQ ID NO. 201
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLASLTTLLRALGAQKEAISPPDAASAAPLRTITADTFRKLFRVYSNFLR
GKLKLYTGEACRTGDR

SEQ ID NO. 202
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLESLTTLLRALGAQKEAISPPDAASAAPLRTITADTFRKLFRVYSNFLR
GKLKLYTGEACRTGDR

SEQ ID NO. 203
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRALTTLLRALGAQKEAISPPDAASAAPLRTITADTFRKLFRVYSNFLR
GKLKLYTGEACRTGDR

SEQ ID NO. 204
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFAVYSNFLR
GKLKLYTGEACRTGDR

SEQ ID NO. 205
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFEVYSNFLR
GKLKLYTGEACRTGDR

SEQ ID NO. 206
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVYSAFLR
GKLKLYTGEACRTGDR

SEQ ID NO. 207
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVYSNFLA
GKLKLYTGEACRTGDR

SEQ ID NO. 208
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVYSNFLE
GKLKLYTGEACRTGDR
```

EPO Peptides Overlapping Interaction Regions

```
                                    SEQ ID NO. 209
APPRLICDSRVLERYLLEAKEAENITT
```

-continued

```
                                              SEQ ID NO. 210
NENITVPDTKVNFYAWKRMEV

SEQ ID NO. 211
NSSQPWEPLQLHVDKAVSGLRSLTTLL

SEQ ID NO. 212
FRKLFRVYSNFLRGKLKL
``` d) NEPOR-targeting EPO chimera's. Such mutants bind and initiate/enhance the mediation of NEPOR's cytoprotective activity. For example, in a scenario where NEPOR constitutes an Ephrin A1 molecule (either as a homodimer or in heterodimeric association with EPOR), then chimeric proteins involving fusions of part of EPH-B4's Ephrin-ligand-binding domain and part of the EPO molecule may be developed as optimised binding partners. This implies fusing an N-terminal portion of EPO (derived from SEQ ID NO. 213) to a C-terminal portion of EPH-B4's Ephrin ligand binding domain (SEQ ID NO. 214), giving a sequence similar to SEQ ID NO. 215, or fusing an N-terminal portion of EPH-B4's Ephrin ligand binding domain (derived from SEQ ID NO. 214) to a C-terminal portion of EPO (SEQ ID NO. 213), giving a sequence similar to SEQ ID NO. 216.

e) high-affinity peptides which specifically target NEPOR to initiate/enhance the mediation of EPO's cytoprotective activity.

f) Small molecules targeting and enhancing the activity of downstream components of NEPOR.

g) Combination therapies involving one or more of approaches a-f.

```
>P01588|EPO_HUMAN Erythropoietin - Homo sapiens
(Human).
                                              SEQ ID NO. 213
MGVHECPAWLWLLLSLLSLPLGLPVLGAPPRLICDSRVLERYLLEAKEAE
NITTGCAEHCSLNENITVPDTKVNFYAWKRMEVGQQAVEVWQGLALLSEA
VLRGQALLVNSSQPWEPLQLHVDKAVSGLRSLTTLLRALGAQKEAISPPD
AASAAPLRTITADTFRKLFRVYSNFLRGKLKLYTGEACRTGDR >EPH-B4_ephrin_ligand_binding_domain
                                              SEQ ID NO. 214
EETLLNTKLETADLKWVTFPQVDGQWEELSGLDEEQHSVRTYEVCDVQRA
PGQAHWLRTGWVPRRGAVHVYATLRFTMLECLSLPRAGRSCKETFTVFYY
ESDADTATALTPAWMENPYIKVDTVAAEHLTRKRPGAEATGKVNVKTLRL
GPLSKAGFYLAFQDQGACMALLSLHLFYKKC >NtermEPO_CtermEPHB4LBD
                                              SEQ ID NO. 215
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASALTPAWMENPYIKVDTVAAEHLTR
KRPGAEATGKVNVKTLRLGPLSKAGFYLAFQDQGACMALLSLHLFYKKC >NtermEPHB4LBD_CtermEPO
                                              SEQ ID NO. 216
EETLLNTKLETADLKWVTFPQVDGQWEELSGLDEEQHSVRTYEVCDVQRA
PGQAHWLRTGWVPRRGAVHVYATLRFTMLECLSLPRAGRSCKETFTVFYY
ESDADTATALSEAVLRGQALLVNSSQPWEPLQLHVDKAVSGLRSLTTLLR
ALGAQKEAISPPDAASAAPLRTITADTFRKLFRVYSNFLRGKLKLYTGEA
CRTGDR
```

Compounds in Combination with EPO

Such compounds, in combination with EPO, inhibit EPH-B4's tyrosine kinase activity while permitting EPOR mediated signalling/haematopoiesis. The following 101 compounds, either alone or in combination, inhibit the tyrosine kinase activity of EPH-B4 containing NEPOR dimers. Therefore, the present disclosure provides a combination therapeutic agent of a tyrosine kinase inhibitor in combination with EPO to provide the hematopoietic properties of EPO along with the prevention of NEPOR signalling so as to block the potentially fatal side effect of EPO to promote tumour survival and angiogenesis.

1: CID: 1095868, AKI-STT-00166305; ZINC00818264; BAS 09636496 IUPAC: N-[5-[(3-chlorophenyl)methyl]-1,3-thiazol-2-yl]-2-(4,6-dimethylpyrimidin-2-yl)sulfanylacetamide. MW: 404.93678|MF: C18H17ClN4OS2. (MW is molecular weight and MF is molecular formula).

2: CID: 1465558, IUPAC: 2-[(3-chlorobenzoyl)amino]-4-methyl-N-pyridin-3-yl-1,3-thiazole-5-carboxamide, MW: 372.82872|MF: C17H13ClN4O2S.

3: CID: 1468201, IUPAC: N-[5-[(2-chlorophenyl)carbamoyl]-4-methyl-1,3-thiazol-2-yl]pyridine-4-carboxamide, MW: 372.82872|MF: C17H13ClN4O2S.

4: CID: 3062316, Dasatinib; Sprycel; BMS Dasatinib, IUPAC: N-(2-chloro-6-methylphenyl)-2-[[6-[4-(2-hydroxyethyl)piperazin-1-yl]-2-methylpyrimidin-4-yl]amino]-1,3-thiazole-5-carboxamide, MW: 488.00554|MF: C22H26ClN7O2S.

5: CID: 3072360, 142287-40-9; Pyrimido(4,5-d)pyrimidin-4(1H)-one, 7-methyl-1-phenyl-2-((3-(4-(2-thiazolyl)-1-piperazinyl)propyl)thio)-IUPAC: 2-methyl-8-phenyl-7-[3-[4-(1,3-thiazol-2-yl)piperazin-1-yl]propylsulfanyl]pyrimido[6,5-d]pyrimidin-5-one, MW: 479.6209|MF: C23H25N7OS2.

6: CID: 5041467, STK154706; ZINC04687922, IUPAC: [2-[(2-methylphenyl)amino]-1,3-thiazol-4-yl]-(4-pyrimidin-2-ylpiperazin-1-yl)methanone, MW: 380.4667|MF: C19H20N6OS.

7: CID: 9822929, IUPAC: N-(2-chloro-6-methylphenyl)-2-[(6-imidazol-1-ylpyridazin-3-yl)amino]-1,3-thiazole-5-carboxamide, MW: 411.869|MF: C18H14ClN7OS.

8: CID: 9927718, IUPAC: N-(2-chloro-6-methylphenyl)-2-(cyclopropanecarbonylamino)-1,3-thiazole-5-carboxamide, MW: 335.809|MF: C15H14ClN3O2S.

9: CID: 10006113, IUPAC: N-[4-chloro-2-[(5-chloropyridin-2-yl)carbamoyl]phenyl]-5-methyl-6,7-dihydro-4H-[1,3]thiazolo[5,4-c]pyridine-2-carboxamide hydrochloride, MW: 498.81322|MF: C20H18Cl3N5O2S.

10: CID: 10006114, IUPAC: N-[4-chloro-2-[(5-chloropyridin-2-yl)carbamoyl]phenyl]-5-methyl-6,7-dihydro-4H-[1,3]thiazolo[5,4-c]pyridine-2-carboxamide, MW: 462.35228|MF: C20H17Cl2N5O2S.

11: CID: 10052635, IUPAC: 2-[[2-methyl-5-[[6-[(4-methylpiperazin-1-yl)methyl]pyridin-2-yl]amino]phenyl]amino]-N-(2-methylphenyl)-1,3-thiazole-5-carboxamide, MW: 527.68362|MF: C29H33N7OS.

12: CID: 10195898, IUPAC: N-[(4-chlorophenyl)methyl]-2-[[[(2S)-2-hydroxy-2-pyrimidin-2-ylethyl]-methylamino]methyl]-4-methyl-7-oxothieno[2,3-e]pyridine-6-carboxamide, MW: 497.99706|MF: C24H24ClN5O3S.

13: CID: 10206276, IUPAC: N-[4-[(5-chloropyridin-2-yl)carbamoyl]-2-phenyl-1,3-thiazol-5-yl]-1-propan-2-ylpiperidine-4-carboxamide, MW: 484.01354|MF: C24H26ClN5O2S.

14: CID: 10252208, IUPAC: 2-[4-(5-amino-1,3-thiazol-2-yl)phenyl]-3-(5-chloropyridin-2-yl)quinazolin-4-one, MW: 431.89746|MF: C22H14ClN5OS.

15: CID: 10253695, IUPAC: 2-[4-[3-(5-chloropyridin-2-yl)-4-oxoquinazolin-2-yl]phenyl]-1,3-thiazole-5-carboxamide, MW: 459.90756|MF: C23H14ClN5O2S.

16: CID: 10301604, IUPAC: N-[4-[(5-chloropyridin-2-yl)carbamoyl]-2-(3,4-difluorophenyl)-1,3-thiazol-5-yl]-1-propan-2-ylpiperidine-4-carboxamide, MW: 519.99446|MF: C24H24ClF2N5O2S.

17: CID: 10344807, IUPAC: N-[2-[4-[3-(5-chloropyridin-2-yl)-4-oxoquinazolin-2-yl]phenyl]-1,3-thiazol-4-yl]acetamide, MW: 473.93414|MF: C24H16ClN5O2S.

18: CID: 10368624, IUPAC: N-[(4-chlorophenyl)methyl]-2-[[(2-hydroxy-2-pyrimidin-2-ylethyl)-methylamino]methyl]-7-methyl-4-oxothieno[3,2-e]pyridine-5-carboxamide, MW: 497.99706|MF: C24H24ClN5O3S.

19: CID: 10370949, IUPAC: (3Z)-4-[[(2S)-2-(3-chlorophenyl)-2-hydroxyethyl]amino]-3-[6-methyl-2-[4-(1,3-thiazol-2-ylmethyl)piperazin-1-yl]-7,9-dihydropurin-8-ylidene]pyridin-2-one, MW: 578.08832|MF: C27H28ClN9O2S.

20: CID: 10412586, IUPAC: N-[2-[4-[3-(5-chloropyridin-2-yl)-4-oxoquinazolin-2-yl]phenyl]-1,3-thiazol-5-yl]acetamide, MW: 473.93414|MF: C24H16ClN5O2S.

21: CID: 10413555, IUPAC: N-[(4-chlorophenyl)methyl]-2-[[[(2R)-2-hydroxy-2-pyrimidin-2-ylethyl]-methylamino]methyl]-7-methyl-4-oxothieno[3,2-e]pyridine-5-carboxamide, MW: 497.99706|MF: C24H24ClN5O3S.

22: CID: 10456156, IUPAC: 4-[(3-chlorothiophen-2-yl)methylamino]-2-[(4-morpholin-4-ylphenyl)amino]pyrimidine-5-carboxamide, MW: 444.93774|MF: C20H21ClN6O2S.

23: CID: 10458706, IUPAC: N-[5-[2-[(4-chlorophenyl)amino]pyrimidin-4-yl]-4-methyl-1,3-thiazol-2-yl]-3-(2-morpholin-4-ylethylamino)propanamide, MW: 502.03212|MF: C23H28ClN7O2S.

24: CID: 11153014, IUPAC: N-(2-chloro-6-methylphenyl)-2-[(2,6-dimethylpyrimidin-4-yl)amino]-1,3-thiazole-5-carboxamide, MW: 373.85984|MF: C17H16ClN5OS.

25: CID: 11167695, IUPAC: N-(2-chloro-6-methylphenyl)-2-[[2-methyl-6-(2-morpholin-4-ylethylamino)pyrimidin-4-yl]amino]-1,3-thiazole-5-carboxamide, MW: 488.00554|MF: C22H26ClN7O2S.

26: CID: 11168231, IUPAC: N-(2-chloro-6-methylphenyl)-2-[(6-chloro-2-methylpyrimidin-4-yl)amino]-N-[(4-methoxyphenyl)methyl]-1,3-thiazole-5-carboxamide, MW: 514.42684|MF: C24H21Cl2N5O2S.

27: CID: 11200510, IUPAC: N-(2-chloro-6-methylphenyl)-2-[[6-(2-hydroxyethylamino)pyridin-2-yl]amino]-1,3-thiazole-5-carboxamide, MW: 403.88582|MF: C18H18ClN5O2S.

28: CID: 11247793, IUPAC: N-(2-chloro-6-methylphenyl)-2-[[6-(methyl-(3-methylaminopropyl)amino)pyridin-2-yl]amino]-1,3-thiazole-5-carboxamide, MW: 444.9808|MF: C21H25ClN6OS.

29: CID: 11260009, IUPAC: N-(2-chloro-6-methylphenyl)-2-[[6-[4-(hydroxymethyl)piperidin-1-yl]-2-methylpyrimidin-4-yl]amino]-1,3-thiazole-5-carboxamide, MW: 472.9909|MF: C22H25ClN6O2S.

30: CID: 11269410, IUPAC: N-(2-chloro-6-methylphenyl)-2-[(6-chloro-2-methylpyrimidin-4-yl)amino]-1,3-thiazole-5-carboxamide, MW: 394.27832|MF: C16H13Cl2N5OS.

31: CID: 11282881, IUPAC: N-(2-chloro-6-methylphenyl)-2-[[6-(2-morpholin-4-ylethylamino)pyrimidin-4-yl]amino]-1,3-thiazole-5-carboxamide, MW: 473.97896|MF: C21H24ClN7O2S.

32: CID: 11283174, IUPAC: N-(2-chloro-6-methylphenyl)-2-[[6-(3-morpholin-4-ylpropylamino)pyridin-2-yl]amino]-1,3-thiazole-5-carboxamide, MW: 487.01748|MF: C23H27ClN6O2S.

33: CID: 11328827, IUPAC: N-(2-chloro-6-methylphenyl)-2-[[6-(3-imidazol-1-ylpropylamino)pyridin-2-yl]amino]-1,3-thiazole-5-carboxamide, MW: 467.97438|MF: C22H22ClN7OS.

34: CID: 11407465, IUPAC: N-(2-chloro-6-methylphenyl)-2-[[6-(2-hydroxyethylamino)-2-methylpyrimidin-4-yl]amino]-1,3-thiazole-5-carboxamide, MW: 418.90046|MF: C18H19ClN6O2S.

35: CID: 11466196, IUPAC: N-(2-chloro-6-methylphenyl)-2-[[2-methyl-6-(3-morpholin-4-ylpropylamino)pyrimidin-4-yl]amino]-1,3-thiazole-5-carboxamide. MW: 502.03212|MF: C23H28ClN7O2S.

36: CID: 11466607, IUPAC: N-(2-chloro-6-methylphenyl)-2-[[6-[4-(2-hydroxyethyl)piperazin-1-yl]-2-methylpyrimidin-4-yl]amino]-1,3-thiazole-5-carboxamide hydrochloride, MW: 524.46648|MF: C22H27Cl2N7O2S.

37: CID: 11487256, IUPAC: N-(2-chloro-6-methylphenyl)-2-[(6-morpholin-4-ylpyrimidin-4-yl)amino]-1,3-thiazole-5-carboxamide, MW: 430.91116|MF: C19H19ClN6O2S.

38: CID: 11505502, IUPAC: 2-[[6-[4-(2-hydroxyethyl)piperazin-1-yl]pyrimidin-4-yl]amino]-N-[2-methyl-5-[[3-(trifluoromethyl)benzoyl]amino]phenyl]-1,3-thiazole-5-carboxamide. MW: 626.65257|MF: C29H29F3N8O3S.

39: CID: 11512538, IUPAC: 2-[4-[6-[[5-[(2-chloro-6-methylphenyl)carbamoyl]-1,3-thiazol-2-yl]amino]-2-methylpyrimidin-4-yl]piperazin-1-yl]ethyl 2,2-dimethylpropanoate, MW: 572.12196|MF: C27H34ClN7O3S.

40: CID: 11539665, IUPAC: (3-chloro-2-fluorophenyl)-[4-[[6-[(5-fluoro-1,3-thiazol-2-yl)amino]pyridin-2-yl]methyl]piperazin-1-yl]methanone, MW: 449.904626|MF: C20H18ClF2N5OS.

41: CID: 11540687, IUPAC: N-(2-chloro-6-methylphenyl)-2-[[6-[4-(2-hydroxyethyl)piperazin-1-yl]-2-methylpyrimidin-4-yl]amino]-1,3-thiazole-5-carboxamide hydrate, MW: 506.02082|MF: C22H28ClN7O3S.

42: CID: 11569328, IUPAC: N-(2-chloro-6-methylphenyl)-2-[[3-[4-(2-hydroxyethyl)piperazin-1-yl]-5-methylphenyl]amino]-1,3-thiazole-5-carboxamide, MW: 486.02942|MF: C24H28ClN5O2S.

43: CID: 11570976, IUPAC: 2-[[6-[4-(2-hydroxyethyl)piperazin-1-yl]-2-methylpyrimidin-4-yl]amino]-N-[2-methyl-5-[[3-(trifluoromethyl)phenyl]carbamoyl]phenyl]-1,3-thiazole-5-carboxamide, MW: 640.67915|MF: C30H31F3N8O3S.

44: CID: 11577776, IUPAC: 2-[[6-(2-hydroxyethylamino)-2-methylpyrimidin-4-yl]amino]-N-[2-methyl-5-[[3-(trifluoromethyl)benzoyl]amino]phenyl]-1,3-thiazole-5-carboxamide, MW: 571.57407|MF: C26H24F3N7O3S.

45: CID: 11590089, IUPAC: (3-chloro-2-fluorophenyl)-[4-[5-methyl-6-(1,3-thiazol-2-ylamino)pyridin-2-yl]piperazin-1-yl]methanone, MW: 431.914163|MF: C20H19ClFN5OS.

46: CID: 11606973, IUPAC: N-[5-[[3-[4-(2-hydroxyethyl)piperazin-1-yl]-5-(trifluoromethyl)benzoyl]amino]-2-methylphenyl]-2-(pyridin-2-ylamino)-1,3-thiazole-5-carboxamide, MW: 625.66451|MF: C30H30F3N7O3S.

47: CID: 11650098, IUPAC: 2-[[6-(4-methylpiperazin-1-yl)pyrimidin-4-yl]amino]-N-[2-methyl-5-[[3-(trifluoromethyl)benzoyl]amino]phenyl]-1,3-thiazole-5-carboxamide, MW: 596.62659|MF: C28H27F3N8O2S.

48: CID: 11650132, IUPAC: pentyl N-[5-[(2-chloro-6-methylphenyl)carbamoyl]-1,3-thiazol-2-yl]-N-[6-[4-(2-hydroxyethyl)piperazin-1-yl]-2-methylpyrimidin-4-yl]carbamate, MW: 602.14794|MF: C28H36ClN7O4S.

49: CID: 11650511, IUPAC: N-[5-[[3-(4-ethylpiperazin-1-yl)-5-(trifluoromethyl)benzoyl]amino]-2-methylphenyl]-2-[[6-(2-hydroxyethylamino)-2-methylpyrimidin-4-yl]amino]-1,3-thiazole-5-carboxamide, MW: 683.74695|MF: C32H36F3N9O3S.

50: CID: 11664355, IUPAC: 2-[(2-methyl-6-motpholin-4-ylpyrimidin-4-yl)amino]-N-[2-methyl-5-[[3-(trifluoromethyl)benzoyl]amino]phenyl]-1,3-thiazole-5-carboxamide, MW: 597.61135|MF: C28H26F3N7O3S.

51: CID: 11664511, IUPAC: 2-[[4-[4-(2-hydroxyethyl)piperazin-1-yl]pyridin-2-yl]amino]-N-[2-methyl-5-[[3-(trifluoromethyl)benzoyl]amino]phenyl]-1,3-thiazole-5-carboxamide, MW: 625.66451|MF: C30H30F3N7O3S.

52: CID: 11669430, IUPAC: N-(2-chloro-6-methylphenyl)-2-[(2-methyl-6-piperazin-1-ylpyrimidin-4-yl)amino]-1,3-thiazole-5-carboxamide, MW: 443.95298|MF: C20H22ClN7OS.

53: CID: 11676373, IUPAC: (3-chloro-2-fluorophenyl)-[4-[[6-(1,3-thiazol-2-ylamino)pyridin-2-yl]methyl]piperazin-1-yl]methanone, MW: 431.914163|MF: C20H19ClFN5OS.

54: CID: 11684148, IUPAC: (3-chloro-2-fluorophenyl)-[4-[[6-[(5-chloro-1,3-thiazol-2-yl)amino]pyridin-2-yl]methyl]piperazin-1-yl]methanone, MW: 466.359223|MF: C20H18C12FN5OS.

55: CID: 11700117, IUPAC: 2-[[6-(4-ethylpiperazin-1-yl)-2-methylpyrimidin-4-yl]amino]-N-[2-methyl-5-[[3-(trifluoromethyl)benzoyl]amino]phenyl]-1,3-thiazole-5-carboxamide, MW: 624.67975|MF: C30H31F3N8O2S.

56: CID: 11707091, IUPAC: 2-[[2-methyl-6-(4-methylpiperazin-1-yl)pyrimidin-4-yl]amino]-N-[2-methyl-5-[[3-(trifluoromethyl)benzoyl]amino]phenyl]-1,3-thiazole-5-carboxamide, MW: 610.65317|MF: C29H29F3N8O2S.

57: CID: 11714286, IUPAC: 2-[[5-[4-(2-hydroxyethyl)piperazin-1-yl]pyridin-2-yl]amino]-N-[2-methyl-5-[[3-(trifluoromethyl)benzoyl]amino]phenyl]-1,3-thiazole-5-carboxamide, MW: 625.66451|MF: C30H30F3N7O3S.

58: CID: 11714353, IUPAC: 2-[[6-[4-(2-hydroxyethyl)piperazin-1-yl]-2-methylpyrimidin-4-yl]amino]-N-[2-methyl-5-[[3-(trifluoromethyl)benzoyl]amino]phenyl]-1,3-thiazole-5-carboxamide, MW: 640.67915|MF: C30H31F3N8O3S.

59: CID: 11752136, IUPAC: N-(2-chloro-6-methylphenyl)-2-[[5-[4-(2-hydroxyethyl)piperazin-1-yl]-2-methylpyrimidin-4-yl]amino]-1,3-thiazole-5-carboxamide, MW: 488.00554|MF: C22H26ClN7O2S.

60: CID: 11772766, IUPAC: 4-[2-(3-chlorophenyl)ethylamino]-2-pyridin-4-yl-1,3-thiazole-5-carboxamide, MW: 358.8452|MF: C17H15ClN4OS.

61: CID: 11775143, IUPAC: N-(2-chloro-6-methylphenyl)-2-[(2-methyl-6-morpholin-4-ylpyrimidin-4-yl)amino]-1,3-thiazole-5-carboxamide, MW: 444.93774|MF: C20H21ClN6O2S.

62: CID: 11854012, IUPAC: 2-[4-[6-[[5-[(2-chloro-6-methylphenyl)carbamoyl]-1,3-thiazol-2-yl]amino]-2-methylpyrimidin-4-yl]piperazin-1-yl]acetic acid, MW: 501.98906|MF: C22H24ClN7O3S.

63: CID: 11854269, IUPAC: 2-[4-[6-[[5-[(2-chloro-6-methylphenyl)carbamoyl]-1,3-thiazol-2-yl]amino]-2-methylpyrimidin-4-yl]piperazin-1-yl]ethyl hydrogen sulfate, MW: 568.06874|MF: C22H26ClN7O5S2.

64: CID: 11854270, IUPAC: N-(2-chloro-6-methylphenyl)-2-[[6-[2-(2-hydroxyethylamino)ethylamino]-2-methylpyrimidin-4-yl]amino]-1,3-thiazole-5-carboxamide, MW: 461.96826|MF: C20H24ClN7O2S 65: CID: 11854271, IUPAC: 2-[[6-(2-aminoethylamino)-2-methylpyrimidin-4-yl]amino]-N-(2-chloro-6-methylphenyl)-1,3-thiazole-5-carboxamide, MW: 417.9157|MF: C18H20ClN7OS.

66: CID: 11854272, IUPAC: 2-[[2-[4-[6-[[5-[(2-chloro-6-methylphenyl)carbamoyl]-1,3-thiazol-2-yl]amino]-2-methylpyrimidin-4-yl]piperazin-1-yl]acetyl]amino]ethanesulfonic acid, MW: 609.12066|MF: C24H29ClN8O5S2.

67: CID: 11854533, IUPAC: N-(2-chloro-4-hydroxy-6-methylphenyl)-2-[[6-[4-(2-hydroxyethyl)piperazin-1-yl]-2-methylpyrimidin-4-yl]amino]-1,3-thiazole-5-carboxamide, MW: 504.00494|MF: C22H26ClN7O3S.

68: CID: 11854534, IUPAC: N-[2-chloro-6-(hydroxymethyl)phenyl]-2-[[6-[4-(2-hydroxyethyl)piperazin-1-yl]-2-methylpyrimidin-4-yl]amino]-1,3-thiazole-5-carboxamide, MW: 504.00494|MF: C22H26ClN7O3S.

69: CID: 11854535, IUPAC: N-(2-chloro-6-methylphenyl)-2-[[6-[4-(2-hydroxyethyl)-4-oxidopiperazin-4-ium-1-yl]-2-methylpyrimidin-4-yl]amino]-1,3-thiazole-5-carboxamide, MW: 504.00494|MF: C22H26ClN7O3S.

70: CID: 11854536, IUPAC: 2-[4-[6-[[5-[(2-chloro-6-methylphenyl)carbamoyl]-1,3-thiazol-2-yl]amino]-2-methylpyrimidin-4-yl]-1-oxidopiperazin-1-ium-1-yl]acetic acid, MW: 517.98846|MF: C22H24ClN7O4S.

71: CID: 11949914, IUPAC: 4-[[2-(5-chloro-2-fluorophenyl)-5-dimethylaminopyrimidin-4-yl]amino]-N-[2-(2-hydroxyethylamino)ethyl]pyridine-3-carboxamide, MW: 473.931003|MF: C22H25ClFN7O2.

72: CID: 11951866, IUPAC: 4-[[2-(5-chloro-2-fluorophenyl)-5-pyrrolidin-1-ylpyrimidin-4-yl]amino]-N-(2-hydroxyethyl)pyridine-3-carboxamide, MW: 456.900483|MF: C22H22ClFN6O2.

73: CID: 11952045, IUPAC: 4-[[2-(5-chloro-2-fluorophenyl)-5-pyrrolidin-1-ylpyrimidin-4-yl]amino]-N-[(2S)-2-hydroxypropyl]pyridine-3-carboxamide, MW: 470.927063|MF: C23H24ClFN6O2.

74: CID: 15979866, IUPAC: 5-[2-[[4-(4-acetylpiperazin-1-yl)pyridin-2-yl]amino]-1,3-thiazol-5-yl]-N-methylpyridine-3-carboxamide, MW: 437.51802|MF: C21H23N7O2S.

75: CID: 15980109, IUPAC: N-(2-aminoethyl)-5-[2-[(4-morpholin-4-ylpyridin-2-yl)amino]-1,3-thiazol-5-yl]pyridine-3-carboxamide, MW: 425.50732|MF: C20H23N7O2S 76: CID: 15980233, IUPAC: N-(2-hydroxyethyl)-5-[2-[(4-morpholin-4-ylpyridin-2-yl)amino]-1,3-thiazol-5-yl]pyridine-3-carboxamide, MW: 426.49208|MF: C20H22N6O3S.

77: CID: 15980347, IUPAC: N-(2-methylaminoethyl)-5-[2-[(4-morpholin-4-ylpyridin-2-yl)amino]-1,3-thiazol-5-yl]pyridine-3-carboxamide, MW: 439.5339|MF: C21H25N7O2S.

78: CID: 15980351, IUPAC: 5-[2-[[4-[4-(2-hydroxyacetyl)piperazin-1-yl]pyridin-2-yl]amino]-1,3-thiazol-5-yl]-N-(2,2,2-trifluoroethyl)pyridine-3-carboxamide, MW: 521.51539|MF: C22H22F3N7O3S.

79: CID: 15982537, IUPAC: (3-chloro-2-fluorophenyl)-[4-[6-[(5-fluoro-1,3-thiazol-2-yl)amino]-5-methylpyridin-2-yl]piperazin-1-yl]methanone, MW: 449.904626|MF: C20H18ClF2N5OS.

80: CID: 16034848, IUPAC: N-(2-chloro-6-methylphenyl)-2-[[6-[4-(2-hydroxyethyl)piperazin-1-yl]-2-methylpyrimidin-4-yl]amino]-1,3-thiazole-5-carboxamide; 2,3-dihydroxybutanedioic acid, MW: 638.09238|MF: C26H32ClN7O8S.

81: CID: 16037977, IUPAC: N-(2-chloro-6-methylphenyl)-2-[[6-[4-(2-hydroxyethyl)piperazin-1-yl]-5-methylpyrimidin-4-yl]amino]-1,3-thiazole-5-carboxamide, MW: 488.00554|MF: C22H26ClN7O2S.

82: CID: 16061431, IUPAC: N-(2-chloro-6-methylphenyl)-2-[[6-[4-(2-hydroxyethyl)piperazin-1-yl]-2-methylpyrimidin-4-yl]amino]-1,3-thiazole-5-carboxamide; 4-[(4-methylpiperazin-1-yl)methyl]-N-[4-methyl-3-[(4-pyridin-3-ylpyrimidin-2-yl)amino]phenyl]benzamide, MW: 981.60828|MF: C51H57ClN14O3S.

83: CID: 16223227, IUPAC: but-2-enedioic acid; N-(2-chloro-6-methylphenyl)-2-[[6-[4-(2-hydroxyethyl)piperazin-1-yl]-2-methylpyrimidin-4-yl]amino]-1,3-thiazole-5-carboxamide, MW: 604.0777|MF: C26H30ClN7O6S.

84: CID: 16223228, IUPAC: N-(2-chloro-6-methylphenyl)-2-[[6-[4-(2-hydroxyethyl)piperazin-1-yl]-2-methylpyrimidin-4-yl]amino]-1,3-thiazole-5-carboxamide hydrobromide, MW: 568.91748|MF: C22H27BrClN7O2S.

85: CID: 16223229, IUPAC: but-2-enedioic acid; N-(2-chloro-6-methylphenyl)-2-[[6-[4-(2-hydroxyethyl)piperazin-1-yl]-2-methylpyrimidin-4-yl]amino]-1,3-thiazole-5-carboxamide, MW: 604.0777|MF: C26H30ClN7O6S.

86: CID: 16223316, IUPAC: N-(2-chloro-6-methylphenyl)-2-[[6-[4-(2-hydroxyethyl)piperazin-1-yl]-2-methylpyrimidin-4-yl]amino]-1,3-thiazole-5-carboxamide; methanesulfonic acid, MW: 584.1112|MF: C23H30ClN7O5S2.

87: CID: 16223317, IUPAC: N-(2-chloro-6-methylphenyl)-2-[[6-[4-(2-hydroxyethyl)piperazin-1-yl]-2-methylpyrimidin-4-yl]amino]-1,3-thiazole-5-carboxamide; phosphoric acid, MW: 586.000721|MF: C22H29ClN7O6PS.

88: CID: 16223318, IUPAC: N-(2-chloro-6-methylphenyl)-2-[[6-[4-(2-hydroxyethyl)piperazin-1-yl]-2-methylpyrimidin-4-yl]amino]-1,3-thiazole-5-carboxamide; 2-hydroxybenzoic acid, MW: 626.12628|MF: C29H32ClN7O5S.

89: CID: 16223319, IUPAC: N-(2-chloro-6-methylphenyl)-2-[[6-[4-(2-hydroxyethyl)piperazin-1-yl]-2-methylpyrimidin-4-yl]amino]-1,3-thiazole-5-carboxamide; sulfuric acid, MW: 586.08402|MF: C22H28ClN7O6S2.

90: CID: 16223320, IUPAC: N-(2-chloro-6-methylphenyl)-2-[[6-[4-(2-hydroxyethyl)piperazin-1-yl]-2-methylpyrimidin-4-yl]amino]-1,3-thiazole-5-carboxamide; 4-methylbenzenesulfonic acid, MW: 660.20716|MF: C29H34ClN7O5S2.

91: CID: 16584134, AKE-PB223730486, IUPAC: N-(4-chlorophenyl)-2-[(4,5-dimethyl-1,3-thiazol-2-yl)amino]-4-methylpyrimidine-5-carboxamide, MW: 373.85984|MF: C17H16ClN5OS.

92: CID: 16584137, AKE-PB223730492, IUPAC: N-(3-chlorophenyl)-2-[(4,5-dimethyl-1,3-thiazol-2-yl)amino]-4-methylpyrimidine-5-carboxamide, MW: 373.85984 MF: C17H16ClN5OS.

93: CID: 16584139, AKE-PB223730496, IUPAC: 2-[(4,5-dimethyl-1,3-thiazol-2-yl)amino]-4-methyl-N-(2-methylphenyl)pyrimidine-5-carboxamide, MW: 353.44136|MF: C18H19N5OS.

94: CID: 16655683, IUPAC: 2-[(6-chloro-2-methylpyrimidin-4-yl)amino]-N-(2,6-dichlorophenyl)-1,3-thiazole-5-carboxamide, MW: 414.6968|MF: C15H10Cl3N5OS.

95: CID: 16655839, IUPAC: N-(2,6-dichlorophenyl)-2-[[6-[4-(2-hydroxyethyl)piperazin-1-yl]-2-methylpyrimidin-4-yl]amino]-1,3-thiazole-5-carboxamide, MW: 508.42402|MF: C21H23Cl2N7O2S.

96: CID: 16660745, IUPAC: N-(4-fluorophenyl)-4-(2-hydroxyethylamino)-6-methylsulfanyl-2-pyridin-4-ylpyrimidine-5-carboxamide, MW: 399.441923|MF: C19H18FN5O2S.

97: CID: 16660747, IUPAC: N-(4-ethylphenyl)-4-(2-hydroxyethylamino)-6-methylsulfanyl-2-pyridin-4-ylpyrimidine-5-carboxamide, MW: 409.50462|MF: C21H23N5O2S.

98: CID: 16660907, IUPAC: 4-(2-hydroxyethylamino)-N-(4-methylphenyl)-6-methylsulfanyl-2-pyridin-4-ylpyrimidine-5-carboxamide, MW: 395.47804|MF: C20H21N5O2S.

99: CID: 16661063, IUPAC: N-(4-chlorophenyl)-4-(2-hydroxyethylamino)-6-methylsulfanyl-2-pyridin-4-ylpyrimidine-5-carboxamide, MW: 415.89652|MF: C19H18ClN5O2S.

100: CID: 16661212, IUPAC: N-(2,4-dimethylphenyl)-4-(2-hydroxyethylamino)-6-methylsulfanyl-2-pyridin-4-ylpyrimidine-5-carboxamide, MW: 409.50462|MF: C21H23N5O2S.

101: CID: 16661214, IUPAC: 4-(1-hydroxybutan-2-ylamino)-N-(4-methylphenyl)-6-methylsulfanyl-2-pyridin-4-ylpyrimidine-5-carboxamide, MW: 423.5312|MF: C22H25N5O2S.

NEPOR: Combined Prognostic and Therapeutic Value in Cancer Treatment.

Without being bound by theory, the observation that EPO treated patients often have poorer survival outcomes (at least in some cancers) means that treatment of these patients with a NEPOR targeted therapy provides a pharmacogenetic approach to targeted cancer treatment providing tumour tissue can be assessed for expression of NEPOR. Such a therapeutic perspective changes the balance in favour of performing biopsies under all suitable circumstances—meaning for cancers where EPOR, EPH-B4 and/or EphrinA1 are typically expressed.

The present disclosure further provides a method for imaging tumour tissue that is susceptible to enhanced survival in response to EPO treatment, comprising administering an anti-NEPOR antibody or NEPOR binding peptide linked to a radio-ligand or other imaging agent, and measuring for tissue distribution and location of the radio-ligand or other imaging agent.

If a tumour is NEPOR positive, then EPO is contraindicated and a NEPOR targeted therapy is administered. If NEPOR is not present, then it is safe to administer EPO. Both outcomes stand to benefit patient outcome, regardless of whether a patient is NEPOR positive or negative. Again, this shifts the balance in favour of performing routine biopsies.

In one embodiment the invention relates to an siRNA molecule specific to EPH-B4 and/or Ephrin A1 for use in treating a cancer patient that is or will receive EPO.

EPH-B4 siRNAs and Antisense Oligodeoxynucleotides

Various EphB4-specific anti-sense phosphorothioate-modified oligodeoxynucleotides (ODNs) and siRNA may be synthesized from (e.g. by Qiagen. The most active antisense ODN and siRNA that knocks down EphB4 expression in the transiently transfected 293T cell line is chosen. The antisense ODN that may be used is AS-10 which spans nucleotides 1980 to 1999 with a sequence 5'-ATG GAG GCC TCG CTC AGA AA-3' (SEQ ID NO. 217). To eliminate cytokine responses, the cytosine at the CpG site may be methylated (AS-10M) without any loss in EphB4 knockdown efficiency (data not shown). Scrambled ODNs containing random nucleotide sequence and a similar CpG site, 5'-TAC CTG AAG GTC AGG CGA AC-3' (SEQ ID NO. 218), may be used as control. siRNA 465 corresponding to the sequences 5'-GGU GAA UGU CAA GAC GCU GUU-3' (SEQ ID NO. 219) and 3'-UUC CAC UUA CAG UUC UGC GAC-5' (SEQ ID NO. 220) may be used for RNA interference. Control siRNA may be generated by mutating three bases in this sequence to effectively abrogate EphB4 knockdown. This mutated siRNA (siRNAA) had the sequences 5'-AGU UAA UAU CAA GAC GCU GUU-3' (SEQ ID NO. 221) and 3'-UUU CAA UUA UAG UUC UGC GAC-5' (SEQ ID NO. 222). Additionally, siRNA directed against green fluorescent protein with sequences 5'-CGC UGA CCC UGA AGU UCA TUU-3' (SEQ ID NO. 223) and 3'-UUG CGA CUG GGA CUU CAA GUA-5' (SEQ ID NO. 224) may be used as a negative control.

In one aspect, one or more of the following EPHB4-specific siRNA, which are depicted in double-stranded form, can be administered to a patient to enhance the effectiveness of Epo therapy.

```
5'- caauagccacucuaacaccuu -3'    (SEQ ID NO: 242)
3'- uuguuacggugagauugugg  -5'    (SEQ ID NO: 243)

5'- ggggcccgucccauuugaguu -3'    (SEQ ID NO: 244)
3'- uuccccgggcaggguaaacuc -5'    (SEQ ID NO: 245)

5'- cugaucugaaguggugacuu  -3'    (SEQ ID NO: 246)
3'- uugacuagacuucacccacug -5'    (SEQ ID NO: 247)

5'- aagacccuaaugaggcuguuu -3'    (SEQ ID NO: 248)
3'- uuuucugggauuacuccgaca -5'    (SEQ ID NO: 249)

5'- ucgaugucuccuacgucaauu -3'    (SEQ ID NO: 250)
3'- uuagcuacagaggaugcaguu -5'    (SEQ ID NO: 251)

5'- auugaagaggugauuggguguu -3'   (SEQ ID NO: 252)
3'- uuuaacuucuccacuaaccac -5'    (SEQ ID NO: 253)

5'- ggaguuacgggauugugauuu -3'    (SEQ ID NO: 254)
3'- uuccucaaugcccuaacacua -5'    (SEQ ID NO: 255)

5'- gguacuaaggucuacaucguu -3'    (SEQ ID NO: 256)
3'- uuccaugauuccagauguagc -5'    (SEQ ID NO: 257)

5'- guccugacuucaccuauacuu -3'    (SEQ ID NO: 258)
3'- uucaggacugaaguggauaug -5'    (SEQ ID NO: 259)

5'- ugccgcucggguacuuccuu  -3'    (SEQ ID NO: 260)
3'- uuacggcgcagcccaugaagg -5'    (SEQ ID NO: 261)
```

In other examples, siRNA can be obtained from commercial sources, such as Sigma-Aldrich (St. Louis, Mo.) and used to enhance Epo therapy. For example, the following siRNA's are commercially available from Sigma-Aldrich:

| siRNA_ID | entrezgene_ID | approx_start_nucleotide |
|---|---|---|
| EPHRIN A1 | | |
| SASI_Hs01_00211016 | NM_004428 | 247 |
| SASI_Hs01_00211017 | NM_004428 | 223 |
| SASI_Hs01_00211018 | NM_004428 | 248 |
| SASI_Hs01_00211019 | NM_004428 | 1071 |
| SASI_Hs01_00211020 | NM_004428 | 256 |
| SASI_Hs01_00211021 | NM_004428 | 208 |
| SASI_Hs01_00211022 | NM_004428 | 829 |
| SASI_Hs01_00211023 | NM_004428 | 1015 |
| SASI_Hs01_00211024 | NM_004428 | 846 |
| SASI_Hs01_00211025 | NM_004428 | 225 |
| SASI_Hs01_00071683 | NM_182685 | 248 |
| SASI_Hs01_00071684 | NM_182685 | 214 |
| SASI_Hs01_00071685 | NM_182685 | 242 |
| SASI_Hs01_00071686 | NM_182685 | 1000 |
| SASI_Hs01_00071687 | NM_182685 | 263 |
| SASI_Hs01_00071688 | NM_182685 | 203 |
| SASI_Hs01_00071689 | NM_182685 | 769 |
| SASI_Hs01_00071690 | NM_182685 | 948 |
| SASI_Hs01_00071691 | NM_182685 | 778 |
| SASI_Hs01_00071692 | NM_182685 | 227 |
| EPHB4 | | |
| SASI_Hs01_00039855 | NM_004444 | 1756 |
| SASI_Hs01_00039856 | NM_004444 | 577 |
| SASI_Hs01_00039857 | NM_004444 | 1373 |
| SASI_Hs01_00039858 | NM_004444 | 2290 |
| SASI_Hs01_00039859 | NM_004444 | 2318 |
| SASI_Hs01_00039860 | NM_004444 | 2353 |
| SASI_Hs01_00039861 | NM_004444 | 2898 |
| SASI_Hs01_00039862 | NM_004444 | 2245 |
| SASI_Hs01_00039863 | NM_004444 | 1679 |
| SASI_Hs01_00039864 | NM_004444 | 1416 |

In another aspect, methods are provided for enhancing the effectiveness of EPO therapy in a patient, comprising administering to said patient, in conjunction with EPO therapy, antisense molecules specific for EPH-B4 mRNA. In one embodiment, the antisense molecule is an oligonuceotide having the nucleic acid sequence of SEQ ID NO. 217.

Antibodies to NEPOR

The present disclosure includes several antibodies that bind to NEPOR components. The following Table 6 provides a list of such antibodies and their availability.

TABLE 6

| Company | Item | Antigen | Catalog Number | Applications | Type |
|---|---|---|---|---|---|
| EPOR | | | | | |
| Abcam | Goat Anti-EPO Receptor Polyclonal Antibody, Unconjugated | EPOR | ab10653 | ELISA, WB | polyclonal |
| ABR-Affinity BioReagents | Mouse Anti-Human EPOR Monoclonal Antibody, Unconjugated, Clone 3D10 | EPOR | MA1-51823 | WB, ELISA | Monoclonal |
| Abnova Corporation | Mouse Anti-Human EPOR Monoclonal Antibody, Unconjugated, Clone 3D10 | EPOR | H00002057-M01 | WB, Capture ELISA | Monoclonal |
| Abcam | Goat Anti-Human EPO Receptor Polyclonal Antibody, Unconjugated | EPOR | ab27497 | ELISA, WB | Polyclonal |
| Abcam | Mouse Anti-Human EPO Receptor Monoclonal Antibody, Unconjugated, Clone MM-0031-6G7 | EPOR | ab56310 | WB | Monoclonal |
| ABR-Affinity BioReagents | Mouse Anti-Human EPOR Polyclonal Antibody, Unconjugated | EPOR | PA1-51822 | WB | Polyclonal |
| IMGENEX | Goat Anti-Human EPOR Polyclonal Antibody, Unconjugated | EPOR | IMG-3771 | WB, ELISA | Polyclonal |
| Lifespan Biosciences | Rabbit Anti-Human Erythropoietin Receptor (EPOR) Polyclonal Antibody, Unconjugated | EPOR | LS-C6720 | ELISA | Polyclonal |
| GeneTex | Mouse Anti-Human EPOR Monoclonal Antibody, Unconjugated, Clone 3D10 | EPOR | GTX91710 | ELISA, WB | Monoclonal |
| Lifespan Biosciences | Rabbit Anti-Human EPOR Polyclonal Antibody, Unconjugated | EPOR | LS-C6719-100 | ELISA | Polyclonal |
| Novus | Mouse Anti-Human EPOR Polyclonal Antibody, | EPOR | H00002057- | | Polyclonal |

TABLE 6-continued

| Company | Item | Antigen | Catalog Number | Applications | Type |
|---|---|---|---|---|---|
| Biologicals | Unconjugated | | A01 | | |
| Novus Biologicals | Mouse Anti-Human EPOR Monoclonal Antibody, Unconjugated, Clone 3D10 | EPOR | H00002057-M01 | ELISA, WB | Monoclonal |
| Lifespan Biosciences | Sheep Anti-Human Erythropoietin Receptor (EPOR) Polyclonal Antibody, Unconjugated | EPOR | LS-C6718 | ELISA, WB | Polyclonal |
| Lifespan Biosciences | Sheep Anti-Human Erythropoietin Receptor (EPOR) Polyclonal Antibody, Unconjugated | EPOR | LS-C6716 | | Polyclonal |
| Lifespan Biosciences | Sheep Anti-Human EPOR Polyclonal Antibody, Unconjugated | EPOR | LS-C6717-50 | ELISA | Polyclonal |
| Santa Cruz Biotechnology, Inc. | Rabbit Anti-Human EpoR (C-20) Polyclonal Antibody, Unconjugated | EpoR (C-20) | sc-695 | WB, IP, IF, ICH. | Polyclonal |
| Santa Cruz Biotechnology, Inc. | Rabbit Anti-EpoR (M-20) Polyclonal Antibody, Unconjugated | EpoR (M-20) | sc-697 | WB, IP, IF, ICH. | Polyclonal |
| Santa Cruz Biotechnology, Inc. | Rabbit Anti-EpoR Polyclonal Antibody, Unconjugated | EpoR | sc-5624 | WB, IP, IF, ICH. | Polyclonal |
| EPH-B4 | | | | | |
| Abgent | Rabbit Anti-EPH-B4 C-term RB1659-1660 Polyclonal Antibody, Unconjugated | EPH-B4 C-term | AP7625a | ELISA; IHC. | Polyclonal |
| ABR-Affinity BioReagents | Rabbit Anti-Human EPH-B4 Polyclonal Antibody, Unconjugated | EPH-B4 | PA1-24241 | WB | Polyclonal |
| ABR-Affinity BioReagents | Mouse Anti-Human EPH-B4 Monoclonal Antibody, Unconjugated, Clone 1D1 | EPH-B4 | MA1-51815 | ELISA | Monoclonal |
| AbD Serotec | Human Anti-Human EPH-B4 Monoclonal Antibody, Unconjugated, Clone 1327 | EPH-B4 | HCA001 | IHC, WB, ELISA | Monoclonal |
| AbD Serotec | Human Anti-Human EPH-B4 Monoclonal Antibody, Unconjugated, Clone 3934 | EPH-B4 | HCA025 | IHC, WB, ELISA | Monoclonal |
| Invitrogen | Anti-EPH-B4 receptor Monoclonal Antibody, Unconjugated, Clone 3D7F8 | EPH-B4 | 35-2900 | WB, ELISA | Monoclonal |
| GeneTex | Rabbit Anti-EPH-B4 Polyclonal Antibody, Unconjugated | EPH-B4 | GTX77656 | WB | Polyclonal |
| Invitrogen | Mouse Anti-EPH-B4 Receptor Monoclonal Antibody,, Clone 3D7G8 | EPH-B4 | 182394 | IHC(FFPE) | Monoclonal |
| Invitrogen | Anti-Eph Receptor Sampler Pack Antibody, | EPH-B4 | 901100 | | |
| GeneTex | Mouse Anti-Human EPH-B4 Monoclonal Antibody, Unconjugated, Clone 1D1 | EPH-B4 | GTX91629 | ELISA | Monoclonal |
| Invitrogen | Mouse Anti-Human EPH-B4 Receptor Monoclonal Antibody,, Clone 3D7G8 | EPH-B4 | 371800 | WB ELISA IP, IHC | Monoclonal |
| Novus Biologicals | Mouse Anti-Human EPH-B4 Monoclonal Antibody, Unconjugated, Clone 1D1 | EPH-B4 | H00002050-M01 | | Monoclonal |
| R&D Systems | Goat Anti-Human EPH-B4 Polyclonal Antibody, Unconjugated | EPH-B4 | AF3038 | FC, IHC, WB | Polyclonal |
| Raybiotech, Inc. | Human Anti-Human EPH-B4, (packaged with HRP-Conjugated Secondary Antibody); Monoclonal Antibody, Unconjugated | EPH-B4 | DS-MB-01224 | | Monoclonal |
| R&D Systems | Rat Anti-Human EPH-B4 Monoclonal Antibody, Unconjugated, Clone 395810 | EPH-B4 | MAB3038 | FC, IHC, WB | Monoclonal |
| Santa Cruz Biotechnology, Inc. | Goat Anti-EPH-B4 Polyclonal Antibody, Unconjugated | EPH-B4 | sc-7284 | WB, IF | Polyclonal |
| Santa Cruz Biotechnology, Inc. | Goat Anti-EPH-B4 Polyclonal Antibody, Unconjugated | EPH-B4 | sc-7285 | WB, IF | Polyclonal |
| Santa Cruz Biotechnology, Inc. | Rabbit Anti-EPH-B4 Polyclonal Antibody, Unconjugated | EPH-B4 | sc-5536 | WB, IF | Polyclonal |
| Raybiotech, Inc. | Human Anti-Human EPH-B4, (packaged with HRP-Conjugated Secondary Antibody); Monoclonal Antibody, Unconjugated | EPH-B4 | DS-MB-01225 | | Monoclonal |
| EFNA1 | | | | | |
| Invitrogen | Anti-Ephrin A1 Polyclonal Antibody, Unconjugated, Clone ZMD.39 | EFNA1 | 34-3300 | | Polyclonal |
| Novus Biologicals | Mouse Anti-Human EFNA1 Monoclonal Antibody, Unconjugated, Clone 3C6 | EFNA1 | H00001942-M01 | | Monoclonal |
| Santa Cruz Biotechnology, Inc. | Rabbit Anti-ephrin-A1 (V-18) Polyclonal Antibody, Unconjugated | EFNA1 (V-18) | sc-911 | WB, IF | Polyclonal |
| Santa Cruz Biotechnology, Inc. | Rabbit Anti-ephrin-A1 Polyclonal Antibody, Unconjugated | EFNA1 | sc-20719 | WB, IP, IF | Polyclonal |
| Abcam | Rabbit Anti-Human Ephrin A1 Receptor Polyclonal Antibody, Unconjugated | EFNA1 | ab37857 | ELISA, IHC, WB | Polyclonal |
| GeneTex | Mouse Anti-Human EFNA1 Monoclonal Antibody, | EFNA1 | GTX91614 | | Monoclonal |

TABLE 6-continued

| Company | Item | Antigen | Catalog Number | Applications | Type |
|---|---|---|---|---|---|
| | Unconjugated, Clone 3C7 | EFNB2 | | | |
| Novus Biologicals | Mouse Anti-Human EFNB2 Polyclonal Antibody, Unconjugated | EFNB2 | H00001948-A01 | | Polyclonal |
| Santa Cruz Biotechnology, Inc. | Rabbit Anti-ephrin-B2 (P-20) Polyclonal Antibody, Unconjugated | EFNB2 (P-20) | sc-1010 | WB, IF | Polyclonal |
| Santa Cruz Biotechnology, Inc. | Goat Anti-ephrin-B2 Polyclonal Antibody, Unconjugated | EFNB2 | sc-19227 | WB, IF, IP | Polyclonal |
| Santa Cruz Biotechnology, Inc. | Rabbit Anti-ephrin-B2 Polyclonal Antibody, Unconjugated | EFNB2 | sc-15397 | WB, IF, IP | Polyclonal |

In one aspect there is provided a method for assessing tumour tissue for expression of EPH-B4 and/or Ephrin A1, comprising: (a) isolating a tissue sample from an individual who is receiving or shall receive erythropoietin, (b) determining the level of expression of the EPH-B4 and/or Ephrin A1, (c) correlating the presence of these component gene expression products to a negative physiological response to the treatment with erythropoietin. In one embodiment, the level of expression of the component genes (mRNA) is determined by a molecular biological technique selected from the group consisting of PCR, QPCR, R-PCR, gene expression microarray analysis, northern-blot analysis, reverse transcription and amplification, zymography, ligase-chain-reaction, NASBA, RNase Protection Assay (RPA), capillary electrophoresis with laser induced fluorescence (CE-LIF). In another, the individual is a cancer patient who is to be treated with erythropoietin or is being treated with erythropoietin. In one example, the presence of EPH-B4 and/or Ephrin A1 gene expression products is indicative of poorer loco-regional tumor control and poorer patient survival upon treatment with erythropoietin. In another, the presence of a higher level of EPH-B4 and/or Ephrin A1 gene expression products is indicative of poorer loco-regional tumour control and poorer patient survival upon treatment with erythropoietin. In some embodiments, the means for testing for the presence of the gene expression products are a protein array or binding to a mass microbalance instrument. In others, the determination of the presence of the EPH-B4 and/or Ephrin A1 gene products is done by detecting the respective proteins with an immunoassay procedure, where the immunoassay procedure is selected from the group of immunoprecipitation, enzyme immunoassay (EIA), radioimmunoassay (RIA) or fluorescent immunoassay, a chemiluminescent assay, an agglutination assay, nephelometric assay, turbidimetric assay, a Western blot, a competitive immunoassay, a noncompetitive immunoassay, a homogeneous immunoassay a heterogeneous immunoassay, a bioassay and a reporter-assay. In one example, the immunoassay is an ELISA. In another embodiment, the tissue sample may be selected from the cancerous tissue or circulating cells derived from same or from a group of biological tissues and fluids such as blood, lymph, urine, cerebral fluid.

In another aspect, a prognostic method is provided to stratify patients having a tumour as suitable (EPH-B4 and/or Ephrin A1) or non-suitable (EPH-B4 and/or Ephrin A1) for EPO treatment, comprising: (a) isolating a tissue sample from an individual who is receiving or shall receive erythropoietin; (b) determining the level of expression of the EPH-B4 and/or Ephrin A1 gene(s) component, a EPH-B4 and/or Ephrin A1 from the isolated tissue; and (c) correlating the presence of EPH-B4 and/or Ephrin A1 component gene expression products to a negative physiological response to the treatment with erythropoietin. In one embodiment, the level of expression of EPH-B4 and/or Ephrin A1 component genes is determined by a molecular biological technique selected from the group consisting of PCR, QPCR, R-PCR, gene expression microarray analysis, northern-blot analysis, reverse transcription and amplification, zymography, ligase-chain-reaction, NASBA, RNase Protection Assay (RPA), capillary electrophoresis with laser induced fluorescence (CE-LIF). In another, the determination of the presence of the EPH-B4 and/or Ephrin A1 gene products is done by detecting the respective protein with an immunoassay procedure, where the immunoassay procedure is selected from the group of ELISA, immunoprecipitation, enzyme immunoassay (EIA), radioimmunoassay (RIA) or fluorescent immunoassay, a chemiluminescent assay, an agglutination assay, nephelometric assay, turbidimetric assay, a Western blot, a competitive immunoassay, a noncompetitive immunoassay, a homogeneous immunoassay a heterogeneous immunoassay, a bioassay and a reporter-assay such as a luciferase-assay. The tissue sample can be selected from the cancerous tissue or circulating cells derived from same, or from a group of biological tissues and fluids such as blood, lymph, urine, cerebral fluid.

In another aspect, a method is provided for imaging tumour tissue that is susceptible to enhanced survival in response to EPO treatment, comprising administering an anti-EPH-B4 and/or anti-Ephrin A1 antibody or EPH-B4 and/or Ephrin A1 binding peptide linked to a radio-ligand or other imaging agent, and measuring for tissue distribution and location of the radio-ligand or other imaging agent. In one embodiment, the anti-EPH-B4 and/or anti-Ephrin A1 antibody is a monoclonal or polyclonal antibody selected from the group of antibodies listed in Table 6.

In another aspect, a method is provided for designing a compound which interferes with NEPOR's survival promoting activity, comprising: (a) providing the molecular makeup of the NEPOR species and providing amino acid sequences of a component NEPOR polypeptides; (b) using software comprised by the digital computer to design a chemical compound/protein construct which is predicted to bind to NEPOR; and (c) optionally designing protein constructs which mimic NEPOR in its dimerised/multimerised state (e.g. Fc constructs).

A method also is provided for identifying compounds that modulate NEPOR's tissue protective signalling activity, comprising (a) contacting a test compound with the NEPOR receptor complex; (b) measuring the level of tissue protective activity initiated by NEPOR activation; (c) identifying a test compound which increases or decreases the level of tissue protective NEPOR complex activity; (d) assaying the identified therapeutics for tissue protective activity mediated via NEPOR; and (e) assaying the identified therapeutics for NEPOR inhibitory activity. In one embodiment, the tissue protective NEPOR receptor complex activity is measured by measuring the binding of the test compound to the NEPOR receptor complex. In another, the test compound is labelled and binding of the labelled test compound to the tissue protective NEPOR receptor complex is measured by detecting the label attached to the test compound. The tissue protective NEPOR receptor complex activity can be measured by measuring the binding of the test compound to the tissue protective NEPOR receptor complex.

In another aspect, a method is provided for identifying compounds that modulate NEPOR's tissue protective signalling activity, comprising (a) contacting a test compound with the NEPOR receptor complex expressing cell; (b) measuring the level of tissue protective activity initiated by NEPOR activation in the cell; (c) identifying a test compound which increases or decreases the level of tissue protective NEPOR complex activity in a cell; (d) assaying the identified compounds for tissue protective activity mediated via NEPOR; and (e) assaying the identified therapeutics for NEPOR inhibitory activity. In one embodiment, the assay in step (d) is a tissue protective NEPOR receptor complex activity is measured by a cell proliferation/differentiation assay. In one example, the cells in the cell proliferentiation/differentiation assay are recombinantly engineered to express EPH-B4, and/or EPOR, and/or Ephrin A1. In another, the cells endogenously expresses an EPO receptor and are transformed with a nucleic acid comprising a nucleotide sequence that (i) is operably linked to a promoter, and (ii) encodes either EPH-B4 and/or Ephrin A1. In another example, the cells endogenously express EPH-B4 and/or Ephrin A1 and are transformed with a nucleic acid comprising a nucleotide sequence that (i) is operably linked to a promoter, and (ii) encodes an EPO receptor polypeptide.

In one aspect, a method is provided for identifying a compound that modulates the interaction between a tissue protective NEPOR receptor complex and a tissue protective NEPOR receptor complex ligand, comprising: (a) contacting a tissue protective NEPOR receptor complex with one or more test compounds; and (b) measuring the tissue protective NEPOR receptor complex activity, whereby if the activity measured in (b) differs from the tissue protective NEPOR receptor complex activity in the absence of the one or more test compounds, then a compound that modulates the interaction between the tissue protective NEPOR receptor complex and the tissue protective NEPOR receptor complex ligand is identified. In one embodiment, the tissue protective NEPOR receptor complex activity is measured by cell proliferation or cell differentiation. In another, the tissue protective NEPOR receptor complex activity measured is the ability of the tissue protective NEPOR receptor complex to interact with a tissue protective NEPOR receptor complex ligand. In another, the step of assaying the identified compound for tissue protective activity comprises detecting the presence of nucleolin in the cell. In some embodiments, the step of assaying the identified compound for tissue protective activity comprises detecting or measuring an increased level of activity of neuroglobin or cytoglobin in a cell. In others, the tissue protective NEPOR receptor complex is in solution. In another the tissue protective NEPOR receptor complex is in a cell. In some aspects, the compound inhibits the binding of a tissue protective NEPOR receptor complex ligand to a tissue protective NEPOR receptor complex, while in others the compound enhances the binding of a tissue protective NEPOR receptor complex ligand to a tissue protective NEPOR receptor complex. The tissue protective NEPOR receptor complex contacted in step (a) can be on a cell surface or on an isolated cell membrane. In some embodiments, the tissue protective NEPOR receptor complex activity is compared to EPOR receptor activation to identify NEPOR specific compounds. In some embodiments, the tissue protective NEPOR receptor complex is immobilized to a solid surface. In one example, the solid surface is a microtiter dish, and in another it is a chip.

In another aspect, there is provided a method for identifying a compound that binds a tissue protective NEPOR receptor complex, comprising: (a) contacting a test compound with a ligand-binding tissue protective NEPOR receptor complex fragment comprising at least one EPO receptor or EPH-B4 receptor or Ephrin A1 receptor extracellular domain and at least one EPO receptor or EPH-B4 receptor or Ephrin A1 receptor, extracellular domain fused to an Fc fragment attached to a solid support; and (b) contacting a test compound with a ligand-binding EPOR receptor complex fragment comprising at least two EPO receptor extracellular domains fused to an Fc fragment attached to a solid support (c) removing unbound test compounds from the solid supports; (d) identifying the compound attached to the tissue protective NEPOR receptor complex fragment, but not the EPOR receptor complex (and vice versa), whereby a compound bound to the solid support is identified as a compound that binds specifically to a tissue protective NEPOR receptor complex or a compound that binds specifically to an EPOR receptor complex.

In another aspect, a method is provided for identifying a compound that binds a tissue protective NEPOR receptor complex, comprising: (a) contacting a test compound with a ligand-binding tissue protective NEPOR receptor complex fragment comprising at least one EPO receptor or EPH-B4 receptor or Ephrin A1 receptor, extracellular domain fused to an Fc fragment attached to a solid support; (b) removing unbound test compounds from the solid supports; (c) identifying the compound attached to the tissue protective NEPOR receptor complex fragment, whereby a compound bound to the solid support is identified as a compound that binds specifically to a tissue protective NEPOR receptor complex.

In another aspect, there is provided a method for identifying a compound that binds to a tissue protective NEPOR receptor complex, comprising: (a) contacting a tissue protective NEPOR receptor complex fragment comprising at least one EPO receptor or EPH-B4 receptor or Ephrin A1 receptor extracellular domain and at least one EPO receptor or EPH-B4 receptor or Ephrin A1 receptor, extracellular domain fused to an Fc fragment attached to a solid support with (i) a tissue protective NEPOR receptor complex ligand attached to a first label and (ii) an equivalent amount of a test compound attached to a second label under conditions conducive to binding; (b) removing unbound material from the tissue protective NEPOR receptor complex; and (c) detecting the level of the first and second labels wherein if the second label is present the compound binds the complex and if the level of the first label decreases relative to the level of the first label where the labelled ligand is contacted with a tissue protective NEPOR receptor complex under conditions conducive to binding in the absence of a test compound after removal of unbound material, then a compound that binds to a tissue protective NEPOR receptor complex is identified.

In another aspect, a method is provided for identifying a compound that modulates the binding of a tissue protective NEPOR receptor complex ligand to a tissue protective NEPOR receptor complex, comprising: (a) contacting a tissue protective NEPOR receptor complex ligand with a tissue protective NEPOR receptor complex fragment comprising at least one EPO receptor or EPH-B4 receptor or Ephrin A1 receptor extracellular domain and at least one EPO receptor or EPH-B4 receptor or Ephrin A1 receptor, extracellular domain fused to an Fc fragment attached to a solid support; in the presence of one or more test compounds under conditions conducive to binding; and (b) measuring the amount of tissue protective NEPOR receptor complex ligated bound to the tissue protective NEPOR receptor complex; whereby if the amount of bound tissue protective NEPOR receptor complex ligand measured in (b) differs from the amount of bound tissue protective NEPOR receptor complex ligand measured in the absence of the one or more test compounds, then a compound that modulates the binding of a tissue protective NEPOR receptor complex ligand to the tissue protective NEPOR receptor complex is identified. In one embodiment, the amount of bound tissue protective NEPOR receptor complex ligand is measured using a tissue protective NEPOR receptor complex ligand-specific antibody. In another, the tissue protective NEPOR receptor complex ligand is labelled and binding of the tissue protective NEPOR receptor complex ligand to the tissue protective NEPOR receptor complex is measured by detecting the label attached to the tissue protective NEPOR receptor complex ligand. In one aspect, the tissue protective NEPOR receptor complex ligand is labelled and binding of the labelled ligand to the tissue protective NEPOR receptor complex is measured by detecting the label attached to the tissue protective NEPOR receptor complex ligand. In one example, the label is fluorescent. In another embodiment, the test compound is an antibody specific for the tissue protective NEPOR receptor complex. In another, the test compound is a small molecule or a peptide or a member of a library. In one embodiment, the tissue protective NEPOR receptor complex ligand is EPO, or derivatives thereof. In some aspects, the compound binds the tissue protective NEPOR receptor complex. In others, the compound binds the tissue protective NEPOR receptor complex ligand. In some embodiments, the tissue protective NEPOR receptor complex activity is compared to EPOR receptor activation to identify NEPOR specific compounds.

In one aspect, a method is provided for identifying a compound that modulates a tissue protective activity in a mammal, comprising: (a) administering the compound to a first animal immediately following infliction of an injury, wherein the first animal endogenously expresses a tissue protective NEPOR receptor complex; and (b) administering the compound to a second animal immediately following infliction of the same injury as in step (a), wherein the second animal is deficient in expression of a tissue protective NEPOR receptor complex or components thereof; such that if recovery from the injury differs in the animal of step (a) as compared to the animal of step (b), a compound that modulates a tissue protective activity is identified.

In another aspect, there is provided a method for treating the negative patient outcomes associated with EPO stimulated NEPOR function, involving the co-administration of EPO with an inhibitor of NEPOR activity. In one embodiment, the method comprises administering an effective amount of anti-NEPOR antibody from claim 1, in combination with EPO, whereby such combinations permits haematopoietic signalling whilst switching off NEPOR signalling and thus EPO mediated cell survival signals on tumour cells. In another, the method further comprises administering an effective amount of EPHB4 tyrosine kinase inhibitor in combination with EPO, whereby such combinations permits haematopoietic signalling whilst switching off NEPOR signalling and thus EPO mediated cell survival signals on tumour cells. In another, the method further comprises administering an effective amount of anti-NEPOR siRNA's, in combination with EPO, whereby such combinations permits haematopoietic signalling whilst switching off NEPOR signalling and thus EPO mediated cell survival signals on tumour cells.

In another aspect, a method is provided for decreasing the survival of tumour cells or tissues in a human comprising administering a therapeutically effective amount of a compound that modulates the activity of a tissue protective NEPOR receptor complex to a human in need thereof, wherein said decreased survival of cancer cells/tissues results in the decrease of tumour growth and/or an increase in patient survival, with the proviso that the compound is an EPO derivative and not a wild-type EPO.

In one aspect, there is provided a method for modulating cell survival in NEPOR positive tissue comprising administering an EPO mutants and peptides selected from the group consisting of peptides from each of SEQ ID NO. 17 through SEQ ID NO. 212.

In another, a method is provided for modulating cell survival in NEPOR positive tissue comprising administering an effective amount of an EPO chimera's, comprising an ephrin receptor ligand binding domain selected from the group consisting of SEQ ID NO.215, is and SEQ ID NO. 216. In one embodiment, the compound is an antibody specific for the tissue protective NEPOR receptor complex. In another, the compound is an antibody is specific for a tissue protective NEPOR receptor complex ligand. In another, the compound is a small molecule, peptide, or a member of a library. In another, the compound binds to the tissue protective NEPOR receptor complex. In another, the compound decreases the activity of the tissue protective NEPOR receptor complex. In another, the compound is administered in conjunction with an EPO. In another embodiment, the disease or disorder is a cancer including, head and neck cancer, breast cancer, liver cancer, colorectal cancer, small intestine cancer, leukemia, prostate cancer, lung cancer, ovarian cancer, pancreatic cancer, endometrial cancer, stomach cancer, non-Hodgkin lymphoma, kidney cancer, Renal cell carcinoma (RCC), malignant melanoma, gallbladder cancer, bladder cancer, vulvar cancer, Penile cancer, testicular cancer, thymus cancer, Kaposi's sarcoma, eye cancer, adrenal gland cancer, brain cancer, cervical cancer, appendix cancer, adenoid cancer, bile duct cancer, urethral cancer, spinal cancer, Ewing's family of tumors, extragonal germ cell cancer, extra hepatic bile duct cancer, fallopian tube cancer, soft tissue cancers, bone cancer, Hodgkin's lymphoma, anal cancer, malignant mesothelioma, vaginal cancer skin cancer, central nervous system cancer (craniopharyngioma), pleuropulmonary blastoma, nasal cavity and paranasal sinus cancer transitional cell cancer of renal pelvis and ureter, pituitary gland cancer, sqamous cell carcinoma of the head and neck (HNSCC), prostate cancer, colorectal cancer, lung cancer, brain cancer, bladder cancer, and salivary gland cancer. In one embodiment, the cancer comprises cancer cells expressing the tissue protective NEPOR receptor complex. In another the cancer is metastatic cancer. In another, the cancer is an angiogenesis-dependent cancer.

In another aspect, there is provided a method for treating a patient suffering from an angiogenesis-associated disease, comprising administering to the patient a compound identified by the inventive methods.

In another aspect, there is provided siRNA which is specific for EPH-B4 for use in treating a cancer and/or tumor patient that is receiving or will receive Erythropoietin.

EXAMPLES

Example 1

A variety of sequence analysis approaches were pursued, including the search for homologues of the EPO binding domain from EPOR, a domain analysis based method combined with text-mining, and EPO homology analysis followed by text-mining of resultant hits. Only that part of the human proteome exposed to the extracellular environment was investigated. This allowed a focus on homologies that were significant, though possibly overlooked within the context of a complete proteome analysis. This formed the Xtra-Cell database. The XtraCell database performed a signal peptide and transmembrane prediction for the entire human proteome. All proteins possessing at least one of these features were stored in a first version of the extracellular database. Given that not all extracellular proteins actually possess either of these features, there was extracted a list of protein domains specific to the extracellular environment from a SMART (Simple Modular Architecture Research Tool—. SMART is a well-known protein domain database with a strong bias towards domains contained in signalling proteins.) These were then screened against the human proteome using the HMMER algorithm. HMMER is a freely distributable implementation of profile HMM software for protein sequence analysis—Profile hidden Markov models (profile HMMs) can be used to do sensitive database searching using statistical descriptions of a sequence family's consensus. All hits were added to the XtraCell database and the dataset made non-redundant. A final version of the XtraCell database was established for the purpose of these EPO specific analyses.

Example 2

Figure 4:
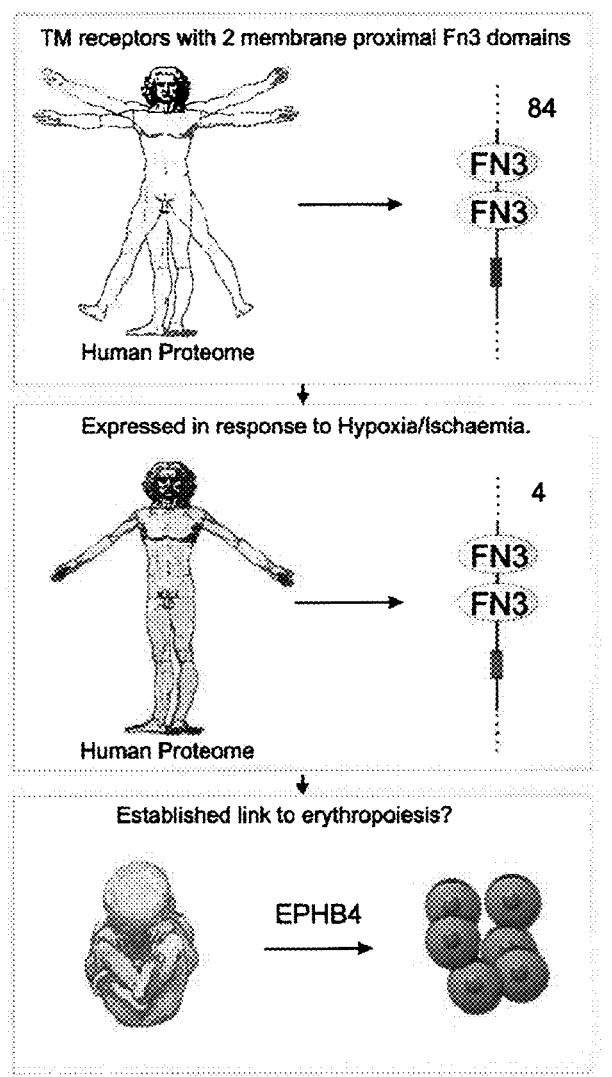
FIG. 4 shows a process for identifying putative EPO binding transmembrane receptors. All proteins containing two membrane proximal FN3 domains were extracted (84 in all) and assessed for evidence of response to hypoxia. EPH-B4 was amongst one of four possible proteins extracted. Moreover, it is the only member of the Ephrin receptor family which is embryonic lethal, with death in embryo's preceding that of EPOR knock-outs.

This example illustrates a domain-based approach coupled with a text-mining and genome-wide analysis. The operating theory was that any novel EPO receptor involved in mediating EPO's neuroprotective effect might also possess the two membrane proximal fibronectin 3 (FN3) domains (as found in EPOR), whilst at the same time being hypoxia inducible. Such conserved domain architecture is compatible with both a heterodimeric complex containing EPOR and/or an independent hypoxia inducible homodimeric receptor. All proteins containing two membrane proximal FN3 domains from the human proteome (84 in all) were extracted and asked whether there was any evidence for their role in response to low oxygen conditions/ischaemia. (See FIG. 4) The latter analysis was performed using a text-mining approach that encompasses the use of comprehensive protein synonyms, and concepts such as hypoxia and ischaemia. Of the 84 proteins containing the 2FN3-TM domain composition, only four showed evidence for mediating response to low oxygen conditions: EPH-B4, IL6RB, TIE1 and GM-CSF. Apart from EPH-B4, the cellular role of each of these proteins has been studied and an important role in response to hypoxia established.

Figure 5:
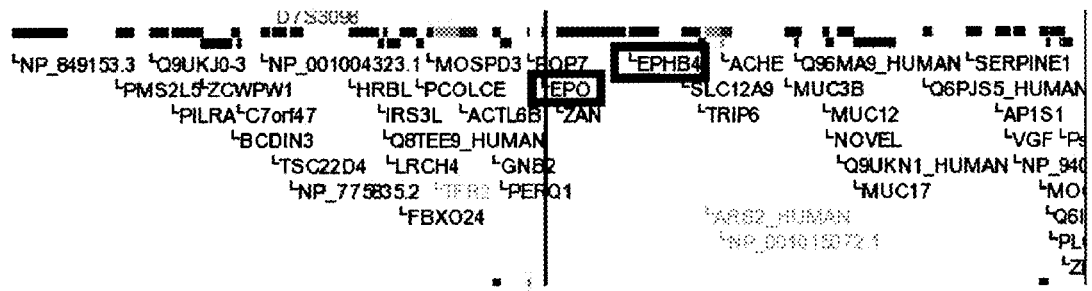
FIG. 5 shows the human EPO locus showing the neighbouring EPH-B4 gene.

Direct examination of the EPH-B4 locus revealed that it directly juxtaposes the EPO locus, albeit on the opposite strand. (See FIG. 5) This close genomic association was conserved in all vertebrate genomes examined. The need for immediate response of cells to low oxygen conditions and thus the need to co-transcribe/-translate key effector molecules was seen. Moreover, such genomic co-localisation of functionally associated molecules is seen for other receptor: ligand partners (e.g. MST1 and its receptor MST1R: see worldwide web at ensembl.org/Homo_sapiens/contigview?gene=OTTHUMG00000136237;db=vega).

Figure 6:
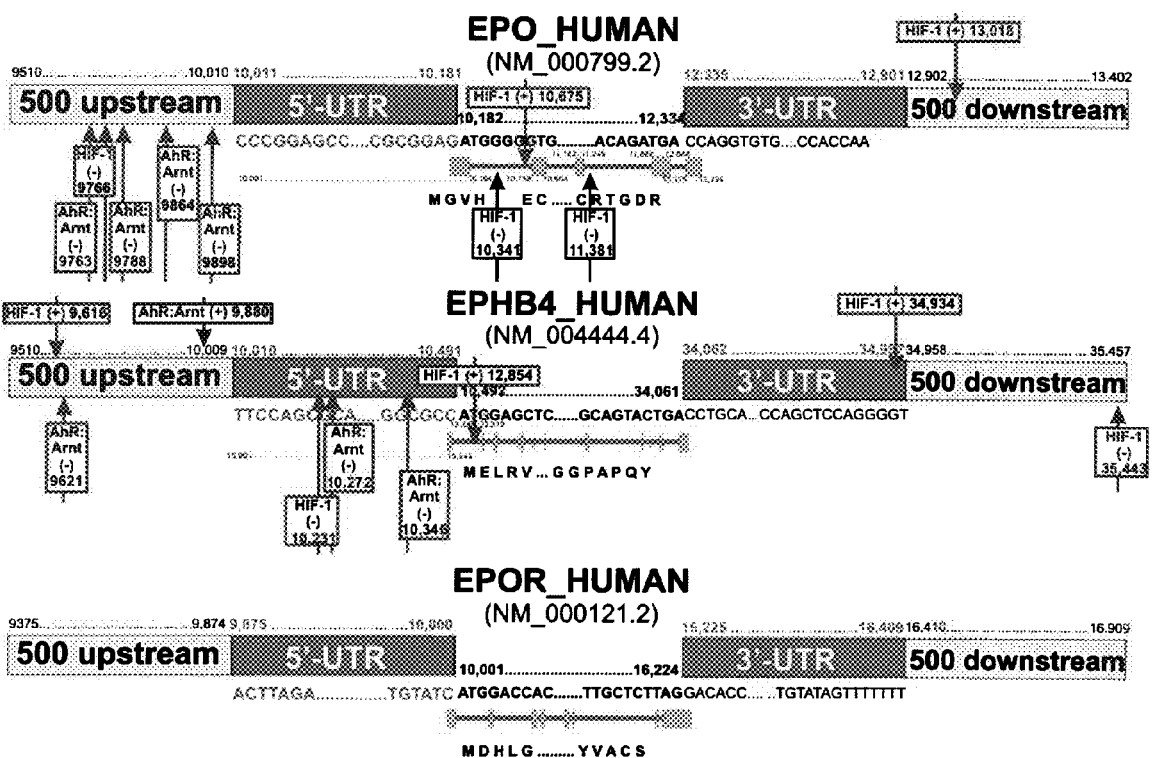
FIG. 6 shows a schematic of the results from analysis of the 5' and 3' UTR's (and an additional 500 bp on either side) of the EPO, EPOR and EPH-B4 genes for the presence of hypoxia inducible transcription factor binding sites. This study was performed employing the "Match" algorithm from TRANS-FAC (*Nucleic Acids Res.* 2003 January 1, 31(1):374-8) to analyse the composition of HIF1 binding sites. Strikingly, only the EPO and EPH-B4 genes were found to contain such sites, supporting the hypothesis that EPH-B4 is indeed hypoxia inducible. The figure discloses the nucleotide sequences as SEQ ID NOS 225-233, respectively, in order of appearance and the protein sequences as SEQ ID NOS 268-273, respectively, in order of appearance.

To examine this possibility in greater detail, we analysed the promoter, 5' UTR and 3' UTR regions of EPO, EPHB4 and EPOR in search of hypoxia inducible factor binding sites. Here we utilised the 'match' algorithm from Genomatix, searching for strict conservation of the core binding site residues and at least 90% conservation of non-core residues. We found that the EPO and EPH-B4 loci possessed numerous hypoxia-inducible transcription factor binding sites. In contrast, the EPOR gene regulatory regions were found to be complete devoid of such HIF-1 binding sites, again hinting at a possible role for EPHB4 as a hypoxia inducible EPO receptor. (See FIG. 6)

Example 3

Figure 7A:
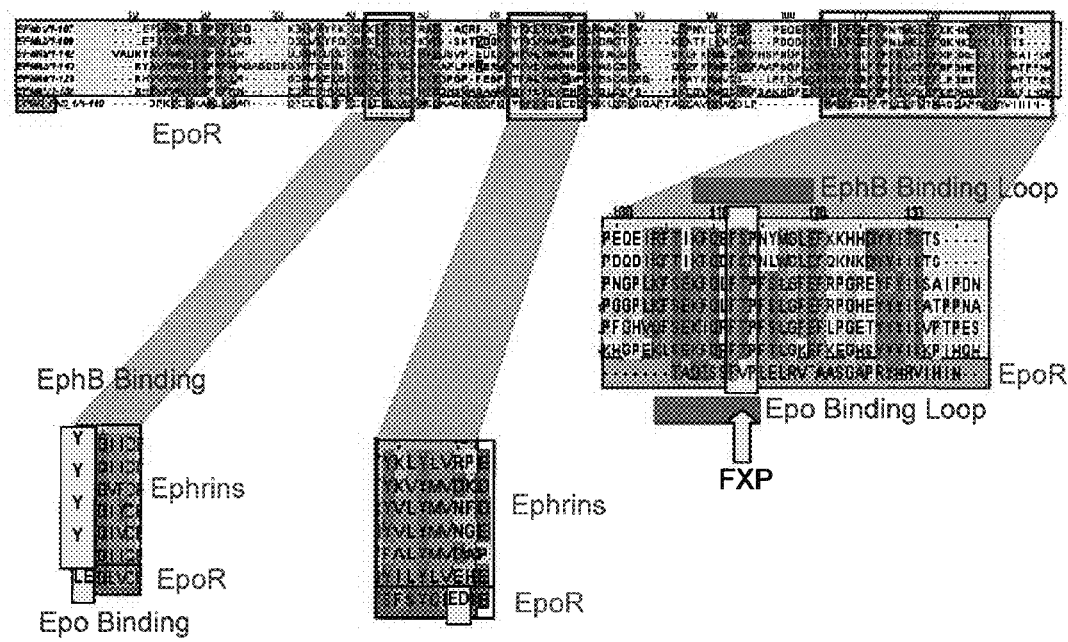
FIG. 7A shows a structural analysis of EphrinA5:EphB2 association in comparison with that of EPO:EPOR. This structural analysis reveals several commonalities consistent with a propensity for Ephrin A1 to bind EPO. The top panel shows homology of the EPO binding region of EPOR to the human Ephrin A molecules.
Figure 7B:
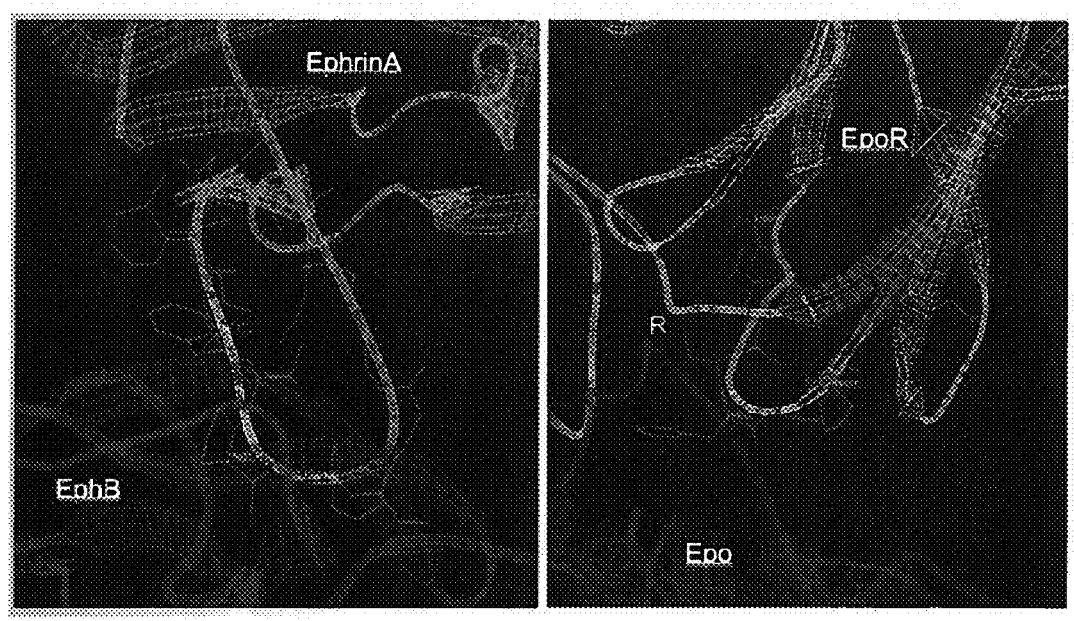
FIG. 7B compares the structural aspects of Ephrin A with EPOR. Figure discloses SEQ ID NOS 234-240 in the first box, residues 73-107 of SEQ ID NO: 234, 75-109 of SEQ ID NO: 235, 81-119 of SEQ ID NO: 236, 85-123 of SEQ ID NO: 237, 76-114 of SEQ ID NO: 238, 79-117 of SEQ ID NO: 239 and 76-105 of SEQ ID NO: 240 in the second box, residues 31-34 of SEQ ID NO: 234, 31-34 of SEQ ID NO: 235, 33-36 of SEQ ID NO: 236, 36-39 of SEQ ID NO: 237, 30-33 of SEQ ID NO: 238, 30-33 of SEQ ID NO: 239 and 26-32 of SEQ ID NO: 240 in the third box, and residues 45-53 of SEQ ID NO: 234, 47-55 of SEQ ID NO: 235, 50-58 of SEQ ID NO: 236, 54-62 of SEQ ID NO: 237, 47-55 of SEQ ID NO: 238, 48-56 of SEQ ID NO: 239 and 47-55 of SEQ ID NO: 240 in the fourth box.

This example shows the homology-based approach using human extra-cellular database. Here we sought to directly identify regions of EPO binding activity in other proteins, by direct comparison to the EPO binding domain of EPOR. The region of EPOR responsible for EPO binding was thus extracted and used to identify homologies with proteins of the XtraCellDB. This specially developed database holds distinct advantages in that all homologies identified are to human extracellular proteins, thus avoiding the need to assess spurious homologies to irrelevant intracellular species. Analysis of resultant homologues revealed a striking homology to the EphrinA1 protein, within the top four hits. Given what we had learned about EPH-B4's possible role in EPO signalling we decided to assess this homology in greater detail using the Swiss-model protein structure package. Here we employed information derived from the co-crystal structure of Ephrin A5 in association with EphB2 and compared it to EPO:EPOR co-crystal information. Conservation of key residues in structurally aligned positions allowed us to conclude a firm structural basis for association between Ephrin A1 and EPO. Moreover, the realisation that both EphrinA1 and EPHB4 possess a putative affinity for EPO, suggests a more exciting functional context for eprhin biology than heretofore recognised (See FIG. 7).

Example 4

This example provides wet lab or in vivo data that validates the bioinformatics analysis provide in Examples 1-3 herein. In vivo validation of EPH-B4's role in EPO signalling has focussed on the neuroprotective aspect of EPO's function, with a bias towards the hypothesis that EPH-B4 and EPOR are heterodimeric partners. The following table lists the validation experiments for which data are available (see Table 7).

TABLE 7

Figure 8:
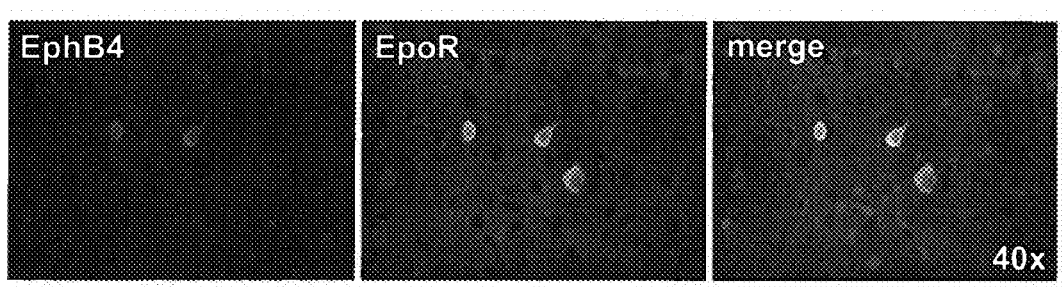
FIG. 8 shows staining of hippocampus with anti-EPH-B4 and anti-EpoR antibodies. It should be noted that there is a striking co-expression of both proteins restricted to certain cells only. These data suggest functional coupling of EPH-B4 and EPOR activity.

| LAB-BASED validation experiments | | |
|---|---|---|
| Method | Goal | Result |
| Immuno-histochemistry | To assess the expression of EPHB4 protein in brain and how it relates to EPOR expression. | Precipitation stainings on adult rodent brain showed that EPHB4 was expressed in adult neurons in the same pattern as EPO receptor. Staining in hippocampus showed co-expression of EPOR and EPHB4 (See FIG. 8). Strikingly, the staining was restricted to particular cells within |

TABLE 7-continued

LAB-BASED validation experiments

| Method | Goal | Result |
|---|---|---|
| Co-IP | Exogenous expression of EPOR/EPHB4 in COS cells. Co-ip with EpoR- and EphB4-antibodies => WB analysis. | the field of tissue. Positive. Use of EPOR antibody successfully Co-IP's EPHB4 protein. |

Immunohistochemistry. For immunofluorescence, sections of paraffin-embedded rat brain tissues (2 μm) were deparaffinated and microwaved (citrate buffer at 600 W for 15 min). Afterwards, sections were incubated simultaneously with the EpoR antiserum (1:200; sc-697, Santa Cruz Biotechnology) and the EphB4 antibody (1:100; AF446, R&D Systems) at 4° C. over night. After adding a biotinylated anti-goat secondary antibody (1:200; Dianova), sections were incubated with Streptavidin-coupled Alexa Fluor 555 (1:200; Invitrogen, Karlsruhe, Germany) and a FITC-coupled anti-rabbit secondary antibody (1:200; Dianova). The nuclei were counterstained with Hoechst 33342 (1:10,000; Molecular Probes). Controls for the stainings included omission of primary antibodies, fluorophor swapping, and single-fluorescence stainings. Images were obtained with an Olympus IX-81 microscope with narrow-bandwidth monochromator excitation (Polychrome IV, Till Photonics, Grafelfing, Germany) and appropriate filters.

Both EPHB4 and EPOR displayed a striking co-localisation when assessed in rat brain tissue sections. Without being bound by theory, this co-expression suggests functional coupling of both receptors.

Co-immunoprecipitation. The principle of an immunoprecipitation is an antibody (monoclonal or polyclonal) against a specific target antigen is allowed to form an immune complex with that target in a sample, such as a cell lysate. The immune complex is then captured on a solid support to which either Protein A or Protein G has been immobilized (Protein A or G binds to the antibody, which is bound to its antigen). The process of capturing this complex from the solution is referred to as precipitation. Any proteins not "precipitated" by the immobilized Protein A or G support are washed away. Finally, components of the bound immune complex (both antigen and antibody) are eluted from the support and analyzed by SDS-PAGE (gel electrophoresis), often followed by Western blot detection to verify the identity of the antigen.

Traditional immunoprecipitation involves the following steps:
1. Form the antigen-antibody complex (immune complex) by incubating specific antibody with the antigen-containing sample for 1 hour to several hours.
2. Capture the immune complex on an immobilized Protein A or Protein G agarose gel support by incubation for 0.5-2 hours.
3. Remove any non-bound protein (non-immune complex sample components) from the precipitated complex by washing gel support with additional sample buffer.
4. Boil gel support in reducing SDS-PAGE sample loading buffer.
5. Recover sample eluted in loading buffer from gel support and analyze by SDS-PAGE.
6. Perform Western blot analysis, probing with antigen-specific antibody.

In a co-immunoprecipitation the target antigen precipitated by the antibody "co-precipitates" a binding partner/protein complex from a lysate, that is, the interacting protein is bound to the target antigen, which becomes bound by the antibody that becomes captured on the Protein A or G gel support. The assumption that is usually made when associated proteins are co-precipitated is that these proteins are related to the function of the target antigen at the cellular level.

Figure 9:
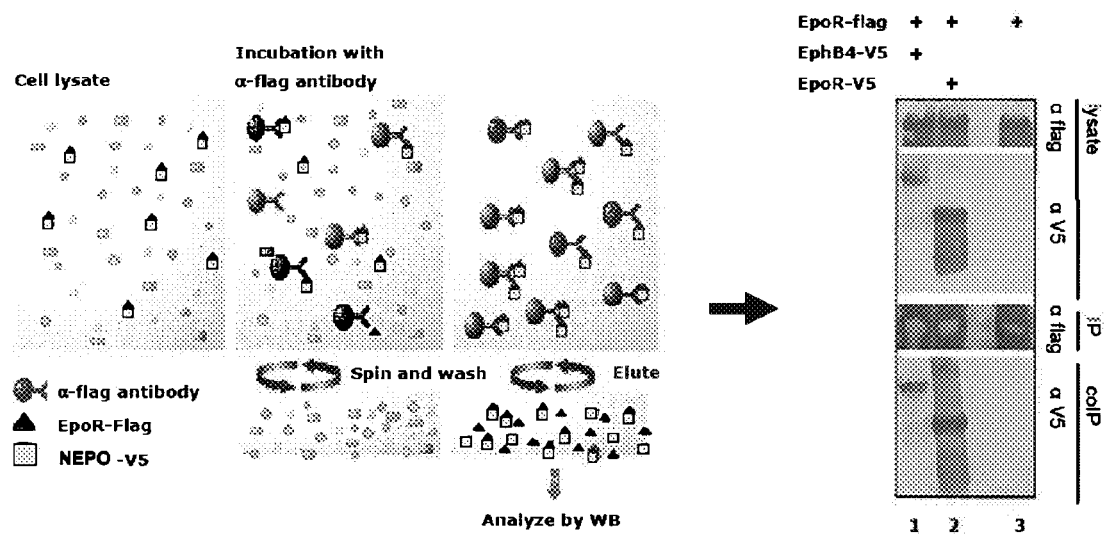
FIG. 9 shows co-immunoprecipitation of EPH-B4 using flag-tagged EpoR. This finding is consistent with the notion that EPH-B4 and EPOR might heterodimerize.

Assessment of a putative EPHB4:EPOR association using co-immmunoprecipitation showed that both proteins were physically associated. Here, FLAG-tagged EPOR was co-expressed with EPH-B4 in COS cells and then immunoprecipitated using an a-FLAG antibody. As can be seen from FIG. 9, EPHB4 was shown to co-immunoprecipitate in these experiments.

Human Fc Antibody Constructs. The Fc conjugate approach is most appropriate when dealing with dimeric cell surface receptors. Here the extracellular portion of EPHB4/EPOR can be fused to an Fc fragment. This method has advantages due to its in vivo (therapeutic) viability and the fact that it optimally mimics the dimerised receptor state. FIG. 10 highlights the Human constructs that can be used to show EPHB4's/EphrinA1's affinity for EPO.

One of two alternatives can assay the interaction of the Fc constructs with EPO, including, for example, a protein array approach or a surface plasmon resonance analysis.

Example 5

Further In Nitro and In Vivo Validation of NEPORs Role in Mediating EPO Function.

In these experiments we sought to determine the response to erythropoietin (EPO) treatment in a panel of ovarian cancer cell lines. This would be mediated by the expression of erythropoietin receptor (EPO as well as two receptors that potentially may be able to activate signaling pathways in response to EPO binding, EPH-B4 and Ephrin A1. It was first necessary to characterize the expression of these receptors in a panel of ovarian cancer cell lines. First we collected RNA from each cell line and reverse transcribed them into cDNA. Using specific primers for each receptor we analyzed their RNA expression. As evident in the figures the expression of EPOR and EPH-B4 RNA is different in different cell lines suggesting changes in transcriptional regulation during tumorigenesis no significant changes were seen in the EphrinA1. It was then necessary to determine protein expression of these receptors in the panel. Again we see significant differences in the expression of the EPOR and EPH-B4 receptors though they do not coincide with the RNA expression suggesting there is changes in post transcriptional regulation of these receptors in the cell lines. We then categorized these expression changes particularly with regard to the EPOR and EPH-B4 to then analyze the response to EPO treatment. We analyzed their response to chemotherapy in conjunction with EPO. We found that particularly in the HeyA8 ovarian cancer cell line that EPO was able to abrogate the apoptosis induced by docetaxel. It was then necessary to analyze the activation of signaling pathways known to be activated by these receptors in response to EPO treatment. Three cell lines were starved for two hours to isolate their response to EPO. Cell lines with higher expression (HeyA8 and HeyA8 MDR) of the EPOR demonstrated activation of the MAPK/ERK pathway while cell lines that expressed higher EPH-B4 (SKOV3ip1) demonstrated increased activation of the AKT and STAT5b signaling pathways. We then sought to determine a EPO dose that optimized its tumor promoting effect in vivo. Female nude mice were injected i.p. with HeyA8 MDR (positive for both EPOR and EPH-B4). At day eight the mice were treated with increasing doses of EPO (10, 50, 100 U)

every two days. Treatment continued until tumors became evident, the mice were then sacrificed and the tumor weight was determined. We saw an increase in tumor weight as compared to control in the mice treated with 10 and 50 U EPO. The differential expression of EphB4 in cell lines as well as the activation of particular signaling pathways suggested that it would also mediate the tumor promoting effect in vivo. To determine this we again injected mice with HeyA8 MDR cell lines i.p. At day eight we began treatment with EPO (50 U 3× week) in conjunction with siRNA specific to EPH-B4 [sense: (SEQ ID NO: 266) 5'CAGCCAAUAGCCACUC-UAA3'; antisense: (SEQ ID NO: 267) 5'UUAGAGUGGC-UAUUGGCUG3']. As previously described EphB4 siRNA was able decrease tumor growth alone. Moreover, EPH-B4 siRNA also completely abrogated the EPO induced tumor growth.

Example 6

To further validate that EPHB4 is a novel EPO receptor a co-immunoprecipitation experiment was conducted using an anti-EPHB4 antibody to immuno-precipitate EPHB4 from cellular lysate.

In particular, cells (HeyA8 MDR and A2780cp20) were grown in RPMI-1640 supplemented with 15% fetal calf serum and gentamycin. At 70% confluency, the cells were treated with Epo (50 U/ml) for 15 and 30 minutes. In addition, one group of cells were exposed to MG132 (10 μM) for 30 minutes. Cell lysates were prepared after washing twice with cold-PBS and incubated in modified radioimmunoprecipitation assay buffer (RIPA). Protein concentrations were determined using a BCA Protein Assay Reagent kit (Pierce Biotechnology, Rockford, Ill.). For immunoprecipitation, 500 μg of cell lysate was incubated with 6 μl of primary antibody (EphB4-Abcam) overnight at 4° C. Protein A Sepharose beads were added, and the mixture was incubated for 3 hours at 4° C. Laemilli buffer was added to dislodge complexes from beads, and beads were separated by centrifugation at 3,500 g for 5 minutes at 4° C. The supernatant were then used for immunoblot analysis. Supernatants were subjected to 8% SDS-PAGE separation. Samples transferred to a nitrocellulose membrane electrophoresis (Bio-Rad Laboratories, Hercules, Calif.) were incubated with EphB4 (Abcam Co.) and Epo (R & D Systems) antibodies overnight at 4° C., detected with horseradish peroxidase (HRP)-conjugated anti-mouse/rabbit IgG (Amersham, Piscataway, N.J.), and developed using enhanced chemiluminescence detection kit (Pierce Biotechnology).

Figure 19:
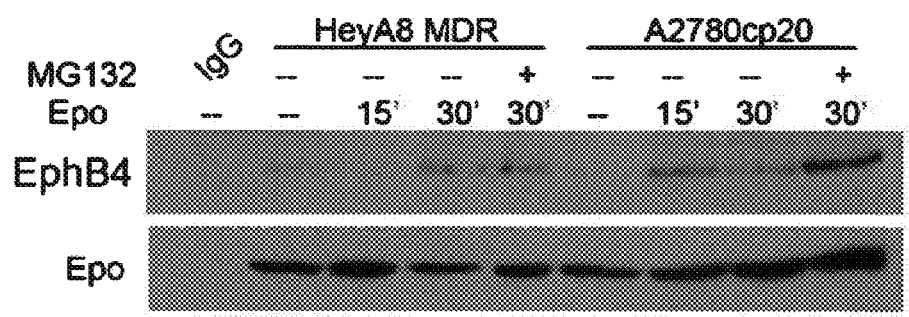
FIG. 19 shows an immunoblot analysis of HeyA8 MDR and A2780cp20 cells exposed to Epo (50 U/ml) for 15 and 30 minutes or MG132 (10 µM) for 30 minutes followed by co-immunoprecipitation with an anti-EPHB4 antibody.

The results are provided in FIG. 19. The data clearly demonstrates a direct association between EPHB4 and EPO, suggesting tight functional coupling of both proteins.

Example 7

Radiolabelled EPO is capable of binding to independent cell-lines to various degrees. The capacity of EPHB4 to mediate such binding was investigated in three different cell-lines with varying degrees of EPHB4 and EPOR expression.

Cells (HeyA8, HeyA8 MDR and A2780cp20) were grown in RPMI-1640 supplemented with 15% fetal calf serum and gentamycin. Cells were transiently transfected with control siRNA [sense: 5'UUCUCCGAACGUUGUCACGU3' (SEQ ID NO: 264); antisense: 5'ACGUGACACGUUCG-GAGAA3' (SEQ ID NO: 265)], EphB4 siRNA [sense: 5'CAGCCAAUAGCCACUCUAA3' (SEQ ID NO: 266); antisense: 5'UUAGAGUGGCUAUUGGCUG3' (SEQ ID NO: 267)] or EpoR siRNA[sense: 5'CCGAAGAGCUUCU-GUGCUU3' (SEQ ID NO: 262); antisense: 5'AAGCACA-GAAGCUCUUCGG3' (SEQ ID NO: 263)]. After 72 hours, the cells were detached with 0.1% EDTA. 1×10$^6$ cells were diluted in 80 μl of binding buffer (MEM+20 mM HEpes, Ph 7.4, 0.1% BSA). They were incubated with 7.5 mM $^{125}$I-Epo at room temperature for 2.5 hours. Non-specific binding was determined by exposing the cells to 7.5 mM $^{125}$I-Epo and cold-Epo (×200). The cells were washed with PBS and resuspended in cushion buffer (10% BSA in PBS). After centrifugation, the tubes were frozen in dry ice, and the pellet clipped and placed in scintillation fluid. Total binding was calculated by subtracting non-specific from total binding.

Figure 20:
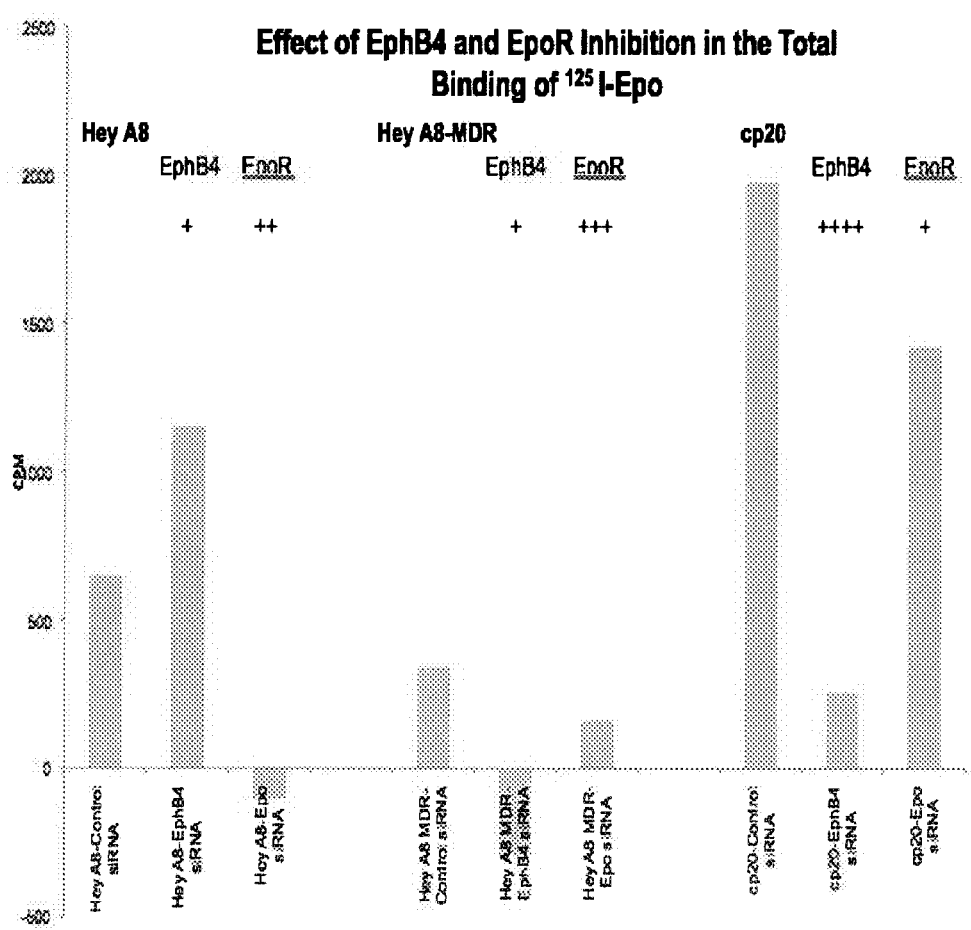
FIG. 20 graphically shows the effect of EphB4 and EpoR inhibition on binding of iodine-125-labelled EPO in cell lines HeyA8, HeyA8 MDR and A2780cp20.

The results, provided in FIG. 20, demonstrate that EPHB4 is indeed responsible for the bulk of EPO binding in certain cell types (e.g. A2780cp20).

Example 8

To demonstrate that EPHB4 is responsible for mediating tumour cell survival and reduced patient outcome in response to EPO treatment, immunohistochemical analysis of EphB4 and EpoR was conducted on tumour samples from 71 patients with high grade and high stage epithelial ovarian cancer. All patients were previously treated with surgery followed by taxane-platinum chemotherapy and EPO therapy.

Specifically, immunohistochemical analysis of EphB4 and EpoR was conducted on 4 μm-thick formalin-fixed paraffin-embedded epithelial ovarian cancer specimens. Slides were deparaffinized with xylene and decreasing concentrations of ethanol and rehydrated with PBS. Antigen retrieval for EphB4 was performed using 1× Diva Decloaker (Biocare Medical, Concord, Calif.) under steam for 40 minutes followed by a 20 minute cool down at room temperature. Antigen retrival for EpoR was performed using 1× Borg Decloaker (Biocare Medical) under heat (125° C.) and pressure for 4 minutes followed by a 60 minute cool down at room temperature. Following antigen retrival, all sections were washed with PBS. Endogenous peroxidases were blocked with 3% hydrogen peroxide in PBS for 12 minutes at room temperature followed by nonspecific protein blockign with either 5% BSA in TBST for 10 minutes at room temperature for EphB4 or 5% normal horse serum for 20 minutes at room temperature for EpoR. Sections were then incubated with primary antibody to EphB4 (mouse monoclonal anti-human, 1:500 dilution, Abcam, Cambridge, Mass.) or EpoR (biotinylated mouse monoclonal anti-human, 1:25 dilution, R&D Systems, Minneapolis, Minn.) in the respectively blocking solution overnight at 4° C. Secondary amplification was performed using either the MACH4 polymer detection system (EphB4: Biocare Medical) or the 4plus Streptavidin AP label (EpoR: Biocare Medical). Visualization was achieved with 3,3'-diaminobezidine (DAB; Open Biosystems, Huntsville, Ala.). Slides were counterstained with Gill No. 2 hematoxylin (Sigrna-Aldrich, St. Louis, Mo.), washed with PBS for 1 minute and mounted with Universal Mount (Reserach Genetics, Huntsville, Ala.). Clinical samples were scored for staining with the EphB4 and EpoR antibodies by a board-certified pathologist who was blinded to the clinical outcome of the patients. EphB4 and EpoR expression was determined semi-quantitatively by assessing the distribution of the positive cells and the staining intensity in the tumor cells. The distribution of positive cells was rated as follows: 0 points, no staining; 1 point, focal or <25%; 2 points, 25-50%, 3 points, 50-75%; 4 points, 75-100%. The staining intensity was rated as focal or weak (1 point), moderate (2 points) or heavy (3 points). Points for intensity and distribution were multiplied, and an overall score ranging from 0 to 12 was assigned. An overall score <3 was deemed negative and >3 positive.

Figure 21:
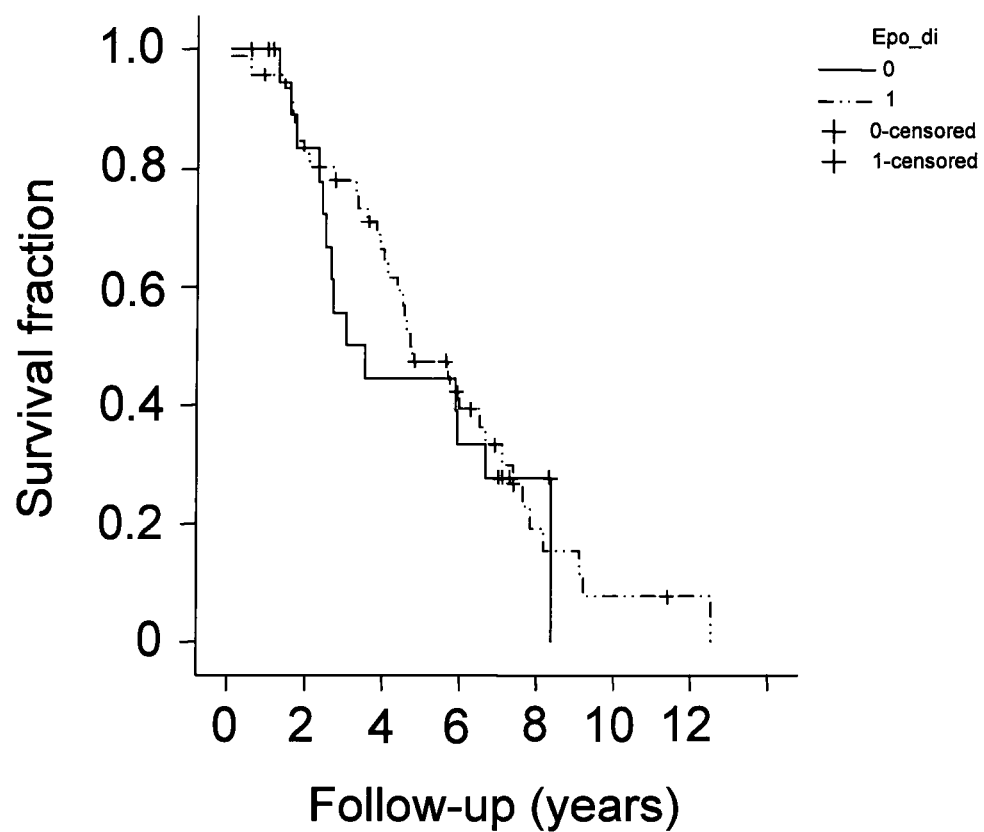
FIG. 21 graphically depicts immunohistochemical analysis of EpoR conducted on 4 µm-thick formalin-fixed paraffin-embedded epithelial ovarian cancer specimens. "O" designates patients negative for EpoR, while "1" designates patients positive for EpoR. The "†" symbol designates censored points, i.e. last medical follow-up for patients who have not died.
Figure 22:
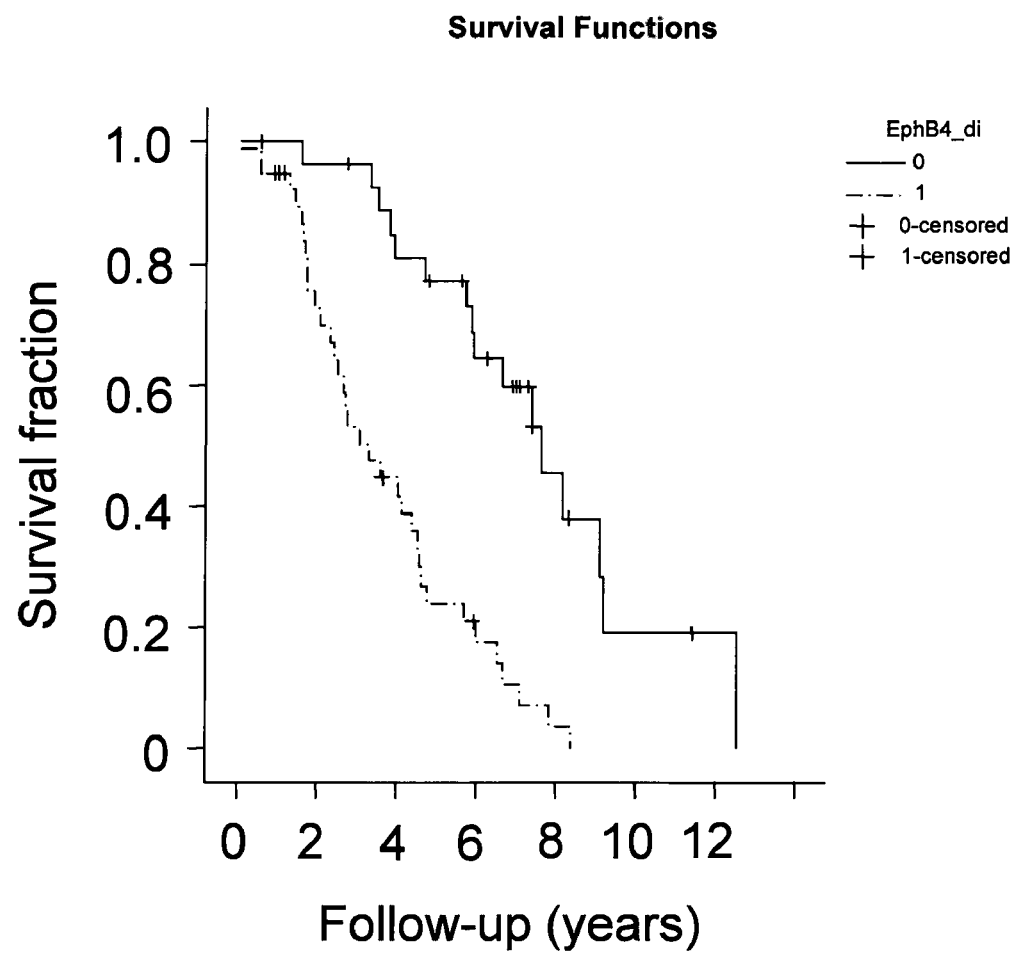
FIG. 22 graphically depicts immunohistochemical analysis of EphB4 conducted on 4 µm-thick formalin-fixed paraffin-embedded epithelial ovarian cancer specimens. "O" designates patients negative for EphB4, while "1" designates patients positive for EphB4. The "†" designates censored points, i.e. last medical follow-up for patients who have not died.
Figure 23:
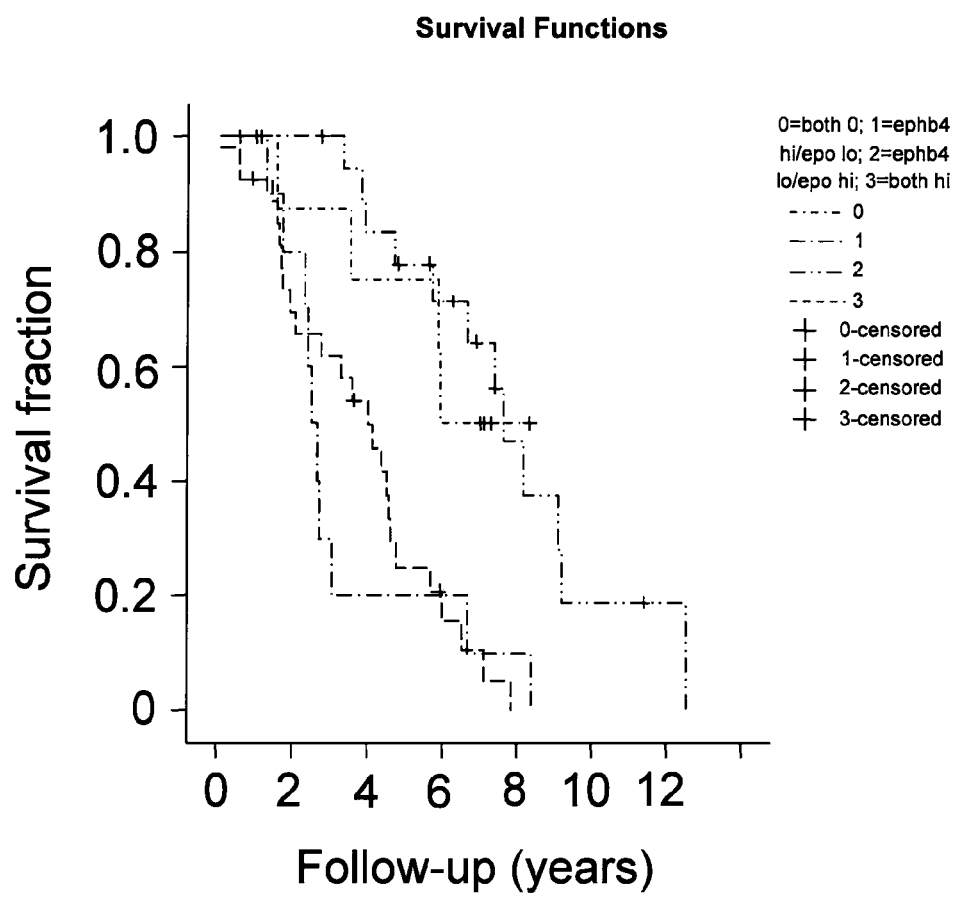
FIG. 23 graphically depicts immunohistochemical analysis of EphB4 and Epo-R conducted on 4 µm-thick formalin-fixed paraffin-embedded epithelial ovarian cancer specimens. "O" designates patients that are both EphB4 and EpoR negative; "1" designates patients that are EphB4 positive and EpoR negative; "2" designates patients that are EphB4 negative and EpoR positive; "3" designates patients that are EphB4 positive and EpoR positive. The "†" designates censored points, i.e. last medical follow-up for patients who have not died.

The results are depicted in FIGS. 21-23. Overexpression of EPHB4, but not EPOR was found to correlate with poorer clinical outcome in response to EPO treatment. High levels of EPHB4 expression with low levels of EPOR showed the worst median survival (2.53 years), while low levels of EPHB4 and high levels of EPOR showed the best median survival (7.67 years). The data supports the need for a theranostic test to assess EPHB4 expression prior to, and/or during, an EPO treatment regimen.

We claim:

1. A method, comprising
   (A) obtaining a cancer tissue sample from a patient that is a candidate for EPO therapy;
   (B) determining in vitro the level of expression of EPH-B4 in said sample by immunohistochemistry, wherein the distribution of EPH-B4 positive cells is assessed as follows: 0 points, no staining; 1 point, focal or <25%; 2 points, 25-50%, 3 points, 50-75%; 4 points, 75-100%; the staining intensity is assessed as follows: focal or weak (1 point), moderate (2 points) or heavy (3 points); and points for intensity and distribution is multiplied to yield a product ranging from 0 to 12, wherein a product of >3 denotes an elevated level of EPH-B4;
   (C) correlating an elevated level of EPH-B4 expression in said sample to a negative physiological response in said patient to EPO therapy, wherein said negative physiological response is one or more of increased tumor progression, proliferation of cancer, cell migration, and poorer patient survival;
   (D) selecting said patient wherein the expression of EPH-B4 is not elevated; and
   (E) administering EPO to said patient.

2. The method of claim 1, further comprising determining the level of expression in said sample of at least one of Ephrin A1 or EPOR.

3. The method of claim 1, wherein said negative physiological response is proliferation of cancer cells of said patient.

4. The method of claim 1, further comprising not administering EPO if the level of EPH-B4 expression is elevated.

* * * * *